(12) United States Patent
Ni et al.

(10) Patent No.: US 9,611,222 B2
(45) Date of Patent: *Apr. 4, 2017

(54) PYRIDINE COMPOUNDS AND THE USES THEREOF

(71) Applicant: Purdue Pharma L.P., Stamford, CT (US)

(72) Inventors: Chiyou Ni, Belle Mead, NJ (US); Bin Shao, Richboro, PA (US); Laykea Tafesse, Robbinsville, NJ (US); Jiangchao Yao, Princeton, NJ (US); Jianming Yu, Plainsboro, NJ (US); Xiaoming Zhou, Plainsboro, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/724,494

(22) Filed: May 28, 2015

(65) Prior Publication Data
US 2015/0259293 A1    Sep. 17, 2015

Related U.S. Application Data

(63) Continuation of application No. 13/821,732, filed as application No. PCT/IB2011/002172 on Sep. 16, 2011, now Pat. No. 9,056,832.

(60) Provisional application No. 61/384,136, filed on Sep. 17, 2010.

(51) Int. Cl.

| | |
|---|---|
| C07D 213/81 | (2006.01) |
| C07D 213/643 | (2006.01) |
| C07D 401/14 | (2006.01) |
| C07D 213/30 | (2006.01) |
| C07D 401/12 | (2006.01) |
| C07D 213/58 | (2006.01) |
| C07D 401/04 | (2006.01) |
| C07D 213/46 | (2006.01) |
| C07D 213/74 | (2006.01) |
| C07D 213/79 | (2006.01) |
| C07D 213/84 | (2006.01) |
| C07D 403/12 | (2006.01) |
| C07D 403/14 | (2006.01) |
| C07D 213/50 | (2006.01) |
| C07D 213/57 | (2006.01) |
| C07D 213/65 | (2006.01) |

(52) U.S. Cl.
CPC ......... *C07D 213/81* (2013.01); *C07D 213/30* (2013.01); *C07D 213/46* (2013.01); *C07D 213/50* (2013.01); *C07D 213/57* (2013.01); *C07D 213/58* (2013.01); *C07D 213/643* (2013.01); *C07D 213/65* (2013.01); *C07D 213/74* (2013.01); *C07D 213/79* (2013.01); *C07D 213/84* (2013.01); *C07D 401/04* (2013.01); *C07D 401/12* (2013.01); *C07D 401/14* (2013.01); *C07D 403/12* (2013.01); *C07D 403/14* (2013.01)

(58) Field of Classification Search
CPC .. C07D 213/81; C07D 213/30; C07D 213/46; C07D 213/50; C07D 213/57; C07D 213/58; C07D 213/643; C07D 213/65; C07D 213/74; C07D 213/79; C07D 213/84; C07D 401/04; C07D 401/12; C07D 401/14; C07D 403/12; C07D 403/14
USPC ...................................... 546/268.1
See application file for complete search history.

(56) References Cited

U.S. PATENT DOCUMENTS

| | | | |
|---|---|---|---|
| 4,697,012 A * | 9/1987 | Boulton ............... | C07D 213/50 544/124 |
| 5,250,530 A | 10/1993 | Giencke et al. | |
| 5,612,340 A * | 3/1997 | Zimmermann ...... | C07D 239/42 514/275 |

(Continued)

FOREIGN PATENT DOCUMENTS

| | | |
|---|---|---|
| CA | 2137443 A1 | 6/1995 |
| EP | 0600092 A1 | 6/1994 |

(Continued)

OTHER PUBLICATIONS

Baba; Synthetic Communications 1994, 24, 1029-1036.*

(Continued)

*Primary Examiner* — Noble Jarrell
*Assistant Examiner* — Daniel Carcanague
(74) *Attorney, Agent, or Firm* — Purdue Pharma L.P.; Alan L. Koller; Weiying Yang

(57) ABSTRACT

The invention relates to substituted pyridine compounds of Formula (I) and the pharmaceutically acceptable salts, prodrugs, and solvates thereof, wherein $R^{1a}$, $A^1$, $A^2$, E, G, $Z^1$, and $Z^2$ are defined as set forth in the specification. The invention is also directed to the use of compounds of Formula I to treat a disorder responsive to the blockade of sodium channels. Compounds of the present invention are especially useful for treating pain.

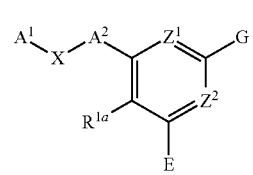

I

19 Claims, No Drawings

(56) References Cited

U.S. PATENT DOCUMENTS

| | | | |
|---|---|---|---|
| 5,627,136 A | 5/1997 | Rheinheimer et al. | |
| 5,639,770 A | 6/1997 | Chihiro et al. | |
| 5,670,525 A * | 9/1997 | Urbahns | C07D 213/85 514/334 |
| 5,705,502 A * | 1/1998 | Zimmermann | C07D 401/04 514/252.02 |
| 6,281,211 B1 | 8/2001 | Cai et al. | |
| 6,335,354 B2 | 1/2002 | Hogenkamp | |
| 6,414,011 B1 | 7/2002 | Hogenkamp et al. | |
| 6,479,484 B1 | 11/2002 | Lan et al. | |
| 6,492,383 B1 | 12/2002 | Munchhof et al. | |
| 6,500,825 B2 | 12/2002 | Lan et al. | |
| 6,613,803 B1 | 9/2003 | Wang et al. | |
| 6,638,947 B2 | 10/2003 | Wang et al. | |
| 6,696,442 B2 | 2/2004 | Wang et al. | |
| 6,737,418 B2 | 5/2004 | Hogenkamp et al. | |
| 6,770,661 B2 | 8/2004 | Shao et al. | |
| 6,867,210 B2 | 3/2005 | Hogenkamp et al. | |
| 6,919,363 B2 | 7/2005 | Hogenkamp et al. | |
| 7,022,714 B2 | 4/2006 | Sun et al. | |
| 7,078,426 B2 | 7/2006 | Hogenkamp et al. | |
| 7,091,210 B2 | 8/2006 | Lan et al. | |
| 7,105,549 B2 | 9/2006 | Shao et al. | |
| 7,169,782 B2 | 1/2007 | Sun et al. | |
| 7,229,993 B2 | 6/2007 | Goehring et al. | |
| 7,393,872 B2 | 7/2008 | Lan | |
| 7,541,465 B2 | 6/2009 | Lan et al. | |
| 7,579,367 B2 | 8/2009 | Shao et al. | |
| 7,872,127 B2 | 1/2011 | Lan et al. | |
| 7,943,643 B2 | 5/2011 | Shao et al. | |
| 8,426,431 B2 | 4/2013 | Lan et al. | |
| 9,045,435 B2 | 6/2015 | Goehring et al. | |
| 9,056,832 B2 | 6/2015 | Ni et al. | |
| 9,120,752 B2 | 9/2015 | Kyle et al. | |
| 9,120,786 B2 | 9/2015 | Yu et al. | |
| 9,133,131 B2 | 9/2015 | Shao | |
| 9,163,008 B2 * | 10/2015 | Ni | C07D 403/12 |
| 9,181,185 B2 * | 11/2015 | Yao | C07D 401/12 |
| 9,206,127 B2 * | 12/2015 | Tafesse | C07D 213/81 |
| 2002/0037926 A1 | 3/2002 | Lan | |
| 2003/0055088 A1 | 3/2003 | Shao et al. | |
| 2003/0069292 A1 | 4/2003 | Hogenkamp et al. | |
| 2003/0073724 A1 | 4/2003 | Shao et al. | |
| 2003/0225080 A1 | 12/2003 | Wang et al. | |
| 2003/0232860 A1 * | 12/2003 | Harada | A61K 31/44 514/332 |
| 2004/0097569 A1 | 5/2004 | Sun et al. | |
| 2004/0122237 A1 | 6/2004 | Amiri et al. | |
| 2004/0142978 A1 * | 7/2004 | Anderson | C07D 213/85 514/344 |
| 2004/0152696 A1 | 8/2004 | Sun et al. | |
| 2004/0176364 A1 | 9/2004 | Sun et al. | |
| 2004/0192691 A1 | 9/2004 | Hogenkamp et al. | |
| 2005/0043305 A1 | 2/2005 | Hogenkamp et al. | |
| 2005/0222027 A1 | 10/2005 | Chiang et al. | |
| 2006/0235028 A1 | 10/2006 | Li et al. | |
| 2008/0318932 A1 | 12/2008 | Lan | |
| 2009/0162319 A1 | 6/2009 | Shaginian et al. | |
| 2012/0129852 A1 * | 5/2012 | Duan | C07D 471/04 514/234.2 |
| 2013/0289044 A1 | 10/2013 | Goehring et al. | |
| 2013/0296281 A1 | 11/2013 | Kyle et al. | |
| 2013/0303568 A1 | 11/2013 | Lan et al. | |
| 2013/0345211 A1 | 12/2013 | Kyle et al. | |
| 2014/0005212 A1 | 1/2014 | Ni et al. | |
| 2014/0249128 A1 | 9/2014 | Yu et al. | |
| 2014/0288092 A1 | 9/2014 | Yao | |
| 2014/0303139 A1 | 10/2014 | Ni et al. | |
| 2014/0309228 A1 | 10/2014 | Engel | |
| 2014/0315783 A1 | 10/2014 | Shao | |
| 2015/0045397 A1 | 2/2015 | Tafesse et al. | |
| 2015/0057300 A1 | 2/2015 | Tafesse et al. | |
| 2015/0133500 A1 | 5/2015 | Tafesse et al. | |
| 2015/0141434 A1 | 5/2015 | Park | |
| 2015/0250789 A1 | 9/2015 | Goehring et al. | |
| 2015/0284383 A1 | 10/2015 | Lynch et al. | |
| 2015/0335642 A1 | 11/2015 | Shao | |
| 2015/0336974 A1 | 11/2015 | Youngman | |
| 2015/0344465 A1 | 12/2015 | Kyle et al. | |
| 2015/0353512 A1 | 12/2015 | Tadesse et al. | |
| 2016/0009659 A1 | 1/2016 | Lockman et al. | |
| 2016/0031873 A1 | 2/2016 | Yao et al. | |
| 2016/0052911 A1 | 2/2016 | Yao | |

FOREIGN PATENT DOCUMENTS

| | | |
|---|---|---|
| EP | 1724278 A1 | 11/2006 |
| EP | 1783116 A1 | 5/2007 |
| WO | WO-99/24440 A1 | 5/1999 |
| WO | WO-01/68612 A2 | 9/2001 |
| WO | WO-01/94342 A1 | 12/2001 |
| WO | WO-03/022276 A1 | 3/2003 |
| WO | WO-03/022285 A1 | 3/2003 |
| WO | WO-03/048137 A1 | 6/2003 |
| WO | WO-03/082272 A1 | 10/2003 |
| WO | WO-2004/013134 A2 | 2/2004 |
| WO | WO-2004/014844 A2 | 2/2004 |
| WO | WO-2004/052880 A1 | 6/2004 |
| WO | WO-2004/062553 A2 | 7/2004 |
| WO | WO-2004/084824 A2 | 10/2004 |
| WO | WO-2004/089308 A2 | 10/2004 |
| WO | WO-2005/014566 A1 | 2/2005 |
| WO | WO-2005/080393 A1 | 9/2005 |
| WO | WO-2005/107760 A1 | 11/2005 |
| WO | WO-2006/042289 A2 | 4/2006 |
| WO | WO-2006/055752 A2 | 5/2006 |
| WO | WO-2006/105222 A2 | 10/2006 |
| WO | WO-2007/038519 A1 | 4/2007 |
| WO | WO-2007/039146 A1 | 4/2007 |
| WO | WO-2007/116230 A1 | 10/2007 |
| WO | WO-2007/078523 A3 | 11/2007 |
| WO | WO-2008/097835 A2 | 8/2008 |
| WO | WO-2009/004430 A1 | 1/2009 |
| WO | WO-2009/014637 A2 | 1/2009 |
| WO | WO-2009/106885 A1 | 9/2009 |
| WO | WO-2009/109035 A1 | 9/2009 |
| WO | WO-2009/120789 A1 | 10/2009 |
| WO | WO-2009/148004 A1 | 12/2009 |
| WO | WO-2010/010380 A1 | 1/2010 |
| WO | WO-2010/018874 A1 | 2/2010 |
| WO | WO-2010/044411 A1 | 4/2010 |
| WO | WO-2010/051188 A1 | 5/2010 |
| WO | WO-2010/052569 A2 | 5/2010 |
| WO | WO-2010/055114 A1 | 5/2010 |
| WO | WO-2010/079443 A1 | 7/2010 |
| WO | WO-2010/100475 A1 | 9/2010 |
| WO | WO 2010109065 * | 9/2010 |
| WO | WO-2009/016498 A1 | 11/2010 |
| WO | WO-2010/138600 A2 | 12/2010 |
| WO | WO-2010/150192 A1 | 12/2010 |
| WO | WO-2012/007836 A1 | 1/2012 |
| WO | WO-2012/035421 A2 | 3/2012 |
| WO | WO-2012/085650 A1 | 6/2012 |
| WO | WO-2013/030665 A1 | 3/2013 |
| WO | WO-2013/064883 A1 | 5/2013 |
| WO | WO-2013/064884 A1 | 5/2013 |
| WO | WO-2013/072758 A1 | 5/2013 |
| WO | WO-2014/096941 A1 | 6/2014 |
| WO | WO-2014/135955 A1 | 9/2014 |
| WO | WO-2014/151393 A2 | 9/2014 |
| WO | WO-2015/031036 A1 | 3/2015 |
| WO | WO-2015/094443 A1 | 6/2015 |
| WO | WO-2015/099841 A1 | 7/2015 |
| WO | WO-2015/100174 A1 | 7/2015 |
| WO | WO-2015/112801 A1 | 7/2015 |

OTHER PUBLICATIONS

Chemical Abstracts STN Database Record for RN 1125433-02-4, entered on Mar. 23, 2009.*

Zorin; Zhurnal Organicheskoi Khimii 1985, 21, 1141 1142, abstract from Chemical Abstracts.*

(56) References Cited

OTHER PUBLICATIONS

Haga; Dalton Transactions 2003, 10, 2069-2079.*
Mehlstaeubl; Dalton Transactions 2008, 18, 2385-2388.*
André, N. et al., "Discriminating between lanthanide ions: self-assembly of heterodimetallic triple-stranded helicates," Chem. Commun., pp. 214-215, The Royal Society of Chemistry (2002).
André, N. et al., "Supramolecular Recognition of Heteropairs of Lanthanide Ions: A Step toward Self-Assembled Bifunctional Probes," Inorg. Chem. 43:515-529, American Chemical Society (2004).
Anger. T., et al., "Medicinal Chemistry of Neuronal Voltage-Gated Sodium Channel Blockers," J. Med. Chem. 44(2):115-137, American Chemical Society, United States (2001).
Baker, M.D. and Wood, J.N., "Involvement of Na+ channels in pain pathways," Trends Pharmacol. Sci. 22(1):27-31, Elsevier Science Ltd., England (2001).
Barthó, L., et al., "Involvement of capsaicin-sensitive neurones in hyperalgesia and enhanced opioid antinociception in inflammation," Naunyn-Schmiedebergs Arch. Pharmacol. 342(6):666-670, Springer-Verlag, Germany (1990).
Benjamin, E.R., et al., "Validation of a Fluorescent Imaging Plate Reader Membrane Potential Assay for High-Throughput Screening of Glycine Transporter Modulators," J. Biomol. Screen. 10(4):365-373, Sage Publications, United States (2005).
Bingham, A.L., et al., "Over one hundred solvates of sulfathiazole," Chem. Commun.: 603-604, The Royal Society of Chemistry, England (2001).
Black, J. A. et al. "Sensory Neuron-Specific Sodium Channel SNS is Abnormally Expressed in the Brains of Mice with Experimental Allergic Encephalomyelitis and Humans with Multiple Sclerosis." Proceedings of the National Academy of Sciences of the United States of America 97.21 (2000): 11598-11602.
Bocquet, B. et al., "The first self-assembled trimetallic lanthanide helicate: different coordination sites in symmetrical molecular architectures," Chem. Commun., pp. 930-931, The Royal Society of Chemistry (2002).
Borkovec, M. et al., "Statistical mechanical approach to competitive binding of metal ions to multi-center receptors," Dalton Trans., pp. 4096-4105, The Royal Society of Chemistry (2004).
Brower, V., "New paths to pain relief," Nat. Biotechnol. 18(4):387-391, Nature America Publishing, United States (2000).
Brown, C.M., et al., "Neuroprotective properties of lifarizine Compared with Those of Other Agents in a Mouse Model of Focal Cerebral Ischaemia," Br. J. Pharmacol. 115(8):1425-1432, Stockton Press, England (1995).
Bundgaard, H., "(C) Means to Enhance Penetration: (1) Prodrugs as a means to improve the delivery of peptide drugs," Adv. Drug Delivery Revs. 8:1-38, Elsevier Science Publishers, B.V., Netherlands (1992).
Caira, M.R., et al., "Preparation and Crystal Characterization of a Polymorph, a Monohydrate, and an Ethyl Acetate Solvate of the Antifungal Fluconazole," J. Pharm. Sci. 93(3):601-611, Wiley-Liss Inc. and the American Pharmacists Assn., United States (2004).
Campeau, L.-C. et al., "Palladium-Catalyzed Direct Arylation of Azine and Azole N-Oxides: Reaction Development. Scope and Applications in Synthesis," J. Am. Chem. Soc. 131:3291-3306, American Chemical Society (2009).
Canard, G. and Piguet, C., "The Origin of the Surprising Stabilities of Highly Charged Self-Assembled Polymetallic Complexes in Solution," Inorg. Chem. 46:3511-3522, American Chemical Society (2007).
Cannon, S.C., "Spectrum of Sodium Channel Disturbances in the nondystrophic myotonias and periodic paralyses," Kidney Int. 57(3):772-779, International Society of Nephrology, United States (2000).
Cantuel, M. et al., "A kinetically inert and optically active Cr III partner in thermodynamically self-assembled heterodimetallic non-covalent d-f podates," J. Chem. Soc., Dalton Trans., pp. 1929-1940, The Royal Society of Chemistry (2002).

Catterall, W.A., "Common modes of drug action on Na+ channels: local anesthetics, antiarrhythmics and anticonvulsants," Trends Pharmacol. Sci. 8:57-65, Elsevier Science Publishers, B.V., Netherlands (1987).
Chahine, M., et al., "Voltage-Gated Sodium Channels in Neurological Disorders," CNS Neurol. Disord. Drug Targets 7(2):144-158, Bentham Science Publishers Ltd., United Arab Emirates (2008).
Choi, H.-S. et al., "Design and synthesis of 7H-pyrrolo[2,3-d]pyrimidines as focal adhesion kinase inhibitors. Part 2," Bioorg. Med. Chem. Letts. 16:2689-2692, Elsevier Ltd. (2006).
Clare, J.J., et al., "Voltage-gated sodium channels as therapeutic targets," Drug Discov. Today 5(11):506-520, Elsevier Science Ltd., England (2000).
Cummins, T.R., et al., "Slow Closed-State Inactivation: A Novel Mechanism Underlying Ramp Currents in Cells Expressing the hNE/PN1 Sodium Channel," J. Neurosci. 18(23):9607-9619, Society for Neuroscience, United States (1998).
Dalla Favera N. et al., "In search for tuneable intramolecular intermetallic interactions in polynuclear lanthanide complexes," Dalton Trans. pp. 7625-7638, The Royal Society of Chemistry (2009).
Dalla-Favera, N. et al., "Linear Polynuclear Helicates as a Link between Discrete Supramolecular Complexes and Programmed Infinite Polymetallic Chains," Chem. Eur. J. 14:2994-3005, Wiley-VCH Verlag GmbH & Co. KGaA (2008).
Dalla-Favera, N. et al., "Tuneable Intramolecular Intermetallic Interactions as a New Tool for Programming Linear Heterometallic 4f-4f Complexes," Inorg. Chem. 46:9312-9322, American Chemical Society (2007).
Donaldson, I., "Tegretol: a double blind trial in tinnitus," J. Laryngol. Otol. 95 (9):947-951, Cambridge University Press, England (1981).
Dörwald, F.Z., "Side Reactions in Organic Synthesis: A Guide to Successful Synthesis Design," preface, Wiley-VCH Verlag GmbH & Co. KGaA, Weinheim, (2005).
Edder, C. et al., "A water-stable and strongly luminescent self-assembled non-covalent lanthanide podate," J. Chem. Soc., Dalton Trans. 24:4657-4663, The Royal Society of Chemistry (1997).
Edder, C. et al., "High-Spin Iron(II) as a Semitransparent Partner for Tuning Europium(III) Luminescence in Heterodimetallic d-f Complexes," Chem. Eur. J. 7:3014-3024, Wiley-VCH Verlag GmbH (2001).
Edder, C. et al., "Unusual Electronic Effects of Electron-Withdrawing Sulfonamide Groups in Optically and Magnetically Active Self-Assembled Noncovalent Heterodimetallic d-f podates," Inorg. Chem. 39:5059-5073, American Chemical Society (2000).
Elhabiri, M. et al., "Lanthanide Helicates Self-Assembled in Water: A New Class of Highly Stable and Luminescent Dimetallic Carboxylates," J. Am. Chem. Soc. 121:10747-10762, American Chemical Society (1999).
Elhabiri, M. et al., "The first lanthanide-containing helicates self-assembled in water," Chem. Commun., pp. 2347-2348, The Royal Society of Chemistry (1998).
Floquet, S. et al., "Programming Heteropolymetallic Lanthanide Helicates: Thermodynamic Recognition of Different Metal Ions Along the Strands," Chem. Eur. J. 10:1091-1105, Wiley-VCH Verlag GmbH & Co. KGaA (2004).
Floquet, S. et al., "The First Self-Assembled Trimetallic Lanthanide Helicates Driven by Positive Cooperativiity," Chem. Eur. J. 9:1860-1875, Wiley-VCH Verlag GmbH & Co. KGaA (2003).
Graham, S.H., et al., "Neuroprotective Effects of a Use-Dependent Blocker of Voltage-Dependent Sodium Channels, BW619C89, in Rat Middle Cerebral Artery Occlusion," J. Pharmacol. Exp. Ther. 269(2):854-859, The American Society for Pharmacology and Experimental Therapeutics, United States (1994).
Hamacek, J., "Unravelling self-assembly of lanthanide helicates: Switching from deduction to induction," J. Alloys and Compounds 451:347-351, Elsevier B.V. (available online Apr. 19, 2007).
Hanks, J.H. and Wallace, R.E., "17131. Relation of Oxygen and Temperature in the Preservation of Tissues by Refrigeration," Proc. Soc. Exp. Biol. Med. 71(2):196-200, Blackwell Science, United States (1949).

(56) References Cited

OTHER PUBLICATIONS

Harootunian, A.T., et al., "Fluorescence Ratio Imaging of Cytosolic Free Na+ in Individual Fibroblasts and Lymphocytes," J. Biol. Chem. 264(32):19458-19467, The American Society for Biochemistry and Molecular Biology, United States (1989).
Hubner, C., et al., "Ion Channel Diseases," Human Molecular Genetics 11:2435-2445, Oxford University Press (2002).
Hunskaar, S., et al., "Formalin test in mice, a useful technique for evaluating mild analgesics," J. Neurosci. Methods 14(1):69-76, Elsevier Science Publishers B.V., Netherlands (1985).
Iglesias, C.P. et al., "Effect of a halogenide substituent on the stability and photophysical properties of lanthanide triple-stranded helicates with ditopic ligands derived from bis(benzimidazolyl)pyridine," J. Chem. Soc., Dalton Trans., pp. 2031-2043, The Royal Society of Chemistry (2000).
Ilyin, V.I., et al., "V102862 (Co 102862): a potent, broad-spectrum state-dependent blocker of mammalian voltage-gated sodium channels," Br. J. Pharmacol. 144(6):801-812, Nature Publishing Group, England (2005).
Imbert, D. et al., "Extension Lifetimes of Lanthanide-Based Near-Infrared Emitters (Nd, Yb) in the Millisecond Range through Cr(III) Sensitization in Discrete Bimetallic Edifices," J. Am. Chem. Soc. 125:15698-15699, American Chemical Society (2003).
Jensen, T.B. et al., "Lanthanide Triple-Stranded Helicates: Controlling the Yield of the Heterobimetallic Species," Inorg. Chem. 45:7806-7814, American Chemical Society (2006).
Jensen, T.B. et al., "Lanthanide Triple-Stranded Helicates: Controlling the Yield of the Heterobimetallic Species," Inorg. Chem. 46:1507, American Chemical Society (2007).
Jensen, T.B. et al., "Thermodynamic Parameters Governing the Self-Assembly of Head-Head-Head Lanthanide Bimetallic Helicates," Chem. Eur. J. 13:8404-8410, Wiley-VCH Verlag GmbH & Co. KGaA (2007).
Jensen, T.B. et al., "Tuning the self-assembly of lanthanide triple stranded heterobimetallic helicates by ligand design," Dalton Trans. pp. 1027-1036, The Royal Society of Chemistry (2008).
Jordan,V.C., "Tamoxifen: A Most Unlikely Pioneering Medicine," Nature Reviews: Drug Discovery 2:205-213, Nature Publishing Group (2003).
Kakeya, N., et al., "Studies on Prodrugs of Cephalosporins. I. Synthesis and Biological Properties of Glycyloxybenzoyloxymethyl and Glycylaminobenzoyloxymethyl Esters of 7β-[2-(2-aminothiazol-4-yl)-(Z)-2-methoxyiminoacetamido]-3-methyl-3-cephem-4-carboxylic Acid," Chem. Pharm. Bull. (Tokyo) 32(2):692-698, Pharmaceutical Society of Japan, Japan (1984).
Kamenecka, T. et al., "Structure-Activity Relationships and X-ray Structures Describing the Selectivity of Aminopyrazole Inhibitors for c-Jun N-terminal Kinase 3 (JNK3) over p38," J. Biol. Chem. 284:12853-12861, The American Society for Biochemistry and Molecular Biology, Inc. (2009).
Kim, H-L., et al., "Rat brain expresses an alternatively spliced form of the dihydropyridine-sensitive L-type calcium channel α2 subunit," Proc. Natl. Acad. Sci. USA 89:3251-3255, National Academy of Sciences, United States (1992).
Kim, S.H. and Chung, J.M., "An experimental model for peripheral neuropathy produced by segmental spinal nerve ligation in the rat," Pain 50:355-363, Elsevier Science Publishers B.V., Netherlands (1992).
Kyle, D.J., and Ilyin, V.I., "Sodium Channel Blockers," J. Med. Chem. 50(11):2583-2588, American Chemical Society, United States (2007).
Lai, J., et al., "The role of voltage-gated sodium channels in neuropathic pain," Curr. Opin. Neurobiol. 13(3):291-297, Elsevier Science Ltd., England (2003).
Lai, J., et al., "Voltage-Gated Sodium Channels and Hyperalgesia," Annu. Rev. Pharmacol. Toxicol. 44:371-397, Annual Reviews, United States (2004).
Laird, J.M.A., et al., "Deficits in Visceral Pain and Referred Hyperalgesia in Nav1.8 (SNS/PN3)-Null Mice," J. Neurosci. 22(19):8352-8356, Society for Neuroscience, United States (2002).

Le Borgne, T. et al., "Tuning facial-meridional isomerisation in monometallic nine-co-ordinate lanthanide complexes with unsymmetrical tridentate ligands, " Dalton Trans., pp. 723-733, The Royal Society of Chemistry (2004).
Leuthold, L.A. et al., "Multi-track single- and dual-channel plastic microchips for electrospray mass spectrometry," Eur. J. Mass Spectrom. 16:47-55, IM Publications LLP (2009).
Liu, H., et al., "Mutations in Cardiac Sodium Channels: Clinical Implications," Am. J. Pharmacogenomics 3(3):173-179, Adis Data Information BV, New Zealand (2003).
Loï, M. et al., "Self-assembly of a bis-tridentate Py2S4 ligand and cadmium cation into 1- and 2-D coordination networks," Chem. Commun. 7:603-604, The Royal Society of Chemistry (1999).
Lonnon, D.G. et al., "Programmed Helicity in Self-Assembled Hydrogen-Bonded Chains of Chiral Copper(II) Complexes," Eur. J. Inorg. Chem. 6:1190-1197, Wiley-VCH Verlag GmbH & Co. GKaA (2006).
Majumdar, B., et al., "An electrocochleographic study of the effects of lignocaine on patients with tinnitus," Clin. Otolaryngol. Allied Sci. 8(3):175-180, Blackwell Scientific Publications, England (1983).
Martin, N. et al., "Self-Assembled Dinuclear Lanthanide Helicates: Substantial Luminescence Enhancement upon Replacing Terminal Benzimidazole Groups by Carboxamide Binding Units," Inorg. Chem. 37:577-589, American Chemical Society (1998).
Mason J.J. and Bergman, J., "Total synthesis of luotonin A and 14-substituted analogues," Org. Biomol. Chem. 5(15):2486-2490, The Royal Society of Chemistry, England (2007).
Meisler MH, and Kearney JA., "Sodium Channel Mutations in Epilepsy and Other Neurological Disorders," J Clin Invest. 115(8):2010-2017, American Society for Clinical Investigation, United States (2005).
Moller, A., "Similiarities Between Chronic Pain and Tinnitus," The American Journal of Ontology 18:577-585 (1997).
Mukkala, V.M., et. al., "New 2,2'-Bipyridine Derivatives and Their Luminescence Properties with Europium(III) and Terbium(III) Ions," Helv. Chim. Act. (75): 1578-1592, (1992).
Nassar, M.A., et al., "Nociceptor-specific gene deletion reveals a major role for Nav1.7 (PN1) in acute and inflammatory pain," Proc. Natl. Acad. Sci. USA 101(34):12706-12711, National Academy of Sciences, United States (2004).
NCBI Database GenBank Report, Accession No. NM_002977 (*Homo sapiens* sodium channel, voltage-gated, type IX, alpha subunit (SCN9A), mRNA), accessed on Aug. 1, 2013, accessed at http://www.ncbi.nlm.nih.gov/nuccore/NM_002977.
Nielsen, N.M. and Bundgaard, H., "Glycolamide Esters as Biolabile Prodrugs of Carboxylic Acid Agents: Synthesis, Stability, Bioconversion, and Physicochemical Properties," J. Pharm. Sci. 77(4):285-298, American Pharmaceutical Assn., United States (1988).
Noble, D., "Unraveling the genetics and mechanisms of cardiac arrhythmia," Proc. Natl. Acad. Sci. USA 99(9):5755-5756, National Academy of Sciences, United States (2002).
Piguet, C. et al., "Lanthanide Podates with Predetermined Structural and Photophysical Properties: Strongly Luminescent Self-Assembled Heterodinuclear d-f Complexes with a Segmental Ligand Containing Heterocyclic Imines and Carboxamide Binding Units," J. Am. Chem. Soc. 118:6681-6697, American Chemical Society (1996).
Piguet, C. et al., "Non-covalent lanthanide podates with predetermined physicochemical properties: iron(II) spin-state equilibria in self-assembled heterodinuclear d-f supramolecular complexes," J. Chem. Soc., Dalton Trans. 3:421-433, The Royal Society of Chemistry (1997).
Piguet, C. et al., "Syntheses of Segmental Heteroleptic Ligands for the Self-Assembly of Heteronuclear Helical Supramolecular Complexes," Helv. Chim. Acta 77:931-942, John Wiley & Sons (1994).
Piguet, C. et al., "The First Structurally Characterized and Strongly Luminescent Self-assembled Helical Heterodinuclear d-f Complex," J. Chem. Soc., Chem. Commun. 118:2575-2577, Royal Society of Chemistry (1995).
Rigault, S. et al., "Combination of crystal-field dependent and independent paramagnetic NMR hyperfine shift analysis methods

(56) References Cited

OTHER PUBLICATIONS for investigating the solution structures of inert self-assembled heterodimetallic d-f supramolecular complexes," J. Chem. Soc., Dalton Trans., pp. 4587-4600, The Royal Society of Chemistry (2000).

Riis-Johannessen T. et al., "Towards inert and preorganized d-block-containing receptors for trivalent lanthanides: The synthesis and characterization of triple-helical monometallic OsII and bimetallic OSII-LnIII complexes," Dalton Trans., pp. 3661-3677, The Royal Society of Chemistry (2008).

Riis-Johannessen, T. et al., "Self-Assembly of the First Discrete 3d-4f-4f Triple-Stranded Helicate, " Inorg. Chem. 48:5512-5525, American Chemical Society (2009).

Riis-Johannessen, T. et al., "Understanding, Controlling and Programming Cooperativitiy in Self-Assembled Polynuclear Complexes in Solution," Chem. Eur. J. 15:12702-12718, Wiley-VCH Verlag GmbH & Co. KGaA (2009).

Seltzer, Z., et al., "A novel behavioral model of neuropathic pain disorders produced in rats by partial sciatic nerve injury," Pain 43(2):205-218, Elsevier Science Publishers B.V., Netherlands (1990).

Shao, B., et al., "Phenoxyphenyl Pyridines as Novel State-Dependent, High-Potency Sodium Channel Inhibitors," J. Med. Chem. 47:4277-4285, American Chemical Society, United States (2004).

Simpson, J.J. and Davies, W.E., "Recent advances in the pharmacological treatment of tinnitus," Trends Pharmacol. Sci. 20(1):12-18, Elsevier Science, England (1999).

Srivatsa, U., et al., "Mechanisms of Antiarrhythmic Drug Actions and Their Clinical Relevance for Controlling Disorders of Cardiac Rhythm," Curr. Cardiol. Rep. 4(5):401-410, Current Science Inc., United States (2002).

Stein, C., et al., "Unilateral Inflammation of the Hindpaw in Rats as a Model of Prolonged Noxious Stimulation: Alterations in Behavior and Nociceptive Thresholds," Pharmacol. Biochem. Behav. 31:445-451, Pergamon Press plc, United States (1988).

Taylor and Meldrum, "Na+ Channels as Targets for Neuroprotective," Sci. 76:309-316, Drugs Trends Pharmacol (1995).

Telfer, S.G. et al., "CD Spectra of d-f Heterobimetallic Helicates with Segmental DI-Imine Ligands," Inorg. Chem. 43:5302-5310, American Chemical Society (2004).

Toledo-Aral, J.J., et al., "Identification of PN1, a predominant voltage-dependent sodium channel expressed principally in peripheral neurons," Proc. Natl. Acad. Sci. USA 94(4):1527-1532, The National Academy of Sciences, United States (1997).

Tonndorf, J., "The analogy between tinnitus and pain: A suggestion for physiological basis of chronic tinnitus," Hearing Research 28(2-3):271-275, Elsevier Science Publishers B.V., Netherlands (1987).

Torelli, S. et al., "Ruthenium(II) as a Novel Labile Partner in Thermodynamic Self-Assembly of Heterobimetallic d-f Triple-Stranded Helicates," Chem. Eur. J. 10:3503-3516, Wiley-VCH Verlag GmbH & Co. KGaA (2004).

Tripier, R. et al., "Self-Assembled Triple-Stranded Lanthanide Dimetallic Helicates with a Ditopic Ligand Derived from Bis(benzimiddazole)pyridine and Featuring an (4 Isothiocyanatophenyl)ethynyl Substituent," Helv. Chim. Acta 85:1915-1929, John Wiley & Sons (2002).

Van Tonder, E.C., et al., "Preparation and Physicochemical Characterization of 5 Niclosamide Solvates and 1 Hemisolvate," AAPS PharmSciTech 5(1):1-10, Springer, United States (2004).

Wood, J.N., et al., "Voltage-Gated Sodium Channels and Pain Pathways," J. Neurobiol. 61(1):55-71, Wiley Periodicals, Inc., United States (2004).

Yogeeswari, P., et al., "Ion Channels as Important Targets for Antiepileptic Drug Design," Curr. Drug Targets 5(7):589-602, Bentham Science Publishers Ltd., Netherlands (2004).

Zeckert, K. et al., "A Simple Thermodynamic Model for Rationalizing the Formation of Self-Assembled Multimetallic Edifices: Application to Triple-Stranded Helicates," J. Am. Chem. Soc. 126:11589-11601, American Chemical Society (2004).

Zeckert, K. et al., "Predictions, Synthetic Strategy, and Isolation of a Linear Tetrametallic Triple-Stranded Lanthanide Helicate," Angew. Chem. Int. Ed. 44:7954-7958, Wiley-VCH Verlag GmbH & Co. KGaA (2005).

Zhu, L. et al., "Geometry-Dependent Phosphodiester Hydrolysis Catalyzed by Binuclear Copper Complexes," Inorg. Chem. 42:7912-7920, American Chemical Society (2003).

Zuliani, V. et al., "Sodium channel blockers for neuropathic pain," Expert Opin. Ther. Patents 20:755-779, Informa UK Ltd (2010).

\* cited by examiner

PYRIDINE COMPOUNDS AND THE USES THEREOF

CROSS REFERENCE TO RELATED APPLICATIONS

The application is a continuation of U.S. patent application Ser. No. 13/821,732, filed on Mar. 8, 2013, with a §371 date of Jul. 22, 2013, allowed, which is the U.S. national phase, pursuant to 35 U.S.C. §371, of PCT International Application Serial No. PCT/IB2011/002172, filed on Sep. 16, 2011, designating the United States and published in English on Mar. 22, 2012 as publication WO 2012/035421 A1, which claims priority to U.S. Provisional Application Ser. No. 61/384,136, filed on Sep. 17, 2010. The contents of the afore-mentioned patent applications are incorporated herein by their entirety.

BACKGROUND OF THE INVENTION

Field of the Invention

This invention is in the field of medicinal chemistry. The invention relates to novel substituted pyridine compounds and the use of these compounds as blockers of voltage-gated sodium ($Na^+$) channels.

Background Art

Voltage-gated sodium channels (VGSCs) are found in all excitable cells. In neuronal cells of the central nervous system (CNS) and peripheral nervous system (PNS) sodium channels are primarily responsible for generating the rapid upstroke of the action potential. In this manner sodium channels are essential to the initiation and propagation of electrical signals in the nervous system. Proper function of sodium channels is therefore necessary for normal function of the neuron. Consequently, aberrant sodium channel function is thought to underlie a variety of medical disorders (See Hubner et al., *Hum. Mol. Genet.* 11:2435-2445 (2002) for a general review of inherited ion channel disorders) including epilepsy (Yogeeswari et al, *Curr. Drug Target* 5:589-602 (2004)), arrhythmia (Noble, *Proc. Natl. Acad. Sci. USA* 99:5755-5756 (2002)), myotonia (Cannon, *Kidney Int.* 57:772-779 (2000)), and pain (Wood et al., *J. Neurobiol.*, 61:55-71 (2004)).

VGSCs are composed of one α-subunit, which forms the core of the channel and is responsible for voltage-dependent gating and ion permeation, and several auxiliary β-subunits (see, e.g., Chahine et al., *CNS & Neurological Disorders-Drug Targets* 7:144-158 (2008) and Kyle and Ilyin, *J. Med. Chem.* 50:2583-2588 (2007)). α-Subunits are large proteins composed of four homologous domains. Each domain contains six α-helical transmembrane spanning segments. There are currently nine known members of the family of voltage-gated sodium channel α-subunits. Names for this family include SCNx, SCNAx, and $Na_v$x.x (see Table 1, below). The VGSC family has been phylogenetically divided into two subfamilies $Na_v$1.x (all but SCN6A) and $Na_v$2.x (SCN6A). The $Na_v$1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product ($Na_v$1.5, H1) is almost exclusively expressed in cardiac tissue and has been shown to underlie a variety of cardiac arrhythmias and other conduction disorders (Liu et al., *Am. J. Pharmacogenomics* 3:173-179 (2003)). Consequently, blockers of $Na_v$1.5 have found clinical utility in treatment of such disorders (Srivatsa et al., *Curr. Cardiol. Rep.* 4:401-410 (2002)). The remaining TTX-resistant sodium channels, $Na_v$1.8 (SCN10A, PN3, SNS) and $Na_v$1.9 (SCN11A, NaN, SNS2) are expressed in the peripheral nervous system and show preferential expression in primary nociceptive neurons. Human genetic variants of these channels have not been associated with any inherited clinical disorder. However, aberrant expression of $Na_v$1.8 has been found in the CNS of human multiple sclerosis (MS) patients and also in a rodent model of MS (Black et al., *Proc. Natl. Acad. Sci. USA* 97:11598-115602 (2000)). Evidence for involvement in nociception is both associative (preferential expression in nociceptive neurons) and direct (genetic knockout). $Na_v$1.8-null mice exhibited typical nociceptive behavior in response to acute noxious stimulation but had significant deficits in referred pain and hyperalgesia (Laird et al., *J. Neurosci.* 22:8352-8356 (2002)).

TABLE 1

Voltage-gated sodium channel gene family

| Type | Gene Symbol | Tissue Distribution | TTX IC50 (nM) | Disease Association | Indications |
|---|---|---|---|---|---|
| Nav1.1 | SCN1A | CNS/PNS | 10 | Epilepsy | Pain, seizures, neuro-degeneration |
| Nav1.2 | SCN2A | CNS | 10 | Epilepsy | Epilepsy, neuro-degeneration |
| Nav1.3 | SCN3A | CNS | 15 | — | Pain |
| Nav1.4 | SCN4A | Skeletal muscle | 25 | Myotonia | Myotonia |
| Nav1.5 | SCN5A | Heart muscle | 2,000 | Arrhythmia | Arrhythmia |
| Nav1.6 | SCN8A | CNS/PNS | 6 | — | Pain, movement disorders |
| Nav1.7 | SCN9A | PNS | 25 | Erythermalgia | Pain |
| Nav1.8 | SCN10A | PNS | 50,000 | — | Pain |
| Nav1.9 | SCN11A | PNS | 1,000 | — | Pain |

The $Na_v$1.7 (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA* 94:1527-1532 (1997)).

An increasing body of evidence suggests that $Na_v$1.7 plays a key role in various pain states, including acute, inflammatory and/or neuropathic pain. Deletion of the SCN9A gene in nociceptive neurons of mice led to an increase in mechanical and thermal pain thresholds and reduction or abolition of inflammatory pain responses (Nassar et al., *Proc Natl. Acad. Sci. USA* 101:12706-12711 (2004)).

Sodium channel-blocking agents have been reported to be effective in the treatment of various disease states, and have found particular use as local anesthetics, e.g., lidocaine and bupivacaine, and in the treatment of cardiac arrhythmias, e.g., propafenone and amiodarone, and epilepsy, e.g., lamotrigine, phenytoin and carbamazepine (see Clare et al., *Drug Discovery Today* 5:506-510 (2000); Lai et al., *Annu. Rev. Pharmacol. Toxicol.* 44:371-397 (2004); Anger et al., *J. Med. Chem.* 44:115-137 (2001), and Catterall, *Trends Phar-* macol. Sci. 8:57-65 (1987)). Each of these agents is believed to act by interfering with the rapid influx of sodium ions.

Other sodium channel blockers such as BW619C89 and lifarizine have been shown to be neuroprotective in animal models of global and focal ischemia (Graham et al., *J. Pharmacol. Exp. Ther.* 269:854-859 (1994); Brown et al., *British J. Pharmacol.* 115:1425-1432 (1995)).

It has also been reported that sodium channel-blocking agents can be useful in the treatment of pain, including acute, chronic, inflammatory, neuropathic, and other types of pain such as rectal, ocular, and submandibular pain typically associated with paroxysmal extreme pain disorder; see, for example, Kyle and Ilyin., *J. Med. Chem.* 50:2583-2588 (2007); Wood et al., *J. Neurobiol.* 61:55-71 (2004); Baker et al., *TRENDS in Pharmacological Sciences* 22:27-31 (2001); and Lai et al., *Current Opinion in Neurobiology* 13:291-297 (2003); the treatment of neurological disorders such as epilepsy, seizures, epilepsy with febrile seizures, epilepsy with benign familial neonatal infantile seizures, inherited pain disorders, e.g., primary erthermalgia and paroxysmal extreme pain disorder, familial hemiplegic migraine, and movement disorder; and the treatment of other psychiatric disorders such as autism, cerebellar atrophy, ataxia, and mental retardation; see, for example, Chahine et al., *CNS & Neurological Disorders-Drug Targets* 7:144-158 (2008) and Meisler and Kearney, *J. Clin. Invest.* 115:2010-2017 (2005). In addition to the above-mentioned clinical uses, carbamazepine, lidocaine and phenytoin are used to treat neuropathic pain, such as from trigeminal neuralgia, diabetic neuropathy and other forms of nerve damage (Taylor and Meldrum, *Trends Pharmacol. Sci.* 16:309-316 (1995)). Furthermore, based on a number of similarities between chronic pain and tinnitus, (Moller, *Am. J. Otol.* 18:577-585 (1997); Tonndorf, *Hear. Res.* 28:271-275 (1987)) it has been proposed that tinnitus should be viewed as a form of chronic pain sensation (Simpson, et al., *Tip.* 20:12-18 (1999)). Indeed, lidocaine and carbamazepine have been shown to be efficacious in treating tinnitus (Majumdar, B. et al., *Clin. Otolaryngol.* 8:175-180 (1983); Donaldson, *Laryngol. Otol.* 95:947-951 (1981)).

Many patients with either acute or chronic pain disorders respond poorly to current pain therapies, and the development of resistance or insensitivity to opiates is common. In addition, many of the currently available treatments have undesirable side effects.

In view of the limited efficacy and/or unacceptable side-effects of the currently available agents, there is a pressing need for more effective and safer analgesics that work by blocking sodium channels.

BRIEF SUMMARY OF THE INVENTION

The present invention is related to the use of substituted pyridine compounds represented by Formula I, below, and the pharmaceutically acceptable salts, prodrugs and solvates thereof (collectively referred to herein as "Compounds of the Invention"), as blockers of sodium ($Na^+$) channels.

The present invention is also related to treating a disorder responsive to the blockade of sodium channels in a mammal suffering from excess activity of said channels by administering an effective amount of a Compound of the Invention as described herein.

Some compounds useful in the present invention have not been heretofore reported. Thus, one aspect of the present invention is directed to novel compounds of Formula I, as well as their pharmaceutically acceptable salts, prodrugs and solvates.

Another aspect of the present invention is directed to the use of the novel compounds of Formula I, and their pharmaceutically acceptable salts, prodrugs and solvates, as blockers of sodium channels.

A further aspect of the present invention is to provide a method for treating pain (e.g., acute pain, chronic pain, which includes but is not limited to, neuropathic pain, postoperative pain, and inflammatory pain, or surgical pain) by administering an effective amount of a Compound of the Invention to a mammal in need of such treatment. Specifically, the present invention provides a method for preemptive or palliative treatment of pain by administering an effective amount of a Compound of the Invention to a mammal in need of such treatment.

A further aspect of the present invention is to provide a method for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, by administering an effective amount of a Compound of the Invention to a mammal in need of such treatment.

A further aspect of the present invention is to provide a pharmaceutical composition useful for treating a disorder responsive to the blockade of sodium ion channels, said pharmaceutical composition containing an effective amount of a Compound of the Invention in a mixture with one or more pharmaceutically acceptable carriers.

Also, an aspect of the present invention is to provide a method of modulating sodium channels in a mammal, wherein said method comprises administering to the mammal an effective amount of at least one Compound of the Invention.

A further aspect of the present invention is to provide a Compound of the Invention for use in treating pain in a mammal, e.g., acute pain, chronic pain, which includes but is not limited to, neuropathic pain, postoperative pain, and inflammatory pain, or surgical pain.

A further aspect of the present invention is to provide a Compound of the Invention for use in treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

A further aspect of the present invention is to provide radiolabeled Compounds of the Invention and the use of such compounds as radioligands in any appropriately selected competitive binding assays and screening methodologies. Thus, the present invention further provides a method for screening a candidate compound for its ability to bind to a sodium channel or sodium channel subunit using a radiolabeled Compound of the Invention. In certain embodiments, the compound is radiolabeled with $^3H$, $^{11}C$, or $^{14}C$. This competitive binding assay can be conducted using any appropriately selected methodology. In one embodiment, the screening method comprises: i) introducing a fixed concentration of the radiolabeled compound to an in vitro preparation comprising a soluble or membrane-associated sodium channel, subunit or fragment under conditions that permit the radiolabeled compound to bind to the channel, subunit or fragment, respectively, to form a conjugate; ii) titrating the conjugate with a candidate compound; and iii) determining the ability of the candidate compound to displace the radiolabeled compound from said channel, subunit or fragment.

A further aspect of the present invention is to provide the use of a Compound of the Invention in the manufacture of a medicament for treating pain in a mammal. In one embodiment, the invention provides the use of a Compound of the Invention in the manufacture of a medicament for palliative or preemptive treatment of pain, such as acute pain, chronic pain, or surgical pain.

A further aspect of the present invention is to provide the use of a Compound of the Invention in the manufacture of a medicament for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

Additional embodiments and advantages of the invention will be set forth in part in the description that follows, and will flow from the description, or can be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention as claimed.

DETAILED DESCRIPTION OF THE INVENTION

One aspect of the present invention is based on the use of compounds of Formula I, and the pharmaceutically acceptable salts, prodrugs and solvates thereof, as blockers of $Na^+$ channels. In view of this property, compounds of Formula I, and the pharmaceutically acceptable salts, prodrugs and solvates thereof, are useful for treating disorders responsive to the blockade of sodium ion channels.

The compounds useful in this aspect of the invention are compounds represented by Formula I:

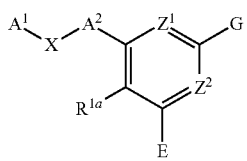

I and the pharmaceutically acceptable salts, solvates, and prodrugs thereof, wherein:

$Z^1$ is selected from the group consisting of N and N-oxide and $Z^2$ is $CR^{1b}$; or
$Z^1$ is $CR^{1b}$ and $Z^2$ is selected from the group consisting of N and N-oxide;
$R^{1a}$ and $R^{1b}$, which are identical or different, are selected from the group consisting of:
 a) hydrogen;
 b) halogen;
 c) hydroxy;
 d) cyano;
 e) optionally substituted alkyl;
 f) alkoxy;
 g) haloalkoxy; and
 h) haloalkyl;
$A^1$ is selected from the group consisting of:
 a) optionally substituted cycloalkyl;
 b) optionally substituted heterocyclo;
 c) optionally substituted aryl; and
 d) optionally substituted heteroaryl;
X is selected from the group consisting of:
 a) —O—;
 b) —S—;
 c) —SO—;
 d) —SO$_2$—
 e) —(CR$^2$R$^3$)$_j$—;
 f) —NR$^4$—; and
 g) —SO$_2$NH—
wherein:
at each occurrence, $R^2$ and $R^3$, which are identical or different, are selected from the group consisting of hydrogen, fluoro, and optionally substituted alkyl; or
$R^2$ and $R^3$ are taken together to form an oxo, i.e., C=O, group; or
$R^2$ and $R^3$ taken together with the carbon atom to which they are attached form a 3- to 8-membered optionally substituted cycloalkyl or optionally substituted heterocyclo;
 j is 0, 1, 2, or 3; and
$R^4$ is selected from the group consisting of hydrogen and optionally substituted alkyl;
$A^2$ is selected from the group consisting of optionally substituted aryl and optionally substituted heteroaryl;
G is selected from the group consisting of:
 a) hydrogen;
 b) alkyl;
 c) cyano;

d)

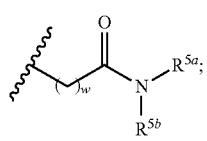

G-1 e)

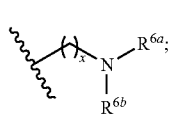

G-2 f)

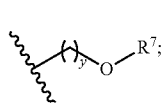

G-3

-continued g)

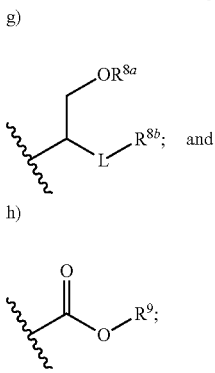

G-4 h)

G-5 wherein:
$R^{5a}$ and $R^{5b}$, which are identical or different, are selected from the group consisting of:
a) hydrogen;
b) optionally substituted alkyl;
c) optionally substituted cycloalkyl;
d) optionally substituted heterocyclo;
e) optionally substituted aryl;
f) optionally substituted heteroaryl;
g) aralkyl;
h) hydroxyalkyl;
i) (cyano)alkyl;
j) (heterocyclo)alkyl;
k) (heteroaryl)alkyl;
l) (amino)alkyl;
m) (alkylamino)alkyl;
n) (dialkylamino)alkyl, and
o) —$(CH_2CH_2O)_m$—$R^{15a}$; or
$R^{5a}$ and $R^{5b}$ taken together with the nitrogen atom to which they are attached form an optionally substituted 3- to 8-membered heterocyclo;
$R^{6a}$ and $R^{6b}$, which are identical or different, are selected from the group consisting of:
a) hydrogen;
b) optionally substituted alkyl;
c) optionally substituted cycloalkyl;
d) optionally substituted heterocyclo;
e) optionally substituted aryl;
f) optionally substituted heteroaryl;
g) hydroxyalkyl;
h) (heterocyclo)alkyl;
i) (heteroaryl)alkyl;
j) (amino)alkyl;
k) (alkylamino)alkyl;
l) (dialkylamino)alkyl;
m) (carboxamido)alkyl,
n) (cyano)alkyl, and
o) —$(CH_2CH_2O)_n$—$R^{15b}$; or
$R^{6a}$ and $R^{6b}$ taken together with the nitrogen atom to which they are attached form an optionally substituted 3- to 8-membered heterocyclo;
$R^7$ is selected from the group consisting of:
a) hydrogen;
b) optionally substituted alkyl;
c) optionally substituted cycloalkyl;
d) optionally substituted heterocyclo;
e) optionally substituted aryl;
f) optionally substituted heteroaryl;
g) (heterocyclo)alkyl;
h) (heteroaryl)alkyl;
i) (amino)alkyl;
j) (alkylamino)alkyl;
k) (dialkylamino)alkyl; and
l) —$(CH_2CH_2O)_o$—$R^{15c}$;
$R^{8a}$ and $R^{8b}$, which are identical or different, are selected from the group consisting of:
a) hydrogen;
b) optionally substituted alkyl; and
c) —$(CH_2CH_2O)_p$—$R^{15d}$;
L is selected from the group consisting of —O— and —$NR^{16}$—;
$R^9$ is selected from the group consisting of hydrogen, alkyl, and —$(CH_2CH_2O)_q$—$R^{15e}$;
$R^{15a}$, $R^{15b}$, $R^{15c}$, $R^{15d}$, and $R^{15e}$, which are identical or different, are selected from the group consisting of hydrogen and optionally substituted alkyl;
$R^{16}$ is selected from the group consisting of hydrogen and optionally substituted alkyl;
m, n, o, p, and q are each independently 1, 2, 3, 4, 5, 6, 7, 8, 9, 10, or 11;
w is 0, 1, 2, 3, 4, or 5;
x and y are each independently 1, 2, 3, or 4;
E is selected from the group consisting of:
a) hydrogen;
b) halogen;
c) optionally substituted alkyl;
d) optionally substituted heteroaryl;
e) optionally substituted heterocyclo;
f) hydroxyalkyl;

g)

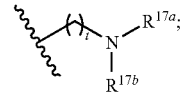

E-1 h)

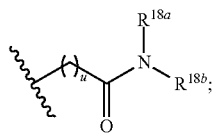

E-2 i)

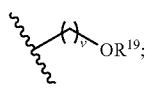

E-3 j)

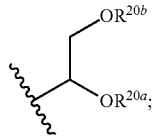

E-4 k)

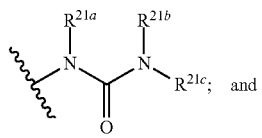

E-5

-continued l)

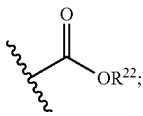
E-6 wherein:

R$^{17a}$ and R$^{17b}$, which are identical or different, are selected from the group consisting of:
a) hydrogen;
b) optionally substituted alkyl;
c) optionally substituted cycloalkyl;
d) —SO$_2$R$^{24a}$;
e) —COR$^{24b}$;
f) optionally substituted aryl;
g) optionally substituted heteroaryl;
h) (heterocyclo)alkyl;
i) (heteroaryl)alkyl;
j) (amino)alkyl;
k) (alkylamino)alkyl;
l) (dialkylamino)alkyl;
m) (carboxamido)alkyl;
n) (cyano)alkyl; and
o) hydroxyalkyl; or R$^{17a}$ and R$^{17b}$ taken together with the nitrogen atom to which they are attached form an optionally substituted 3- to 8-membered heterocyclo;

R$^{18a}$ and R$^{18b}$, which are identical or different, are selected from the group consisting of:
a) hydrogen;
b) optionally substituted alkyl;
c) optionally substituted cycloalkyl;
d) optionally substituted aryl;
e) optionally substituted heteroaryl;
f) (heterocyclo)alkyl;
g) (heteroaryl)alkyl;
h) (amino)alkyl;
i) (alkylamino)alkyl;
j) (dialkylamino)alkyl;
k) (carboxamido)alkyl;
l) (cyano)alkyl; and
m) hydroxyalkyl; or R$^{18a}$ and R$^{18b}$ taken together with the nitrogen atom to which they are attached form an optionally substituted 3- to 8-membered heterocyclo;

R$^{19}$ is selected from the group consisting of hydrogen and optionally substituted alkyl;

R$^{20a}$ and R$^{20b}$, which are identical or different, are selected from the group consisting of hydrogen and optionally substituted alkyl, wherein at least one of R$^{20a}$ and R$^{20b}$ is optionally substituted alkyl;

R$^{21a}$ is selected from the group consisting of hydrogen and alkyl;

R$^{21b}$ and R$^{21c}$, which are identical or different, are selected from the group consisting of:
a) hydrogen;
b) optionally substituted alkyl;
c) optionally substituted cycloalkyl;
d) optionally substituted aryl;
e) optionally substituted heteroaryl;
f) (heterocyclo)alkyl;
g) (heteroaryl)alkyl; and
h) (amino)alkyl;
i) (alkylamino)alkyl;
j) (dialkylamino)alkyl;
k) (carboxamido)alkyl;
l) (cyano)alkyl; and
m) hydroxyalkyl; or R$^{21b}$ and R$^{21c}$ taken together with the nitrogen atom to which they are attached form an optionally substituted 3- to 8-membered heterocyclo;

R$^{22}$ is selected from the group consisting of hydrogen and alkyl;

R$^{24a}$ is selected from the group consisting of optionally substituted alkyl, optionally substituted cycloalkyl, optionally substituted aryl, and optionally substituted heteroaryl;

R$^{24b}$ is selected from the group consisting of optionally substituted alkyl, optionally substituted cycloalkyl, optionally substituted aryl, and optionally substituted heteroaryl;

t and u are each independently 0, 1, 2, or 3; and v is 1, 2, or 3.

In one embodiment, Compounds of the Invention are compounds having Formula I, wherein G and E are not both hydrogen.

In another embodiment, Compounds of the Invention are compounds having Formula I, wherein when G is alkyl, then E is not halogen.

In another embodiment, Compounds of the Invention are compounds having Formula I, wherein when G is:

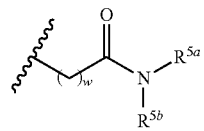
G-1 and w is 0, then E is not a morpholinyl group.

In another embodiment, Compounds of the Invention are compounds having Formula I, wherein when G is:

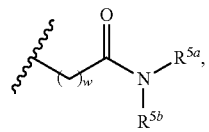
G-1 w is 0, and E is:

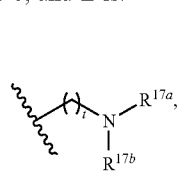
E-1 then R$^{17a}$ and R$^{17b}$ are not both hydrogen, R$^{17a}$ and R$^{17b}$ are not both alkyl, R$^{17a}$ is not hydrogen when R$^{17b}$ is alkyl, and R$^{17a}$ is not alkyl when R$^{17b}$ is hydrogen.

In another embodiment, Compounds of the Invention are compounds having Formula I, wherein when G is:

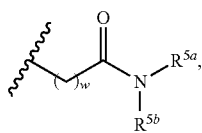

w is 0, and E is:

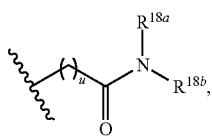

then u is 1, 2, or 3.

In another embodiment, Compounds of the Invention are compounds having Formula I, wherein when G is:

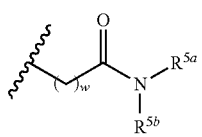

G-1 and w is 0, then E is:

a) optionally substituted heteroaryl;
b) optionally substituted heterocyclo;
c) hydroxyalkyl d)

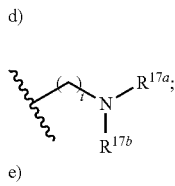

E-1 e)

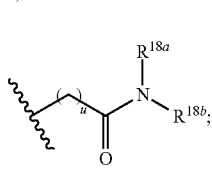

E-2 f)

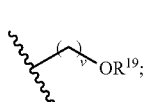

E-3 g)

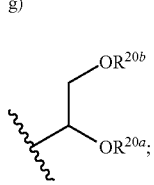

E-4 h)

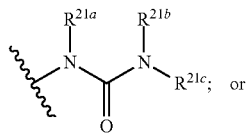

E-5 i)

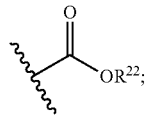

E-6 wherein when E is E-1, then at least one of $R^{17a}$ and $R^{17b}$ is not hydrogen or optionally substituted alkyl and u is 1, 2, or 3.

In another embodiment, Compounds of the Invention are compounds having Formula I, wherein when G is:

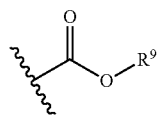

G-5 and $R^9$ is hydrogen or alkyl; then E is:

a) optionally substituted heteroaryl;
b) optionally substituted heterocyclo;
c) hydroxyalkyl;

d)

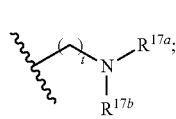

E-1 e)

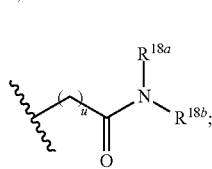

E-2 f)

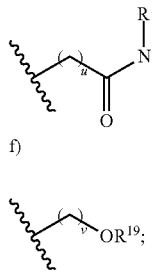

E-3 g)

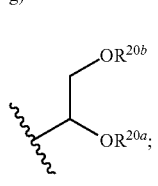

E-4 h)

-continued

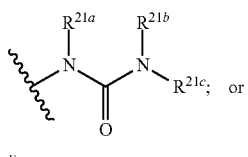
E-5 i)

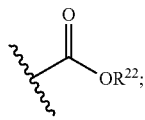
E-6 wherein when E is E-1, then at least one of $R^{17a}$ and $R^{17b}$ is not hydrogen or alkyl and u is 1, 2, or 3.

In another embodiment, Compounds of the Invention are compounds having Formula I, wherein:

G is selected from the group consisting of:

a)

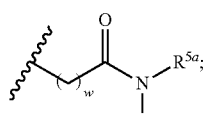
G-1 b)

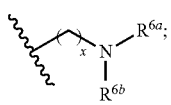
G-2 c)

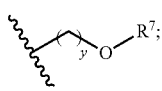
G-3 d)

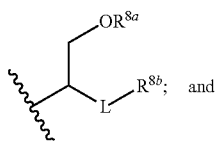
G-4 e)

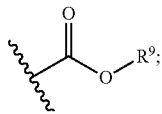
G-5 and

E is selected from the group consisting of:
a) hydroxyalkyl, including, e.g., —CH(OH)CH$_2$OH, —CH(OH)CH(CH$_3$)OH, or —CH$_2$CH(OH)CH$_2$OH;

d)

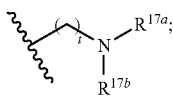
E-1 e)

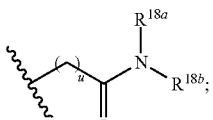
E-2 f)

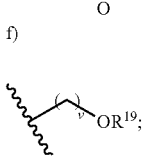
E-3 g)

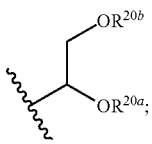
E-4 h)

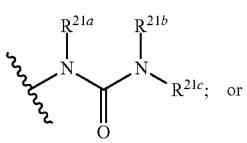
E-5 i)

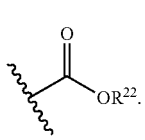
E-6

In another embodiment, Compounds of the Invention are compounds having Formula I, wherein when G is:

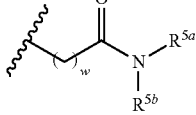
G-1 and $R^{5a}$ and $R^{5b}$ taken together with the nitrogen atom to which they are attached form an optionally substituted 3- to 8-membered heterocyclo, then said optional substituents are selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, alkylcarbonyl, arylcarbonyl, ureido, guanidino, optionally substituted alkyl, optionally substituted cycloalkyl, optionally substituted alkenyl, optionally substituted alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl.

In another embodiment, Compounds of the Invention are compounds having Formula I, or a pharmaceutically acceptable salt, solvate, or prodrug thereof, wherein:

$Z^1$ is selected from the group consisting of N and N-oxide and $Z^2$ is CH; or $Z^1$ is CH and $Z^2$ is selected from the group consisting of N and N-oxide;

$R^{1a}$ is hydrogen;

$A^1$ is selected from the group consisting of optionally substituted aryl and optionally substituted heteroaryl;

X is selected from the group consisting of:
a) —O—;
b) —$(CR^2R^3)_j$—;
c) —$SO_2NH$—; and
d) —$NHSO_2$— wherein:
j is 0;

$A^2$ is unsubstituted phenyl;

G is selected from the group consisting of:
a) hydrogen;
b) cyano;

c)

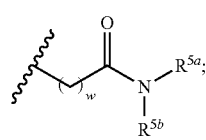

G-1 d)

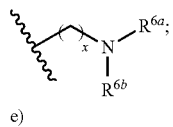

G-2 e)

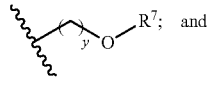

G-3 f)

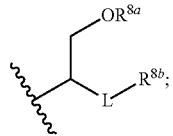

G-4 wherein:

$R^{5a}$ and $R^{5b}$ are hydrogen;

$R^{6a}$ is selected from the group consisting of:
a) hydroxyalkyl;
b) (heterocyclo)alkyl;
c) (heteroaryl)alkyl;
d) (amino)alkyl;
e) (alkylamino)alkyl;
f) (dialkylamino)alkyl;
g) (carboxamido)alkyl; and
h) (cyano)alkyl;

$R^{6b}$ is selected from the group consisting of hydrogen and (cyano)alkyl;

$R^7$ is —$(CH_2CH_2O)_o$—$R^{15c}$;

$R^{8a}$ and $R^{8b}$ are hydrogen;

L is —O—;

$R^{15c}$ is selected from the group consisting of hydrogen and optionally substituted alkyl;

o is 1, 2, 3, 4, 5, 6, 7, 8, 9, 10, or 11;
w is 0;
x is 1 or 2;
y is 1;

E is selected from the group consisting of:
a) hydrogen;
b) halogen;
d) substituted piperazine;
e) hydroxyalkyl;

f)

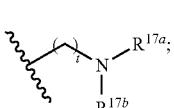

E-1 g)

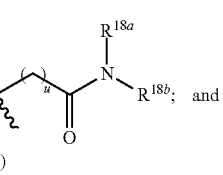

E-2 h)

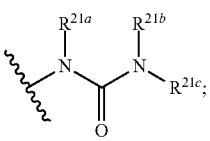

E-3 wherein:

$R^{17a}$ is selected from the group consisting of hydrogen and alkyl;

$R^{17b}$ is selected from the group consisting of:
a) optionally substituted aryl;
b) optionally substituted heteroaryl;
c) (heterocyclo)alkyl;
d) (heteroaryl)alkyl;
e) (amino)alkyl;
f) (alkylamino)alkyl;
g) (dialkylamino)alkyl;
h) (carboxamido)alkyl;
i) (cyano)alkyl; and
j) hydroxyalkyl;

$R^{18a}$ and $R^{18b}$ are hydrogen;

$R^{21a}$ is selected from the group consisting of hydrogen and alkyl;

$R^{21b}$ and $R^{21c}$, which are identical or different, are selected from the group consisting of:
a) hydrogen;
b) optionally substituted alkyl;
c) optionally substituted cycloalkyl;
d) optionally substituted aryl;
e) optionally substituted heteroaryl;
f) (heterocyclo)alkyl;
g) (heteroaryl)alkyl; and
h) (dialkylamino)alkyl; or $R^{21b}$ and $R^{21c}$ taken together with the nitrogen atom to which they are attached form an optionally substituted 3- to 8-membered heterocyclo;

t is 0 or 1; and
u is 0;

with the provisos:

a) when G is hydrogen, cyano, or G-1, then E is substituted piperazine, hydroxyalkyl, E-1, or E-5; or b) when E is hydrogen or halogen, then G is G-2, G-3, or G-4.

In another embodiment, Compounds of the Invention are compounds having Formula II:

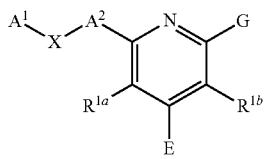

II and the pharmaceutically acceptable salts, prodrugs, and solvates thereof, wherein $A^1$, X, $A^2$, $R^{1a}$, $R^{1b}$, G, and E are as defined above in connection with Formula I.

In another embodiment, Compounds of the Invention are compounds having Formula III:

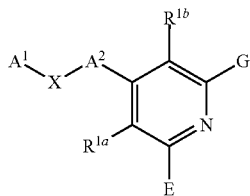

III and the pharmaceutically acceptable salts, prodrugs, and solvates thereof, wherein $A^1$, X, $A^2$, $R^{1b}$, G, and E are as defined above in connection with Formula I.

In another embodiment, Compounds of the Invention are compounds having Formula IV:

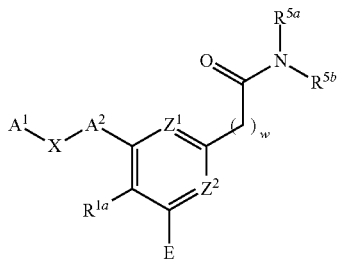

IV and the pharmaceutically acceptable salts, prodrugs, and solvates thereof, wherein $A^1$, X, $A^2$, $R^{1a}$, $R^{5a}$, $R^{5b}$, $Z^1$, $Z^2$, and w are as defined above in connection with Formula I, and E is selected from the group consisting of:

a) optionally substituted heteroaryl;

b) optionally substituted heterocyclo;

c) hydroxyalkyl;

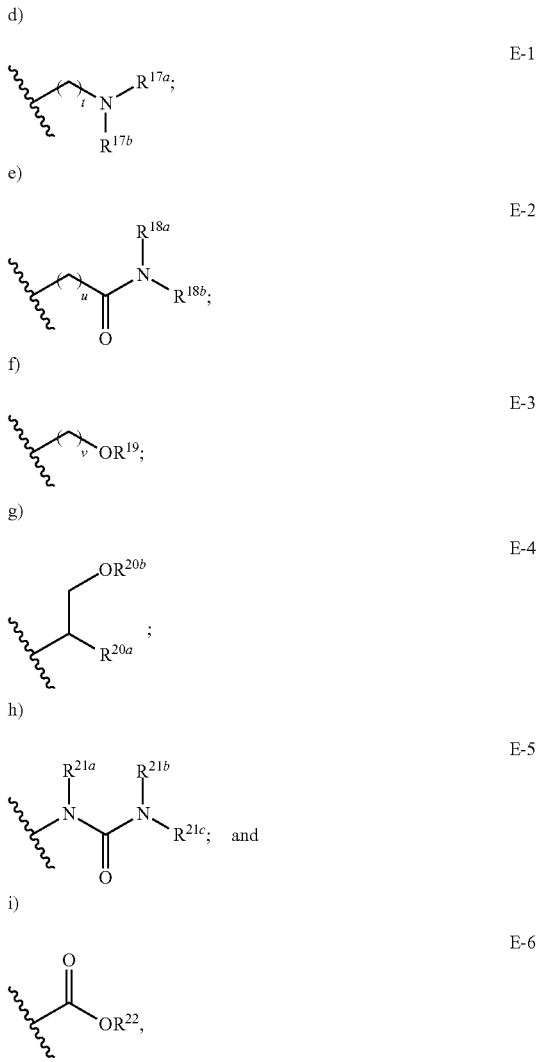

wherein $R^{17a}$, $R^{17b}$, $R^{18a}$, $R^{18b}$, $R^{19}$, $R^{20a}$, $R^{20b}$, $R^{21a}$, $R^{21b}$, $R^{21c}$, $R^{22}$, t, u, and v are as defined above in connection with Formula I.

In another embodiment, Compounds of the Invention are compounds having Formula IV and the pharmaceutically acceptable salts, prodrugs, and solvates thereof, wherein w is 0.

In another embodiment, Compounds of the Invention are compounds having Formula IV and the pharmaceutically acceptable salts, prodrugs, and solvates thereof, wherein E is hydroxyalkyl. Useful hydroxyalkyl groups include:

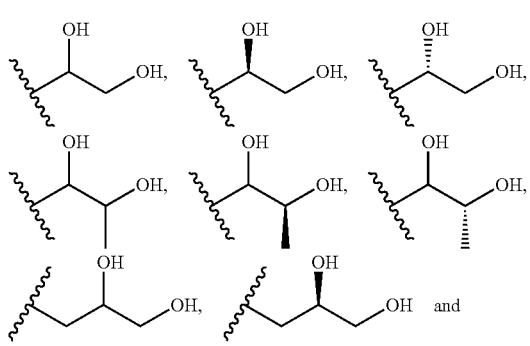

-continued

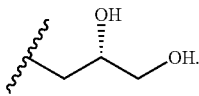

In another embodiment, Compounds of the Invention are compounds having Formula V:

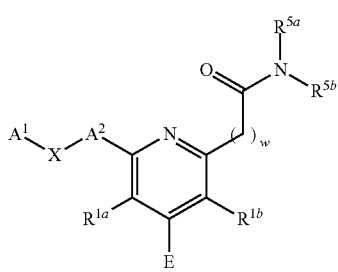

V and the pharmaceutically acceptable salts, prodrugs, and solvates thereof, wherein $A^1$, X, $A^2$, $R^{1a}$, $R^{1b}$, $R^{5a}$, $R^{5b}$, $Z^1$, $Z^2$, and w are as defined above in connection with Formula I, and E is selected from the group consisting of:
a) optionally substituted heteroaryl;
b) optionally substituted heterocyclo;
c) hydroxyalkyl;

d)

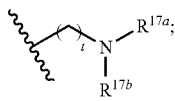

E-1 e)

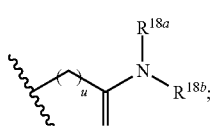

E-2 f)

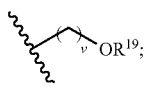

E-3 g)

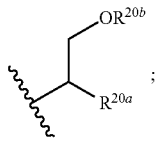

E-4 h)

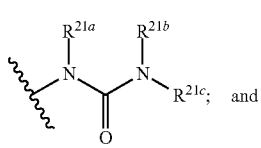

E-5 i)

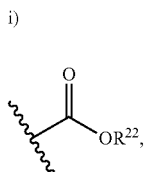

E-6 wherein $R^{17a}$, $R^{17b}$, $R^{18a}$, $R^{18b}$, $R^{19}$, $R^{20a}$, $R^{20b}$, $R^{21a}$, $R^{21b}$, $R^{21c}$, $R^{22}$, t, u, and v are as defined above in connection with Formula I.

In another embodiment, Compounds of the Invention are compounds having Formula V and the pharmaceutically acceptable salts, prodrugs, and solvates thereof, wherein w is 0.

In another embodiment, Compounds of the Invention are compounds having Formula V and the pharmaceutically acceptable salts, prodrugs, and solvates thereof, wherein E is hydroxyalkyl. Useful hydroxyalkyl groups include:

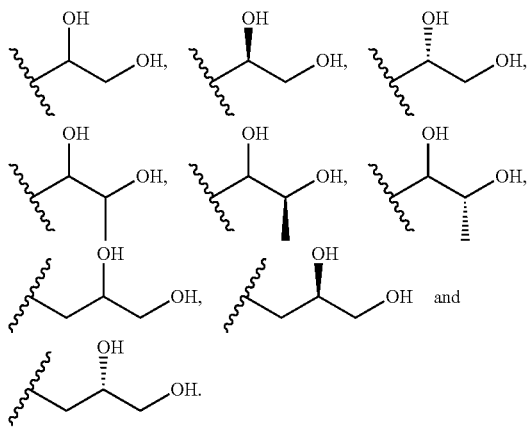

In another embodiment, Compounds of the Invention are compounds having Formula V and the pharmaceutically acceptable salts, prodrugs, and solvates thereof, wherein:

E is

E-1 t is 0;
$R^{17a}$ is selected from the group consisting of:
a) hydrogen;
b) alkyl;
c) optionally substituted aryl;
d) optionally substituted heteroaryl;
e) (heterocyclo)alkyl;
f) (heteroaryl)alkyl; and
g) (dialkylamino)alkyl; and
$R^{17b}$ is selected from the group consisting of:
a) —SO$_2$R$^{24a}$;
b) —COR$^{24b}$;
c) optionally substituted aryl;
d) optionally substituted heteroaryl;
e) (heterocyclo)alkyl;
f) (heteroaryl)alkyl;
g) (dialkylamino)alkyl; and
h) (carboxamido)alkyl; or $R^{17a}$ and $R^{17b}$ taken together with the nitrogen atom to which they are attached form an optionally substituted 3- to 8-membered heterocyclo.

In another embodiment, Compounds of the Invention are compounds having Formula V and the pharmaceutically acceptable salts, prodrugs, and solvates thereof, wherein E is:

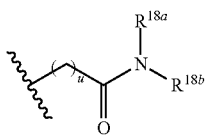
E-2 and u is 1, 2, or 3.

In another embodiment, Compounds of the Invention are compounds having Formula VI:

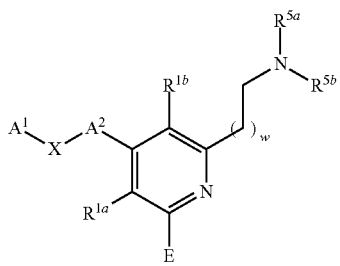
VI and the pharmaceutically acceptable salts, prodrugs, and solvates thereof, wherein $A^1$, X, $A^2$, $R^{1a}$, $R^{1b}$, $R^{5a}$, $R^{5b}$, and w are as defined above in connection with Formula I, and E is selected from the group consisting of:

a) optionally substituted heteroaryl;
b) optionally substituted heterocyclo;
c) hydroxyalkyl;

d)

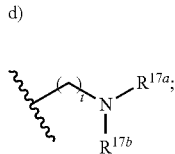
E-1 e)

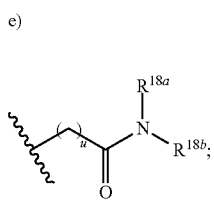
E-2 f)

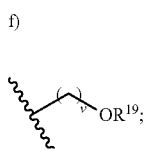
E-3 g)

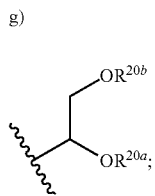
E-4 h)

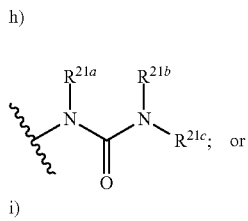
E-5 i)

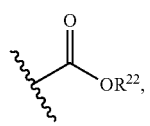
E-6 wherein $R^{17a}$, $R^{17b}$, $R^{18a}$, $R^{18b}$, $R^{19}$, $R^{20a}$, $R^{20b}$, $R^{21a}$, $R^{21b}$, $R^{21c}$, $R^{22}$, t, u, and v are as defined above in connection with Formula I.

In another embodiment, Compounds of the Invention are compounds having Formula VI and the pharmaceutically acceptable salts, prodrugs, and solvates thereof, wherein w is 0.

In another embodiment, Compounds of the Invention are compounds having Formula VII:

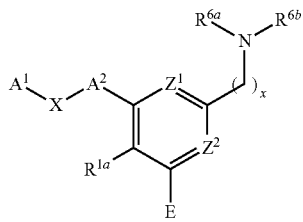
VII and the pharmaceutically acceptable salts, prodrugs, and solvates thereof, wherein $A^1$, X, $A^2$, $R^{1a}$, $R^{6a}$, $R^{6b}$, E, $Z^1$, $Z^2$, and x are as defined above in connection with Formula I.

In another embodiment, Compounds of the Invention are compounds having Formula VIII:

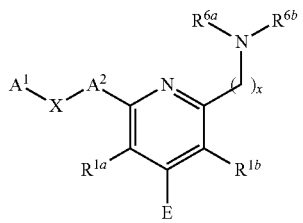
VIII and the pharmaceutically acceptable salts, prodrugs, and solvates thereof, wherein $A^1$, X, $A^2$, $R^{1a}$, $R^{1b}$, $R^{6a}$, $R^{6b}$, E, and x are as defined above in connection with Formula I.

In another embodiment, Compounds of the Invention are compounds having Formula IX:

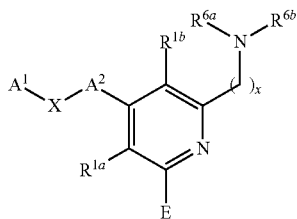

and the pharmaceutically acceptable salts, prodrugs, and solvates thereof, wherein $A^1$, X, $A^2$, $R^{1a}$, $R^{1b}$, $R^{6a}$, $R^{6b}$, E, and x are as defined above in connection with Formula I.

In another embodiment, Compounds of the Invention are compounds having Formula X:

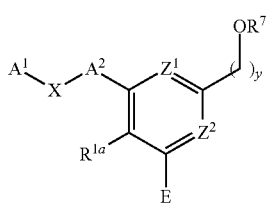

and the pharmaceutically acceptable salts, prodrugs, and solvates thereof, wherein $A^1$, X, $A^2$, $R^{1a}$, $Z^1$, $Z^2$, $R^7$, E, and y are as defined above in connection with Formula I.

In another embodiment, Compounds of the Invention are compounds having Formula XI:

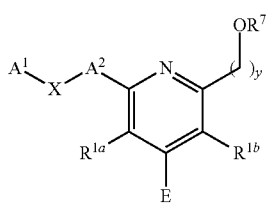

and the pharmaceutically acceptable salts, prodrugs, and solvates thereof, wherein $A^1$, X, $A^2$, $R^{1a}$, $R^{1b}$, $R^7$, E, and y are as defined above in connection with Formula I.

In another embodiment, Compounds of the Invention are compounds having Formula XII:

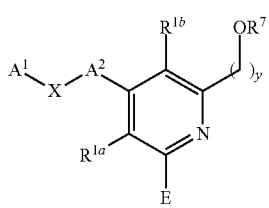

and the pharmaceutically acceptable salts, prodrugs, and solvates thereof, wherein $A^1$, X, $A^2$, $R^{1a}$, $R^{1b}$, $R^7$, E, and y are as defined above in connection with Formula I.

In another embodiment, Compounds of the Invention are compounds having Formula XIII:

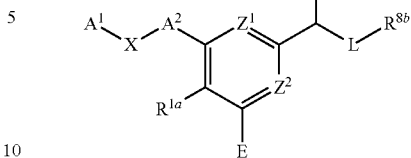

and the pharmaceutically acceptable salts, prodrugs, and solvates thereof, wherein $A^1$, X, $A^2$, $R^{1a}$, $R^{8a}$, $R^{8b}$, E, $Z^1$, $Z^2$, and L are as defined above in connection with Formula I.

In another embodiment, Compounds of the Invention are compounds having Formula XIV:

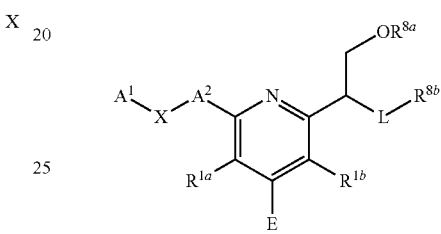

and the pharmaceutically acceptable salts, prodrugs, and solvates thereof, wherein $A^1$, X, $A^2$, $R^{1a}$, $R^{1b}$, $R^{8a}$, $R^{8b}$, E, and L are as defined above in connection with Formula I.

In another embodiment, Compounds of the Invention are compounds having Formula XV:

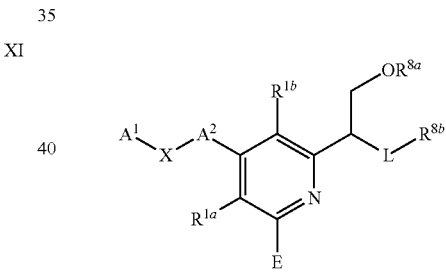

and the pharmaceutically acceptable salts, prodrugs, and solvates thereof, wherein $A^1$, X, $A^2$, $R^{1a}$, $R^{1b}$, $R^{8a}$, $R^{8b}$, E, and L are as defined above in connection with Formula I.

In another embodiment, Compounds of the Invention are compounds having Formula XVI:

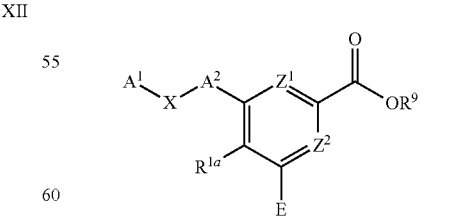

and the pharmaceutically acceptable salts, prodrugs, and solvates thereof, wherein $A^1$, X, $A^2$, $R^{1a}$, $R^9$, $Z^1$, $Z^2$, and E are as defined above in connection with Formula I.

In another embodiment, Compounds of the Invention are compounds having Formula XVII:

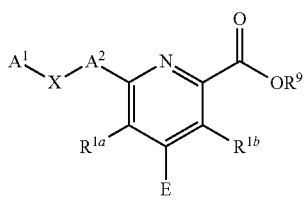

XVII and the pharmaceutically acceptable salts, prodrugs, and solvates thereof, wherein $A^1$, X, $A^2$, $R^{1a}$, $R^{1b}$, $R^9$, and E are as defined above in connection with Formula I.

In another embodiment, Compounds of the Invention are compounds having Formula XVIII:

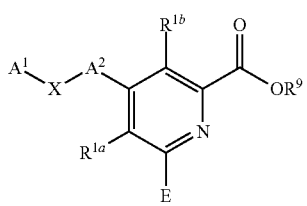

XVIII and the pharmaceutically acceptable salts, prodrugs, and solvates thereof, wherein $A^1$, X, $A^2$, $R^{1a}$, $R^{1b}$, $R^9$, and E are as defined above in connection with Formula I.

In another embodiment, Compounds of the Invention are compounds having any one of Formulae I-XVIII, wherein $A^1$ is selected from the group consisting of optionally substituted aryl and optionally substituted heteroaryl; X is —S—; and $A^2$ is optionally substituted phenyl; and the pharmaceutically acceptable salts, prodrugs, and solvates thereof.

In another embodiment, Compounds of the Invention are compounds having any one of Formulae I-XVIII, wherein $A^1$ is selected from the group consisting of optionally substituted aryl and optionally substituted heteroaryl; X is —SO—; and $A^2$ is optionally substituted phenyl; and the pharmaceutically acceptable salts, prodrugs, and solvates thereof.

In another embodiment, Compounds of the Invention are compounds having any one of Formulae I-XVIII, wherein $A^1$ is selected from the group consisting of optionally substituted aryl and optionally substituted heteroaryl; X is —SO_2—; and $A^2$ is optionally substituted phenyl; and the pharmaceutically acceptable salts, prodrugs, and solvates thereof.

In another embodiment, Compounds of the Invention are compounds having any one of Formulae I-XVIII, wherein $A^1$ is selected from the group consisting of optionally substituted aryl and optionally substituted heteroaryl; X is a bond; and $A^2$ is optionally substituted phenyl; and the pharmaceutically acceptable salts, prodrugs, and solvates thereof.

In another embodiment, Compounds of the Invention are compounds having any one of Formulae I-XVIII, wherein $A^1$ is selected from the group consisting of optionally substituted aryl and optionally substituted heteroaryl; X is —CH_2—; and $A^2$ is optionally substituted phenyl; and the pharmaceutically acceptable salts, prodrugs, and solvates thereof.

In another embodiment, Compounds of the Invention are compounds having any one of Formulae I-XVIII, wherein $A^1$ is selected from the group consisting of optionally substituted aryl and optionally substituted heteroaryl; X is —NH—; and $A^2$ is optionally substituted phenyl; and the pharmaceutically acceptable salts, prodrugs, and solvates thereof.

In another embodiment, Compounds of the Invention are compounds having any one of Formulae I-XVIII, wherein $A^1$ is selected from the group consisting of optionally substituted aryl and optionally substituted heteroaryl; X is —SO_2NH—; and $A^2$ is optionally substituted phenyl; and the pharmaceutically acceptable salts, prodrugs, and solvates thereof.

In another embodiment, Compounds of the Invention are compounds having any one of Formulae I-XVIII, wherein $A^1$ is selected from the group consisting of optionally substituted aryl and optionally substituted heteroaryl; X is —NHSO_2—; and $A^2$ is optionally substituted phenyl; and the pharmaceutically acceptable salts, prodrugs, and solvates thereof.

In another embodiment, Compounds of the Invention are compounds having any one of Formulae I-XVIII, wherein $A^1$ is selected from the group consisting of optionally substituted aryl and optionally substituted heteroaryl; X is —O—; and $A^2$ is optionally substituted phenyl; and the pharmaceutically acceptable salts, prodrugs, and solvates thereof.

In another embodiment, Compounds of the Invention are compounds having any one of Formulae I-XVIII, wherein $A^1$ is selected from the group consisting of optionally substituted phenyl; optionally substituted pyridin-2-yl; optionally substituted pyridin-3-yl; and optionally substituted pyridin-4-yl; X is —O—; and $A^2$ is optionally substituted phenyl; and the pharmaceutically acceptable salts, prodrugs, and solvates thereof.

In another embodiment, Compounds of the Invention are compounds having any one of Formulae I-XVIII, wherein $A^1$-X-$A^2$- is:

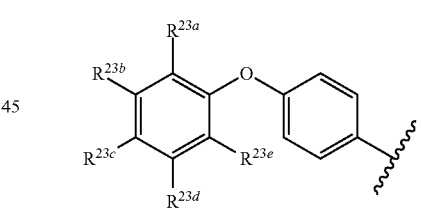

wherein:
$R^{23a}$, $R^{23b}$, $R^{23c}$, $R^{23d}$, $R^{23e}$, which are identical or different, are selected from the group consisting of:
a) hydrogen;
b) halo;
c) nitro;
d) cyano;
e) hydroxy;
f) amino;
g) alkylamino;
h) dialkylamino;
i) haloalkyl;
j) hydroxyalkyl;
k) alkoxy;
l) haloalkoxy;
m) aryloxy;
n) aralkyloxy;

o) alkylthio;
p) carboxamido;
q) sulfonamido;
r) alkylcarbonyl;
s) arylcarbonyl;
t) alkylsulfonyl;
u) arylsulfonyl;
v) ureido;
w) guanidino;
x) carboxy;
y) carboxyalkyl;
z) optionally substituted alkyl;
aa) optionally substituted cycloalkyl;
bb) optionally substituted alkenyl;
cc) optionally substituted alkynyl;
dd) optionally substituted aryl;
ee) optionally substituted heteroaryl; and
ff) optionally substituted heterocyclo; or
$R^{23a}$ and $R^{23b}$, or $R^{23b}$ and $R^{23c}$, or $R^{23c}$ and $R^{23d}$, or $R^{23d}$ and $R^{23e}$, taken together with the carbon atoms to which they are attached form a 5- or 6-membered optionally substituted cycloalkyl or heterocyclo group; and the pharmaceutically acceptable salts, prodrugs, and solvates thereof.

In another embodiment, $R^{23a}$, $R^{23b}$, $R^{23c}$, $R^{23d}$, $R^{23e}$, which are identical or different, are selected from the group consisting of:
a) hydrogen;
b) halo;
c) nitro;
d) cyano;
e) hydroxy;
f) amino;
g) alkylamino;
h) dialkylamino;
i) haloalkyl;
j) alkoxy;
k) haloalkoxy;
l) alkylthio;
m) carboxamido;
n) sulfonamido;
o) alkylcarbonyl;
p) alkylsulfonyl;
q) arylsulfonyl;
r) ureido;
s) guanidino;
t) carboxy;
u) carboxyalkyl; and
v) optionally substituted alkyl; or
$R^{23a}$ and $R^{23b}$, or $R^{23b}$ and $R^{23c}$, or $R^{23c}$ and $R^{23d}$, or $R^{23d}$ and $R^{23e}$ taken together with the carbon atoms to which they are attached form a 5- or 6-membered optionally substituted cycloalkyl or heterocyclo group.

In another embodiment, $R^{23a}$, $R^{23b}$, $R^{23c}$, $R^{23d}$, $R^{23e}$, which are identical or different, are selected from the group consisting of:
a) hydrogen;
b) halo;
c) nitro;
d) cyano;
e) hydroxy;
amino;
g) alkylamino;
h) dialkylamino;
i) haloalkyl;
j) alkoxy;
k) haloalkoxy;
l) carboxamido;
m) sulfonamido;
n) alkylcarbonyl;
o) alkylsulfonyl;
p) arylsulfonyl;
q) carboxyalkyl; and
r) alkyl; or
$R^{23a}$ and $R^{23b}$, or $R^{23b}$ and $R^{23c}$, or $R^{23c}$ and $R^{23d}$, or $R^{23d}$ and $R^{23e}$ taken together with the carbon atoms to which they are attached form a 5- or 6-membered optionally substituted cycloalkyl or heterocyclo group.

In another embodiment, $R^{23a}$ and $R^{23b}$, or $R^{23b}$ and $R^{23c}$, or $R^{23c}$ and $R^{23d}$, or $R^{23d}$ and $R^{23e}$ taken together represent:
—$CH_2CH_2O$—; —$OCH_2O$—; —$OCH_2CH_2CH_2O$—; —$OCH_2CH_2O$—; —$CH_2CH_2CH_2$—; —$CH_2CH_2CH_2CH_2$—; —$NR^{25a}CH_2CH_2$—; —$CH_2NR^{25b}CH_2$—; —$NR^{25c}CH_2CH_2CH_2$—; or —$CH_2NR^{25d}CH_2CH_2$—, wherein $R^{25a}$, $R^{25b}$, $R^{25c}$, and $R^{25d}$, which are identical or different, are selected from the group consisting of hydrogen and optionally substituted alkyl.

In another embodiment, Compounds of the Invention are compounds having any one of Formulae I-XVIII, wherein $R^{1a}$ and $R^{1b}$ are each hydrogen, and the pharmaceutically acceptable salts, prodrugs, and solvates thereof.

In another embodiment, Compounds of the Invention are compounds having any one of Formulae I-XVIII, wherein E is optionally substituted heteroaryl, and the pharmaceutically acceptable salts, prodrugs, and solvates thereof.

In another embodiment, Compounds of the Invention are compounds having any one of Formulae I-XVIII, wherein E is optionally substituted heterocyclo, e.g., an optionally substituted piperidine or optionally substituted piperazine, and the pharmaceutically acceptable salts, prodrugs, and solvates thereof.

In another embodiment, Compounds of the Invention are compounds having any one of Formulae I-XVIII wherein E is hydroxyalkyl. Useful hydroxyalkyl groups include:

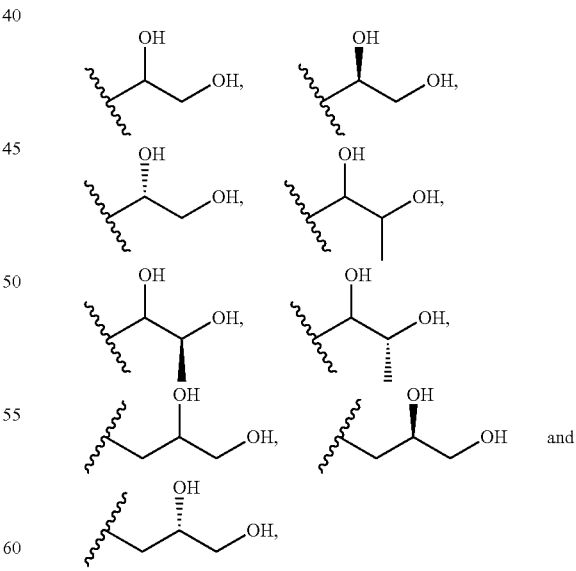

and the pharmaceutically acceptable salts, prodrugs, and solvates thereof

In another embodiment, Compounds of the Invention are compounds having any one of Formulae I-XVIII, wherein E is:

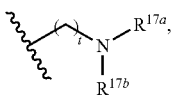
E-1 and the pharmaceutically acceptable salts, prodrugs, and solvates thereof.

In another embodiment, Compounds of the Invention are compounds having any one of Formulae I-XVIII, wherein E is:

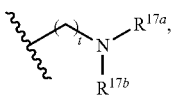
E-1 t is 0, $R^{17a}$ is hydrogen, and $R^{17b}$ is (carboxamido)alkyl, e.g.,

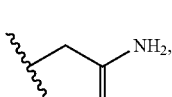 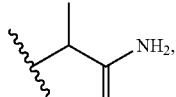

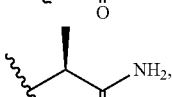 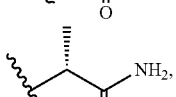 and

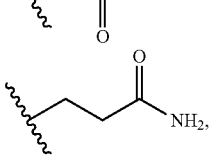

and the pharmaceutically acceptable salts, prodrugs, and solvates thereof.

In another embodiment, Compounds of the Invention are compounds having any one of Formulae I-XVIII, wherein E is:

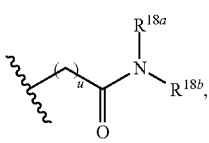
E-2 and the pharmaceutically acceptable salts, prodrugs, and solvates thereof.

In another embodiment, Compounds of the Invention are compounds having any one of Formulae I-XVIII, wherein E is:

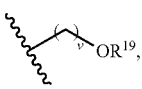
E-3 and the pharmaceutically acceptable salts, prodrugs, and solvates thereof.

In another embodiment, Compounds of the Invention are compounds having any one of Formulae I-XVIII, wherein E is:

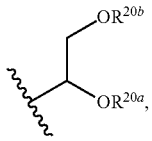
E-4 and the pharmaceutically acceptable salts, prodrugs, and solvates thereof.

In another embodiment, Compounds of the Invention are compounds having any one of Formulae I-XVIII, wherein E is:

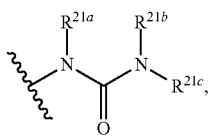
E-5 and the pharmaceutically acceptable salts, prodrugs, and solvates thereof

In another embodiment, Compounds of the Invention are compounds having any one of Formulae I-XVIII, wherein E is:

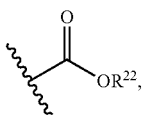
E-6 and the pharmaceutically acceptable salts, prodrugs, and solvates thereof

In another embodiment, Compounds of the Invention are compounds having Formula V, wherein w is 0 and E is optionally substituted heteroaryl, and the pharmaceutically acceptable salts, prodrugs, and solvates thereof.

In another embodiment, Compounds of the Invention are compounds having Formula V, wherein w is 0 and E is optionally substituted heterocyclo, and the pharmaceutically acceptable salts, prodrugs, and solvates thereof.

In another embodiment, Compounds of the Invention are compounds having Formula V, wherein w is 0 and E is hydroxyalkyl, and the pharmaceutically acceptable salts, prodrugs, and solvates thereof.

In another embodiment, Compounds of the Invention are compounds having Formula V, wherein w is 0, and E is:

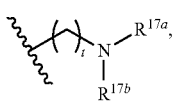
E-1 and the pharmaceutically acceptable salts, prodrugs, and solvates thereof

In another embodiment, Compounds of the Invention are compounds having Formula V, wherein w is 0 and E is:

E-2 and the pharmaceutically acceptable salts, prodrugs, and solvates thereof.

In another embodiment, Compounds of the Invention are compounds having Formula V, wherein w is 0 and E is:

E-3 and the pharmaceutically acceptable salts, prodrugs, and solvates thereof.

In another embodiment, Compounds of the Invention are compounds having Formula V, wherein w is 0 and E is:

E-4 and the pharmaceutically acceptable salts, prodrugs, and solvates thereof.

In another embodiment, Compounds of the Invention are compounds having Formula V, wherein w is 0 and E is:

E-5 and the pharmaceutically acceptable salts, prodrugs, and solvates thereof.

In another embodiment, Compounds of the Invention are compounds having Formula V, wherein w is 0 and E is:

E-6 and the pharmaceutically acceptable salts, prodrugs, and solvates thereof.

In another embodiment, Compounds of the Invention are compounds having Formula XIX:

XIX wherein $A^1$ and E are as defined above in connection with Formula I, $R^7$ is —$(CH_2CH_2O)_o$—$R^{15c}$ and $R^{15c}$ is H, and the pharmaceutically acceptable salts, prodrugs, and solvates thereof.

In another embodiment, Compounds of the Invention are compounds having Formula XX:

XX wherein $A^1$ and E are as defined above in connection with Formula I, and the pharmaceutically acceptable salts, prodrugs, and solvates thereof In another embodiment, Compounds of the Invention are compounds having Formula XXI:

XXI wherein $A^1$ and E are as defined above in connection with Formula I, and the pharmaceutically acceptable salts, prodrugs, and solvates thereof In another embodiment, Compounds of the Invention are compounds having Formula XXII:

XXII wherein $A^1$ and E are as defined above in connection with Formula I, and the pharmaceutically acceptable salts, prodrugs, and solvates thereof.

In another embodiment, Compounds of the Invention are compounds having Formula

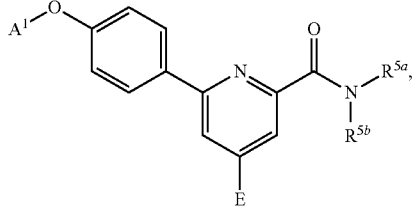

XXIII wherein $A^1$, $R^{5a}$, and $R^{5b}$ are as defined above in connection with Formula I and E is hydroxyalkyl. Useful hydroxyalkyl groups include:

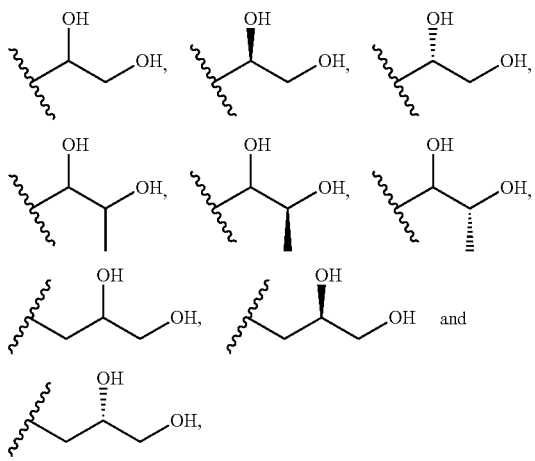

and the pharmaceutically acceptable salts, prodrugs, and solvates thereof.

In another embodiment, Compounds of the Invention are compounds having Formula XXIV:

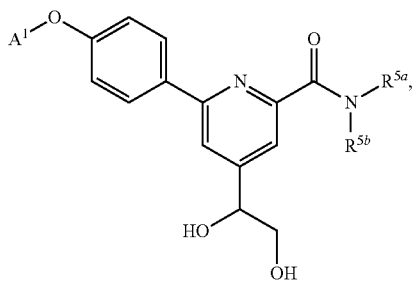

XXIV wherein $A^1$, $R^{5a}$, and $R^{5b}$ are as defined above in connection with Formula I and the pharmaceutically acceptable salts, prodrugs, and solvates thereof.

In another embodiment, Compounds of the Invention are compounds having Formula XXV:

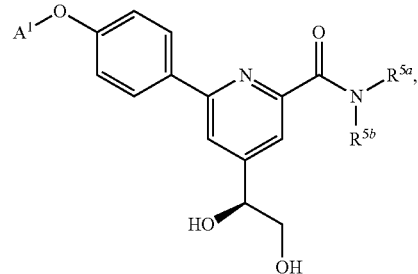

XXV wherein $A^1$, $R^{5a}$, and $R^{5b}$ are as defined above in connection with Formula I, and the pharmaceutically acceptable salts, prodrugs, and solvates thereof.

In another embodiment, Compounds of the Invention are compounds having Formula XXVI:

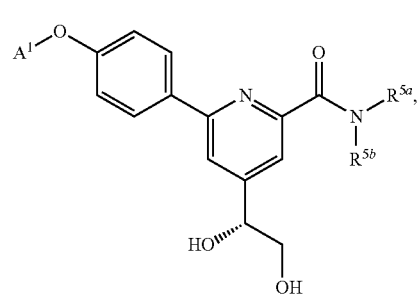

XXVI wherein $A^1$, $R^{5a}$, and $R^{5b}$ are as defined above in connection with Formula I, and the pharmaceutically acceptable salts, prodrugs, and solvates thereof In another embodiment, Compounds of the Invention are compounds having Formula XXVII:

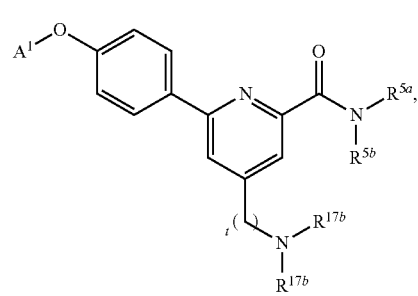

XXVII wherein $A^1$, $R^{5a}$, $R^{5b}$, $R^{17a}$, $R^{17b}$, and t are as defined above in connection with Formula I, and the pharmaceutically acceptable salts, prodrugs, and solvates thereof.

In another embodiment, Compounds of the Invention are compounds having Formula XXVII, wherein $A^1$, $R^{5a}$, $R^{5b}$, $R^{17a}$, and $R^{17b}$ are as defined above in connection with Formula I and t is 0 or 1, and the pharmaceutically acceptable salts, prodrugs, and solvates thereof.

In another embodiment, Compounds of the Invention are compounds having Formula XXVII, wherein $A^1$, $R^{5a}$, and $R^{5b}$ are as defined above in connection with Formula I, t is 0, $R^{17a}$ is selected from the group consisting of:
  a) hydrogen;
  b) alkyl;

c) optionally substituted aryl;
d) optionally substituted heteroaryl;
e) (heterocyclo)alkyl;
f) (heteroaryl)alkyl; and
g) (dialkylamino)alkyl; and $R^{17b}$ is selected from the group consisting of:

a) —$SO_2R^{24a}$;
b) —$COR^{24b}$;
c) optionally substituted aryl;
d) optionally substituted heteroaryl;
e) (heterocyclo)alkyl;
f) (heteroaryl)alkyl;
g) (dialkylamino)alkyl; and
h) (carboxamido)alkyl; or $R^{17a}$ and $R^{17b}$ taken together with the nitrogen atom to which they are attached form an optionally substituted 3- to 8-membered heterocyclo, and the pharmaceutically acceptable salts, prodrugs, and solvates thereof.

In another embodiment, Compounds of the Invention are compounds having Formula XXVII, wherein $A^1$, $R^{5a}$, and $R^{5b}$ are as defined above in connection with Formula I, t is 0, $R^{17a}$ is hydrogen, and $R^{17b}$ is (carboxamido)alkyl, and the pharmaceutically acceptable salts, prodrugs, and solvates thereof.

In another embodiment, Compounds of the Invention are compounds having Formula XXVII, wherein $A^1$ is optionally substituted aryl, $R^{5a}$ and $R^{5b}$ are hydrogen, t is 0, $R^{17a}$ is hydrogen, and $R^{17b}$ is (carboxamido)alkyl, and the pharmaceutically acceptable salts, prodrugs, and solvates thereof.

In another embodiment, Compounds of the Invention are compounds having Formula XXVIII:

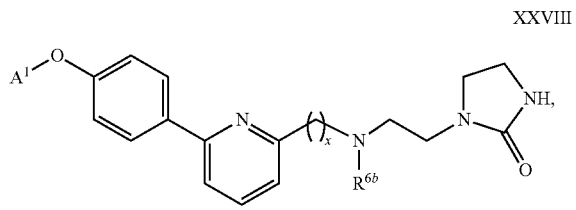

XXVIII wherein $A^1$, $R^{6b}$, and x are as defined above in connection with Formula I, and the pharmaceutically acceptable salts, prodrugs, and solvates thereof.

In another embodiment, Compounds of the Invention are compounds having Formula XXVIII, wherein $A^1$ and $R^{6b}$ are as defined above in connection with Formula I and x is 1 or 2, and the pharmaceutically acceptable salts, prodrugs, and solvates thereof.

In another embodiment, Compounds of the Invention are compounds having Formula XXIII wherein E is optionally substituted heteroaryl, and the pharmaceutically acceptable salts, prodrugs, and solvates thereof. Useful optionally substituted heteroaryl groups include optionally substituted indoles.

In another embodiment, Compounds of the Invention are compounds having Formula XXIII, wherein E is an optionally substituted heterocyclo, and the pharmaceutically acceptable salts, prodrugs, and solvates thereof. In one embodiment, E is an optionally substituted piperazinyl having the formula:

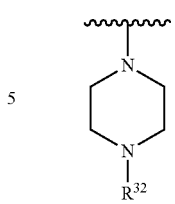

wherein $R^{32}$ is chosen from hydrogen, hydroxyalkyl, carboxamido, sulfonamido, alkylcarbonyl, arylcarbonyl, alkylsulfonyl, arylsulfonyl, ureido, guanidino, carboxyalkyl, optionally substituted alkyl, optionally substituted cycloalkyl, optionally substituted alkenyl, optionally substituted alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (heteroaryl)alkyl, and the like.

In another embodiment, Compounds of the Invention are compounds having Formula XXIX:

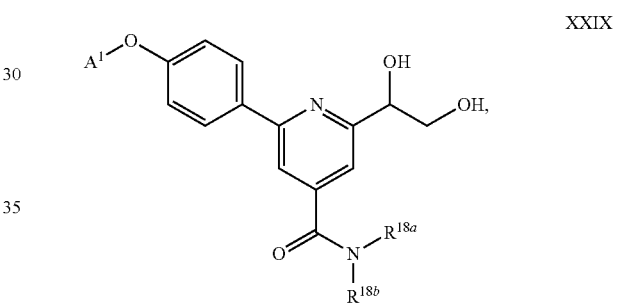

XXIX wherein $A^1$, $R^{18a}$, and $R^{18b}$ are as defined above in connection with Formula I, and the pharmaceutically acceptable salts, prodrugs, and solvates thereof.

In another embodiment, Compounds of the Invention are compounds having Formula XXX:

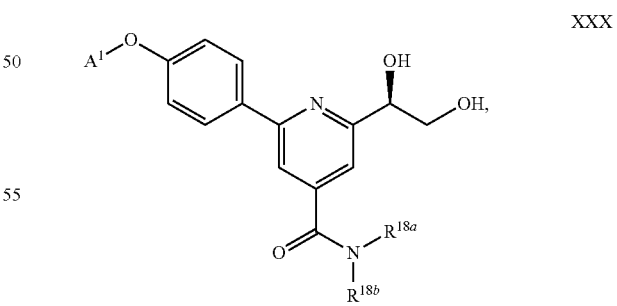

XXX wherein $A^1$, $R^{18a}$, and $R^{18b}$ are a as defined above in connection with Formula I, and the pharmaceutically acceptable salts, prodrugs, and solvates thereof.

In another embodiment, Compounds of the Invention are compounds having Formula XXXI:

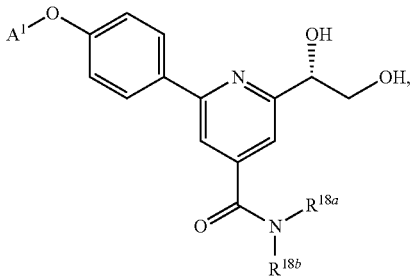

XXXI wherein $A^1$, $R^{18a}$, and $R^{18b}$ are as defined above in connection with Formula I, and the pharmaceutically acceptable salts, prodrugs, and solvates thereof.

In another embodiment, Compounds of the Invention are compounds having Formula XXXII:

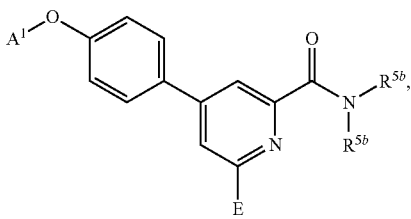

XXXII wherein $A^1$, $R^{5a}$, and $R^{5b}$ are as defined above in connection with Formula I and E is selected from the group consisting of:
a) hydroxyalkyl;
b) optionally substituted heterocyclo;
c) optionally substituted heteroaryl;

d)

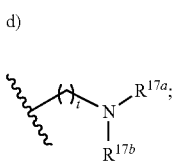

E-1 e)

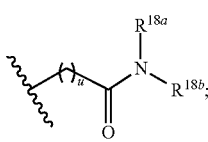

E-2 f)

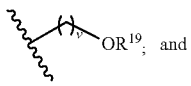

E-3 g)

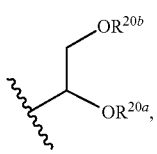

E-4 wherein $R^{17a}$, $R^{17b}$, $R^{18a}$, $R^{18b}$, $R^{19}$, $R^{20a}$, $R^{20b}$, t, u, and v are as defined above in connection with Formula I, and the pharmaceutically acceptable salts, prodrugs, and solvates thereof.

In another embodiment, Compounds of the Invention are compounds having Formula XXXII wherein E is hydroxyalkyl, and the pharmaceutically acceptable salts, prodrugs, and solvates thereof.

In another embodiment, Compounds of the Invention are compounds having Formula XXXII wherein E is optionally substituted heteroaryl, e.g., optionally substituted indole, and the pharmaceutically acceptable salts, prodrugs, and solvates thereof.

In another embodiment, Compounds of the Invention are compounds having Formula XXXIII:

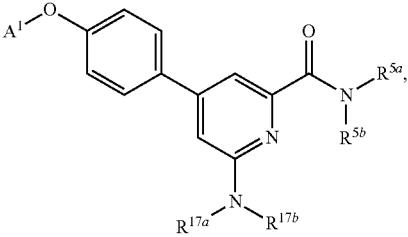

XXXIII wherein $A^1$, $R^{5a}$, $R^{5b}$, $R^{17a}$, and $R^{17b}$ are as defined above in connection with Formula I, and the pharmaceutically acceptable salts, prodrugs, and solvates thereof. In one embodiment, $R^{17a}$ is chosen from hydrogen, alkyl, and optionally substituted aryl. In another embodiment, $R^{17b}$ is chosen from (amino)alkyl, (alkylamino)alkyl, (dialkylamino)alkyl, (carboxamido)alkyl, (cyano)alkyl; and hydroxyalkyl. In another embodiment, $R^{17a}$ is optionally substituted aryl and $R^{17b}$ is (carboxamido)alkyl.

In another embodiment, Compounds of the Invention are compounds having any one of Formulae XIX-XXXIII wherein $A^1$ is selected from the group consisting of optionally substituted aryl and optionally substituted heteroaryl, and the pharmaceutically acceptable salts, prodrugs, and solvates thereof.

In another embodiment, Compounds of the Invention are compounds having any one of Formulae XIX-XXXIII wherein $A^1$ is selected from the group consisting of optionally substituted phenyl, optionally substituted pyridin-2-yl, optionally substituted pyridin-3-yl, and optionally substituted pyridin-4-yl, and the pharmaceutically acceptable salts, prodrugs, and solvates thereof.

In another embodiment, Compounds of the Invention include the compound ("cpd") examples of TABLE 2, and the pharmaceutically acceptable salts, prodrugs, and solvates thereof.

TABLE 2

| Cpd Example No. | Chemical Name | Structure |
|---|---|---|
| 1 | 2-(2,5,8,11-tetraoxadodecyl)-6-(4-(4-(trifluoromethyl)phenoxy)phenyl)pyridine | 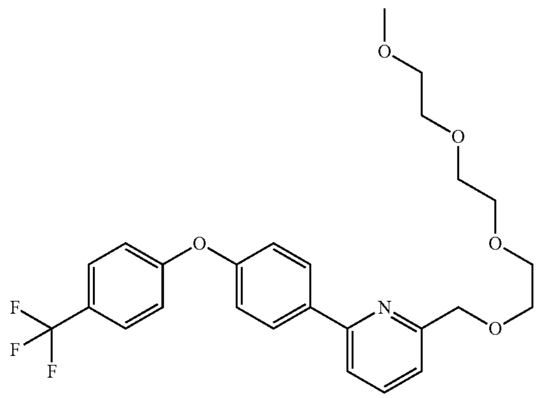 [SMILES: COCCOCCOCCOCc1cccc(-c2ccc(Oc3ccc(C(F)(F)F)cc3)cc2)n1] |
| 2 | 2-(2,5,8,11,14,17,20,23-octaoxatetracosyl)-6-(4-(4-(trifluoromethyl)phenoxy)phenyl pyridine | 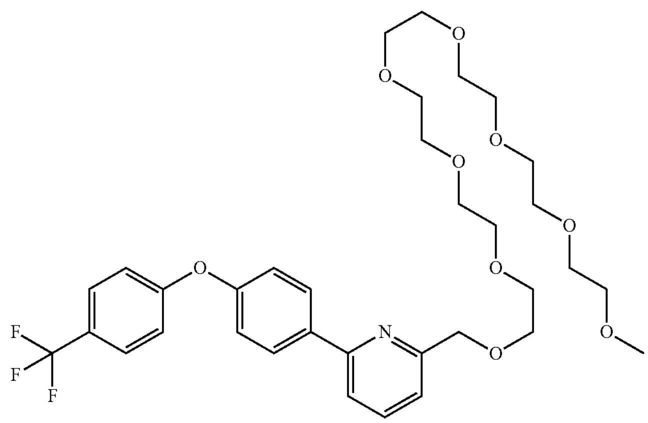 [SMILES: COCCOCCOCCOCCOCCOCCOCCOCc1cccc(-c2ccc(Oc3ccc(C(F)(F)F)cc3)cc2)n1] |
| 3 | 1-(6-(4-(4-(trifluoromethyl)phenoxy)phenyl)pyridin-2-yl)ethane-1,2-diol | 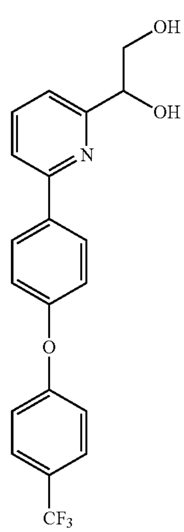 |

TABLE 2-continued
| Cpd Example No. | Chemical Name | Structure |
|---|---|---|
| 4 | (S)-1-(6-(4-(4-(trifluoromethyl)phenoxy)phenyl)pyridin-2-yl)ethane-1,2-diol | 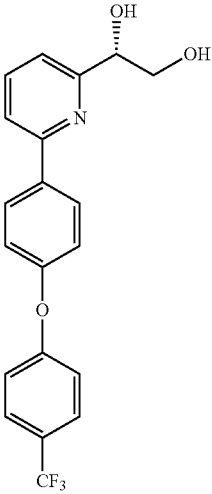 |
| 5 | (R)-1-(6-(4-(4-(trifluoromethyl)phenoxy)phenyl)pyridin-2-yl)ethane-1,2-diol | 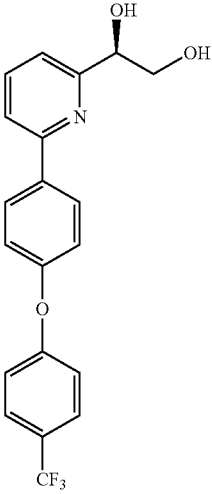 [SMILES: OC[C@H](O)c1cccc(-c2ccc(Oc3ccc(C(F)(F)F)cc3)cc2)n1] |
| 6 | (S)-4-(4-(6-(1,2-dihydroxyethyl)pyridin-2-yl)phenoxy)benzonitrile | 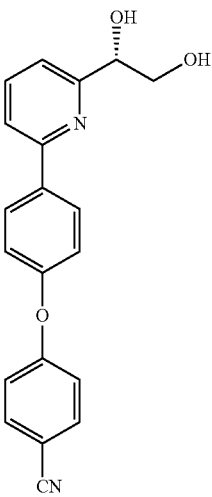 [SMILES: N#Cc1ccc(Oc2ccc(-c3cccc([C@H](O)CO)n3)cc2)cc1] |

TABLE 2-continued
| Cpd Example No. | Chemical Name | Structure |
|---|---|---|
| 7 | (R)-4-(2-(1,2-dihydroxyethyl)-6-(4-(4-fluorophenoxy)phenyl)pyridin-4-yl)-N-isopropyl piperazine-1-carboxamide | 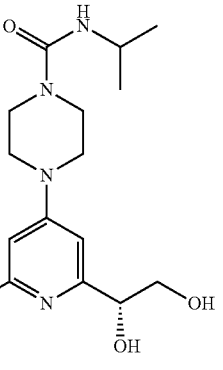 |
| 8 | 4-(4-(6-(1,2-dihydroxyethyl)pyridin-2-yl)phenoxy)benzonitrile | 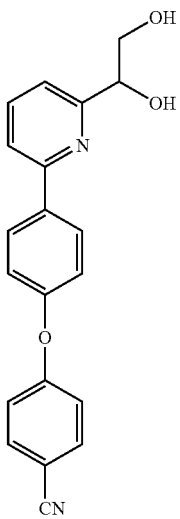 [SMILES: N#Cc1ccc(Oc2ccc(-c3cccc(C(O)CO)n3)cc2)cc1] |
| 9 | 4-(4-(6-(1,2-dihydroxyethyl)pyridin-2-yl)phenoxy)-3-(trifluoromethyl)benzonitrile | 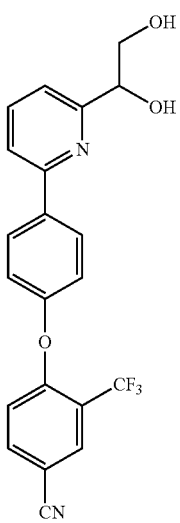 [SMILES: N#Cc1ccc(Oc2ccc(-c3cccc(C(O)CO)n3)cc2)c(C(F)(F)F)c1] |

TABLE 2-continued

| Cpd Example No. | Chemical Name | Structure |
|---|---|---|
| 10 | 2-(4-(6-(1,2-dihydroxyethyl)pyridin-2-yl)phenoxy)-5-(trifluoromethyl)benzonitrile | 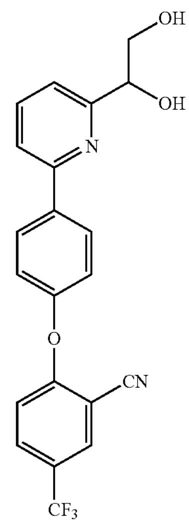 [SMILES: N#Cc1cc(C(F)(F)F)ccc1Oc1ccc(-c2cccc(C(O)CO)n2)cc1] |
| 11 | (R)-4-(4-(6-(1,2-dihydroxyethyl)pyridin-2-yl)phenoxy)-3-(trifluoromethyl)benzonitrile | 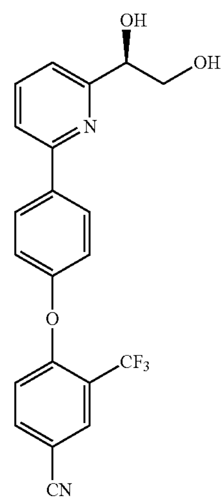 [SMILES: N#Cc1ccc(Oc2ccc(-c3cccc([C@@H](O)CO)n3)cc2)c(C(F)(F)F)c1] |
| 12 | 5-(4-(6-(1,2-dihydroxyethyl)pyridin-2-yl)phenoxy)-2-(trifluoromethyl)benzonitrile | 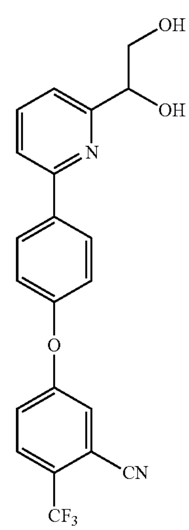 [SMILES: N#Cc1cc(Oc2ccc(-c3cccc(C(O)CO)n3)cc2)ccc1C(F)(F)F] |

TABLE 2-continued

| Cpd Example No. | Chemical Name | Structure |
|---|---|---|
| 13 | (R)-4-(4-(6-(1,2-dihydroxyethyl)pyridin-2-yl)phenoxy)benzonitrile | 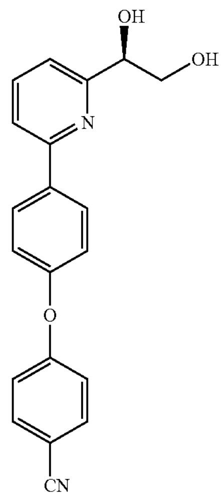 [SMILES: N#Cc1ccc(Oc2ccc(-c3cccc([C@@H](O)CO)n3)cc2)cc1] |
| 14 | (R)-5-(4-(6-(1,2-dihydroxyethyl)pyridin-2-yl)phenoxy)-2-(trifluoromethyl)benzonitrile | 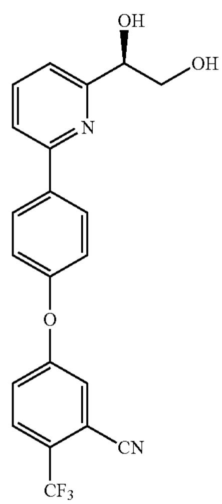 [SMILES: N#Cc1cc(Oc2ccc(-c3cccc([C@@H](O)CO)n3)cc2)ccc1C(F)(F)F] |
| 15 | 1-(6-(4-((3-chloro-5-(trifluoromethyl)pyridin-2-yl)oxy)phenyl)pyridin-2-yl)ethane-1,2-diol | 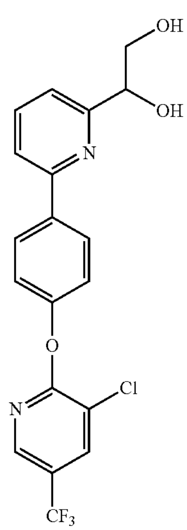 [SMILES: OCC(O)c1cccc(-c2ccc(Oc3ncc(C(F)(F)F)cc3Cl)cc2)n1] |

TABLE 2-continued

| Cpd Example No. | Chemical Name | Structure |
|---|---|---|
| 16 | 1-(6-(4-((5-(trifluoromethyl)pyridin-2-yl)oxy)phenyl)pyridin-2-yl)ethane-1,2-diol | 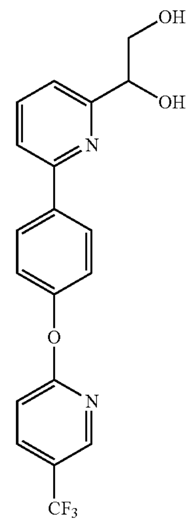 [SMILES: OCC(O)c1cccc(-c2ccc(Oc3ccc(C(F)(F)F)cn3)cc2)n1] |
| 17 | 1-(6-(4-((6-methylpyridin-3-yl)oxy)phenyl)pyridin-2-yl)ethane-1,2-diol | 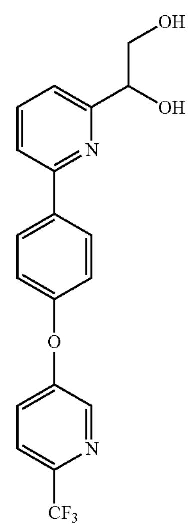 [SMILES: OCC(O)c1cccc(-c2ccc(Oc3ccc(C(F)(F)F)nc3)cc2)n1] |
| 18 | (S)-5-(4-(6-(1,2-dihydroxyethyl)pyridin-2-yl)phenoxy)-2-(trifluoromethyl)benzonitrile | 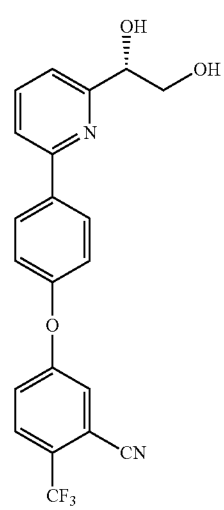 [SMILES: N#Cc1cc(Oc2ccc(-c3cccc([C@H](O)CO)n3)cc2)ccc1C(F)(F)F] |

| Cpd Example No. | Chemical Name | Structure |
|---|---|---|
| 19 | (1R,1'R)-1,1'-(6-(4-(4-fluorophenoxy)phenyl)pyridine-2,4-diyl)bis(ethane-1,2-diol) | 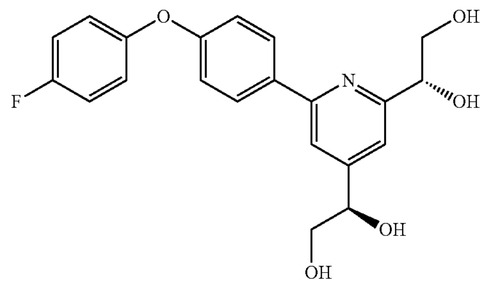 [SMILES: OC[C@H](O)c1cc(-c2ccc(Oc3ccc(F)cc3)cc2)nc([C@@H](O)CO)c1] |
| 20 | 1-(4-(4-(6-(1,2-dihydroxyethyl)pyridin-2-yl)phenoxy)-3-(trifluoromethyl)phenyl)ethanone | 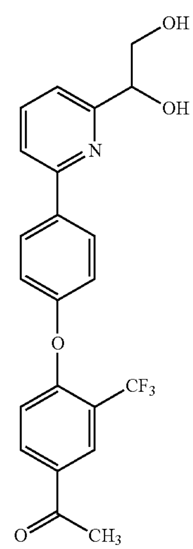 [SMILES: CC(=O)c1ccc(Oc2ccc(-c3cccc(C(O)CO)n3)cc2)c(C(F)(F)F)c1] |
| 21 | (R)-1-(6-(4-(4-fluorophenoxy)phenyl)-4-(piperazin-1-yl)pyridin-2-yl)ethane-1,2-diol | 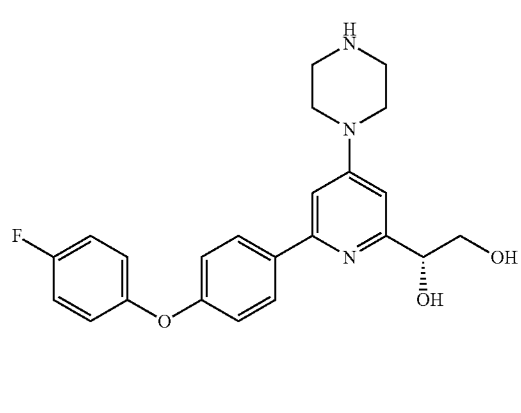 [SMILES: OC[C@H](O)c1cc(N2CCNCC2)cc(-c2ccc(Oc3ccc(F)cc3)cc2)n1] |

TABLE 2-continued
| Cpd Example No. | Chemical Name | Structure |
|---|---|---|
| 22 | (S)-4-(4-(6-(1,2-dihydroxyethyl)pyridin-2-yl)phenoxy)-3-(trifluoromethyl)benzonitrile | 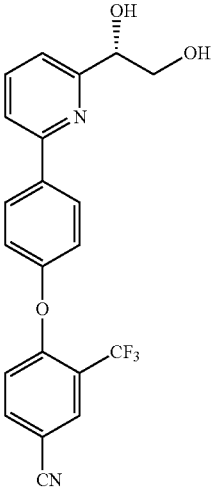 [SMILES: N#Cc1ccc(Oc2ccc(-c3cccc([C@H](O)CO)n3)cc2)c(C(F)(F)F)c1] |
| 23 | (R)-1-(6-(4-((5-(trifluoromethyl)pyridin-2-yl)oxy)phenyl)pyridin-2-yl)ethane-1,2-diol | 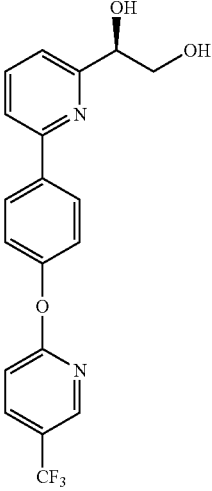 [SMILES: OC[C@H](O)c1cccc(-c2ccc(Oc3ccc(C(F)(F)F)cn3)cc2)n1] |
| 24 | (S)-1-(6-(4-((5-(trifluoromethyl)pyridin-2-yl)oxy)phenyl)pyridin-2-yl)ethane-1,2-diol | 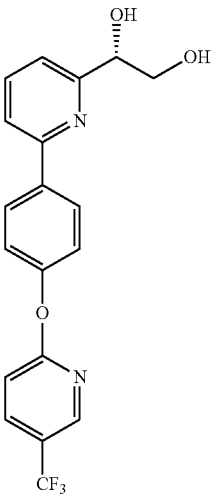 [SMILES: OC[C@@H](O)c1cccc(-c2ccc(Oc3ccc(C(F)(F)F)cn3)cc2)n1] |

TABLE 2-continued

| Cpd Example No. | Chemical Name | Structure |
|---|---|---|
| 25 | 4-(4-(4,6-bis((S)-1,2-dihydroxyethyl)pyridin-2-yl)phenoxy)-3-(trifluoromethyl)benzonitrile | 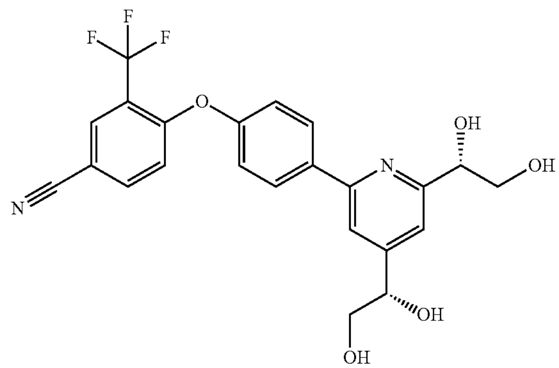 [SMILES: N#Cc1ccc(Oc2ccc(-c3cc([C@H](O)CO)cc([C@H](O)CO)n3)cc2)c(C(F)(F)F)c1] |
| 26 | (1S,1'S)-1,1'-(6-(4-(4-fluorophenoxy)phenyl)pyridine-2,4-diyl)bis(ethane-1,2-diol) | 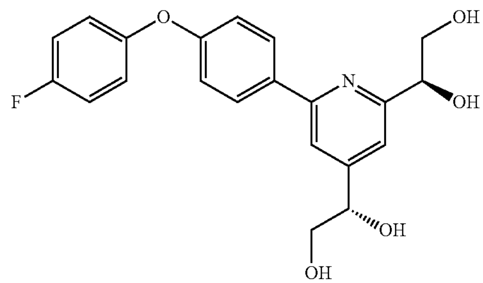 [SMILES: OC[C@@H](O)c1cc(-c2ccc(Oc3ccc(F)cc3)cc2)nc([C@H](O)CO)c1] |
| 27 | 1-(6-(4-((6-methylpyridin-3-yl)oxy)phenyl)pyridin-2-yl)ethane-1,2-diol | 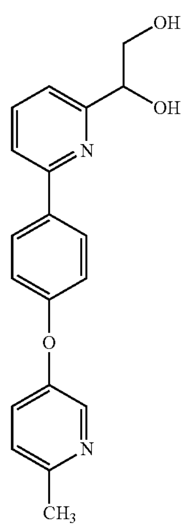 [SMILES: Cc1ccc(Oc2ccc(-c3cccc(C(O)CO)n3)cc2)cn1] |
| 28 | 4-(4-(4,6-bis((R)-1,2-dihydroxyethyl)pyridin-2-yl)phenoxy)-3-(trifluoromethyl)benzonitrile | 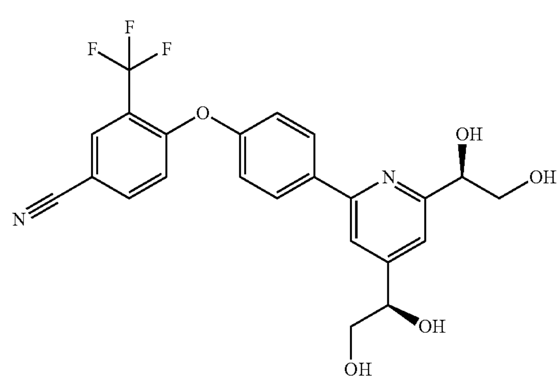 [SMILES: N#Cc1ccc(Oc2ccc(-c3cc([C@@H](O)CO)cc([C@@H](O)CO)n3)cc2)c(C(F)(F)F)c1] |

TABLE 2-continued

| Cpd Example No. | Chemical Name | Structure |
|---|---|---|
| 29 | 1-(6-(4-((3-(trifluoromethyl)pyridin-2-yl)oxy)phenyl)pyridin-2-yl)ethane-1,2-diol | 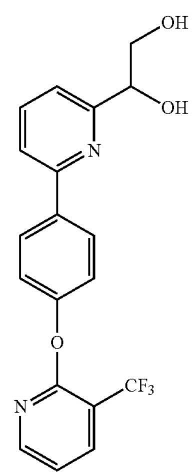 [SMILES: OCC(O)c1cccc(-c2ccc(Oc3ncccc3C(F)(F)F)cc2)n1] |
| 30 | (S)-4-(1,2-dihydroxyethyl)-6-(4-(4-(trifluoromethyl)phenoxy)phenyl)picolinamide | 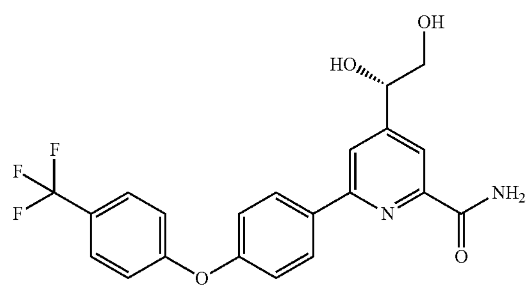 [SMILES: NC(=O)c1cc([C@H](O)CO)cc(-c2ccc(Oc3ccc(C(F)(F)F)cc3)cc2)n1] |
| 31 | (S)-6-(4-(4-cyano-3-(trifluoromethyl)phenoxy)phenyl)-4-(1,2-dihydroxyethyl)picolinamide | 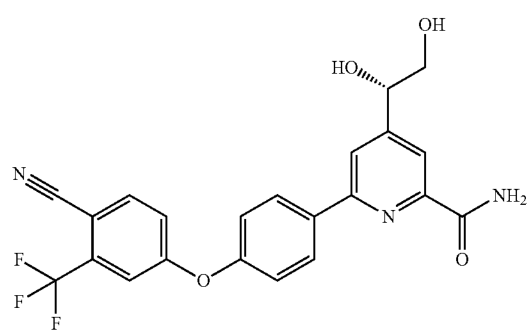 [SMILES: N#Cc1ccc(Oc2ccc(-c3cc([C@H](O)CO)cc(C(N)=O)n3)cc2)cc1C(F)(F)F] |
| 32 | (S)-6-(4-(4-carbamoyl-2-(trifluoromethyl)phenoxy)phenyl)-4-(1,2-dihydroxyethyl)picolinamide | 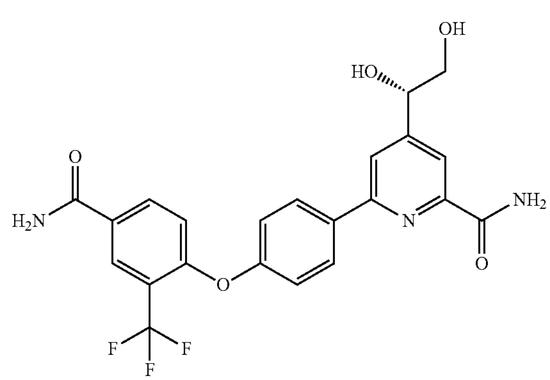 [SMILES: NC(=O)c1ccc(Oc2ccc(-c3cc([C@H](O)CO)cc(C(N)=O)n3)cc2)c(C(F)(F)F)c1] |

TABLE 2-continued

| Cpd Example No. | Chemical Name | Structure |
|---|---|---|
| 33 | (S)-6-(4-(3-cyano-4-(trifluoromethyl)phenoxy)phenyl)-4-(1,2-dihydroxyethyl)picolinamide | 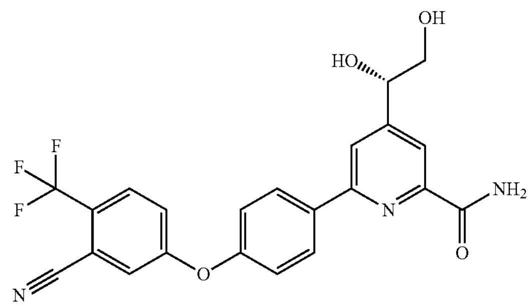 [SMILES: N#Cc1cc(Oc2ccc(-c3cc([C@H](O)CO)cc(C(N)=O)n3)cc2)ccc1C(F)(F)F] |
| 34 | (R)-6-(4-(3-cyano-4-(trifluoromethyl)phenoxy)phenyl)-4-(1,2-dihydroxyethyl)picolinamide | 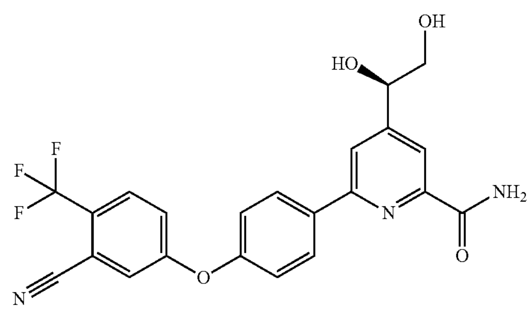 [SMILES: N#Cc1cc(Oc2ccc(-c3cc([C@@H](O)CO)cc(C(N)=O)n3)cc2)ccc1C(F)(F)F] |
| 35 | (S)-6-(4-(4-cyano-2-(trifluoromethyl)phenoxy)phenyl)-4-(1,2-dihydroxyethyl)picolinamide | 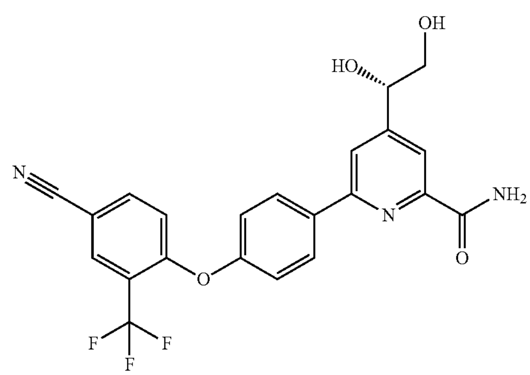 [SMILES: N#Cc1ccc(Oc2ccc(-c3cc([C@H](O)CO)cc(C(N)=O)n3)cc2)c(C(F)(F)F)c1] |
| 36 | (R)-6-(4-(4-cyano-2-(trifluoromethyl)phenoxy)phenyl)-4-(1,2-dihydroxyethyl)picolinamide | 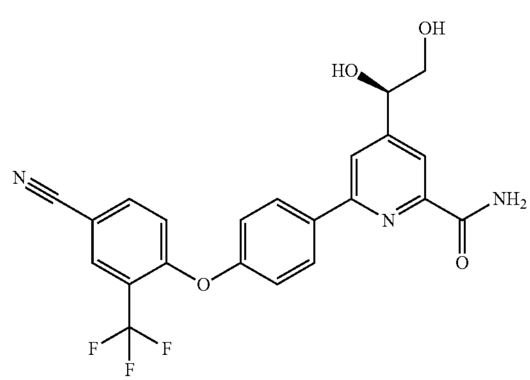 [SMILES: N#Cc1ccc(Oc2ccc(-c3cc([C@@H](O)CO)cc(C(N)=O)n3)cc2)c(C(F)(F)F)c1] |

TABLE 2-continued

| Cpd Example No. | Chemical Name | Structure |
|---|---|---|
| 37 | (S)-6-(4-(4-cyanophenoxy)phenyl)-4-(1,2-dihydroxyethyl)picolinamide | 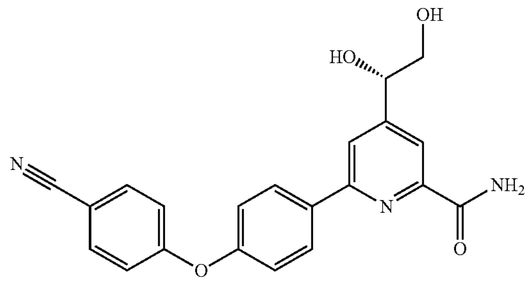 [SMILES: N#Cc1ccc(Oc2ccc(-c3cc([C@H](O)CO)cc(C(N)=O)n3)cc2)cc1] |
| 38 | (R)-6-(4-(4-cyanophenoxy)phenyl)-4-(1,2-dihydroxyethyl)picolinamide | 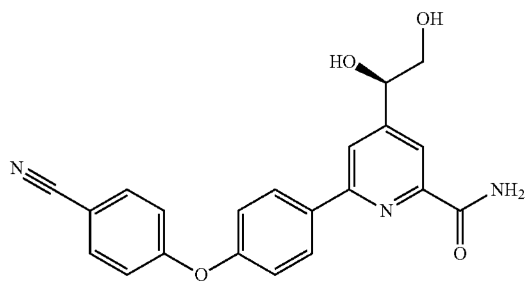 [SMILES: N#Cc1ccc(Oc2ccc(-c3cc([C@@H](O)CO)cc(C(N)=O)n3)cc2)cc1] |
| 39 | (S)-6-(4-(5-chloro-2-fluorophenoxy)phenyl)-4-(1,2-dihydroxyethyl)picolinamide | 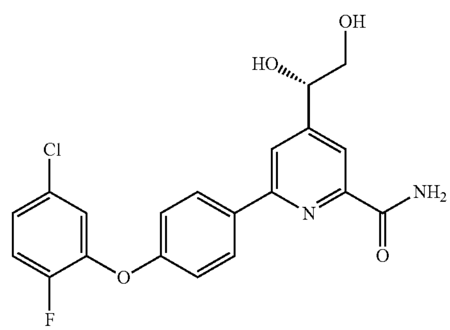 [SMILES: NC(=O)c1cc([C@H](O)CO)cc(-c2ccc(Oc3cc(Cl)ccc3F)cc2)n1] |
| 40 | (R)-4-(1,2-dihydroxyethyl)-6-(4-(4-fluorophenoxy)phenyl)picolinamide | 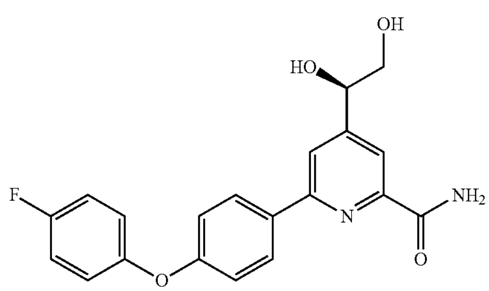 [SMILES: NC(=O)c1cc([C@@H](O)CO)cc(-c2ccc(Oc3ccc(F)cc3)cc2)n1] |
| 41 | (S)-4-(1,2-dihydroxyethyl)-6-(4-(4-fluorophenoxy)phenyl)picolinamide | 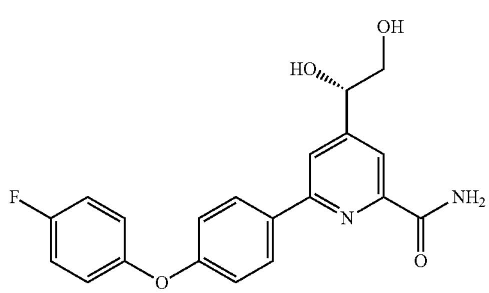 [SMILES: NC(=O)c1cc([C@H](O)CO)cc(-c2ccc(Oc3ccc(F)cc3)cc2)n1] |

TABLE 2-continued

| Cpd Example No. | Chemical Name | Structure |
|---|---|---|
| 42 | (S)-4-(1,2-dihydroxyethyl)-6-(4-(4-fluorophenoxy)phenyl)-N-(2-(piperidin-1-yl)ethyl)picolinamide | 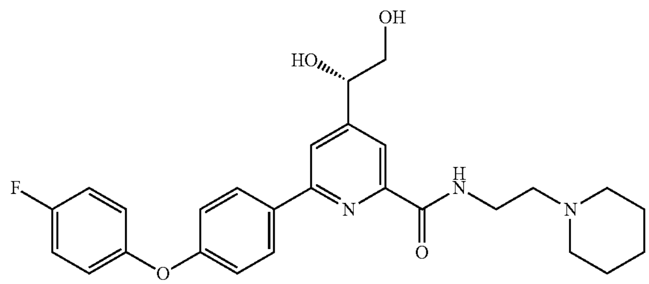 [SMILES: O=C(NCCN1CCCCC1)c1cc([C@H](O)CO)cc(-c2ccc(Oc3ccc(F)cc3)cc2)n1] |
| 43 | 6-(4-(4-fluorophenoxy)phenyl)-4-(methyl(phenyl)amino)picolinamide | 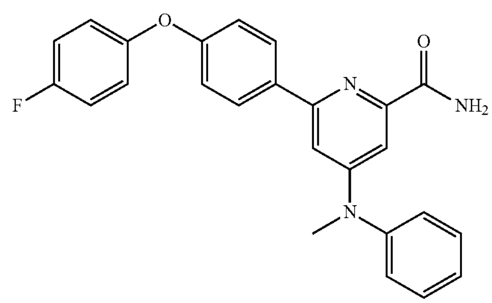 [SMILES: CN(c1ccccc1)c1cc(C(N)=O)nc(-c2ccc(Oc3ccc(F)cc3)cc2)c1] |
| 44 | 4-((2-cyanoethyl)(phenyl)amino)-6-(4-(4-fluorophenoxy)phenyl)picolinamide | 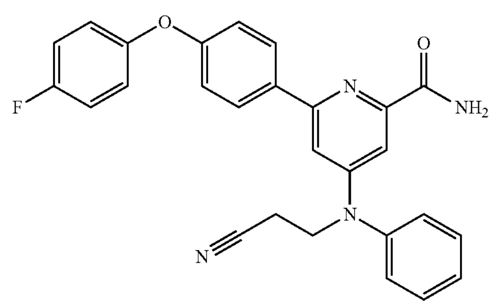 [SMILES: N#CCCN(c1ccccc1)c1cc(C(N)=O)nc(-c2ccc(Oc3ccc(F)cc3)cc2)c1] |
| 45 | 6-(4-(4-fluorophenoxy)phenyl)-4-((pyridin-3-ylmethyl)amino)picolinamide | 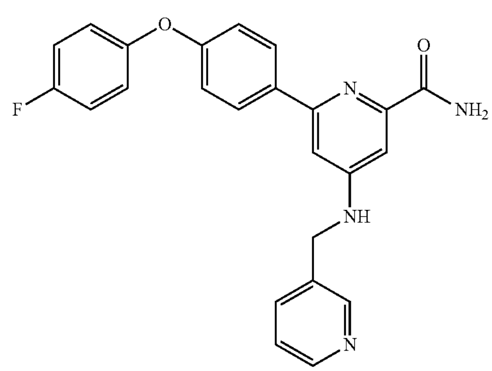 [SMILES: NC(=O)c1cc(NCc2cccnc2)cc(-c2ccc(Oc3ccc(F)cc3)cc2)n1] |

TABLE 2-continued
| Cpd Example No. | Chemical Name | Structure |
|---|---|---|
| 46 | 6-(4-(4-fluorophenoxy)phenyl)-4-((pyridin-4-ylmethyl)amino)picolinamide | 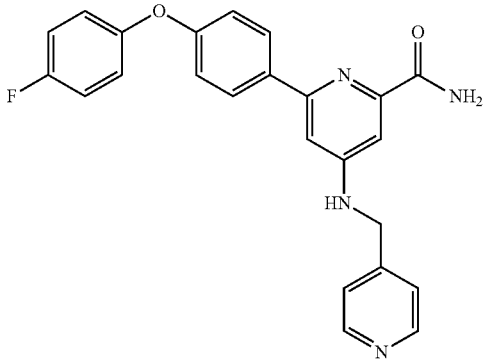 [SMILES: NC(=O)c1cc(NCc2ccncc2)cc(-c2ccc(Oc3ccc(F)cc3)cc2)n1] |
| 47 | 6-(4-(4-fluorophenoxy)phenyl)-4-((pyridin-2-ylmethyl)amino)picolinamide | 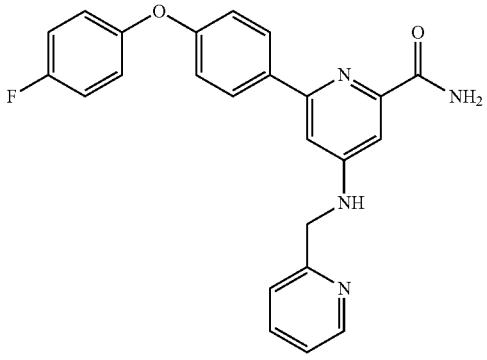 [SMILES: NC(=O)c1cc(NCc2ccccn2)cc(-c2ccc(Oc3ccc(F)cc3)cc2)n1] |
| 48 | 4-((2-(1,1-dioxidothiomorpholino)ethyl)amino)-6-(4-(4-fluorophenoxy)phenyl)picolinamide | 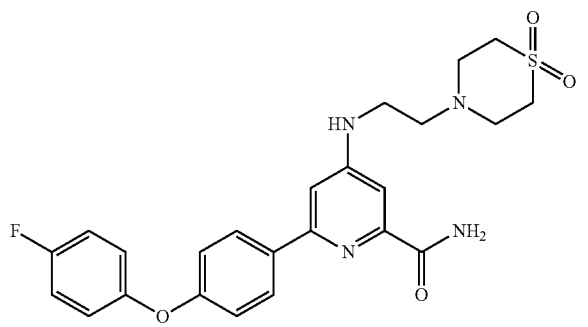 [SMILES: NC(=O)c1cc(NCCN2CCS(=O)(=O)CC2)cc(-c2ccc(Oc3ccc(F)cc3)cc2)n1] |
| 49 | 6-(4-(4-fluorophenoxy)phenyl)-4-((pyrimidin-2-ylmethyl)amino)picolinamide | 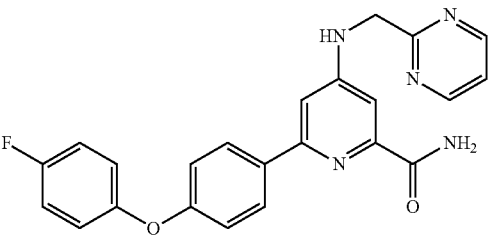 [SMILES: NC(=O)c1cc(NCc2ncccn2)cc(-c2ccc(Oc3ccc(F)cc3)cc2)n1] |

TABLE 2-continued

| Cpd Example No. | Chemical Name | Structure |
|---|---|---|
| 50 | 6-(4-(4-fluorophenoxy)phenyl)-4-(methylsulfonamidomethyl)picolinamide | 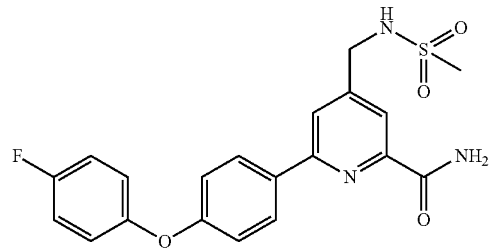 [SMILES: CS(=O)(=O)NCc1cc(C(N)=O)nc(-c2ccc(Oc3ccc(F)cc3)cc2)c1] |
| 51 | 6-(4-(4-fluorophenoxy)phenyl)-4-(piperazin-1-ylmethyl)picolinamide | 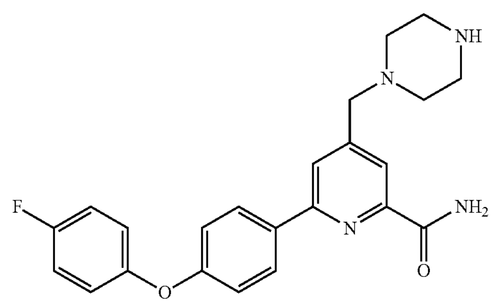 [SMILES: NC(=O)c1cc(CN2CCNCC2)cc(-c2ccc(Oc3ccc(F)cc3)cc2)n1] |
| 52 | 4-(((1-(2-amino-2-oxoethyl)piperidin-4-yl)methyl)amino)-6-(4-(4-fluorophenoxy)phenyl)picolinamide | 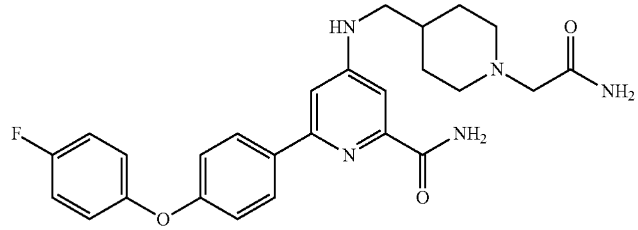 [SMILES: NC(=O)CN1CCC(CNc2cc(C(N)=O)nc(-c3ccc(Oc4ccc(F)cc4)cc3)c2)CC1] |
| 53 | 6-(4-(4-fluorophenoxy)phenyl)-4-((2-morpholinoethyl)amino)pidolnamide | 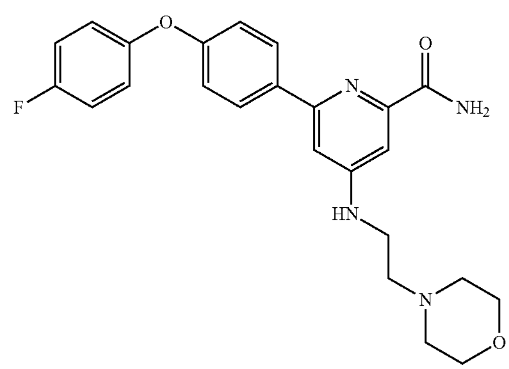 [SMILES: NC(=O)c1cc(NCCN2CCOCC2)cc(-c2ccc(Oc3ccc(F)cc3)cc2)n1] |
| 54 | 4-((3-(1H-imidazol-1-yl)propyl)amino)-6-(4-(4-fluorophenoxy)phenyl)picolinamide | 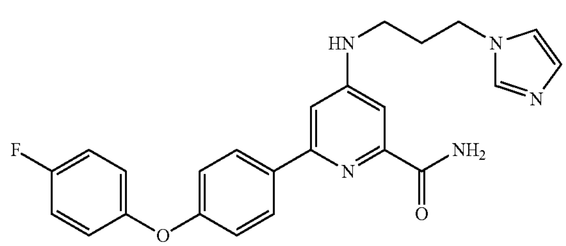 [SMILES: NC(=O)c1cc(NCCCn2ccnc2)cc(-c2ccc(Oc3ccc(F)cc3)cc2)n1] |

TABLE 2-continued

| Cpd Example No. | Chemical Name | Structure |
|---|---|---|
| 55 | 6-(4-(4-fluorophenoxy)phenyl)-4-(piperazin-1-yl)picolinamide | 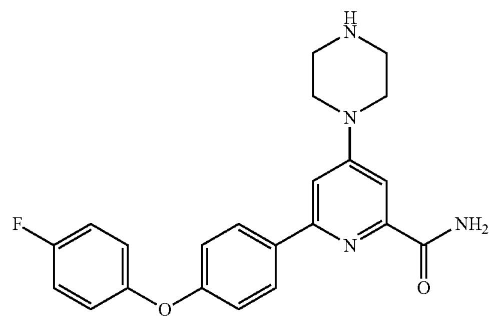 [SMILES: NC(=O)c1cc(N2CCNCC2)cc(-c2ccc(Oc3ccc(F)cc3)cc2)n1] |
| 56 | 4-(4-carbamoylpiperidin-1-yl)-6-(4-(4-fluorophenoxy)phenyl)picolinamide | 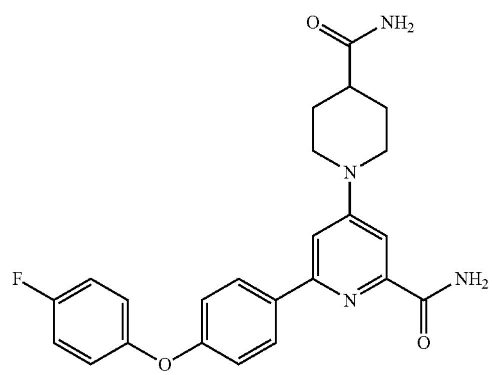 |
| 57 | 6-(4-(4-fluorophenoxy)phenyl)-4-((piperidin-4-ylmethyl)amino)picolinamide | 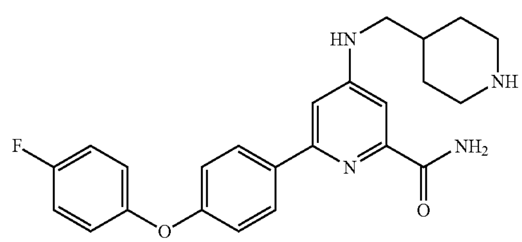 [SMILES: NC(=O)c1cc(NCC2CCNCC2)cc(-c2ccc(Oc3ccc(F)cc3)cc2)n1] |
| 58 | 6-(4-(4-fluorophenoxy)phenyl)-4-((2-(2-oxoimidazolidin-1-yl)ethyl)amino)picolinamide | 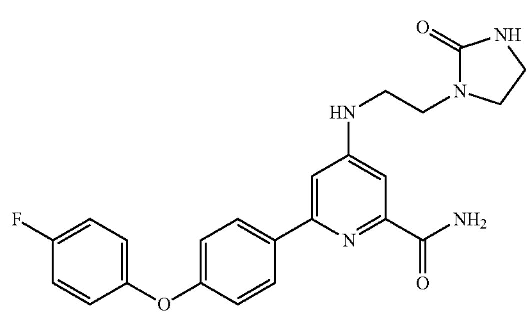 [SMILES: NC(=O)c1cc(NCCN2CCNC2=O)cc(-c2ccc(Oc3ccc(F)cc3)cc2)n1] |

TABLE 2-continued

| Cpd Example No. | Chemical Name | Structure |
|---|---|---|
| 59 | 1-(2-carbamoyl-6-(4-(4-fluorophenoxy)phenyl)pyridin-4-yl)piperidine-4-carboxylic acid | 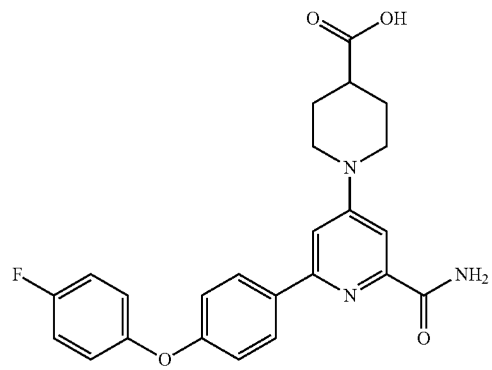 [SMILES: NC(=O)c1cc(N2CCC(C(=O)O)CC2)cc(-c2ccc(Oc3ccc(F)cc3)cc2)n1] |
| 60 | 6-(4-(4-fluorophenoxy)phenyl)-4-(((2-(2-oxoimidazolidin-1-yl)ethyl)amino)methyl)picolinamide | 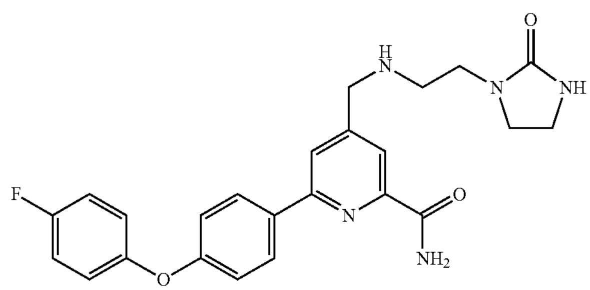 [SMILES: NC(=O)c1cc(CNCCN2CCNC2=O)cc(-c2ccc(Oc3ccc(F)cc3)cc2)n1] |
| 61 | 1-(2-(((6-(4-(4-(trifluoromethyl)phenoxy)phenyl)pyridin-2-yl)methyl)amino)ethyl)imidazolidin-2-one | 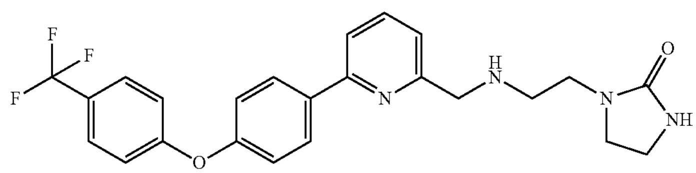 [SMILES: O=C1NCCN1CCNCc1cccc(-c2ccc(Oc3ccc(C(F)(F)F)cc3)cc2)n1] |
| 62 | 1-(2-(((6-(4-(4-fluorophenoxy)phenyl)pyridin-2-yl)methyl)amino)ethyl)imidazolidin-2-one | 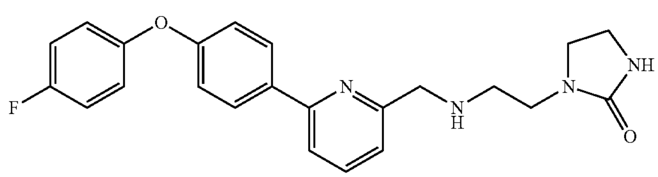 [SMILES: O=C1NCCN1CCNCc1cccc(-c2ccc(Oc3ccc(F)cc3)cc2)n1] |
| 63 | 2-(4-(6-(((2-(2-oxoimidazolidin-1-yl)ethyl)amino)methyl)pyridin-2-yl)phenoxy)-5-(trifluoromethyl)benzonitrile | 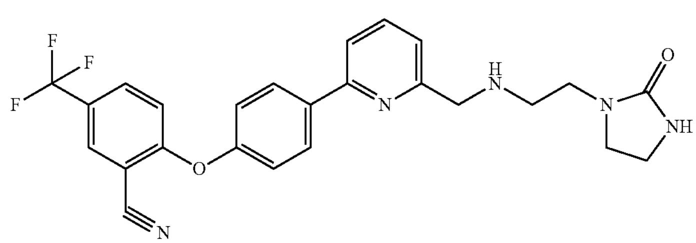 [SMILES: N#Cc1cc(C(F)(F)F)ccc1Oc1ccc(-c2cccc(CNCCN3CCNC3=O)n2)cc1] |
| 64 | 1-(2-((2-(6-(4-(4-fluorophenoxy)phenyl)pyridin-2-yl)ethyl)amino)ethyl)imidazolidin-2-one | 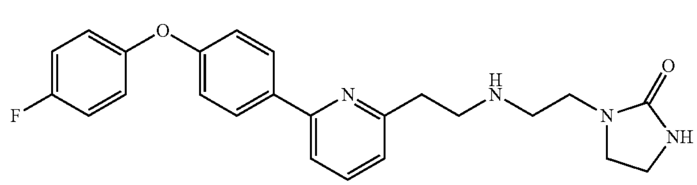 [SMILES: O=C1NCCN1CCNCCc1cccc(-c2ccc(Oc3ccc(F)cc3)cc2)n1] |

TABLE 2-continued

| Cpd Example No. | Chemical Name | Structure |
|---|---|---|
| 65 | 4-(4-(6-(((2-(2-oxoimidazolidin-1-yl)ethyl)amino)methyl)pyridin-2-yl)phenoxy)-3-(trifluoromethyl)benzonitrile | 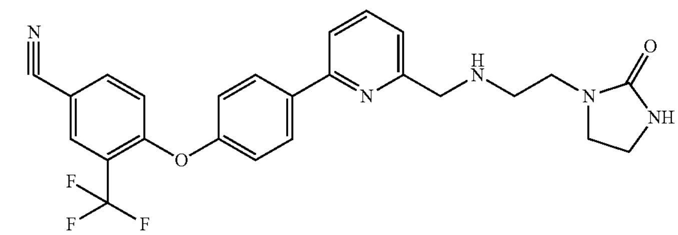 [SMILES: N#Cc1ccc(Oc2ccc(-c3cccc(CNCCN4CCNC4=O)n3)cc2)c(C(F)(F)F)c1] |
| 66 | 1-(2-(((6-(4-((3-chloro-5-(trifluoromethyl)pyridin-2-yl)oxy)phenyl)pyridin-2-yl)methyl)amino)ethyl)imidazolidin-2-one | 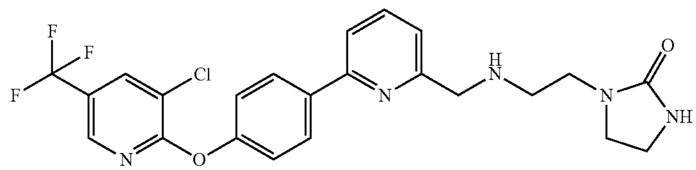 [SMILES: O=C1NCCN1CCNCc1cccc(-c2ccc(Oc3ncc(C(F)(F)F)cc3Cl)cc2)n1] |
| 67 | 4-(4-(6-(((2-(2-oxoimidazolidin-1-yl)ethyl)amino)methyl)pyridin-2-yl)phenoxy)benzonitrile | 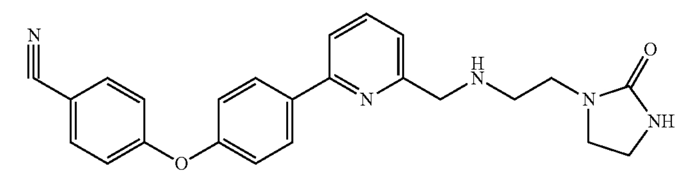 [SMILES: N#Cc1ccc(Oc2ccc(-c3cccc(CNCCN4CCNC4=O)n3)cc2)cc1] |
| 68 | 1-(2-(((6-(4-((5-(trifluoromethyl)pyridin-2-yl)oxy)phenyl)pyridin-2-yl)methyl)amino)ethyl)imidazolidin-2-one | 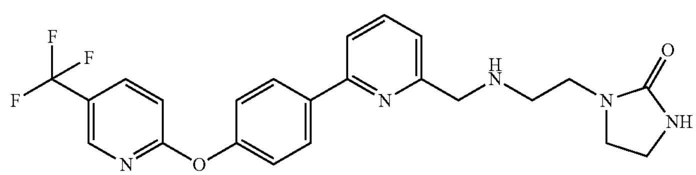 [SMILES: O=C1NCCN1CCNCc1cccc(-c2ccc(Oc3ccc(C(F)(F)F)cn3)cc2)n1] |
| 69 | 2-(((6-(4-(4-fluorophenoxy)phenyl)pyridin-2-yl)methyl)(2-(2-oxoimidazolidin-1-yl)ethyl)amino)acetonitrile | 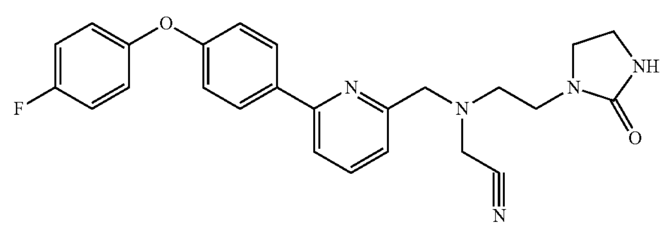 [SMILES: N#CCN(CCN1CCNC1=O)Cc1cccc(-c2ccc(Oc3ccc(F)cc3)cc2)n1] |
| 70 | 5-(4-(5-(((2-(2-oxoimidazolidin-1-yl)ethyl)amino)methyl)pyridin-2-yl)phenoxy)-2-(trifluoromethyl)benzonitrile | 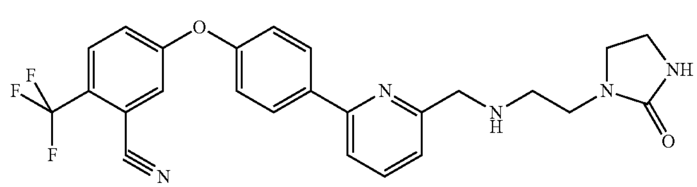 [SMILES: N#Cc1cc(Oc2ccc(-c3cccc(CNCCN4CCNC4=O)n3)cc2)ccc1C(F)(F)F] |
| 71 | 1-(2-(((6-(4-(4-(methylsulfonyl)phenoxy)phenyl)pyridin-2-yl)methyl)amino)ethyl)imidazolidin-2-one | 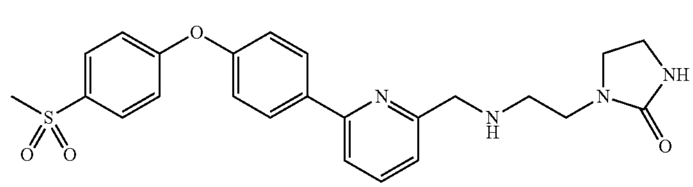 [SMILES: CS(=O)(=O)c1ccc(Oc2ccc(-c3cccc(CNCCN4CCNC4=O)n3)cc2)cc1] |

TABLE 2-continued

| Cpd Example No. | Chemical Name | Structure |
|---|---|---|
| 72 | 2-(((6-(4-(4-fluorophenoxy)phenyl)pyridin-2-yl)methyl)(2-(2-oxoimidazolidin-1-yl)ethyl)amino)acetamide | 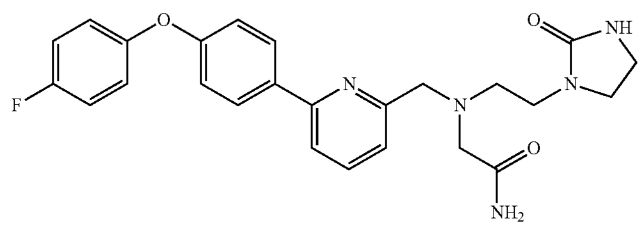 [SMILES: NC(=O)CN(CCN1CCNC1=O)Cc1cccc(-c2ccc(Oc3ccc(F)cc3)cc2)n1] |
| 73 | 4-(2-carbamoyl-6-(4-(4-fluorophenoxy)phenyl)pyridin-4-yl)-N-isopropylpiperazine-1-carboxamide | 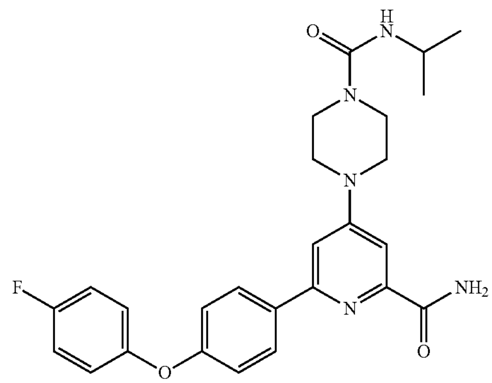 [SMILES: CC(C)NC(=O)N1CCN(c2cc(C(N)=O)nc(-c3ccc(Oc4ccc(F)cc4)cc3)c2)CC1] |
| 74 | 6-(4-(4-fluorophenoxy)phenyl)-4-(4-(pyrimidin-2-yl)piperazin-1-yl)picolinamide | 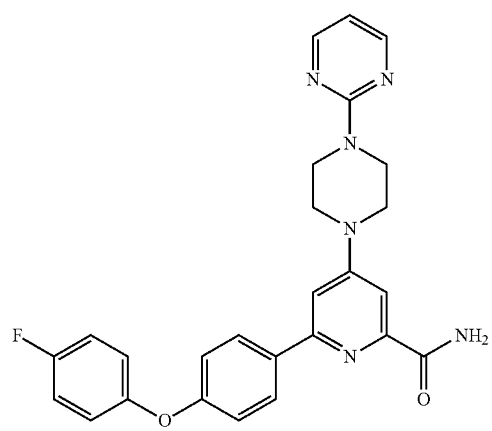 [SMILES: NC(=O)c1cc(N2CCN(c3ncccn3)CC2)cc(-c2ccc(Oc3ccc(F)cc3)cc2)n1] |
| 75 | 4-(4-(2-amino-2-oxoethyl)piperazin-1-yl)-6-(4-(4-fluorophenoxy)phenyl)picolinamide | 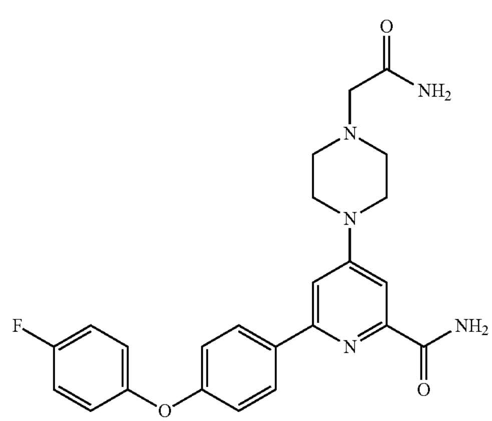 [SMILES: NC(=O)CN1CCN(c2cc(C(N)=O)nc(-c3ccc(Oc4ccc(F)cc4)cc3)c2)CC1] |

TABLE 2-continued

| Cpd Example No. | Chemical Name | Structure |
|---|---|---|
| 76 | 4-(2-carbamoyl-6-(4-(4-fluorophenoxy)phenyl)pyridin-4-yl)piperazine-1-carboxamide | 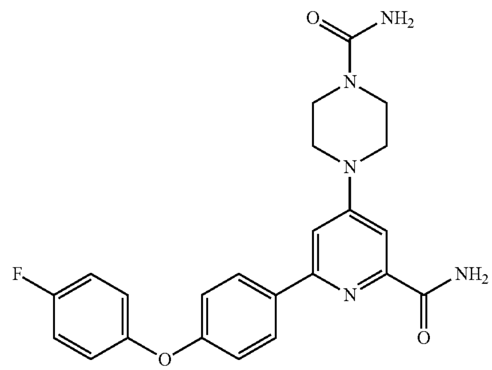 [SMILES: NC(=O)c1cc(N2CCN(C(N)=O)CC2)cc(-c2ccc(Oc3ccc(F)cc3)cc2)n1] |
| 77 | 6-(4-(4-fluorophenoxy)phenyl)-4-(4-(1,4,5,6-tetrahydropyrimidin-2-yl)piperazin-1-yl)picolinamide | 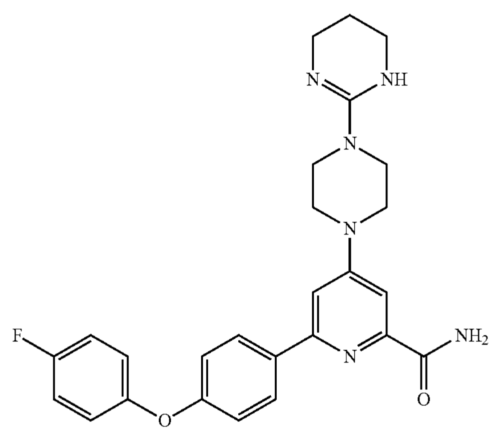 [SMILES: NC(=O)c1cc(N2CCN(C3=NCCCN3)CC2)cc(-c2ccc(Oc3ccc(F)cc3)cc2)n1] |
| 78 | (6-(4-(4-fluorophenoxy)phenyl)-4-(piperazin-1-yl)pyridin-2-yl)(piperazin-1-yl)methanone | 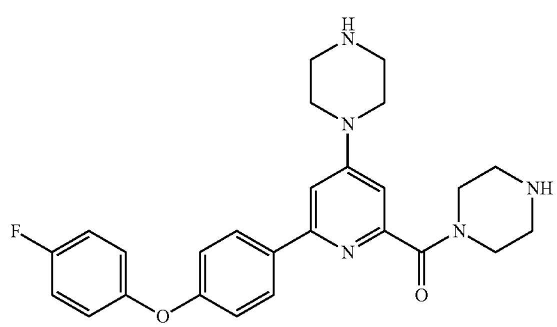 [SMILES: O=C(c1cc(N2CCNCC2)cc(-c2ccc(Oc3ccc(F)cc3)cc2)n1)N1CCNCC1] |
| 79 | 6-(4-(4-fluorophenoxy)phenyl)-4-(hydroxymethyl)-N-(2-(piperidin-1-yl)ethyl)picolinamide | 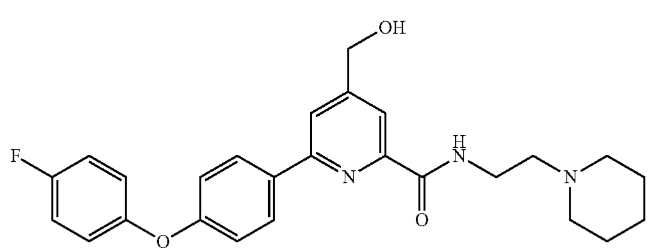 [SMILES: O=C(NCCN1CCCCC1)c1cc(CO)cc(-c2ccc(Oc3ccc(F)cc3)cc2)n1] |

TABLE 2-continued
| Cpd Example No. | Chemical Name | Structure |
|---|---|---|
| 80 | 4-(4-carbamimidoyl piperazin-1-yl)-6-(4-(4-fluorophenoxy) phenyl)picolinamide | 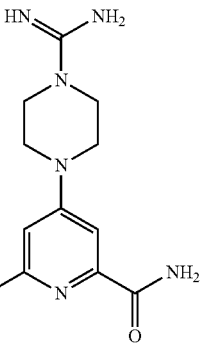 |
| 81 | 6-(4-(4-fluorophenoxy)phenyl)-N2-(2-(piperidin-1-yl) ethyl)pyridin-2,4-dicarboxamide | 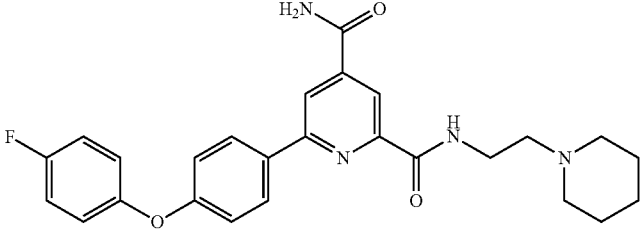 [SMILES: NC(=O)c1cc(C(=O)NCCN2CCCCC2)nc(-c2ccc(Oc3ccc(F)cc3)cc2)c1] |
| 82 | 4-(2-cyano-6-(4-(4-fluorophenoxy)phenyl) pyridin-4-yl)-N-isopropylpiperazine-1-carboxamide | 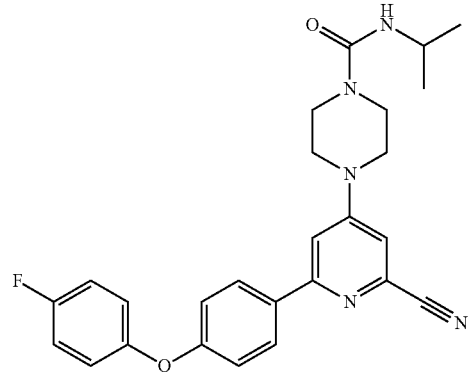 [SMILES: CC(C)NC(=O)N1CCN(c2cc(C#N)nc(-c3ccc(Oc4ccc(F)cc4)cc3)c2)CC1] |
| 83 | 4-(2-cyano-6-(4-(4-fluorophenoxy)phenyl) pyridin-4-yl) piperazine-1-carboximidamide | 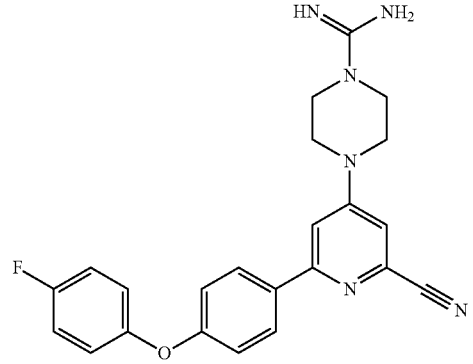 [SMILES: N#Cc1cc(N2CCN(C(=N)N)CC2)cc(-c2ccc(Oc3ccc(F)cc3)cc2)n1] |

TABLE 2-continued

| Cpd Example No. | Chemical Name | Structure |
|---|---|---|
| 84 | 6-(4-(4-fluorophenoxy)phenyl)-4-(3-phenylureido)picolinamide | 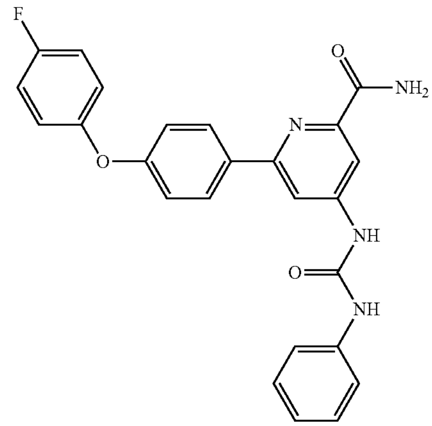 [SMILES: NC(=O)c1cc(NC(=O)Nc2ccccc2)cc(-c2ccc(Oc3ccc(F)cc3)cc2)n1] |
| 85 | 2-(4-(4-fluorophenoxy)phenyl)-6-((2-(piperidin-1-yl)ethyl)carbamoyl)isonicotinic acid | 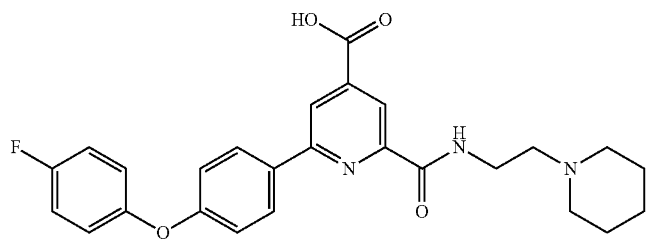 [SMILES: O=C(O)c1cc(C(=O)NCCN2CCCCC2)nc(-c2ccc(Oc3ccc(F)cc3)cc2)c1] |
| 86 | 6-(4-(4-fluorophenoxy)phenyl)-N-(2-(piperidin-1-yl)ethyl)-4-(1H-tetrazol-5-yl)picolinamide | 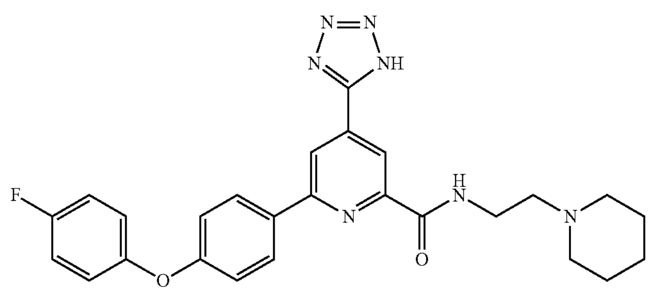 [SMILES: O=C(NCCN1CCCCC1)c1cc(-c2nnn[nH]2)cc(-c2ccc(Oc3ccc(F)cc3)cc2)n1] |
| 87 | 2-(3-(2-carbamoyl-6-(4-(4-fluorophenoxy)phenyl)pyridin-4-yl)ureido)acetic acid | 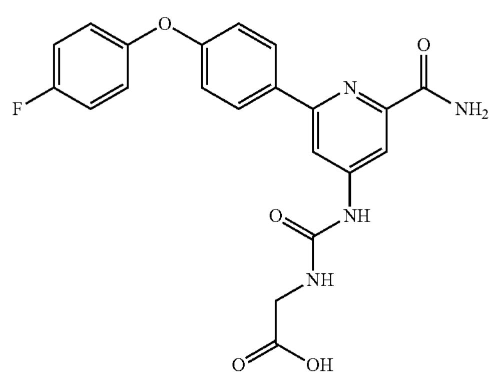 [SMILES: NC(=O)c1cc(NC(=O)NCC(=O)O)cc(-c2ccc(Oc3ccc(F)cc3)cc2)n1] |
| 88 | (S)-2-({6-[4-(4-Fluorophenoxy)-phenyl]-pyridin-2-yl-methyl}-amino)propionamide | 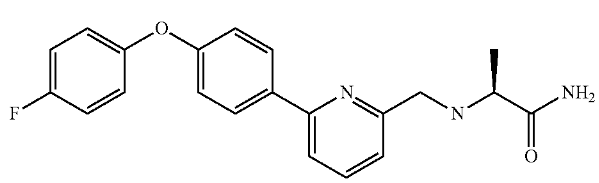 [SMILES: C[C@H](NCc1cccc(-c2ccc(Oc3ccc(F)cc3)cc2)n1)C(N)=O] |

TABLE 2-continued

| Cpd Example No. | Chemical Name | Structure |
|---|---|---|
| 89 | (R)-2-(1,2-dihydroxyethyl)-6-(4-(4-fluorophenoxy)phenyl)isonicotinamide | 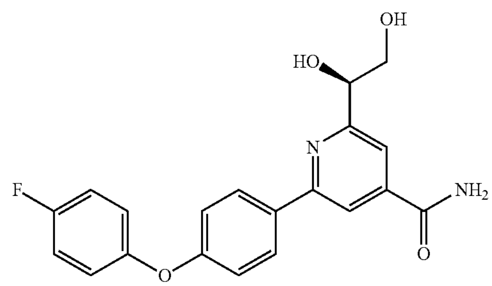 |
| 90 | (S)-6-(4-(3-cyano-4-(trifluoromethyl)phenoxy)phenyl)-N-(2,3-dihydroxypropyl)picolinamide | 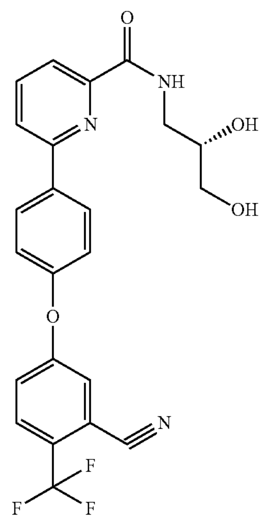 [SMILES: N#Cc1cc(Oc2ccc(-c3cccc(C(=O)NC[C@H](O)CO)n3)cc2)ccc1C(F)(F)F] |
| 91 | 4-((2-carbamoyl-6-(4-(4-fluorophenoxy)phenyl)pyridin-4-yl)(methyl)amino)benzoic acid | 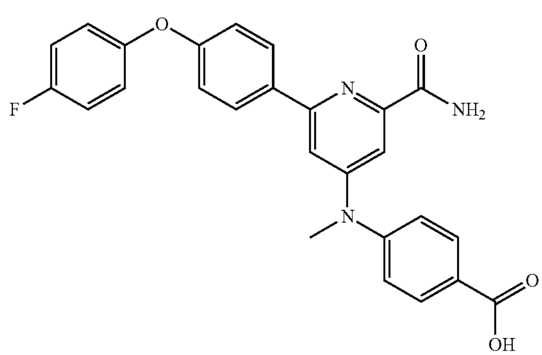 [SMILES: CN(c1ccc(C(=O)O)cc1)c1cc(C(N)=O)nc(-c2ccc(Oc3ccc(F)cc3)cc2)c1] |
| 92 | 4-((carboxymethyl)(phenyl)amino)-6-(4-(4-fluorophenoxy)phenyl)picolinic acid | 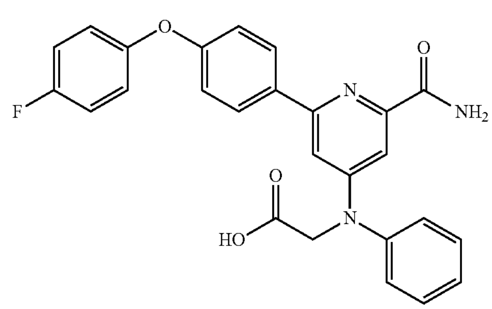 [SMILES: NC(=O)c1cc(N(CC(=O)O)c2ccccc2)cc(-c2ccc(Oc3ccc(F)cc3)cc2)n1] |

TABLE 2-continued

| Cpd Example No. | Chemical Name | Structure |
|---|---|---|
| 93 | 1-(2-carboxy-6-(4-(4-fluorophenoxy)phenyl)pyridin-4-yl)-1H-indole-3-carboxylic acid | 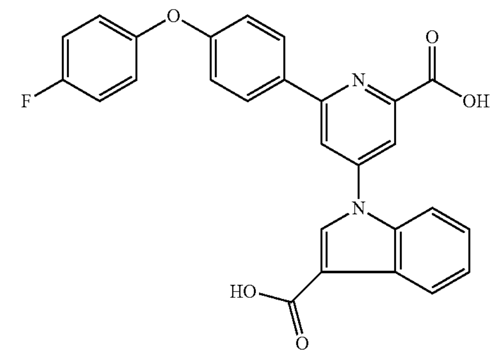 [SMILES: O=C(O)c1cc(-n2cc(C(=O)O)c3ccccc32)cc(-c2ccc(Oc3ccc(F)cc3)cc2)n1] |
| 94 | 6-((2-cyanoethyl)(phenyl)amino)-4-(4-(4-fluorophenoxy)phenyl)picolinic acid | 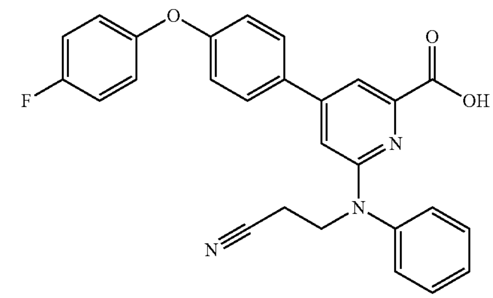 [SMILES: N#CCCN(c1ccccc1)c1cc(-c2ccc(Oc3ccc(F)cc3)cc2)cc(C(=O)O)n1] |
| 95 | (S)-6-(1,2-dihydroxyethyl)-4-(4-(4-fluorophenoxy)phenyl)picolinamide | 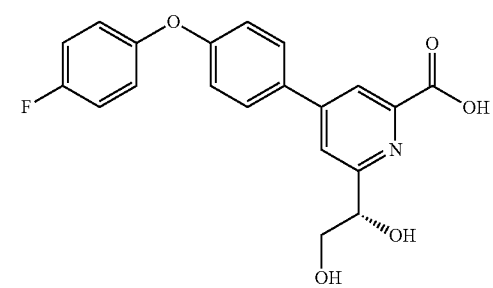 [SMILES: O=C(O)c1cc(-c2ccc(Oc3ccc(F)cc3)cc2)cc([C@H](O)CO)n1] |
| 96 | (R)-6-(1,2-dihydroxyethyl)-4-(4-(4-fluorophenoxy)phenyl)picolinamide | 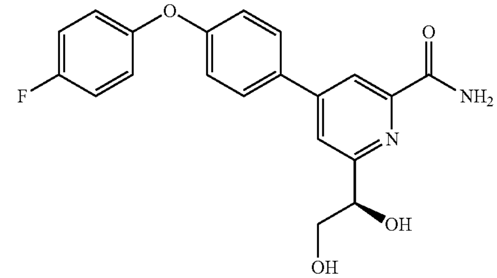 [SMILES: NC(=O)c1cc(-c2ccc(Oc3ccc(F)cc3)cc2)cc([C@@H](O)CO)n1] |
| 97 | (S)-2-(1,2-dihydroxyethyl)-6-(4-(4-fluorophenoxy)phenyl)isonicotinamide | 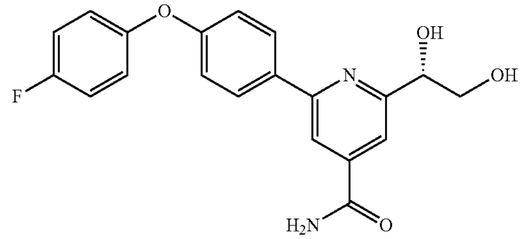 [SMILES: NC(=O)c1cc(-c2ccc(Oc3ccc(F)cc3)cc2)nc([C@H](O)CO)c1] |

TABLE 2-continued

| Cpd Example No. | Chemical Name | Structure |
|---|---|---|
| 98 | 6-((2-amino-2-oxoethyl)(phenyl)amino)-4-(4-(4-fluorophenoxy)phenyl)picolinamide | 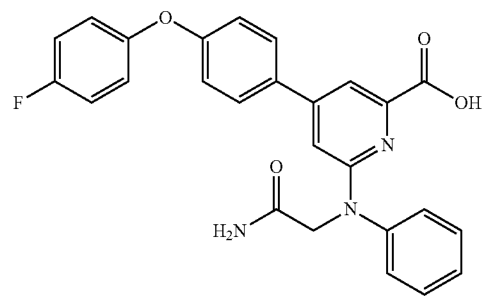 [SMILES: NC(=O)CN(c1ccccc1)c1cc(-c2ccc(Oc3ccc(F)cc3)cc2)cc(C(=O)O)n1] |
| 99 | 4-(4-cyano-1H-indol-1-yl)-6-(4-(4-fluorophenoxy)phenyl)picolinamide | 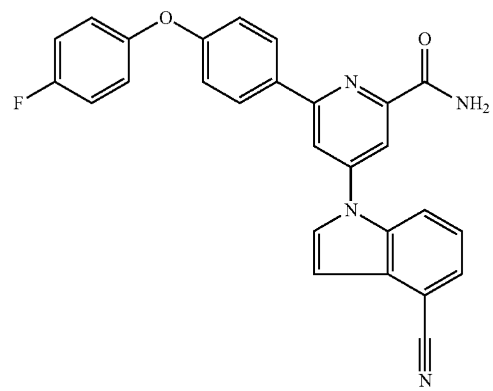 [SMILES: N#Cc1cccc2c1ccn2-c1cc(C(N)=O)nc(-c2ccc(Oc3ccc(F)cc3)cc2)c1] |
| 100 | 6-(4-cyano-1H-indol-1-yl)-4-(4-(4-fluorophenoxy)phenyl)picolinamide | 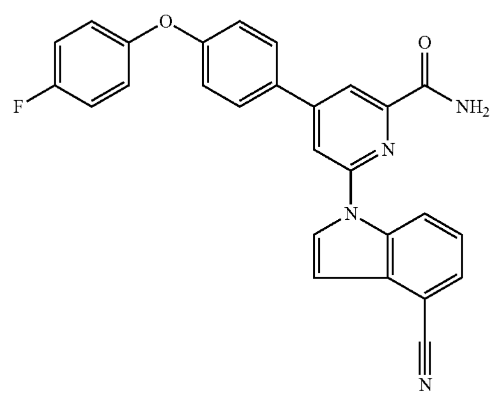 [SMILES: N#Cc1cccc2c1ccn2-c1cc(-c2ccc(Oc3ccc(F)cc3)cc2)cc(C(N)=O)n1] |
| 101 | 4-(4-cyano-1H-indol-1-yl)-6-(4-(4-fluorophenoxy)phenyl)picolinic acid | 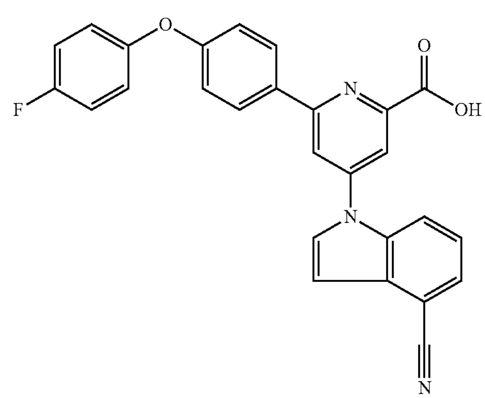 [SMILES: N#Cc1cccc2c1ccn2-c1cc(C(=O)O)nc(-c2ccc(Oc3ccc(F)cc3)cc2)c1] |

TABLE 2-continued

| Cpd Example No. | Chemical Name | Structure |
|---|---|---|
| 102 | 4-((2-amino-2-oxoethyl)(phenyl)amino)-6-(4-(4-fluorophenoxy)phenyl)picolinamide | 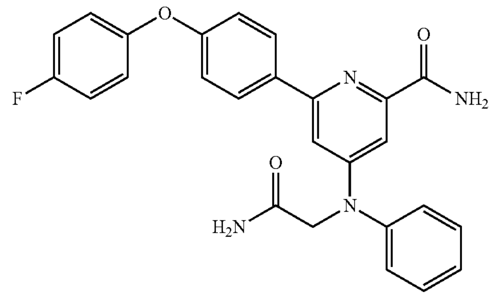 [SMILES: NC(=O)CN(c1ccccc1)c1cc(C(N)=O)nc(-c2ccc(Oc3ccc(F)cc3)cc2)c1] |
| 103 | (R)-4-(1,2-dihydroxyethyl)-6-(4-(4-(trifluoromethyl)phenoxy)phenyl)picolinamide | 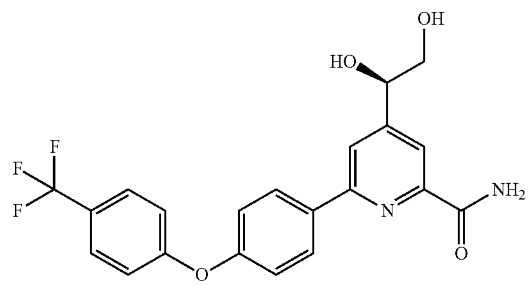 [SMILES: NC(=O)c1cc([C@@H](O)CO)cc(-c2ccc(Oc3ccc(C(F)(F)F)cc3)cc2)n1] |
| 104 | 2-(4-((2-carbamoyl-6-(4-(4-fluorophenoxy)phenyl)pyridine-4-yl)methyl)piperazin-1-yl)acetic acid | 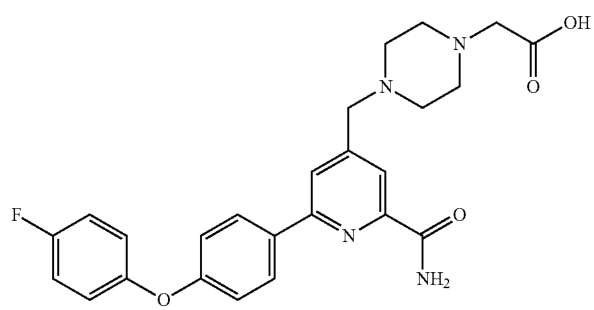 [SMILES: NC(=O)c1cc(CN2CCN(CC(=O)O)CC2)cc(-c2ccc(Oc3ccc(F)cc3)cc2)n1] |
| 105 | 1-(2-(((2-(4-(4-fluorophenoxy)phenyl)pyridin-4-yl)methyl)amino)ethyl)imidazolidin-2-one | 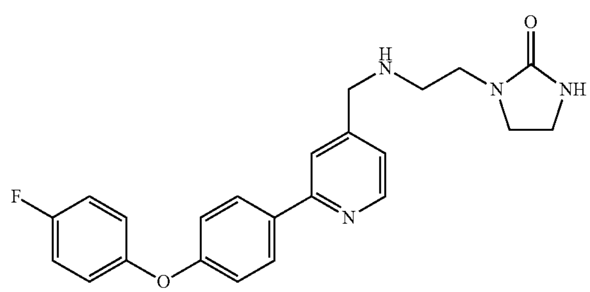 [SMILES: O=C1NCCN1CCNCc1ccnc(-c2ccc(Oc3ccc(F)cc3)cc2)c1] |
| 106 | 6-(4-(4-fluorophenoxy)phenyl)-4-(((2-(2-oxoimidazolidin-1-yl)ethyl)amino)methyl)picolinonitrile | 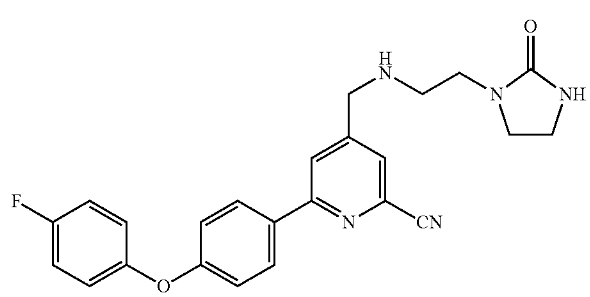 [SMILES: N#Cc1cc(CNCCN2CCNC2=O)cc(-c2ccc(Oc3ccc(F)cc3)cc2)n1] |

TABLE 2-continued

| Cpd Example No. | Chemical Name | Structure |
|---|---|---|
| 107 | 2-(4-(4-fluorophenoxy)phenyl)-6-methyl-N-(2-(piperidin-1-yl)ethyl)isonicotinamide | 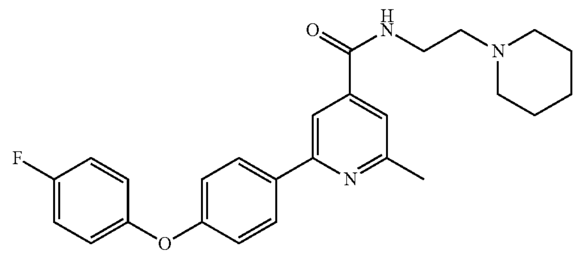 [SMILES: Cc1cc(C(=O)NCCN2CCCCC2)cc(-c2ccc(Oc3ccc(F)cc3)cc2)n1] |
| 108 | 2-(5-(2-(4-(4-fluorophenoxy)phenyl)-6-methylpyridin-4-yl)-2H-tetrazol-2-yl)acetamide | 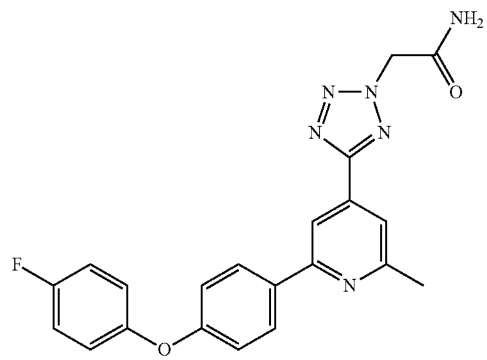 [SMILES: Cc1cc(-c2nnn(CC(N)=O)n2)cc(-c2ccc(Oc3ccc(F)cc3)cc2)n1] |
| 109 | 2-(4-(2-chloro-6-(4-(4-fluorophenoxy)phenyl)pyridine-4-yl)piperazin-1-yl)acetamide | 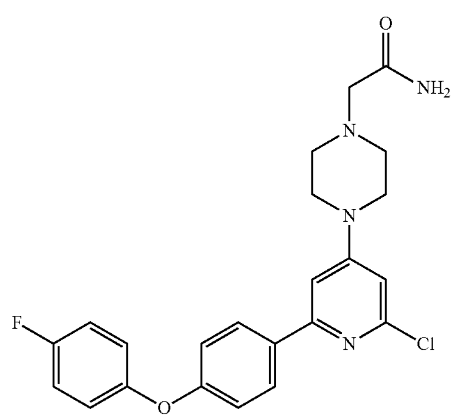 [SMILES: NC(=O)CN1CCN(c2cc(Cl)nc(-c3ccc(Oc4ccc(F)cc4)cc3)c2)CC1] |
| 110 | 4-((3-(1H-imidazol-1-yl)propyl)amino)-6-(4-(4-fluorophenoxy)phenylpicolinonitrile | 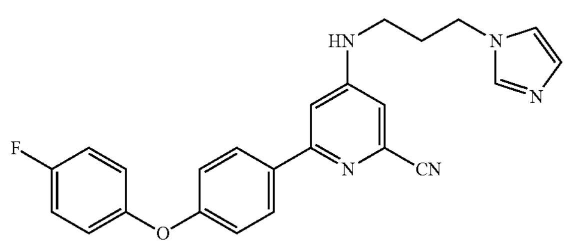 [SMILES: N#Cc1cc(NCCCn2ccnc2)cc(-c2ccc(Oc3ccc(F)cc3)cc2)n1] |

TABLE 2-continued

| Cpd Example No. | Chemical Name | Structure |
|---|---|---|
| 111 | (R)-1-(6-(4-(4-fluorophenoxy)phenyl)-4-((2-morpholinoethyl)amino)pyridine-2-yl)ethan-1,2-diol | 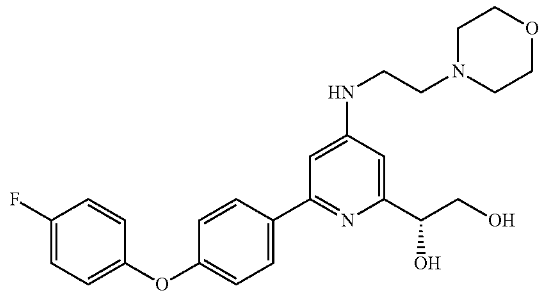 [SMILES: OC[C@H](O)c1cc(NCCN2CCOCC2)cc(-c2ccc(Oc3ccc(F)cc3)cc2)n1] |
| 112 | (S)-4-(1,2-dihydroxyethyl)-6-(4-(4-fluorophenoxy)phenyl)picolinonitrile | 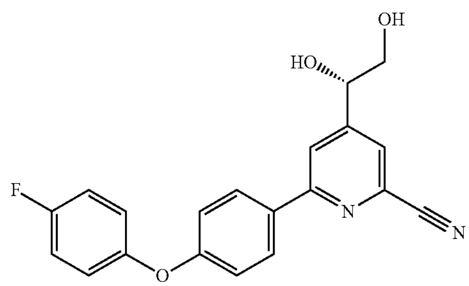 [SMILES: N#Cc1cc([C@H](O)CO)cc(-c2ccc(Oc3ccc(F)cc3)cc2)n1] |
| 113 | 4-(4-(4-fluorophenoxy)phenyl)-6-(methyl(phenyl)amino)picolinamide | 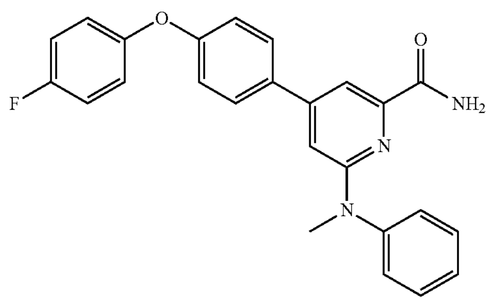 [SMILES: CN(c1ccccc1)c1cc(-c2ccc(Oc3ccc(F)cc3)cc2)cc(C(N)=O)n1] |
| 114 | 6-(4-(4-fluorophenoxy)phenyl)-4-(methyl(phenyl)amino)picolinic acid | 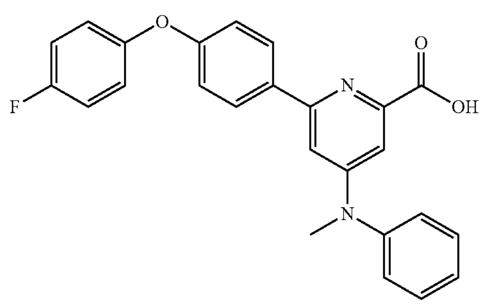 [SMILES: CN(c1ccccc1)c1cc(C(=O)O)nc(-c2ccc(Oc3ccc(F)cc3)cc2)c1] |
| 115 | 6-((2-cyanoethyl)(phenyl)amino)-4-(4-(4-fluorophenoxy)phenyl)picolinamide | 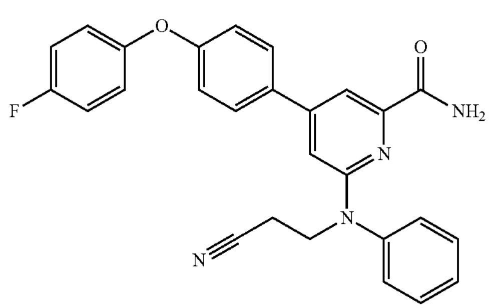 [SMILES: N#CCCN(c1ccccc1)c1cc(-c2ccc(Oc3ccc(F)cc3)cc2)cc(C(N)=O)n1] |

TABLE 2-continued

| Cpd Example No. | Chemical Name | Structure |
|---|---|---|
| 116 | 4-((6-carbamoyl-4-(4-(4-fluorophenoxy)phenyl)pyridin-2-yl)(methyl)amino)benzoic acid | 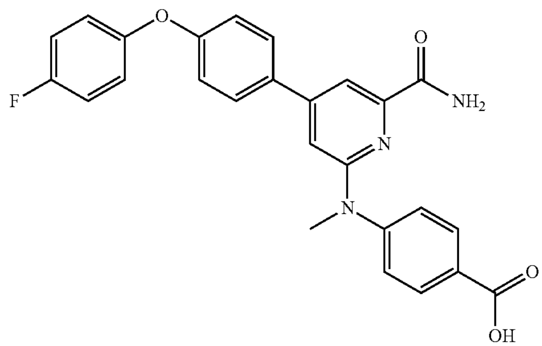 [SMILES: CN(c1ccc(C(=O)O)cc1)c1cc(-c2ccc(Oc3ccc(F)cc3)cc2)cc(C(N)=O)n1] |
| 117 | 4-((4-carboxyphenyl)(methy)amino)-6-(4-(4-fluorophenoxy)phenyl)picolinic acid | 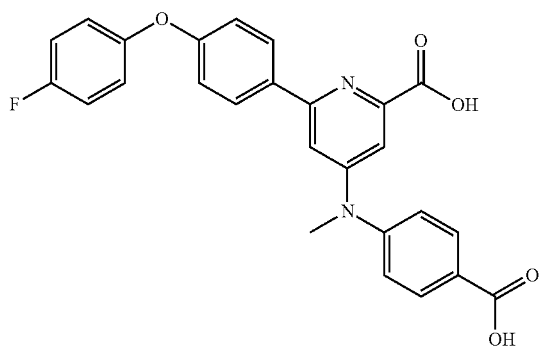 [SMILES: CN(c1ccc(C(=O)O)cc1)c1cc(C(=O)O)nc(-c2ccc(Oc3ccc(F)cc3)cc2)c1] |
| 118 | 4-((2-cyanoethyl)(phenyl)amino)-6-(4-(4fluorophenoxy)phenyl)picolinic acid | 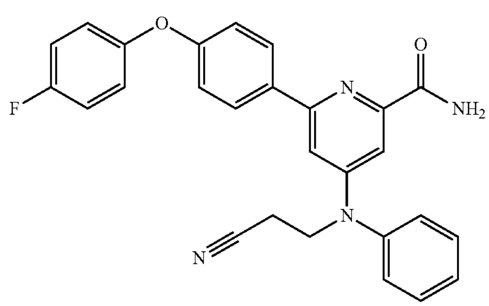 [SMILES: N#CCCN(c1ccccc1)c1cc(C(N)=O)nc(-c2ccc(Oc3ccc(F)cc3)cc2)c1] |
| 119 | 4-(4-(4-fluorophenoxy)phenyl)-6-(methyl(phenyl)amino)picolinic acid | 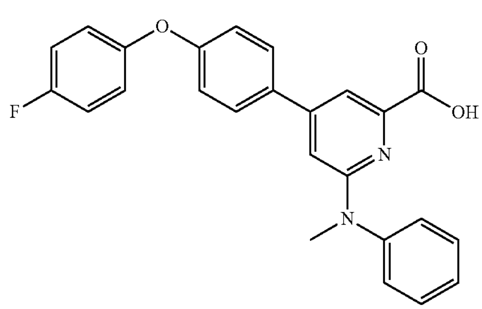 [SMILES: CN(c1ccccc1)c1cc(-c2ccc(Oc3ccc(F)cc3)cc2)cc(C(=O)O)n1] |

TABLE 2-continued

| Cpd Example No. | Chemical Name | Structure |
|---|---|---|
| 120 | 6-((4-carboxyphenyl)(methy)amino)-4-(4-(4-fluorophenoxy)phenyl)picolinic acid | 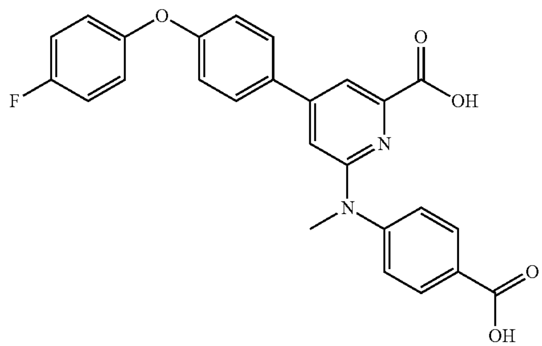 [SMILES: CN(c1ccc(C(=O)O)cc1)c1cc(-c2ccc(Oc3ccc(F)cc3)cc2)cc(C(=O)O)n1] |
| 121 | 6-((carboxymethyl)(phenyl)amino)-4-(4-(4-fluorophenoxy)phenyl)picolinic acid | 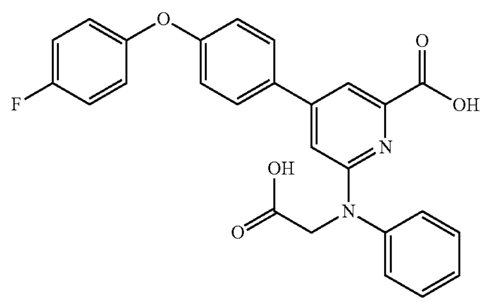 [SMILES: O=C(O)CN(c1ccccc1)c1cc(-c2ccc(Oc3ccc(F)cc3)cc2)cc(C(=O)O)n1] |
| 122 | 6-(4-(4-fluorophenoxy)phenyl)-1',2',3',6'-tetrahydro-[4,4'-bipyridine]-2-carboxamide | 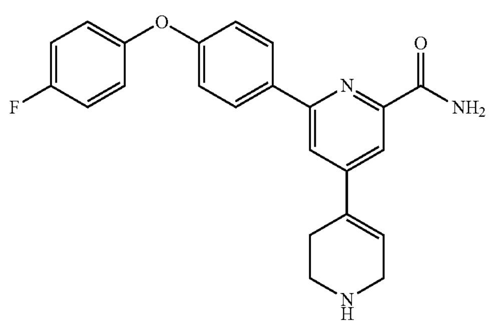 [SMILES: NC(=O)c1cc(C2=CCNCC2)cc(-c2ccc(Oc3ccc(F)cc3)cc2)n1] |
| 123 | (R)-6-(4-(5-chloro-2-fluorophenoxy)phenyl)-4-(1,2-dihydroxyethyl)picolinamide | 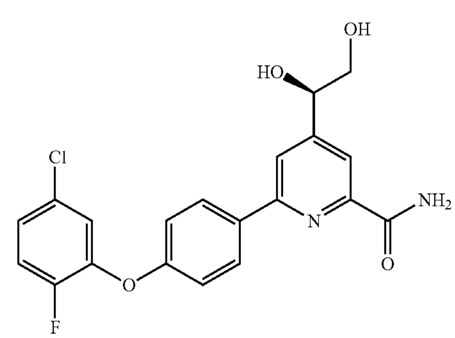 [SMILES: NC(=O)c1cc([C@@H](O)CO)cc(-c2ccc(Oc3cc(Cl)ccc3F)cc2)n1] |

TABLE 2-continued

| Cpd Example No. | Chemical Name | Structure |
|---|---|---|
| 124 | (S)-4-(6-(1,2-dihydroxyethyl)pyridin-2-yl)-N-(4-fluorophenyl)benzenesulfonamide | 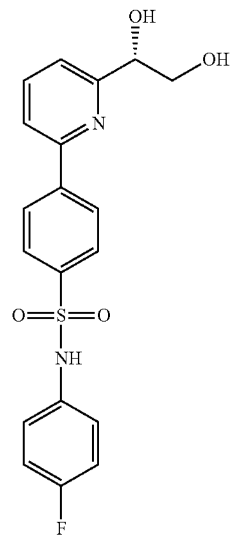 [SMILES: O=S(=O)(Nc1ccc(F)cc1)c1ccc(-c2cccc([C@H](O)CO)n2)cc1] |
| 125 | 6-chloro-N-(1,3-dihydroxypropan-2-yl)-4-(4-(4-fluorophenoxy)phenyl)picolinamide | 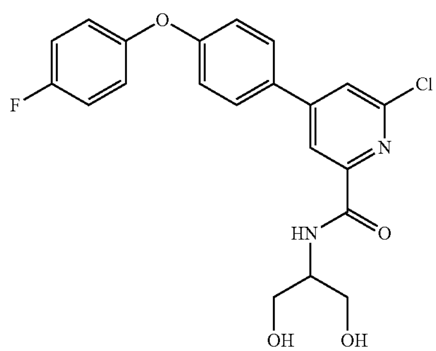 [SMILES: O=C(NC(CO)CO)c1cc(-c2ccc(Oc3ccc(F)cc3)cc2)cc(Cl)n1] |
| 126 | 6-(4-cyano-1H-indol-1-yl)-4-(4-(4-fluorophenoxy)phenyl)picolinic acid | 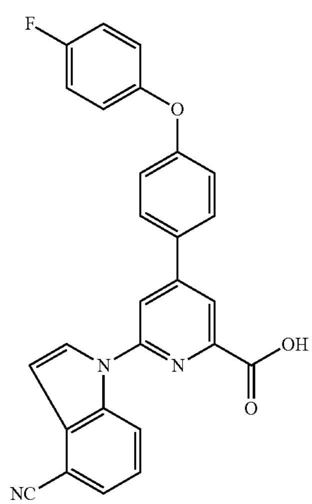 [SMILES: N#Cc1cccc2c1ccn2-c1cc(-c2ccc(Oc3ccc(F)cc3)cc2)cc(C(=O)O)n1] |

TABLE 2-continued

| Cpd Example No. | Chemical Name | Structure |
|---|---|---|
| 127 | (R)-6-(4-(4-cyano-3-(trifluoromethyl)phenoxy)phenyl)-4-(1,2-dihydroxyethyl)picolinamide | 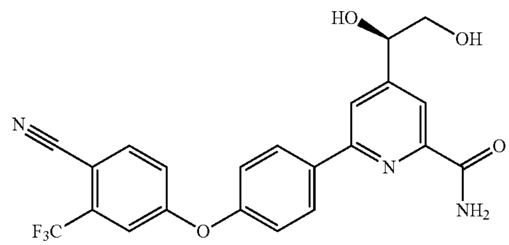 [SMILES: N#Cc1ccc(Oc2ccc(-c3cc([C@@H](O)CO)cc(C(N)=O)n3)cc2)cc1C(F)(F)F] |
| 128 | 6-((1,3-dihydroxypropan-2-yl)amino)-4-(4-(4-fluorophenoxy)phenyl)picolinamide | 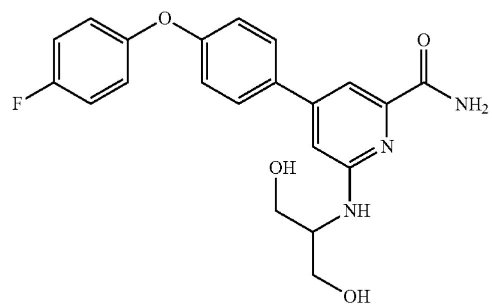 [SMILES: NC(=O)c1cc(-c2ccc(Oc3ccc(F)cc3)cc2)cc(NC(CO)CO)n1] |
| 129 | 4-((1S,2S)-1,2-dihydroxypropyl)-6-(4-(4-fluorophenoxy)phenyl)picolinamide | 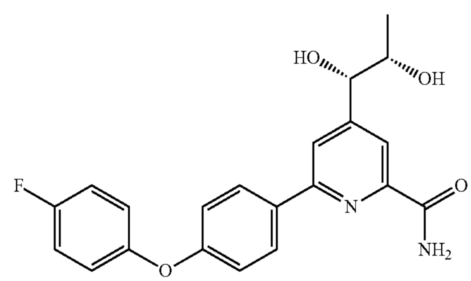 [SMILES: C[C@H](O)[C@@H](O)c1cc(C(N)=O)nc(-c2ccc(Oc3ccc(F)cc3)cc2)c1] |
| 130 | 1-(2-carboxy-6-(4-(4-fluorophenoxy)phenyl)pyridin-4-yl)-1H-indole-6-carboxylic acid | 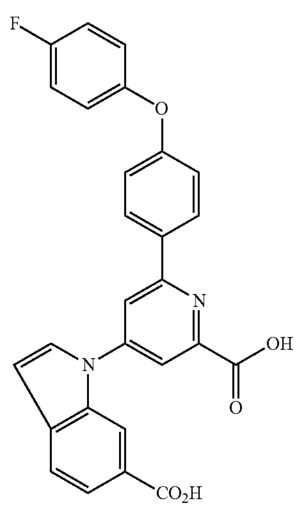 [SMILES: O=C(O)c1ccc2ccn(-c3cc(C(=O)O)nc(-c4ccc(Oc5ccc(F)cc5)cc4)c3)c2c1] |

TABLE 2-continued

| Cpd Example No. | Chemical Name |
|---|---|
| 131 | 4-((1R,2)-1,2-dihydroxypropyl)-6-(4-(4-fluorophenoxy)phenyl)picolinamide |
| 132 | (R)-4-(1,2-dihydroxyethyl)-6-(4-((5-(trifluoromethyl)pyridin-2-yl)oxy)phenyl)picolinamide |
| 133 | 4-((1,3-dihydroxypropan-2-yl)amino)-6-(4-(4-fluorophenoxy)phenyl)picolinamide |
| 134 | (R)-4-(2,3-dihydroxypropyl)-6-(4-(4-fluorophenoxy)phenyl)picolinamide |
| 135 | (S)-4-(2,3-dihydroxypropyl)-6-(4-(4-fluorophenoxy)phenyl)picolinamide |

TABLE 2-continued

| Cpd Example No. | Chemical Name | Structure |
|---|---|---|
| 136 | 6-(4-(4-fluorophenoxy)phenyl)-4-hydroxy picolinamide | 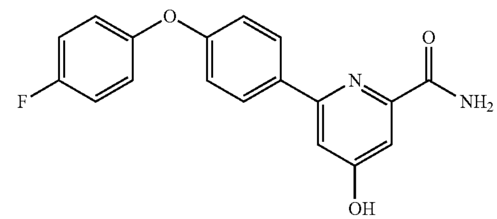 [SMILES: NC(=O)c1cc(O)cc(-c2ccc(Oc3ccc(F)cc3)cc2)n1] |
| 137 | (S)-N-(4-(6-(1,2-dihydroxyethyl)pyridin-2-yl)phenyl)-4-fluorobenzene sulfonamide | 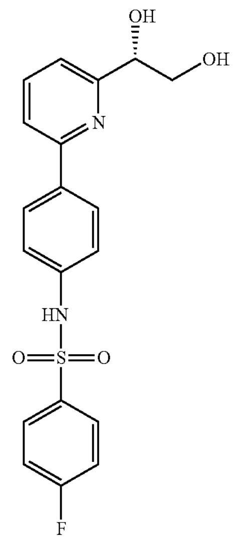 [SMILES: O=S(=O)(Nc1ccc(-c2cccc([C@H](O)CO)n2)cc1)c1ccc(F)cc1] |
| 138 | (R)-4-(1,2-dihydroxyethyl)-6-(4-(4-fluorophenoxy)phenyl)picolinonitrile | 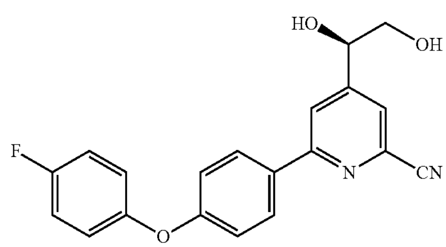 [SMILES: N#Cc1cc([C@@H](O)CO)cc(-c2ccc(Oc3ccc(F)cc3)cc2)n1] |
| 139 | (S)-4-(1,2-dihydroxyethyl)-6-(5-(trifluoromethyl)pyridin-2-yl)oxy)phenyl)picolinamide | 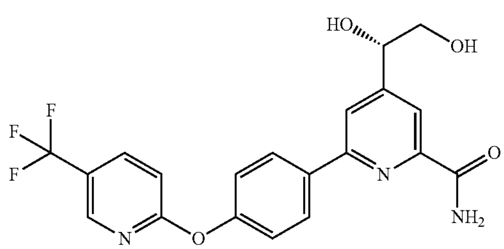 [SMILES: NC(=O)c1cc([C@H](O)CO)cc(-c2ccc(Oc3ccc(C(F)(F)F)cn3)cc2)n1] |
| 140 | (S)-6-(4-(4-chloro-2-fluorophenoxy)phenyl)-4-(1,2-dihydroxyethyl)picolinamide | 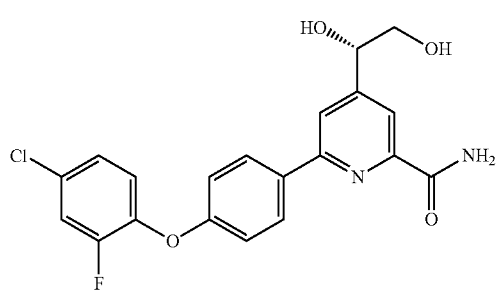 |

TABLE 2-continued
| Cpd Example No. | Chemical Name | Structure |
|---|---|---|
| 141 | (R)-6-(4-(4-chloro-2-fluorophenoxy)phenyl)-4-(1,2-dihydroxyethyl)picolinamide | 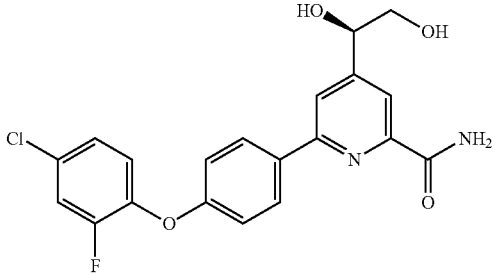 |
| 142 | 4-((R)-1,2-dihydroxyethyl)-6-[3-(4-fluoro-phenoxy)-phenyl]-pyridine-2-carboxylic acid amide | 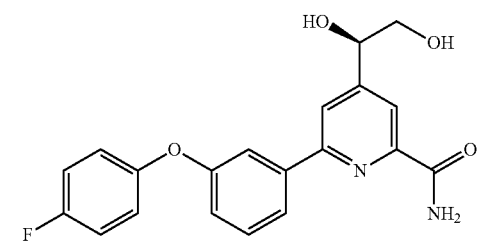 [SMILES: NC(=O)c1cc([C@@H](O)CO)cc(-c2cccc(Oc3ccc(F)cc3)c2)n1] |
| 143 | ({6-Carbamoyl-4-[4-(4-fluoro-phenoxy)-phenyl]-pyridin-2-yl}phenyl-amino)-acetic acid | 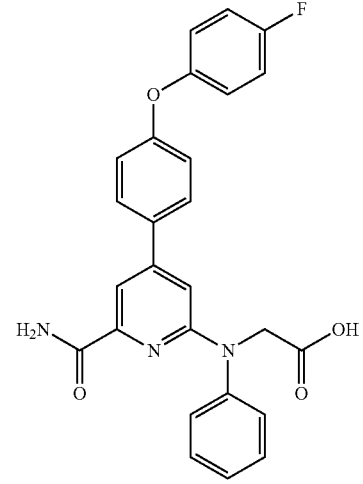 [SMILES: NC(=O)c1cc(-c2ccc(Oc3ccc(F)cc3)cc2)cc(N(CC(=O)O)c2ccccc2)n1] |
| 144 | 3-({6-Carbamoyl-4-[4-(4-fluoro-phenoxy)-phenyl]-pyridin-2-yl}phenyl-amino)-propionic acid | 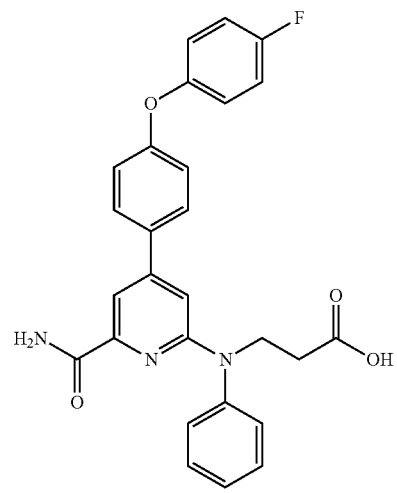 |

TABLE 2-continued

| Cpd Example No. | Chemical Name | Structure |
|---|---|---|
| 145 | 3-({2-Carbamoyl-6-[4-(4-fluoro-phenoxy)-phenyl]-pyridin-4-yl}phenyl-amino)-propionic acid | 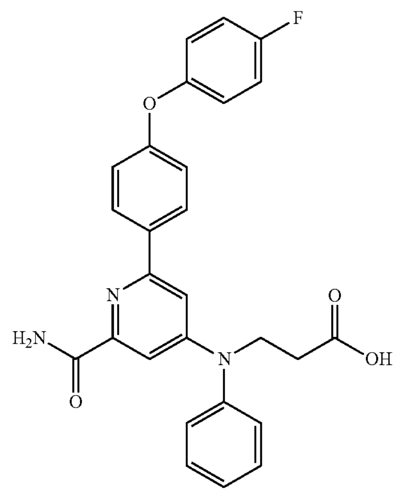 |
| 146 | 4-[4-(4-Cyano-phenoxy)-phenyl]-6-(methyl-phenyl-amino)-pyridine2-carboxylic acid amide | 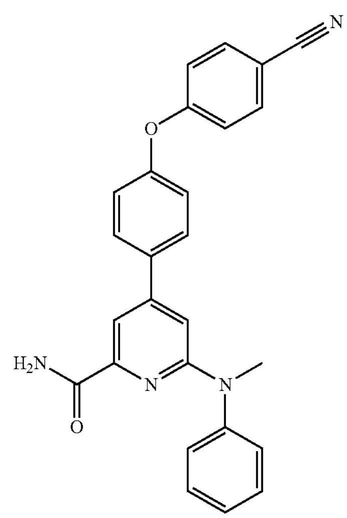 |
| 147 | 6-[4-(4-Cyano-phenoxy)-phenyl]-4-(methyl-phenyl-amino)-pyridine-2-carboxylic acid amide | 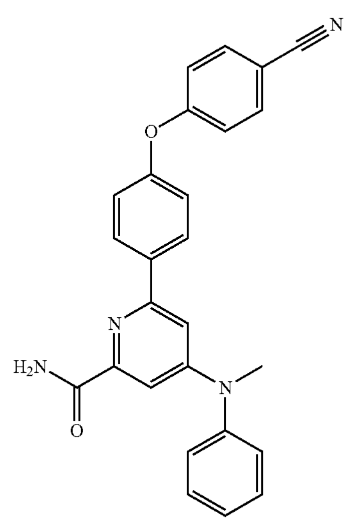 |

TABLE 2-continued

| Cpd Example No. | Chemical Name | Structure |
|---|---|---|
| 148 | 6-(Methyl-phenyl-amino)-4-[4-(4-trifluoromethyl-phenoxy)phenyl]-pyridine-2-carboxylic acid amide | 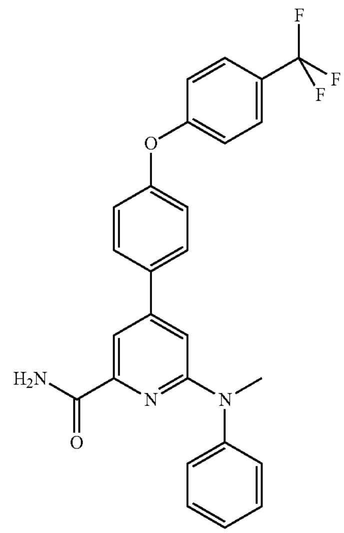 [SMILES: CN(c1ccccc1)c1cc(-c2ccc(Oc3ccc(C(F)(F)F)cc3)cc2)cc(C(N)=O)n1] |
| 149 | 4-(Methyl-phenyl-amino)-6-[4-(4-trifluoromethyl-phenoxy)phenyl]-pyridine-2-carboxylic acid amide | 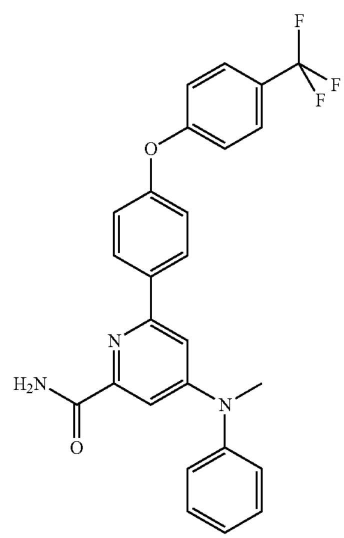 [SMILES: CN(c1ccccc1)c1cc(C(N)=O)nc(-c2ccc(Oc3ccc(C(F)(F)F)cc3)cc2)c1] |
| 150 | 6-[4-(4-Fluoro-phenoxy)-phenyl]-4-{phenyl-[2-(2H-tetrazol-5-yl)-ethyl]-amino}-pyridine-2-carboxylic acid amide | 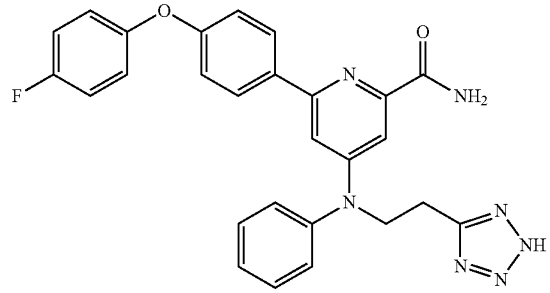 [SMILES: NC(=O)c1cc(N(CCc2nn[nH]n2)c2ccccc2)cc(-c2ccc(Oc3ccc(F)cc3)cc2)n1] |

TABLE 2-continued

| Cpd Example No. | Chemical Name | Structure |
|---|---|---|
| 151 | 4-[4-(4-Fluoro-phenoxy)-phenyl]-6-{phenyl-[2-(2H-tetrazol-5-yl)-ethyl]-amino}-pyridine-2-carboxylic acid amide | 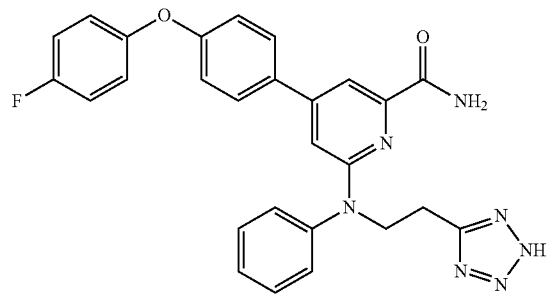 [SMILES: NC(=O)c1cc(-c2ccc(Oc3ccc(F)cc3)cc2)cc(N(CCc2nn[nH]n2)c2ccccc2)n1] |
| 152 | 6-[4-(4-Fluoro-phenoxy)-phenyl]-4-{phenyl-[2-(2H-tetrazol-5-yl)ethyl]-amino}-pyridine-2-carboxylic acid | 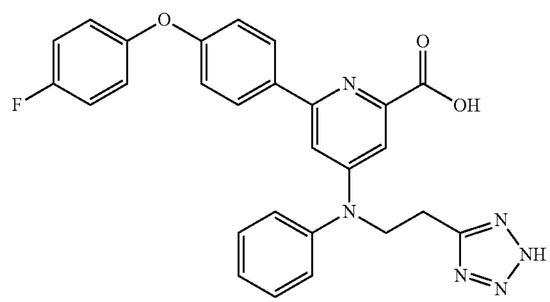 [SMILES: O=C(O)c1cc(N(CCc2nn[nH]n2)c2ccccc2)cc(-c2ccc(Oc3ccc(F)cc3)cc2)n1] |
| 153 | 4-[4-(4-Fluoro-phenoxy)-phenyl]-6-{phenyl-[2-(2H-tetrazol-5-yl)ethyl]-amino}-pyridine-2-carboxylic acid | 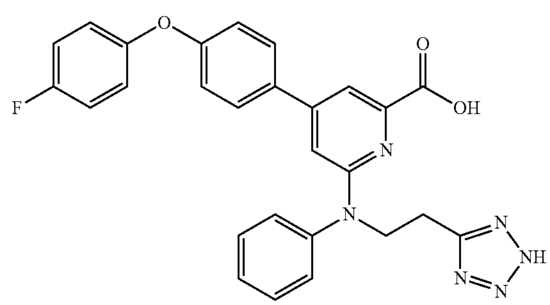 |
| 154 | 4-((S)-1,2-Dihydroxy-ethyl)-6-(4'-fluoro-biphenyl-4-yl)pyridin-2-carboxylic acid amide | 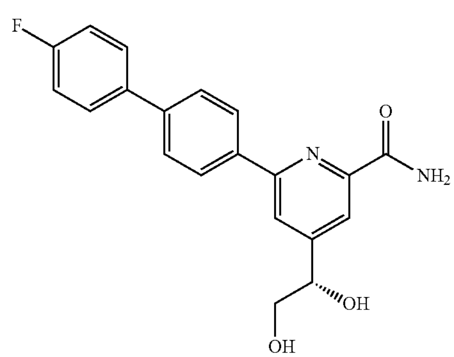 [SMILES: NC(=O)c1cc([C@H](O)CO)cc(-c2ccc(-c3ccc(F)cc3)cc2)n1] |

TABLE 2-continued

| Cpd Example No. | Chemical Name | Structure |
|---|---|---|
| 155 | 4-((R)-1,2-Dihydroxy-ethyl)-6-(4'-fluoro-biphenyl-4-yl)pyriidne-2-carboxylic acid amide | 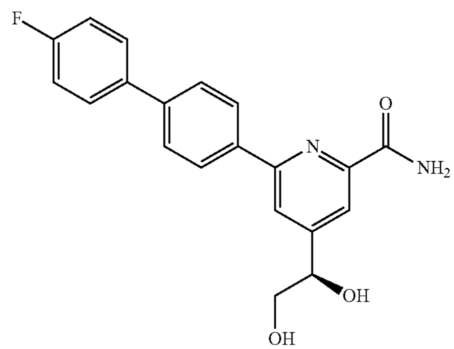 [SMILES: NC(=O)c1cc([C@@H](O)CO)cc(-c2ccc(-c3ccc(F)cc3)cc2)n1] |
| 156 | 6-((S)-1,2-Dihydroxy-ethyl)-4-[4-(4-trifluoromethoxy-phenoxy)phenyl]-pyridine-2-carboxylic acid amide | 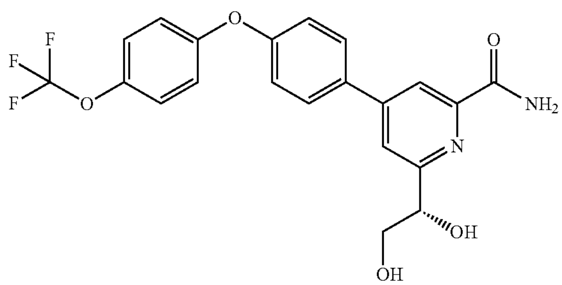 [SMILES: NC(=O)c1cc(-c2ccc(Oc3ccc(OC(F)(F)F)cc3)cc2)cc([C@H](O)CO)n1] |
| 157 | 6-((R)-1,2-Dihydroxy-ethyl)-4-[4-(4-trifluoromethoxy-phenoxy)phenyl]-pyridine-2-carboxylic acid amide | 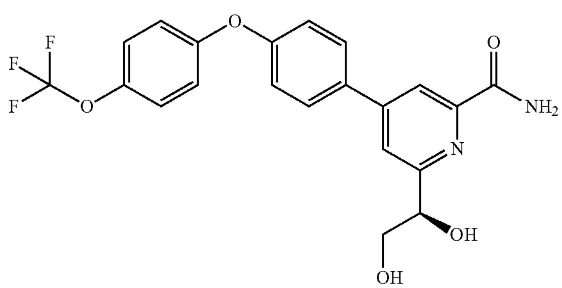 |
| 158 | 6-((S)-1,2-Dihydroxy-ethyl)-4-[4-(3-trifluoromethoxy-phenoxy)phenyl]-pyridine-2-carboxylic acid amide | 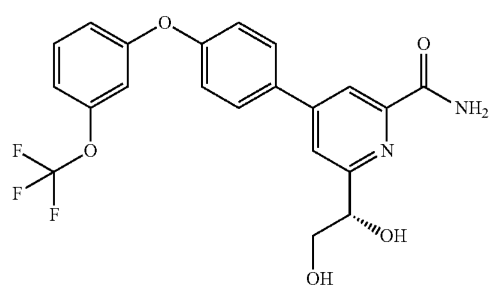 |
| 159 | 4-((S)-1,2-Dihydroxy-ethyl)-6-[4-(4-trifluoromethoxy-phenoxy)phenyl]-pyridine-2-carboxylic acid amide | 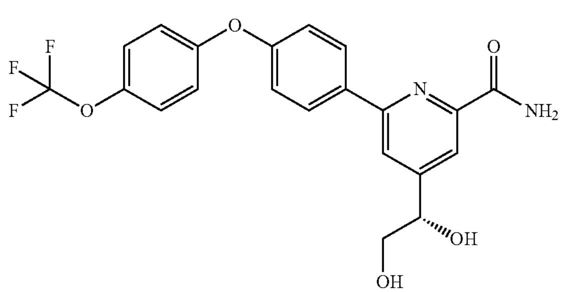 |

TABLE 2-continued

| Cpd Example No. | Chemical Name | Structure |
|---|---|---|
| 160 | 6-((S)-1,2-Dihydroxy-ethyl)-4-(4'-fluoro-biphenyl-4-yl)pyridine-2-carboxylic acid amide | 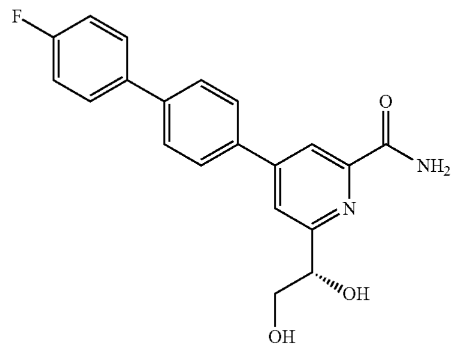 [SMILES: NC(=O)c1cc(-c2ccc(-c3ccc(F)cc3)cc2)cc([C@H](O)CO)n1] |
| 161 | 4-((R)-1,2-Dihydroxy-ethyl)-6-[4-(4-trifluoromethoxy-phenoxy)phenyl]-pyridine-2-carboxylic acid amide | 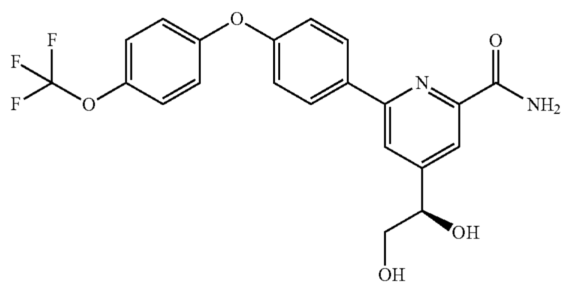 |
| 162 | 6-((R)-1,2-Dihydroxy-ethyl)-4-(4'-fluoro-biphenyl-4-yl)pyriidne-2-carboxylic acid amide | 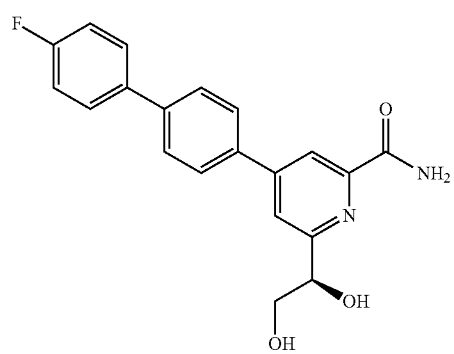 [SMILES: NC(=O)c1cc(-c2ccc(-c3ccc(F)cc3)cc2)cc([C@@H](O)CO)n1] |
| 163 | 4-((S)-1,2-Dihydroxy-ethyl)-6-[4-(3-trifluoromethoxy-phenoxy)phenyl]-pyridine-2-carboxylic acid amide | 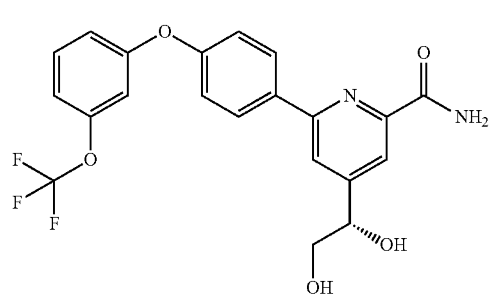 |

TABLE 2-continued

| Cpd Example No. | Chemical Name | Structure |
|---|---|---|
| 164 | 4-((R)-1,2-Dihydroxy-ethyl)-6-[4-(3-trifluoromethoxy-phenoxy)phenyl]-pyridine-2-carboxylic acid amide | 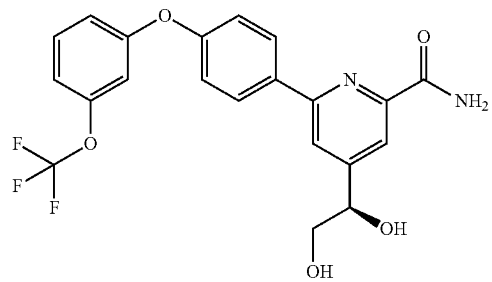 [SMILES: NC(=O)c1cc([C@@H](O)CO)cc(-c2ccc(Oc3cccc(OC(F)(F)F)c3)cc2)n1] |
| 165 | (S)-2-((2-cyano-6-(4-(4-fluorophenoxy)phenyl)pyridin-4-yl)amino)propanamide | 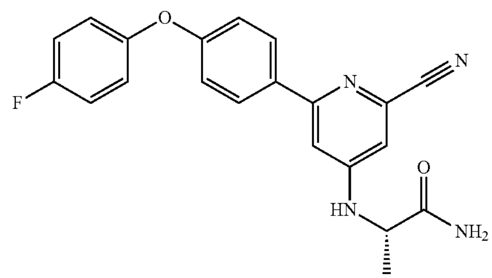 |
| 166 | (S)-2-((4-cyano-6-(4-(4-fluorophenoxy)phneyl)pyridin-2-yl)amino)propanamide | 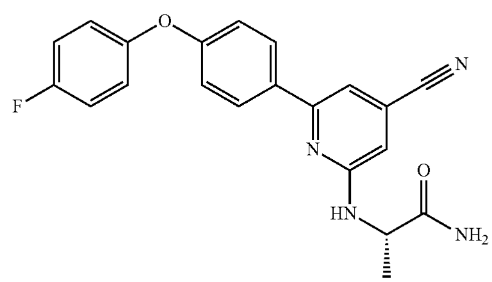 |
| 167 | (S)-4-((1-amino-1-oxopropan-2-yl)amino)-6-(4-(4-fluorophenoxy)phenyl)picolinamide | 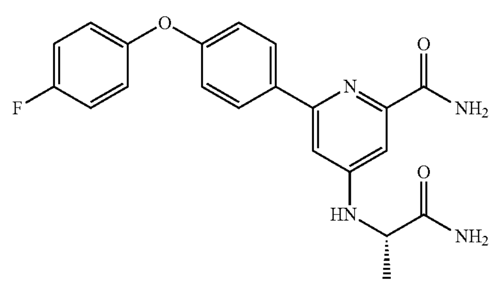 [SMILES: C[C@H](Nc1cc(C(N)=O)nc(-c2ccc(Oc3ccc(F)cc3)cc2)c1)C(N)=O] |
| 168 | (S)-2-((2-((S)-1,2-dihydroxyethyl)-6-(4-(4-fluorophenoxy)phenyl)pyridin-4-yl)amino)propanamide | 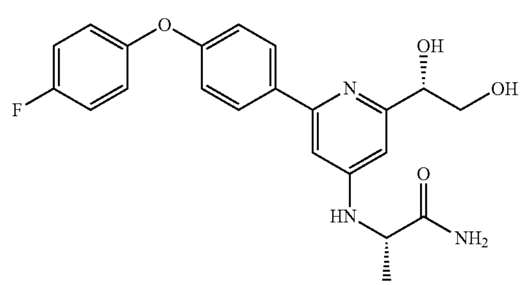 [SMILES: C[C@H](Nc1cc(-c2ccc(Oc3ccc(F)cc3)cc2)nc([C@H](O)CO)c1)C(N)=O] |

For the purpose of the present disclosure, the term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{1-10}$ alkyl group. In another embodiment, the alkyl group is chosen from a straight chain $C_{1-6}$ alkyl group. In another embodiment, the alkyl group is chosen from a branched chain $C_{1-6}$ alkyl group. In another embodiment, the alkyl group is chosen from a straight chain $C_{1-4}$ alkyl group. In another embodiment, the alkyl group is chosen from a branched chain $C_{1-4}$ alkyl group. In another embodiment, the alkyl group is chosen from a $C_{2-4}$ alkyl group. Non-limiting exemplary alkyl groups include methyl, ethyl, propyl, isopropyl, butyl, sec-butyl, tert-butyl, iso-butyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, ureido, guanidino, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include —$CH_2CH_2NO_2$, —$CH_2CH_2CO_2H$, —$CH_2CH_2SO_2CH_3$, —$CH_2CH_2COPh$, and the like.

For the purpose of the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_3$-$C_8$ cycloalkyl group. In another embodiment, the cycloalkyl group is chosen from a $C_3$-$C_6$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and the like.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkyl amino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkyl is substituted with two substituents. In another embodiment, the optionally substituted cycloalkyl is substituted with one substituent. Non-limiting exemplary optionally substituted cycloalkyl groups include:

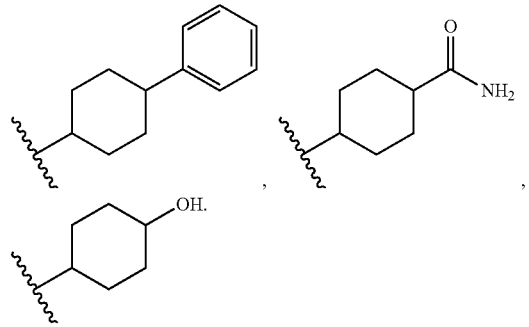

For the purpose of the present disclosure, the term "alkenyl" as used by itself or as part of another group refers to an alkyl group as defined above containing one, two or three carbon-to-carbon double bonds. In one embodiment, the alkenyl group is chosen from a $C_{2-12}$ alkenyl group. In one embodiment, the alkenyl group is chosen from a $C_{2-10}$ alkenyl group. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, hexenyl, heptenyl, octenyl, nonenyl, and the like.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-12}$ alkynyl group. In one embodiment, the alkynyl group is chosen from a $C_{2-10}$ alkynyl group. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group as defined above substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "hydroxyalkyl" as used by itself or as part of another group refers to an alkyl group as defined above substituted with one or more, e.g., one, two, or three, hydroxy groups. In one embodiment, the hydroxyalkyl is a monohydroxyalkyl, i.e., substituted with one hydroxy group. In another embodiment, the hydroxyalkyl is a dihydroxyalkyl, i.e., substituted with two hydroxy groups. In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

For the purpose of the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkoxy groups include —SCH$_3$, and —SCH$_2$CH$_3$.

For the purpose of the present disclosure, the term "alkoxyalkyl" as used by itself or as part of another group refers to any of the above-mentioned alkyl groups substituted with any of the above-mentioned alkoxy groups. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "aralkyloxy" as used by itself or as part of another group refers to an aralkyl group attached to a terminal oxygen atom. A non-limiting exemplary aryloxy group is PhCH$_2$O—.

For the purpose of the present disclosure, the term "aryl" as used by itself or as part of another group refers to a monocyclic or bicyclic aromatic ring system having from six to fourteen carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl and naphthyl.

For the purpose of the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkyl amino, (alkylamino)alkyl, (dialkylamino)alkyl, (cyano)alkyl, (carboxamido)alkyl, mercaptoalkyl, (heterocyclo)alkyl, or (heteroaryl)alkyl. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl and 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Examples include

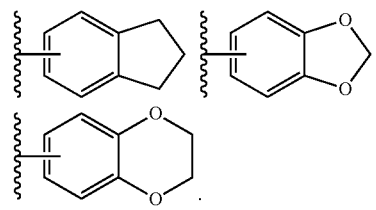

For the purpose of the present disclosure, the term "heteroaryl" or "heteroaromatic" refers to monocyclic and bicyclic aromatic ring systems having 5 to 14 ring atoms (i.e., $C_5$-$C_{14}$ heteroaryl) and 1, 2, 3, or 4 heteroatoms independently chosen from oxygen, nitrogen and sulfur. In one embodiment, the heteroaryl has three heteroatoms. In another embodiment, the heteroaryl has two heteroatoms. In another embodiment, the heteroaryl has one heteroatom. In one embodiment, the heteroaryl is a $C_5$ heteroaryl. In another embodiment, the heteroaryl is a $C_6$ heteroaryl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Exemplary N-oxides include pyridyl N-oxide and the like.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted heteroaryl has one substituent. In one embodiment, the optionally substituted is an optionally substituted pyridyl, i.e., 2-, 3-, or 4-pyridyl. Any available carbon or nitrogen atom can be substituted. In another embodiment, the optionally substituted heteroaryl is an optionally substituted indole.

For the purpose of the present disclosure, the term "heterocyclo" as used by itself or as part of another group refers to saturated and partially unsaturated (containing one or two double bonds) cyclic groups containing one to three rings having from two to twelve carbon atoms (i.e., $C_2$-$C_{12}$ heterocyclo) and one or two oxygen, sulfur and/or nitrogen atoms. The term "heterocyclo" is meant to include cyclic ureido groups such as 2-imidazolidinone. In one embodiment, the heterocyclo group is chosen from a 5- or 6-membered cyclic group containing one ring and one or two oxygen and/or nitrogen atoms. The heterocyclo can be optionally linked to the rest of the molecule through a carbon or nitrogen atom. Non-limiting exemplary heterocyclo groups include 2-imidazolidinone, piperidinyl, morpholinyl, piperazinyl, and pyrrolidinyl.

For the purpose of the present disclosure, term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkyl amino, (alkylamino)alkyl, (dialkylamino)alkyl, (cyano)alkyl, (carboxamido)alkyl, mercaptoalkyl, (heterocyclo) alkyl, (heteroaryl)alkyl, and the like. Substitution may occur on any available carbon or nitrogen atom. An optionally substituted heterocyclo can be fused to an aryl group to provide an optionally substituted aryl as described above. In one embodiment, the optionally substituted heterocyclo is a substituted piperazine. Non-limiting exemplary optionally substituted heterocyclo groups include:

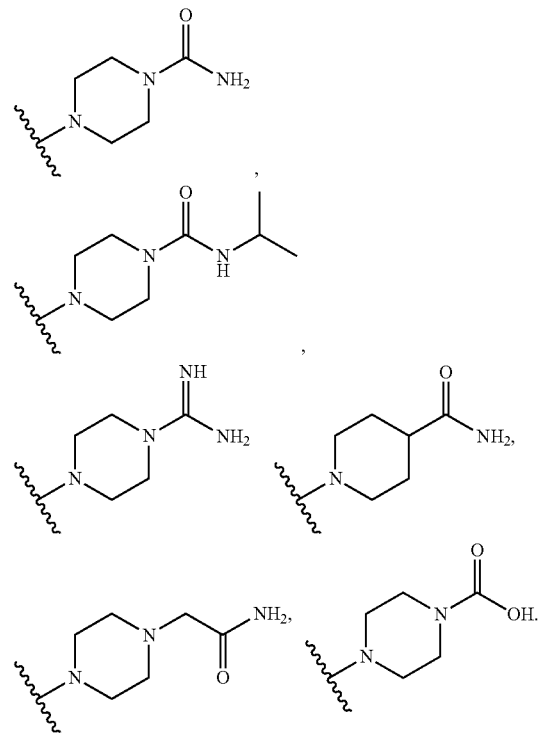

For the purpose of the present disclosure, the term "amino" as used by itself or as part of another group refers to —NH$_2$.

For the purpose of the present disclosure, the term "(amino)alkyl" as used by itself or as part of another group refers to any of the above-mentioned alkyl groups substituted with an amino group. Non-limiting exemplary amino alkyl groups include —CH$_2$CH$_2$NH$_2$, —CH$_2$CH$_2$CH$_2$NH$_2$, —CH$_2$CH$_2$CH$_2$CH$_2$NH$_2$ and the like.

For the purpose of the present disclosure, the term "diaminoalkyl" as used by itself or as part of another group refers any of the above-mentioned alkyl groups substituted with two amino groups.

For the purpose of the present disclosure, the term "alkylamino" as used by itself or as part of another group refers to —NHR$^{26}$, wherein R$^{26}$ is any alkyl group as "alkyl" is defined above.

For the purpose of the present disclosure, the term "dialkylamino" as used by itself or as part of another group refers to —NR$^{27a}$R$^{27b}$ wherein R$^{27a}$ and R$^{27b}$ are each independently any alkyl group as "alkyl" is defined above.

For the purpose of the present disclosure, the term "hydroxyalkylamino" as used by itself or as part of another group refers to —NHR$^{28}$, wherein R$^{28}$ is any hydroxyalkyl group as "hydroxyalkyl" is defined above.

For the purpose of the present disclosure, the term "(alkylamino)alkyl" as used by itself or as part of another group refers to any alkyl group as "alkylamino" is defined above.

For the purpose of the present disclosure, the term "(dialkylamino)alkyl" as used by itself or as part of another group refers to any alkyl group as "alkyl" is defined above substituted by any dialkylamino group as "dialkylamino" is defined above.

For the purpose of the present disclosure, the term "(cyano)alkyl" as used by itself or as part of another group refers to any alkyl group as "alkyl" is defined above substituted with one or more cyano, e.g., —CN, groups. Non-limiting exemplary (cyano)alkyl groups include —CH$_2$CH$_2$CN, —CH$_2$CH$_2$CH$_2$CN, and —CH$_2$CH$_2$CH$_2$CH$_2$CN.

For the purpose of the present disclosure, the term "carboxamido" as used by itself or as part of another group refers to a radical of formula —C(=O)NR$^{33a}$R$^{33b}$, wherein R$^{33a}$ and R$^{33b}$ are each independently hydrogen, optionally substituted alkyl, optionally substituted aryl, or optionally substituted heteroaryl, or R$^{33a}$ and R$^{33b}$ taken together with the nitrogen to which they are attached from a 3- to 8-membered heterocyclo group. In one embodiment, R$^{33a}$ and R$^{33b}$ are each independently hydrogen or optionally substituted alkyl. Non-limiting exemplary carboxamido groups include —CONH$_2$, —CON(H)CH$_3$, CON(CH$_3$)$_2$, and CON(H)Ph.

For the purpose of the present disclosure, the term "(carboxamido)alkyl" as used by itself or as part of another group refers to any of the above-mentioned alkyl groups substituted with a carboxamido group. Non-limiting exemplary (carboxamido)alkyl groups include:

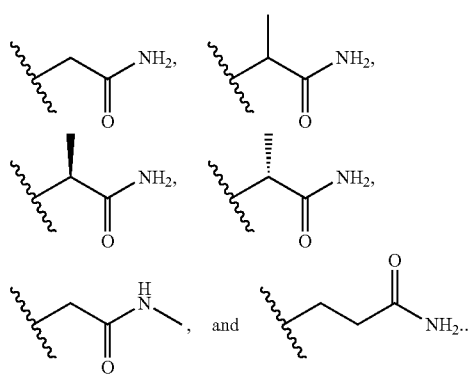

For the purpose of the present disclosure, the term "sulfonamido" as used by itself or as part of another group refers to a radical of the formula —SO$_2$NR$^{34a}$R$^{34b}$, wherein R$^{34a}$ and R$^{34b}$ are each independently hydrogen, optionally substituted alkyl, or optionally substituted aryl, or R$^{34a}$ and R$^{34b}$ taken together with the nitrogen to which they are attached from a 3- to 8-membered heterocyclo group Non-limiting exemplary sulfonamido groups include —SO$_2$NH$_2$, —SO$_2$N(H)CH$_3$, and —SO$_2$N(H)Ph.

For the purpose of the present disclosure, the term "alkylcarbonyl" as used by itself or as part of another group refers to a carbonyl group, i.e., —C(=O)—, substituted by any of the above-mentioned optionally substituted alkyl groups. A non-limiting exemplary alkylcarbonyl group is —COCH$_3$.

For the purpose of the present disclosure, the term "arylcarbonyl" as used by itself or as part of another group refers to a carbonyl group, i.e., —C(=O)—, substituted by any of the above-mentioned optionally substituted aryl groups. A non-limiting exemplary arylcarbonyl group is —COPh.

For the purpose of the present disclosure, the term "alkylsulfonyl" as used by itself or as part of another group refers to a sulfonyl group, i.e., —SO$_2$, substituted by any of the above-mentioned optionally substituted alkyl groups. A non-limiting exemplary alkylsulfonyl group is —SO$_2$CH$_3$.

For the purpose of the present disclosure, the term "arylsulfonyl" as used by itself or as part of another group refers to a sulfonyl group, i.e., —SO$_2$, substituted by any of the above-mentioned optionally substituted aryl groups. A non-limiting exemplary arylsulfonyl group is —SO$_2$Ph.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula —COOH.

For the purpose of the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

For the purpose of the present disclosure, the term "aralkyl" as used by itself or as part of another group refers to any of the above-mentioned alkyl groups substituted with one, two, or three optionally substituted aryl groups. In one embodiment, the aralkyl group is a C$_1$-C$_4$ alkyl substituted with one optionally substituted aryl group. Non-limiting exemplary aralkyl groups include benzyl and phenethyl.

For the purpose of the present disclosure, the term "ureido" as used by itself or as part of another group refers to a radical of the formula —NR$^{29a}$—C(=O)—NR$^{29b}$R$^{29c}$, wherein R$^{29a}$ is hydrogen, optionally substituted alkyl, or optionally substituted aryl, and R$^{29b}$ and R$^{29c}$ are each independently hydrogen, optionally substituted alkyl, or optionally substituted aryl, or R$^{29b}$ and R$^{29c}$ taken together with the nitrogen to which they are attached form a 4- to 8-membered heterocyclo group. Non-limiting exemplary ureido groups include —NH—C(C=O)—NH$_2$ and NH—C(C=O)—NHCH$_3$.

For the purpose of the present disclosure, the term "guanidino" as used by itself or as part of another group refers to a radical of the formula —NR$^{30a}$—C(=NR$^{31}$)—NR$^{30b}$R$^{30c}$, wherein R$^{30a}$, R$^{30b}$, and R$^{30c}$ are each independently hydrogen, optionally substituted alkyl, or optionally substituted aryl, and R$^{31}$ is hydrogen, alkyl, cyano, alkylsulfonyl, alkylcarbonyl, carboxamido, or sulfonamido. Non-limiting exemplary guanidino groups include —NH—C(C=NH)—NH$_2$, —NH—C(C=NCN)—NH$_2$, —NH—C(C=NH)—NHCH$_3$ and the like.

For the purpose of the present disclosure, the term "azido" as used by itself or as part of another group refers to a radical of the formula —N$_3$.

For the purpose of the present disclosure, the term "(heterocyclo)alkyl" as used by itself or as part of another group refers to any of the above-mentioned alkyl groups substituted with one, two, or three optionally substituted heterocyclo groups. In one embodiment, the (heterocyclo)alkyl group is a C$_{1-4}$ alkyl substituted with one optionally substituted heterocyclo group. Non-limiting exemplary (heterocyclo)alkyl groups include:

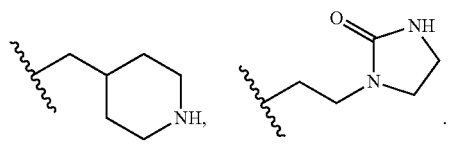 [SMILES: *CC1CCNCC1 ; *CCN1CCNC1=O]

For the purpose of the present disclosure, the term "(heteroaryl)alkyl" as used by itself or as part of another group refers to any of the above-mentioned alkyl groups substituted with one, two, or three optionally substituted heteroaryl groups. In one embodiment, the (heteroaryl)alkyl group is a $C_{1-4}$ alkyl substituted with one optionally substituted heteroaryl group. Non-limiting exemplary (heteroaryl) alkyl groups include:

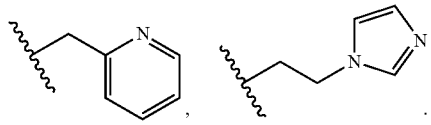 [SMILES: *Cc1ccccn1 ; *CCn1ccnc1]

For the purpose of the present disclosure, the term "alkylcarbonylamino" as used by itself or as part of another group refers to an alkylcarbonyl group attached to an amino nitrogen. A non-limiting exemplary alkylcarbonylamino group is —NHCOCH$_3$.

For the purpose of the present disclosure, the group —SO$_2$NH— is intended to connect A$_1$ and A$_2$ in either direction, i.e., A$_1$-SO$_2$NH-A$_2$- or A$_1$-NHSO$_2$-A$_2$-. Accordingly, in one embodiment, X is —SO$_2$NH—. In another embodiment, X is —NHSO$_2$—.

The present invention disclosed herein is also meant to encompass prodrugs of any of the disclosed compounds. As used herein, prodrugs are considered to be any covalently bonded carriers that release the active parent drug in vivo. In general, such prodrugs will be functional derivatives of compounds of any of Formulae I-XXXIII, which will be readily convertible in vivo, e.g., by being metabolized, into the required compound of Formulae I-XXXIII. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984). Non-limiting examples of prodrugs include esters or amides of compounds of any of Formulae I-XXXIII having hydroxyalkyl or aminoalkyl as a substituent, and these can be prepared by reacting such parent compounds with anhydrides such as succinic anhydride.

The invention disclosed herein is also intended to encompass any of the disclosed compounds being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, and preferably $^3$H, $^{11}$C, and $^{14}$C. Isotopically-labeled compounds of the present invention can be prepared by methods known in the art.

The present invention is also directed to $^3$H, $^{11}$C, or $^{14}$C radiolabeled compounds of any of Formulae I-XXXIII, as well as their pharmaceutically acceptable salts, prodrugs and solvates, and the use of any such compounds as radioligands for their ability to bind to the sodium channel. For example, one use of the labeled compounds of the present invention is the characterization of specific receptor binding. Another use of a labeled compound of the present invention is an alternative to animal testing for the evaluation of structure-activity relationships. For example, the receptor assay can be performed at a fixed concentration of a labeled compound of the invention and at increasing concentrations of a test compound in a competition assay. For example, a tritiated compound of any of Formulae I-XXXIII can be prepared by introducing tritium into the particular compound, for example, by catalytic dehalogenation with tritium. This method may include reacting a suitably halogen-substituted precursor of the compound with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}$C-labeled compounds can be prepared by employing starting materials having a $^{14}$C carbon.

Some of the compounds disclosed herein may contain one or more asymmetric centers and may thus give rise to enantiomers, diastereomers, and other stereoisomeric forms. The present invention is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treat," "treating" or "treatment" is meant to encompass administering to a subject a compound of the present invention for the purposes of amelioration or cure, including preemptive and palliative treatment.

The term "about," as used herein in connection with a measured quantity, refers to the normal variations in that measured quantity, as expected by the skilled artisan making the measurement and exercising a level of care commensurate with the objective of measurement and the precision of the measuring equipment.

The invention disclosed herein also encompasses the use of salts of the disclosed compounds, including all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present invention with a solution of a pharmaceutically acceptable non-toxic base such as sodium hydroxide, potassium hydroxide, choline hydroxide, sodium carbonate and the like.

The invention disclosed herein is also meant to encompass solvates of any of the disclosed compounds. Solvates typically do not significantly alter the physiological activity or toxicity of the compounds, and as such may function as pharmacological equivalents. The term "solvate" as used herein is a combination, physical association and/or solvation of a compound of the present invention with a solvent molecule such as, e.g. a disolvate, monosolvate or hemisolvate, where the ratio of solvent molecule to compound of the present invention is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of any of Formulae I-XXXIII can be present as solvated forms with a pharmaceutically acceptable solvent, such as water, methanol, ethanol, and the like, and it is intended that the invention includes both solvated and unsolvated forms of compounds of any of Formulae I-XXXIII. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1): Article 12 (2004), and A. L. Bingham et al., *Chem. Commun.:* 603-604 (2001). A typical, non-limiting, process of preparing a solvate would involve dissolving a compound of any of Formulae I-XXXIII in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Since compounds of Formulae are blockers of sodium ($Na^+$) channels, a number of diseases and conditions mediated by sodium ion influx can be treated by employing these compounds. The present invention is thus directed generally to a method for treating a disorder responsive to the blockade of sodium channels in an animal suffering from, or at risk of suffering from, said disorder, said method comprising administering to the animal an effective amount of a compound represented by any of defined Formulae I-XXXIII, or a pharmaceutically acceptable salt, prodrug, or solvate thereof.

The present invention is further directed to a method of modulating sodium channels in an animal in need thereof, said method comprising administering to the animal a modulating-effective amount of at least one compound represented by any of defined Formulae I-XXXIII, or a pharmaceutically acceptable salt, prodrug, or solvate thereof.

More specifically, the present invention provides a method of treating stroke, neuronal damage resulting from head trauma, epilepsy, neuronal loss following global and focal ischemia, pain (e.g., acute pain, chronic pain, which includes but is not limited to neuropathic pain, postoperative pain, and inflammatory pain, or surgical pain), a neurodegenerative disorder (e.g., Alzheimer's disease, amyotrophic lateral sclerosis (ALS), or Parkinson's disease), migraine, manic depression, tinnitus, myotonia, a movement disorder, or cardiac arrhythmia, or providing local anesthesia. In one embodiment, the invention provides a method of treating pain. In another embodiment, the type of pain is chronic pain. In another embodiment, the type of pain is neuropathic pain. In another embodiment, the type of pain is postoperative pain. In another embodiment, the type of pain is inflammatory pain. In another embodiment, the type of pain is surgical pain. In another embodiment, the type of pain is acute pain. In another embodiment, the treatment of pain (e.g., chronic pain, such as neuropathic pain, postoperative pain, or inflammatory pain, acute pain or surgical pain) is preemptive. In another embodiment, the treatment of pain is palliative. In each instance, such method of treatment requires administering to an animal in need of such treatment an amount of a compound of the present invention that is therapeutically effective in achieving said treatment. In one embodiment, the amount of such compound is the amount that is effective to block sodium channels in vivo.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (Brower, *Nature Biotechnology* 2000; 18: 387-391).

The inflammatory process is a complex series of biochemical and cellular events activated in response to tissue injury or the presence of foreign substances (Levine, *Inflammatory Pain, In: Textbook of Pain*, Wall and Melzack eds., 3$^{rd}$ ed., 1994). Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, that associated with osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. Chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The present invention is also directed to the use of a compound represented by any of defined Formulae I-XXXIII, or a pharmaceutically acceptable salt, prodrug, or solvate thereof, in the manufacture of a medicament for treating a disorder responsive to the blockade of sodium channels (e.g., any of the disorders listed above) in an animal suffering from said disorder.

The present invention is also directed to the use of a compound represented by any of defined Formulae I-XXXIII, or a pharmaceutically acceptable salt, prodrug, or solvate thereof, in the manufacture of a medicament, in particular a medicament for modulating sodium channels, in an animal in need thereof.

General Synthesis of Compounds

The compounds of the present invention are prepared using methods known to those skilled in the art in view of this disclosure. For example, compounds of Formulae XXV or XXVI, wherein $R^{5a}$ and $R^{5b}$ are hydrogen, can be prepared according to General Scheme 1.

General Scheme 1

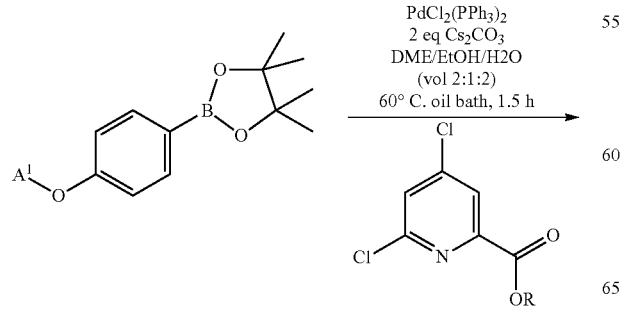

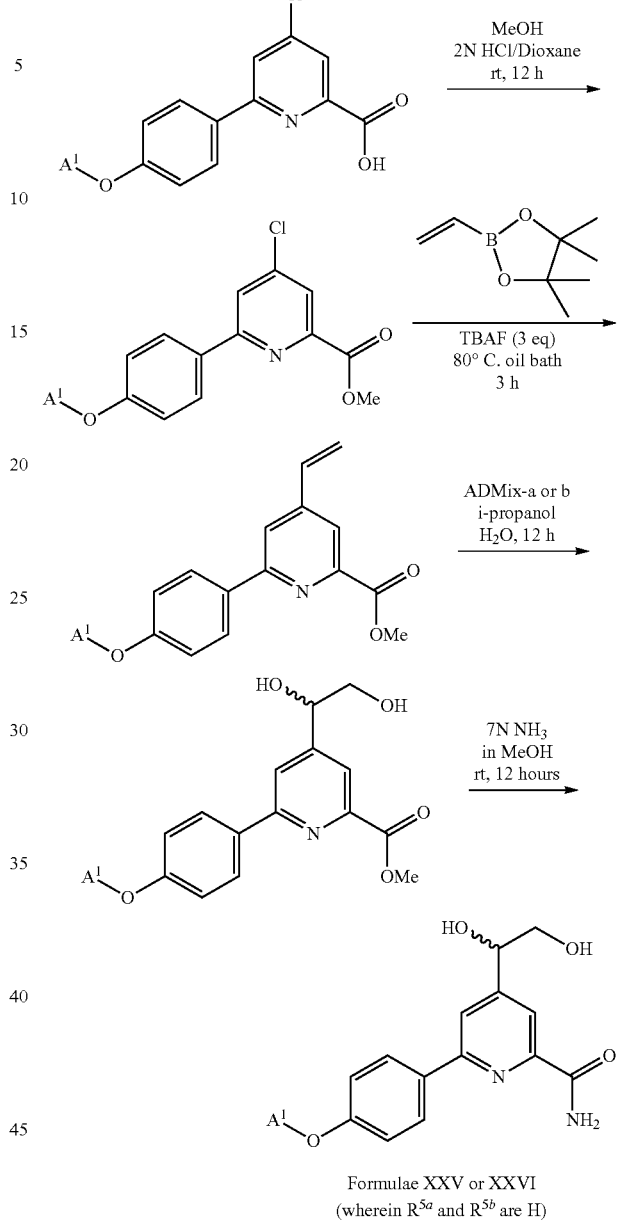

Formulae XXV or XXVI
(wherein $R^{5a}$ and $R^{5b}$ are H)

Compounds of Formula XXXII, wherein $R^{5a}$ and $R^{5b}$ are hydrogen and E is hydroxyalkyl, can be prepared according to General Scheme 2.

General Scheme 2

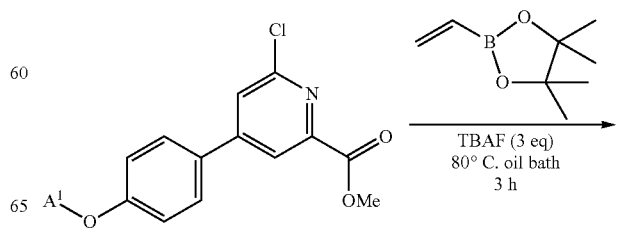

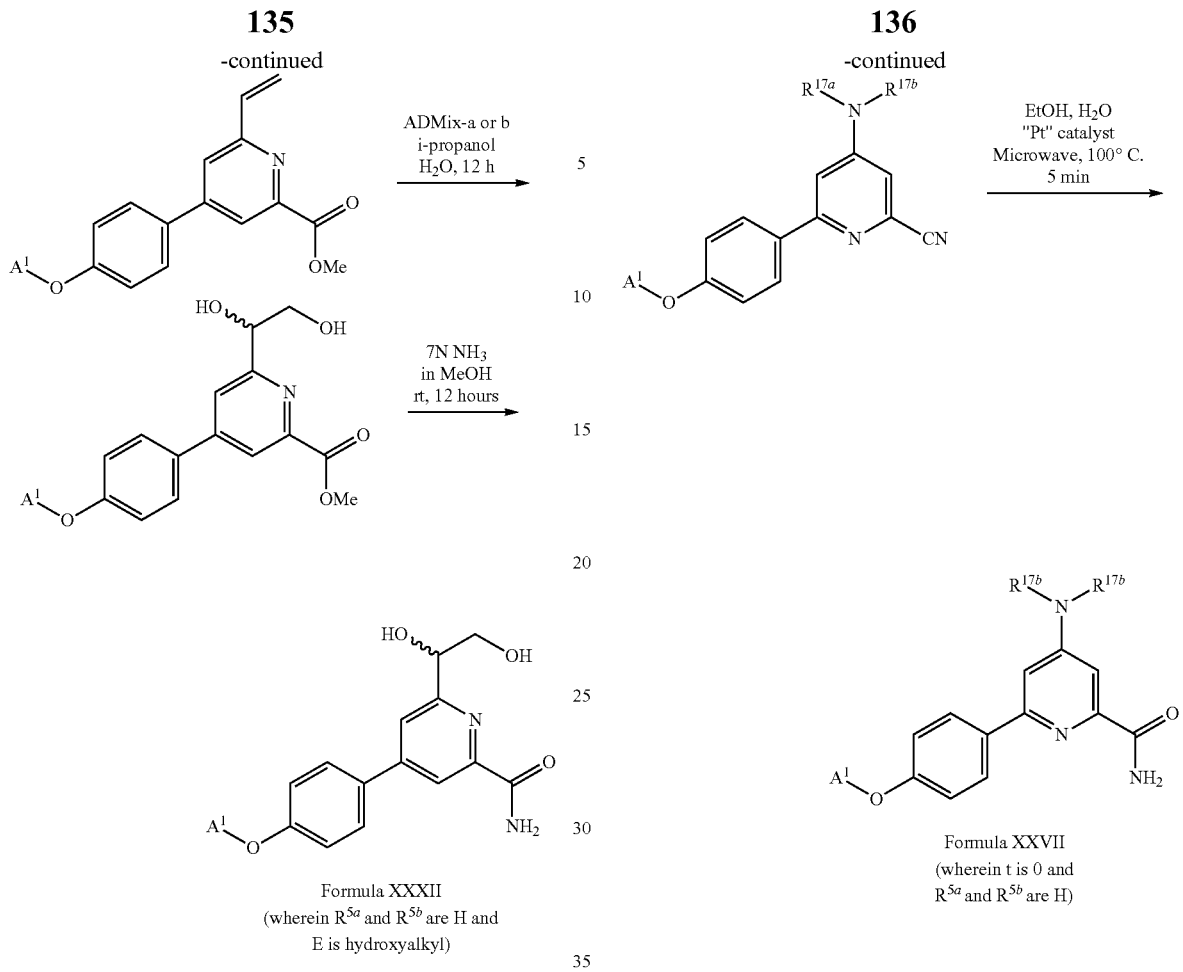
Compounds of Formula XXVII, wherein t is 0 and $R^{5a}$ and $R^{5b}$ are hydrogen, can be prepared according to General Scheme 3.
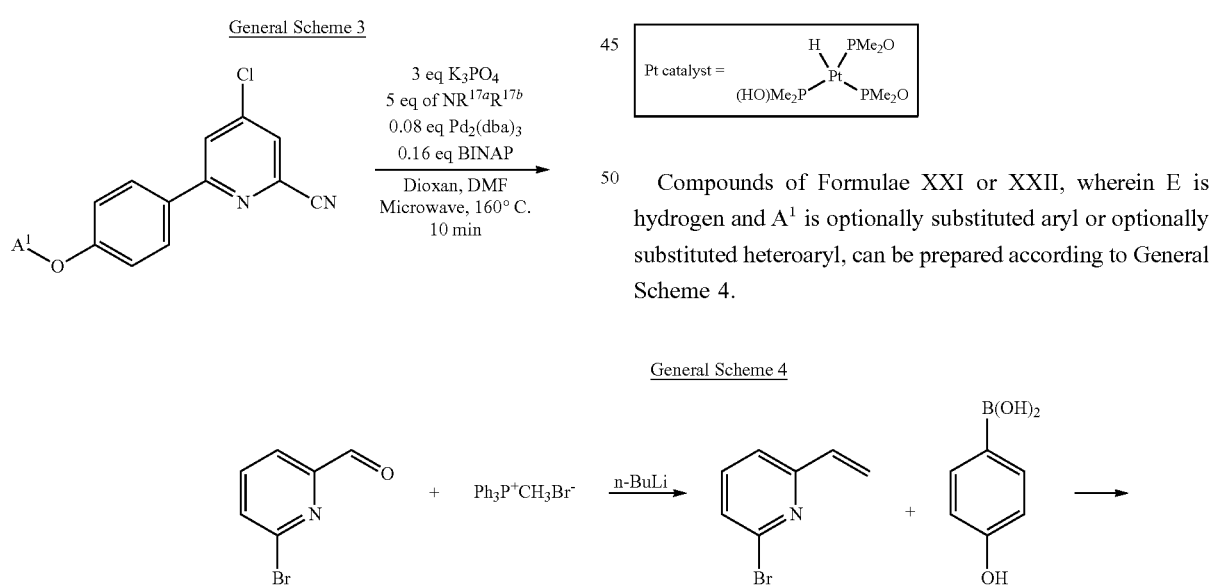
Compounds of Formulae XXI or XXII, wherein E is hydrogen and $A^1$ is optionally substituted aryl or optionally substituted heteroaryl, can be prepared according to General Scheme 4.

-continued

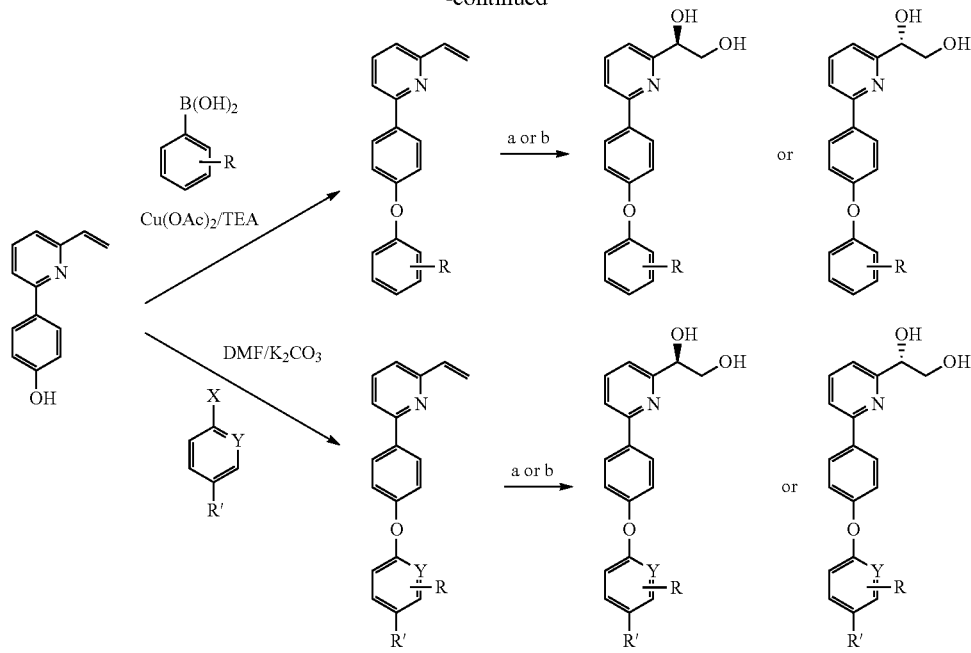

a. Admix-a
b. Admix-b
X = F or Br
R = one or more optional substituents
R' = electron withdrawing group
Y = N or C Testing of Compounds Compounds of the present invention were assessed by sodium mobilization and/or electrophysiological assays for sodium channel blocker activity. One aspect of the present invention is based on the use of the compounds herein described as sodium channel blockers. Based upon this property, compounds of the invention are considered useful in treating a condition or disorder responsive to the blockade of sodium ion channels, e.g., stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, cardiac arrhythmia, or providing local anesthesia. Compounds of the Invention are also expected to be effective in treating pain, e.g., acute pain, chronic pain, which includes but is not limited to, neuropathic pain, postoperative pain, and inflammatory pain, or surgical pain.

More specifically, the present invention is directed to compounds of Formulae I-XXXIII that are blockers of sodium channels. According to the present invention, those compounds having useful sodium channel blocking properties exhibit an $IC_{50}$ for $Na_v1.1$, $Na_v1.2$, $Na_v1.3$, $Na_v1.4$, $Na_v1.5$, $Na_v1.6$, $Na_v1.7$, $Na_v1.8$, and/or $Na_v1.9$ of about 100 µM or less, e.g., about 50 µM or less, about 10 µM or less, about 5 µM or less, or about 1 µM or less, in sodium mobilization and/or electrophysiological assays. In certain embodiments, Compounds of the Invention exhibit an $IC_{50}$ for $Na_v1.7$ of 100 µM or less, about 50 µM or less, about 10 µM or less, about 5 µM or less, about 1 µM or less, about 0.5 µM or less, or about 0.1 µM or less. Compounds of the Invention can be tested for their $Na^+$ channel blocking activity using methods known in the art and by the following fluorescence imaging and electrophysiological in vitro assays and/or in vivo assays.

In Vitro Assay Protocols

FLIPR® Assays

Recombinant $Na_v1.7$ Cell Line:

In vitro assays were performed in a recombinant cell line expressing cDNA encoding the alpha subunit ($Na_v1.7$, SCN9a, PN1, NE) of human $Na_v1.7$ (Accession No. NM_002977). The cell line was provided by investigators at Yale University (Cummins et al, *J. Neurosci.* 18(23): 9607-9619 (1998)). For dominant selection of the $Na_v1.7$-expressing clones, the expression plasmid co-expressed the neomycin resistance gene. The cell line was constructed in the human embryonic kidney cell line, HEK293, under the influence of the CMV major late promoter, and stable clones were selected using limiting dilution cloning and antibiotic selection using the neomycin analogue, G418. Recombinant beta and gamma subunits were not introduced into this cell line. Additional cell lines expressing recombinant $Na_v1.7$ cloned from other species can also be used, alone or in combination with various beta subunits, gamma subunits or chaperones.

Non-Recombinant Cell Lines Expressing Native $Na_v1.7$:

Alternatively, in vitro assays can be performed in a cell line expressing native, non-recombinant $Na_v1.7$, such as the ND7 mouse neuroblastoma X rat dorsal root ganglion (DRG) hybrid cell line ND7/23, available from the European Cell Culture Collection (Cat. No. 92090903, Salisbury, Wiltshire, United Kingdom). The assays can also be performed in other cell lines expressing native, non-recombinant $Na_v1.7$, from various species, or in cultures of fresh or preserved sensory neurons, such as dorsal root ganglion (DRG) cells, isolated from various species. Primary screens or counter-screens of other voltage-gated sodium channels can also be performed, and the cell lines can be constructed using methods known in the art, purchased from collaborators or commercial establishments, and they can express either recombinant or native channels. The primary counter-screen is for one of the central neuronal sodium channels, $Na_v1.2$ (rBIIa), expressed in HEK293 host cells (Ilyin et al., Br. J. Pharmacol. 144:801-812 (2005)). Pharmacological profiling for these counter-screens is carried out under conditions similar to the primary or alternative $Na_v1.7$ assays described below.

Cell Maintenance:

Unless otherwise noted, cell culture reagents were purchased from Mediatech of Herndon, Va. The recombinant $Na_v1.7$/HEK293 cells were routinely cultured in growth medium consisting of Dulbecco's minimum essential medium containing 10% fetal bovine serum (FBS, Hyclone, Thermo Fisher Scientific, Logan, Utah), 100 U/mL penicillin, 100 µg/mL streptomycin, 2-4 mM L-glutamine, and 500 mg/mL G418. For natural, non-recombinant cell lines, the selective antibiotic was omitted, and additional media formulations can be applied as needed.

Assay Buffer:

The assay buffer was formulated by removing 120 mL from a 1 L bottle of fresh, sterile $dH_2O$ (Mediatech, Herndon, Va.) and adding 100 mL of 10×HBSS that does not contain $Ca^{++}$ or $Mg^{++}$ (Gibco, Invitrogen, Grand Island, N.Y.) followed by 20 mL of 1.0 M Hepes, pH 7.3 (Fisher Scientific, BP299-100). The final buffer consisted of 20 mM Hepes, pH 7.3, 1.261 mM $CaCl_2$, 0.493 mM $MgCl_2$, 0.407 mM $Mg(SO)_4$, 5.33 mM KCl, 0.441 mM $KH_2PO_4$, 137 mM NaCl, 0.336 mM $Na_2HPO4$ and 0.556 mM D-glucose (Hanks et al., Proc. Soc. Exp. Biol. Med. 71:196 (1949)), and the simple formulation was typically the basic buffer throughout the assay (i.e., all wash and addition steps).

CoroNa™ Green AM $Na^+$ Dye for Primary Fluorescence Assay:

The fluorescence indicator used in the primary fluorescence assay was the cell permeant version of CoroNa™ Green (Invitrogen, Molecular Probes, Eugene, Oreg.), a dye that emits light in the fluorescence range (Harootunian et al., J. Biol. Chem. 264(32):19458-19467 (1989)). The intensity of this emission, but not the wavelength range, is increased when the dye is exposed to $Na^+$ ions, which it can bind with partial selectivity. Cells expressing $Na_v1.7$ or other sodium channels were loaded with the CoroNa™ Green dye immediately in advance of the fluorescence assay, and then, after agonist stimulation, the mobilization of $Na^+$ ions was detected as the $Na^+$ ions flowed from the extracellular fluid into the cytoplasm through the activated sodium channel pores. The dye was stored in the dark as a lyophilized powder, and then an aliquot was dissolved immediately before the cell loading procedure, according to the instructions of the manufacturer to a stock concentration of 10 mM in DMSO. It was then diluted in the assay buffer to a 4× concentrated working solution, so that the final concentration of dye in the cell loading buffer was 5 µM.

Membrane Potential Dye for Alternative Fluorescence Assays:

A fluorescence indicator that can be used in alternative fluorescence assays is the blue version membrane potential dye (MDS, Molecular Devices, Sunnyvale, Calif.), a dye that detects changes in molecules following a change in membrane potential. An increase in fluorescence is expected if agonist stimulation provokes a change in membrane potential. Cells expressing $Na_v1.7$ or other sodium channels are incubated with the membrane potential dye 30-60 minutes before the fluorescence assay. In the case of the KCl pre-stimulation version of the assay, the dye and all other components are washed out immediately before the assay, and the dye is then replaced. In the version lacking KCl pre-stimulation, the dye remains on the cells and is not washed out or replaced. The dye is stored in the dark as a lyophilized powder, and then an aliquot dissolved in assay buffer to form a 20×-concentrated stock solution that can be used for several weeks.

Agonists:

In the fluorescence assays, two agonists were used in combination, namely 1) veratridine; and 2) the venom from the yellow scorpion, Leiurus quinquestriatus hebraeus. Veratridine is an alkaloid small molecule that facilitates the capture of channel openings by inhibiting inactivation, and the scorpion venom is a natural preparation that includes peptide toxins selective for different subsets of voltage-gated sodium channels. These scorpion toxins inhibit the fast inactivation of their cognate target channels. Stock solutions of the agonists were prepared to 40 mM in DMSO (veratridine) and 1 mg/mL in $dH_2O$ (scorpion venom), and then diluted to make a 4× or 2× stock (depending on the particular assay) in assay buffer, the final concentration being 100 µM (veratridine) and 10 µg/mL (scorpion venom). Both of the agonists were purchased from Sigma Aldrich, St. Louis, Mo.

Test Compounds:

Test compounds were dissolved in DMSO to yield 10 mM stock solutions. The stock solutions were further diluted using DMSO in 1:3 serial dilution steps with 10 points (10,000 µM, 3,333 µM, 1,111 µM, 370 µM, 123 µM, 41 µM, 14 µM, 4.6 µM, 1.5 µM and 0.5 µM). The stock solutions were further diluted in assay buffer (1:125) as 4× stock serial dilutions with a DMSO concentration of 0.8% (final [DMSO], in the assay, from the compounds component=0.2%), so that the compounds' final concentrations in the assay were 20 µM, 6.7 µM, 2.2 µM, 0.74 µM, 0.25 µM and 0.08 µM, 0.03 µM, 0.01 µM, 0.003 µM and 0.001 µM. If a particular test article appeared to be especially potent, then the concentration curve was adjusted, e.g., to 10-fold lower concentrations, in order to perform the dose-response in a more relevant concentration range. Compound dilutions were added during the dye-loading and pre-stimulation step, and then again during the fluorescence assay, early in the kinetic read. Compound dilutions were added in duplicate rows across the middle 80 wells of the 96-well plate, whereas the fully stimulated and the fully inhibited controls (positive and negative) were located in the top 4 side wells and the bottom 4 side wells, respectively, on the left and right sides of the assay plate.

Data Analysis:

The data were analyzed according to methods known to those skilled in the art or using the GraphPad® Prism 4.0 Program (available from GraphPad Software, San Diego, Calif.) to determine the $IC_{50}$ value for the test article. At least one standard reference compound was evaluated during each experiment.

FLIPR® or FLIPR$^{TETRA}$® Sodium Dye Assay with KCl and Test Article Pre-Incubation:

Cells were prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate was then incubated in growth media, with or without selective antibiotic, overnight at 37° C. at 5% $CO_2$, 95% humidity, in preparation for the assay. For counter-screens of other voltage-gated sodium channels, the procedure was very similar, though optimal densities of cells, media and subsequent assay components can be fine-tuned for the particular cell line or isoform.

The next day, at the start of the assay, the media was flicked from the cells and the wells were washed once with 50 μl/well assay buffer (1× Hank's balanced salt solution without sodium bicarbonate or phenol red, 20 mM Hepes, pH 7.3) and then pre-incubated with the test articles, CoroNa™ Green AM sodium dye (for cell loading) and KCl for re-polarization and synchronization of the channels in the entire population of cells. For this dye-loading and pre-stimulation step, the components were added as follows, immediately after the wash step: 1) first, the compound dilutions and controls were added as 4× concentrates in assay buffer at 50 μL/well; 2) CoroNa™ Green AM dye was diluted from the stock solution to 20 μM in assay buffer (4× concentrate) and added to the plate at 50 μL/well; and 3) finally, a solution of 180 mM KCl (2×) was prepared by diluting a 2M stock solution into assay buffer and the solution was added to the cells at 100 Owen. The cells were incubated at 25° C. in the dark for 30 min. before their fluorescence was measured.

The plates containing dye-loaded cells were then flicked to remove the pre-incubation components and washed once with 100 μL/well assay buffer. A 100 μL/well aliquot of assay buffer was added back to the plate, and the real-time assay was commenced. The fluorescence of cells was measured using a fluorescence plate reader (FLIPR$^{TETRA}$® or FLIPR384®, MDS, Molecular Devices, Sunnyvale, Calif.) Samples were excited by either a laser or a PMT light source (Excitation wavelength=470-495 nM) and the emissions are filtered (Emission wavelength=515-575 nM). The additions of compound and the channel activators in this cell-based, medium-to-high throughput assay were performed on the fluorescence plate reader and the results (expressed as relative fluorescence units) were captured by means of camera shots every 1-3 sec., then displayed in real-time and stored. Generally, there was a 15 sec. base line, with camera shots taken every 1.5 sec., then the test compounds were added, then another 120 sec. baseline was conducted, with camera shots taken every 3 sec.; and finally, the agonist solution (containing veratridine and scorpion venom) was added. The amplitude of fluorescence increase, resulting from the binding of $Na^+$ ions to the CoroNa™ Green dye, was captured for ~180 sec. thereafter. Results were expressed in relative fluorescence units (RFU) and can be determined by using the maximum signal during the latter part of the stimulation; or the maximum minus the minimum during the whole agonist stimulation period; or by taking the area under the curve for the whole stimulation period.

The assay can be performed as a screening assay as well with the test articles present in standard amounts (e.g., 10 μM) in only one or two wells of a multi-well plate during the primary screen. Hits in this screen were typically profiled more exhaustively (multiple times), subjected to dose-response or competition assays and tested in counter screens against other voltage-gate sodium channels or other biologically relevant target molecules.

FLIPR® or FLIPR$^{TETRA}$® Membrane Potential Assay with KCl and Test Article Pre-Incubation:

Cells are prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% $CO_2$, 95% humidity, in preparation for the assay (see, e.g., Benjamin et. al., *J. Biomol. Screen* 10(4): 365-373 (2005)). For screens and counter-screens of other voltage-gated sodium channels, the assay protocol is similar, though optimal densities of cells, media and subsequent assay components can be fine-tuned for the particular cell line or sodium channel isoform being tested.

The next day, at the start of the assay, the media is flicked from the cells and the wells are washed once with 50 μL/well assay buffer (1× Hank's balanced salt solution without sodium bicarbonate or phenol red, 20 mM Hepes, pH 7.3) and then pre-incubated with the test articles, the membrane potential dye (for cell loading), and the KCl for re-polarization and synchronization of the channels in the entire population of cells. For this dye-loading and pre-stimulation step, the components are added as follows, immediately after the wash step: 1) first, the compound dilutions and controls are added as 4× concentrates in assay buffer at 50 μL/well; 2) membrane potential dye is diluted from the stock solution in assay buffer (4× concentrate) and added to the plate at 50 μt/well; and 3) finally, a solution of 180 mM KCl (2×) is prepared by diluting a 2M stock solution into assay buffer and the solution added to the cells at 100 μL/well. The cells are incubated at 37° C. in the dark for 30-60 min. before their fluorescence is measured.

The plates containing dye-loaded cells are then flicked to remove the pre-incubation components and washed once with 50 μL/well assay buffer. A 50 μL/well aliquot of membrane potential dye is added back to the plate, and the real-time assay is commenced. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first) and then the channel activators (later) in this are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well with the test articles present in standard amounts (e.g., 10 μM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

FLIPR® or FLIPR$^{TETRA}$® Sodium Dye Assay without KCl and Test Article Pre-Incubation:

Cells are prepared by plating the recombinant HEK293 cells or other host cells expressing either recombinant or non-recombinant, native, Na$_v$1.7 alpha subunit, alone or in combination with various beta and gamma subunits at a density of 40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% CO$_2$, 95% humidity, in preparation for the assay. For counter-screens of other voltage-gated sodium channels, the procedure is very similar, though optimal densities of cells, media and subsequent assay components can be fine-tuned for the particular cell line or isoform.

The next day, at the start of the assay, the media is flicked from the cells and the wells washed once with 50 µL/well assay buffer (1× Hank's balanced salt solution without sodium bicarbonate or phenol red, 20 mM Hepes, pH 7.3). Membrane potential dye is then added to each well of the 96-well plate (50 µL/well), from a freshly diluted sample of the stock (now at 4× concentration) in the assay buffer. The cells are incubated at 37° C. in the dark for 30-60 min. before their fluorescence is measured.

In this standard membrane potential assay, the 96-well plate containing dye-loaded cells is then loaded directly onto the plate reader without aspirating the dye solution and without any further washing of the cells. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first, 50 µL/well from a 4× stock plate) and then the channel activators (later, 100 µL/well from a 2× stock solution) in this kinetic assay are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well, with the test articles present in standard amounts (e.g. 10 µM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

Electrophysiology Assay

Cells:

The hNa$_v$1.7 expressing HEK-293 cells were plated on 35 mm culture dishes pre-coated with poly-D-lysine in standard DMEM culture media (Mediatech, Inc., Herndon, Va.) and incubated in a 5% CO$_2$ incubator at 37° C. Cultured cells were used approximately 12-48 hours after plating.

Electrophysiology:

On the day of experimentation, the 35 mm dish was placed on the stage of an inverted microscope equipped with a perfusion system that continuously perfuses the culture dish with fresh recording media. A gravity driven superfusion system was used to apply test solutions directly to the cell under evaluation. This system consists of an array of glass pipette glass connected to a motorized horizontal translator. The outlet of the shooter was positioned approximately 100 µm from the cell of interest.

Whole cell currents were recorded using the whole-cell patch clamp configuration using an Axopatch 200B amplifier (Axon Instruments, Foster City Calif.), 1322A A/D converter (Axon Instruments) and pClamp software (v. 8; Axon Instruments) and stored on a personal computer. Gigaseals were formed and the whole-cell configuration was established in voltage clamp mode, and membrane currents generated by hNa$_v$1.7 were recorded in gap-free mode. Borosilicate glass pipettes have resistance values between 1.5 and 2.0 MΩ when filled with pipette solution and series resistance (<5 MΩ) was compensated 75-80%. Signals were sampled at 50 kHz and low pass filtered at 3 kHz.

Voltage Protocols:

After establishing the whole-cell configuration in voltage clamp mode, two voltage protocols were run to establish: 1) the holding potential; and 2) the test potential for each cell.

Resting Block:

To determine a membrane potential at which the majority of channels are in the resting state, a standard steady-state inactivation (SSIN) protocol was run using 100 ms prepulses×10 mV depolarizing steps. The holding potential for testing resting block (Vh$_t$) was 20 mV more hyperpolarized than the first potential where inactivation was observed with the inactivation protocol.

From this holding potential a standard I-V protocol was run to determine the potential at which the maximal current (Imax) is elicited. This potential was the test potential (Vt).

The compound testing protocol was a series of 10 ms depolarizations from the Vh$_1$ (determined from the SSIN) to the Vt (determined from the I-V protocol) repeated every 10-15 seconds. After a stable baseline was established, a high concentration of a test compound (highest concentration solubility permits or that which provides ~50% block) was applied and block of the current assessed. Washout of the compound was attempted by superfusing with control solution once steady-state block was observed. The fractional response was calculated as follows:

$$FR = I(\text{after drug})/I(\text{control}),$$

where I is the peak current amplitude and was used for estimating resting block dissociation constant, K$_r$:

$$K_r = [\text{drug}] * \{FR/(1-FR)\},$$

where [drug] is the concentration of a drug.

Block of Inactivated Channels:

To assess the block of inactivated channels the holding potential was depolarized such that 20-50% of the current amplitude was reduced when pulsed to the same Vt as above. The magnitude of this depolarization depends upon the initial current amplitude and the rate of current loss due to slow inactivation. This was the second holding potential (Vh$_2$). The current reduction was recorded to determine the fraction of available channels at this potential (h).

$$h = I@Vh_2/I\text{max}.$$

At this membrane voltage a proportion of channels was in the inactivated state, and thus inhibition by a blocker includes interaction with both resting and inactivated channels.

To determine the potency of the test compound on inactivated channels, a series of currents were elicited by 10 ms voltage steps from $Vh_2$ to Vt every 10-15 seconds. After establishing a stable baseline, the low concentration of the compound was applied. Multiple cumulative concentrations may have to be applied to identify a concentration that will block between 40-60% of the current. Washout will be attempted to re-establish baseline. Fractional responses were measured with respect to a projected baseline to determine $K_{app}$.

$$K_{app}=[drug]*\{FR/(1-FR)\},$$

where [drug] is the concentration of a drug.

This $K_{app}$ value, along with the calculated $K_r$ and h values, were used to calculate the affinity of the compound for the inactivated channels ($K_i$) using the following equation:

$$K_i=(1-h)/((1/K_{app})-(h/K_r)).$$

In the alternative, the voltage clamp protocol to examine $hNa_v1.7$ currents was as follows. First, the standard current-voltage relationship was tested by pulsing the cell from the holding voltage ($V_h$) of −120 mV by a series of 5 msec long square-shaped test pulses incrementing in +10 mV steps over the membrane voltage range of −90 mV to +60 mV at the pace of stimulation of 0.5 Hz. This procedure determines the voltage that elicits the maximal current ($V_{max}$). Second, $V_h$ was re-set to −120 mV and a steady-state inactivation (SSIN) curve was taken by the standard double-pulse protocol: 100 ms depolarizing pre-pulse was incremented in steps of +10 mV (voltage range from −90 mV to 0 mV) immediately followed by the 5 ms long test pulse to −10 mV at the pace of stimulation of 0.2 Hz. This procedure determines the voltage of full inactivation ($V_{full}$). Third, the cell was repeatedly stimulated with the following protocol, first in the absence of the test compound then in its presence. The protocol consisted of depolarizing the cell from the holding potential of −120 mV to the $V_{full}$ value for 4.5 seconds then repolarizing the cell to the holding potential for 10 ms before applying the test pulse to the $V_{max}$ for 5 ms. The amount of inhibition produced by the test compound was determined by comparing the current amplitude elicited by the test pulse in the absence and presence of the compound.

Solutions and Chemicals:

For electrophysiological recordings the external solution was either standard, DMEM supplemented with 10 mM HEPES (pH adjusted to 7.34 with NaOH and the osmolarity adjusted to 320) or Tyrodes salt solution (Sigma, USA) supplemented with 10 mM HEPES (pH adjusted to 7.4 with NaOH; osmolarity=320). The internal pipette solution contained (in mM): NaCl (10), CsF (140), $CaCl_2$ (1), $MgCl_2$ (5), EGTA (11), HEPES (10: pH 7.4, 305 mOsm). Compounds were prepared first as series of stock solutions in DMSO and then dissolved in external solution; DMSO content in final dilutions did not exceed 0.3%. At this concentration, DMSO did not affect sodium currents. Vehicle solution used to establish base line was also contacting 0.3% DMSO.

Data Analysis:

Data was analyzed off-line using Clampfit software (pClamp, v. 8; Axon Instruments) and graphed using GraphPad Prizm (v. 4.0) software.

In Vivo Assay for Pain

The compounds can be tested for their antinociceptive activity in the formalin model as described in Hunskaar et al., *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period, mice are weighed and given either the compound of interest administered i.p. or p.o., or the appropriate volume of vehicle (for example, 10% Tween-80 or 0.9% saline, and other pharmaceutically acceptable vehicles) as control. Fifteen minutes after the i.p. dosing, and 30 minutes after the p.o. dosing mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value <0.05 is considered significant. Compounds are considered to be efficacious for treating acute and chronic pain if they have activity in blocking both the early and second phase of formalin-induced paw-licking activity.

In Vivo Assays for Inflammatory or Neuropathic Pain

Test Animals:

Each experiment uses rats weighing between 200-260 g at the start of the experiment. The rats are group-housed and have free access to food and water at all times, except prior to oral administration of a test compound when food is removed for 16 hours before dosing. A control group acts as a comparison to rats treated with a compound of Formulae I-XXXIII. The control group is administered the carrier as used for the test compound. The volume of carrier administered to the control group is the same as the volume of carrier and test compound administered to the test group.

Inflammatory Pain:

To assess the actions of the compounds of Formulae I-XXXIII on the treatment of inflammatory pain the Freund's complete adjuvant ("FCA") model of inflammatory pain is used. FCA-induced inflammation of the rat hind paw is associated with the development of persistent inflammatory mechanical and thermal hyperalgesia and provides reliable prediction of the anti-hyperalgesic action of clinically useful analgesic drugs (Bartho et al., *Naunyn-Schmiedeberg's Archives of Pharmacol.* 342:666-670 (1990)). The left hind paw of each animal is administered a 50 μL intraplantar injection of 50% FCA. 24 hour post injection, the animal is assessed for response to noxious mechanical stimuli by determining the paw withdrawal threshold (PWT), or to noxious thermal stimuli by determining the paw withdrawal latency (PWL), as described below. Rats are then administered a single injection of either a test compound or 30 mg/kg of a positive control compound (indomethacin). Responses to noxious mechanical or thermal stimuli are then determined 1, 3, 5 and 24 hours post administration (admin). Percentage reversal of hyperalgesia for each animal is defined as:

$$\% \text{ reversal} = \frac{\begin{bmatrix} (\text{post administration } PWT \text{ or } PWL) - \\ (\text{pre-administration } PWT \text{ or } PWL) \end{bmatrix}}{\begin{bmatrix} (\text{baseline } PWT \text{ or } PWL) - \\ (\text{pre-administration } PWT \text{ or } PWL) \end{bmatrix}} \times 100$$

Neuropathic Pain:

To assess the actions of the test compounds for the treatment of neuropathic pain the Seltzer model and the Chung model were used.

In the Seltzer model, the partial sciatic nerve ligation model of neuropathic pain was used to produce neuropathic hyperalgesia in rats (Seltzer et al., Pain 43:205-218 (1990)). Partial ligation of the left sciatic nerve was performed under inhalation anesthesia, e.g., isoflurane/$O_2$. Following induction of anesthesia, the left thigh of the rat was shaved and the sciatic nerve exposed at high thigh level through a small incision and was carefully cleared of surrounding connective tissues at a site near the trocanther just distal to the point at which the posterior biceps semitendinosus nerve branches off of the common sciatic nerve. A 7-0 silk suture was inserted into the nerve, e.g., with a ⅜ curved, reversed-cutting mini-needle, and tightly ligated so that the dorsal ⅓ to ½ of the nerve thickness was held within the ligature. The wound was closed, e.g., with a single muscle suture (4-0 nylon (Vicryl)) and vetbond tissue glue. Following surgery, the wound area was dusted with antibiotic powder. Sham-treated rats undergo an identical surgical procedure except that the sciatic nerve is not manipulated. Following surgery, animals were weighed and placed on a warm pad until they recovered from anesthesia. Animals were then returned to their home cages until behavioral testing began. The animals were assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \text{ reversal} = \frac{[(\text{post administration } PWT) - (\text{pre-administration } PWT)]}{[(\text{baseline } PWT) - (\text{pre-administration } PWT)]} \times 100$$

The following compounds were tested and produced a statistically significant increase in paw withdrawal threshold when administered at 30 mg/kg p.o. in the Seltzer model of neuropathic pain at the time points indicated:

| Cpd No. | Vehicle | Time post-dose (h) |
| --- | --- | --- |
| 5 | 0.5% carboxymethylcellulose | 1 |
| 13 | 10% Tween 80 in water | 1, 3, and 5 |
| 18 | 10% Tween 80 in water | 1 |
| 30 | 0.5% carboxymethylcellulose | 1 |
| 40 | 0.5% carboxymethylcellulose | 1 |
| 68 | 0.5% carboxymethylcellulose | 1 |

Cpd No. 63 (vehicle: 10% Tween 80 in water) did not produce a statistically significant increase in paw withdrawal threshold in the Seltzer model at 30 mg/kg p.o.

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anesthesia. Following induction of anesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is (are) isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is (are) not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a compound of Formulae for the left rear paw of the animal. The animals can also be assessed for response to noxious thermal stimuli or for tactile allodynia, as described below. The Chung model for neuropathic pain is described in Kim et al., Pain 50(3):355-363 (1992).

Tactile Allodynia:

Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia:

Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (Biochemistry & Behavior 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

In Vivo Assay for Anticonvulsant Activity

The compounds of the present invention of the present invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

Pharmaceutical Compositions

Although a Compound of the Invention can be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Pharmaceutical compositions within the scope of the present invention include all compositions where a Compound of the Invention is combined with a pharmaceutically acceptable carrier. In one embodiment, the compound is present in the composition in an amount that is effective to achieve its intended therapeutic purpose. While individual needs may vary, a determination of optimal ranges of effective amounts of each compound is within the skill of the art. Typically, a compound can be administered to a mammal, e.g., a human, orally at a dose of from about 0.0025 to about 1500 mg per kg body weight of the mammal, or an equivalent amount of a pharmaceutically acceptable salt, prodrug, or solvate thereof, per day to treat the particular disorder. A useful oral dose of a Compound of the Invention administered to a mammal is from about 0.0025 to about 50 mg per kg body weight of the mammal, or an equivalent amount of the pharmaceutically acceptable salt, prodrug, or solvate thereof. For intramuscular injection, the dose is typically about one-half of the oral dose.

A unit oral dose may comprise from about 0.01 to about 50 mg, and preferably about 0.1 to about 10 mg, of the compound. The unit dose can be administered one or more times daily, e.g., as one or more tablets or capsules, each containing from about 0.01 to about 50 mg of the compound, or an equivalent amount of a pharmaceutically acceptable salt, prodrug or solvate thereof.

A pharmaceutical composition of the present invention can be administered to any animal that may experience the beneficial effects of a compound of the present invention. Foremost among such animals are mammals, e.g., humans and companion animals, although the invention is not intended to be so limited.

A pharmaceutical composition of the present invention can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

In one embodiment, a pharmaceutical composition of the present invention can be administered orally and is formulated into tablets, dragees, capsules or an oral liquid preparation. In one embodiment, the oral formulation comprises extruded multiparticulates comprising the compound of the invention.

Alternatively, a pharmaceutical composition of the present invention can be administered rectally, and is formulated in suppositories.

Alternatively, a pharmaceutical composition of the present invention can be administered by injection.

Alternatively, a pharmaceutical composition of the present invention can be administered transdermally.

Alternatively, a pharmaceutical composition of the present invention can be administered by inhalation or by intranasal or transmucosal administration.

Alternatively, a pharmaceutical composition of the present invention can be administered by the intravaginal route.

A pharmaceutical composition of the present invention can contain from about 0.01 to 99 percent by weight, and preferably from about 0.25 to 75 percent by weight, of active compound(s).

A method of the present invention, such as a method for treating a disorder responsive to the blockade of sodium channels in an animal in need thereof, can further comprise administering a second therapeutic agent to the animal in combination with a compound of the present invention. In one embodiment, the other therapeutic agent is administered in an effective amount.

Effective amounts of the other therapeutic agents are known to those skilled in the art. However, it is well within the skilled artisan's purview to determine the other therapeutic agent's optimal effective-amount range.

A compound of the present invention (i.e., the first therapeutic agent) and the second therapeutic agent can act additively or, in one embodiment, synergistically. Alternatively, the second therapeutic agent can be used to treat a disorder or condition that is different from the disorder or condition for which the first therapeutic agent is being administered, and which disorder or condition may or may not be a condition or disorder as defined herein. In one embodiment, a compound of the present invention is administered concurrently with a second therapeutic agent; for example, a single composition comprising both an effective amount of a compound of any of Formulae I-XXXIII, and an effective amount of the second therapeutic agent can be administered. Accordingly, the present invention further provides a pharmaceutical composition comprising a combination of a compound of the present invention, the second therapeutic agent, and a pharmaceutically acceptable carrier. Alternatively, a first pharmaceutical composition comprising an effective amount of a compound of any of Formulae I-XXXIII and a second pharmaceutical composition comprising an effective amount of the second therapeutic agent can be concurrently administered. In another embodiment, an effective amount of a compound of the present invention is administered prior or subsequent to administration of an effective amount of the second therapeutic agent. In this embodiment, the compound of the present invention is administered while the second therapeutic agent exerts its therapeutic effect, or the second therapeutic agent is administered while the compound of the present invention exerts its therapeutic effect for treating a disorder or condition.

The second therapeutic agent can be an opioid agonist, a non-opioid analgesic, a non-steroidal anti-inflammatory agent, an antimigraine agent, a Cox-II inhibitor, a β-adrenergic blocker, an anticonvulsant, an antidepressant, an anti-cancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphine, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydro codeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol. II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful antimigraine agents include, but are not limited to, alpipride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating epilepsy or seizure include, but are not limited to, carbamazepine, ethosuximide, gabapentin, lamotrigine, phenobarbital, phenytoin, primidone, valproic acid, trimethadione, benzodiazepines, gamma-vinyl GABA, acetazolamide, and felbamate.

Examples of useful therapeutic agents for treating stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating a pruritic condition include, but are not limited to, naltrexone; nalmefene; danazol; tricyclics such as amitryptyline, imipramine, and doxepin; antidepressants such as those given below; menthol; camphor; phenol; pramoxine; capsaicin; tar; steroids; and antihistamines.

Examples of useful therapeutic agents for treating psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating ALS include, but are not limited to, baclofen, neurotrophic factors, riluzole, tizanidine, benzodiazepines such as clonazepan and dantrolene.

Examples of useful therapeutic agents for treating cognitive disorders include, but are not limited to, agents for treating dementia such as tacrine; donepezil; ibuprofen; antipsychotic drugs such as thioridazine and haloperidol; and antidepressant drugs such as those given below.

Examples of useful therapeutic agents for treating a migraine include, but are not limited to, sumatriptan; methysergide; ergotamine; caffeine; and beta-blockers such as propranolol, verapamil, and divalproex.

Examples of useful therapeutic agents for treating vomiting include, but are not limited to, 5-HT3 receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating dyskinesia include, but are not limited to, reserpine and tetrabenazine.

Examples of useful therapeutic agents for treating depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A pharmaceutical composition of the present invention is preferably manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate can be used. Dye stuffs or pigments can be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

Synthesis of 1-(6-(4-(4-(trifluoromethyl)phenoxy) phenyl)pyridin-2-yl)ethane-1,2-diol Compound Example No. 3 and Related ethane-1,2-diol-Containing Compounds

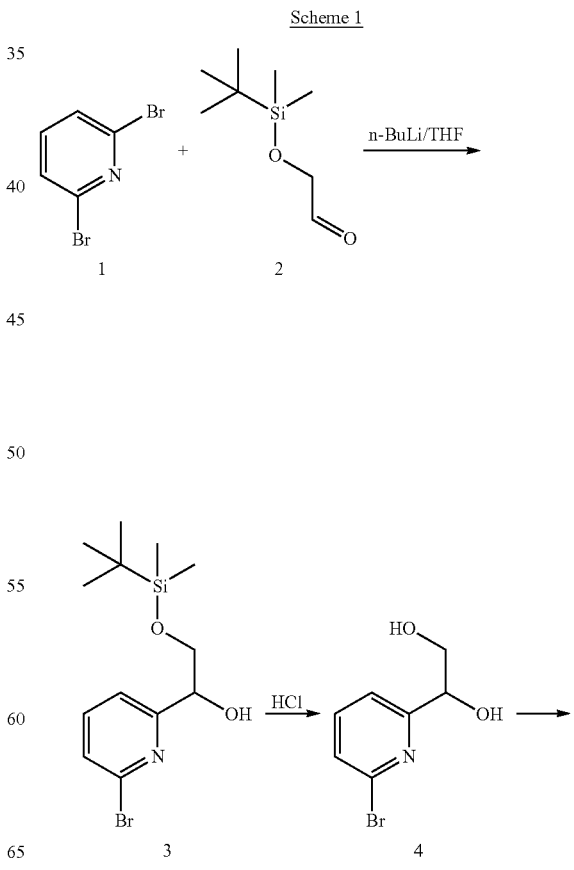

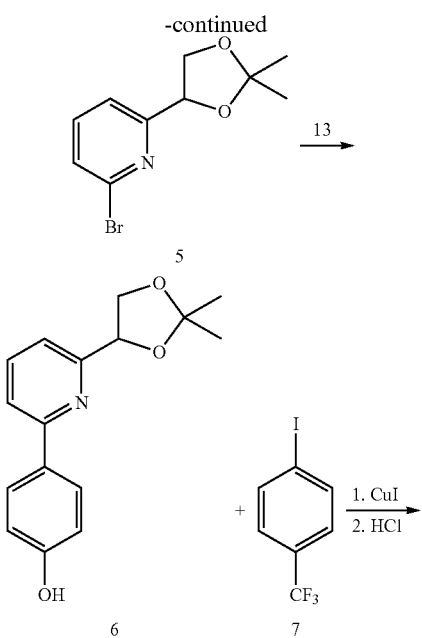

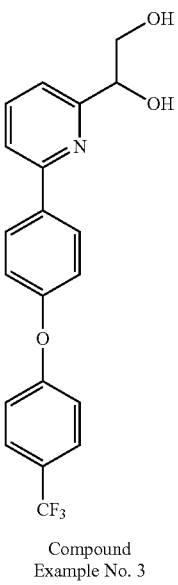

Compound Example No. 3

As described in Scheme 1, compound 1 (2.4 g, 10 mmol, Aldrich) was added to a solution of n-BuLi (2.5N in hexanes, 5 mL Aldrich) in 20 mL THF at −70° C. over 40 min. After 1 h, compound 2 (2 g, Aldrich) was added, and the reaction mixture was kept at −70° C. for 30 min. The reaction was quenched with MeOH (4 mL) and HCl (4 mL) and warmed to room temperature for 3 h. The reaction mixture was diluted with water, neutralized with NaOH (2N) and extracted with CHCl$_3$ (3×50 mL). The combined organic layers were concentrated and purified by column chromatography (CHCl$_3$/MeOH 10/0.2) to give compound 4 as yellow oil. $^1$H NMR (400 MHz, CDCl$_3$): 7.62 (dd, 1H, 7.6 and 7.8 Hz), 7.46 (d, 1H, 7.8 Hz), 7.40 (d, 1H, 7.6 Hz), 4.82-4.86 (m, 1H), 3.94-3.98 (m, 1H), 3.79-3.84 (m, 1H), 3.74-3.76 (m, 1H), 2.34-2.4 (m, 1H). 2,2, Dimethoxypropane (6 mL, 8.4 mmol, Aldrich) and toluenesulfonic acid (0.50 g, Aldrich) were added to a solution of compound 4 (8 g, 1.0 eq.) in DMF (150 mL). The solution was stirred at room temperature for 24 h. K$_2$CO$_3$ (2 g) was added and the reaction mixture was concentrated under vacuum at 40° C. for 1 h. The residue was diluted with 200 mL EtOH (0.5 mL water) and K$_2$CO$_3$ (14 g) and 4-HYDROXYPHENYLBORONIC ACID (compound 13, 1.05 eq., Accela Chembio) and [(o-tolyl)$_3$P]$_2$PdCl$_2$ (1 g, Aldrich) were added. The reaction mixture was flushed with argon and shaken at 80° C. for 16 h. After cooling to room temperature, the reaction mixture was filtered, concentrated, diluted with 0.2N HCl (100 mL), and extracted with CHCl$_3$ (500 mL). The organic layer was concentrated and purified to give compound 6 as brown oil.

A mixture of compound 6 (0.3 g, 1.1 mmol), 4-IODOBENZOTRIFLUORIDE (0.35 g, Aldrich), K$_2$CO$_3$ and CuI (0.1 g) in DMF (5 mL) was shaken at 110° C. for 48 h. After cooling to room temperature, the reaction mixture was diluted with water, extracted with CHCl$_3$ and concentrated to give a brown oil. The brown oil was dissolved in THF/MeOH (4 mL/1 mL) and treated with 1N (HCl 5 mL) at room temperature for 10 h. The solvent was evaporated, diluted with CHCl$_3$ (20 mL), neutralized with 1N NaOH, concentrated and purified by column chromatography (CHCl$_3$/MeOH 10/1) to give 1-(6-(4-(4-(trifluoromethyl)phenoxy)phenyl)pyridin-2-yl)ethane-1,2-diol (Compound Example No. 3) as a white solid (200 mg, yield 50%). $^1$H NMR (400 MHz, CDCl$_3$): 7.92-7.96 (m, 2H), 7.75 (dd, 1H, 7.6 and 7.8 Hz), 7.6 (d, 1H, 7.6 Hz), 7.53-7.56 (m, 2H), 7.23 (d, 1H, 7.6 Hz), 7.03-7.11 (m, 4H), 4.81-4.84 (m, 1H), 3.91-3.95 (m, 1H), 3.74-3.78 (m, 1H); LC/MS: m/z=376.5 [M+H]$^+$. Unless otherwise indicated all $^1$H NMR chemical shifts reported herein are denoted by the delta (δ) scale.

Example 2

General Procedure for the Synthesis of 1-(6-(4-((5-(trifluoromethyl)pyridin-2-yl)oxy)phenyl)pyridin-2-yl)ethane-1,2-diol (Compound Example No. 8) and Related Compounds Compound Example Nos. 9, 10, 12, 15, 16, 20, and 29

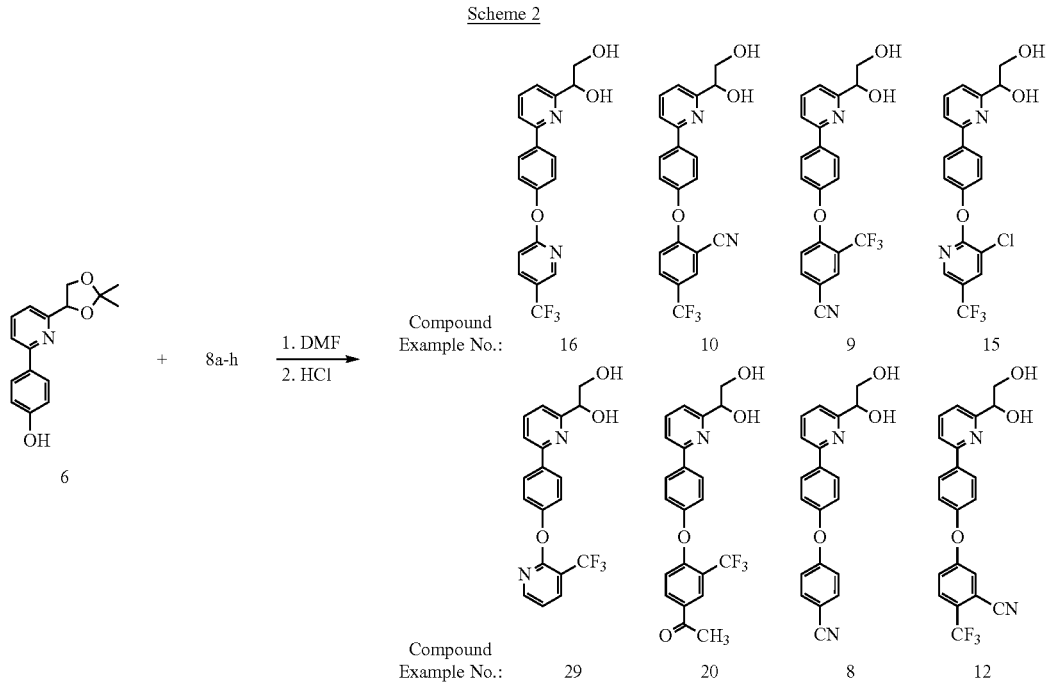

Scheme 2

As described in Scheme 2, a mixture of compound 6 (200 mg, 1.0 eq.), 1.05 eq. of:
2-BROMO-5-(TRIFLUOROMETHYL)PYRIDINE (compound 8a; Maybridge);
2-FLUORO-5-(TRIFLUOROMETHYL)BENZONITRILE (compound 8b; Matrix Scientific);
4-FLUORO-3-(TRIFLUOROMETHYL)BENZONITRILE (compound 8c; Matrix Scientific);
3-CHLORO-2-FLUORO-5-(TRIFLUOROMETHYL) PYRIDINE (8d; Aldrich);
2-CHLORO-3-(TRIFLUOROMETHYL)PYRIDINE (compound 8e; Oakwood);
4'-FLUORO-3'-(TRIFLUOROMETHYL)ACETOPHENONE (compound 8f; Matrix Scientific);
4-FLUORO BENZONITRILE (compound 8g; Aldrich); or
5-FLUORO-2-(TRIFLUOROMETHYL)BENZONITRILE (compound 8h; Oakwood), K$_2$CO$_3$ (4 eq.) and DMF (5 mL) was shaken at 110° C. for 16 h. After cooling to room temperature, the mixture was diluted with water (20 mL), extracted with CHCl$_3$ (3×20 mL), and concentrated. The residue was dissolved in THF/MeOH (10 mL/4 mL), and treated with HCl (1N, 3 mL) at room temperature for 12 h. The solvent was evaporated and the residue was diluted with CHCl$_3$ (20 mL), neutralized with NH$_4$OH (28% aqueous) and purified by column chromatography (CH$_3$Cl/MeOH 10/1) to give:

1-(6-(4-((5-(trifluoromethyl)pyridin-2-yl)oxy)phenyl)pyridin-2-yl)ethane-1,2-diol (Compound Example No. 16, White Solid): $^1$H NMR (400 MHz, CDCl$_3$): 8.41 (s, 1H), 7.88-8.01 (m, 2H), 7.85-7.88 (m, 1H), 7.72-7.76 (m, 1H), 7.62 (d, 1H, 7.5 Hz), 7.2-7.25 (m, 3H), 7.01 (d, 1H, 8.8 Hz), 4.81-4.84 (m, 1H), 4.5 (br, 1H, —OH), 3.91-3.95 (m, 1H), 3.74-3.78 (m, 1H), 2.65 (Br, 1H, —OH); LC/MS: m/z=377.4 [M+H]$^+$.

2-(4-(6-(1,2-dihydroxyethyl)pyridin-2-yl)phenoxy)-5-(trifluoromethyl)benzonitrile (Compound Example No. 10, White Solid) %): $^1$H NMR (400 MHz, CD$_3$OD): 8.06-8.1 (m, 2H), 7.98-7.99 (m, 1H), 7.85 (dd, 1H, 7.6 and 7.8 Hz), 7.74-7.78 (m, 1H), 7.68 (d, 1H, 7.8 Hz), 7.48 (d, 1H, 8.1 Hz), 7.22-7.26 (m, 2H), 7.02 (d, 1H, 8.9 Hz), 4.84-4.88 (m, 1H), 3.94-3.97 (m, 1H), 3.77-3.82 (m, 1H); LC/MS: m/z=401.5 [M+H]$^+$.

4-(4-(6-(1,2-dihydroxyethyl)pyridin-2-yl)phenoxy)-3-(trifluoromethyl)benzonitrile (Compound Example No. 9, White Solid): $^1$H NMR (400 MHz, CD$_3$OD): 8.01-8.1 (m, 3H), 7.76-7.85 (m, 2H), 7.67 (d, 1H, 7.9 Hz), 7.44-7.48 (m, 1H), 7.18-7.22 (m, 2H), 7.03 (d, 1H, 8.9 Hz), 4.84-4.88 (m, 1H), 3.94-3.97 (m, 1H), 3.77-3.82 (m, 1H); LC/MS: m/z=401.4 [M+H]$^+$.

1-(6-(4-((3-chloro-5-(trifluoromethyl)pyridin-2-yl)oxy)phenyl)pyridin-2-yl) ethane-1,2-diol (Compound Example No. 15, White Solid): $^1$H NMR (400 MHz, CD$_3$OD): 8.26 (s, 1H), 8.03-8.07 (m, 3H), 7.82 (dd, 1H, 7.6 and 7.8 Hz), 7.68 (d, 1H, 7.8 Hz), 7.45 (d, 1H, 7.6 Hz), 7.25-7.29 (m, 2H), 4.84-4.88 (m, 1H), 3.92-3.95 (m, 1H), 3.76-3.81 (m, 1H); LC/MS: m/z=411.5 [M+H]$^+$.

1-(6-(4-((3-(trifluoromethyl)pyridin-2-yl)oxy)phenyl)pyridin-2-yl)ethane-1,2-diol (Compound Example No. 29, White Solid): $^1$H NMR (400 MHz, CD$_3$OD): 8.2-8.23 (m, 1H), 7.96-8.03 (m, 3H), 7.77 (dd, 1H, 7.8 and 7.9 Hz), 7.62 (d, 1H, 7.7 Hz), 7.41 (d, 1H, 7.7 Hz), 7.11-7.21 (m, 3H), 4.76-4.81 (m, 1H), 3.85-3.89 (m, 1H), 3.69-3.74 (m, 1H); LC/MS: m/z=377.4 [M+H]$^+$.

1-(4-(4-(6-(1,2-dihydroxyethyl)pyridin-2-yl)phenoxy)-3-(trifluoromethyl)phenyl) ethanone (Compound Example No. 20, White Solid): $^1$H NMR (400 MHz, CD$_3$OD): 8.3 (d, 1H, 1.9 Hz), 8.04-8.11 (m, 3H), 7.84 (dd, 1H, 7.8 and 7.9 Hz), 7.68 (d, 1H, 7.6 Hz), 7.48 (d, 1H, 7.7 Hz), 7.18-7.21 (m, 2H), 7.02 (d, 1H, 7.8 Hz), 4.84-4.88 (m, 1H), 3.94-3.97 (m, 1H), 3.77-3.82 (m, 1H), 2.62 (s, 3H); LC/MS: m/z=418.5 [M+H]$^+$.

4-(4-(6-(1,2-dihydroxyethyl)pyridin-2-yl)phenoxy)benzonitrile (Compound Example No. 8, White Solid): $^1$H NMR (400 MHz, CD$_3$OD): 8.3 (d, 1H, 1.9 Hz), 8.01-8.02 (m, 2H), 7.84 (dd, 1H, 7.8 and 7.9 Hz), 7.64-7.66 (m, 3H), 7.44 (d, 1H, 7.7 Hz), 7.14-7.17 (m, 2H), 7.06-7.09 (m, 2H), 4.84-4.88 (m, 1H), 3.94-3.97 (m, 1H), 3.77-3.87 (m, 1H); LC/MS: m/z=333.5 [M+H]$^+$.

5-(4-(6-(1,2-dihydroxyethyl)pyridin-2-yl)phenoxy)-2-(trifluoromethyl)benzonitrile (Compound Example No. 12, White Solid): $^1$H NMR (400 MHz, CD$_3$OD): 8.06-8.1 (m, 2H), 7.85 (dd, 1H, 7.8 and 7.9 Hz), 7.79 (d, 1H, 8.9 Hz), 7.69 (d, 1H, 7.7 Hz), 7.44-7.5 (m, 2H), 7.33-7.37 (m, 1H), 7.18-7.22 (m, 2H), 4.84-4.88 (m, 1H), 3.94-3.98 (m, 1H), 3.78-3.82 (m, 1H); LC/MS: m/z=401.4 [M+H]$^+$.

Example 3

General Procedure for the Synthesis of 1-(6-(4-((6-methylpyridin-3-yl)oxy)phenyl)pyridin-2-yl)ethane-1,2-diol (Compound Example No. 17) and 1-(6-(4-((6-methylpyridin-3-yl)oxy)phenyl)pyridin-2-yl)ethane-1,2-diol (Compound Example No. 27)

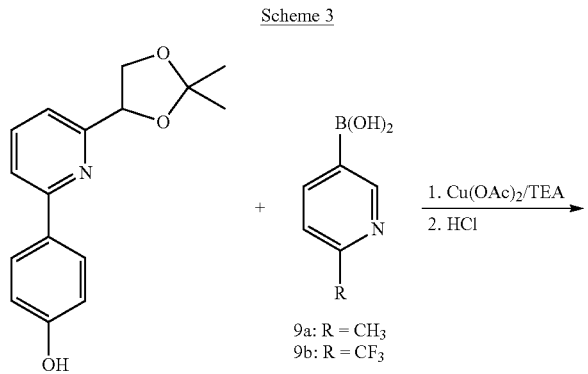

Scheme 3

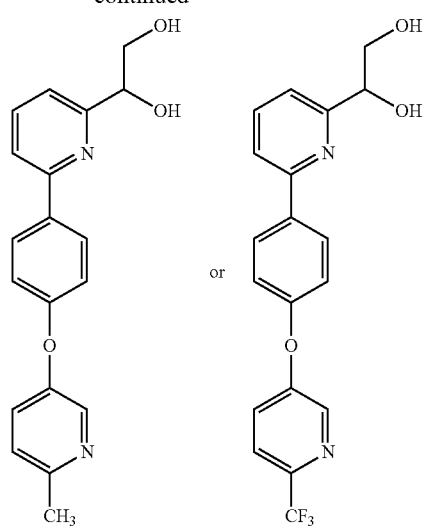

Compound Example No. 27    Compound Example No. 17

As described in Scheme 3, a mixture of compound 6 (200 mg, 1.0 eq.), compound 9a or 9b (1.1 eq., Combi-Blocks, LLC), triethylamine (4 eq.), Cu(OAc)$_2$ (0.3 eq., Aldrich), and 4 Å molecular sieves (0.4 g, Aldrich) in 10 mL of DCM was shaken at 40° C. for 96 h. After cooling to room temperature, the mixture was filtered, diluted with water (20 mL) and extracted with CHCl$_3$ (3×20 mL). The combined organic layers were concentrated. The residue was dissolved in THF/MeOH (10 mL/4 mL), and treated with HCl (1N, 3 mL) at room temperature for 12 h. The solvent was evaporated, and the residue was treated with CHCl$_3$ (20 mL), neutralized with NH$_4$OH (28% aqueous) and purified by column chromatography (CH$_3$Cl/MeOH 10/1) to give:

1-(6-(4-((6-methylpyridin-3-yl)oxy)phenyl)pyridin-2-yl)ethane-1,2-diol (Compound Example No. 27, brown solid, 20%):): $^1$H NMR (400 MHz, CD$_3$OD): 8.16 (d, 1H, 2.8 Hz), 7.88-7.91 (m, 2H), 7.96-8.03 (m, 3H), 7.74 (dd, 1H, 7.6 and 7.8 Hz), 7.56 (d, 1H, 7.8 Hz), 7.35 (d, 1H, 7.6 Hz), 7.28 (dd, 1H, 2.8 and 8.5 Hz), 7.16 (d, 1H, 8.5 Hz), 7.0-7.08 (m, 2H), 4.76-4.79 (m, 1H), 3.85-3.89 (m, 1H), 3.69-3.74 (m, 1H), 2.47 (s, 3H); LC/MS: m/z=323.1 [M+H]$^+$.

1-(6-(4-((6-methylpyridin-3-yl)oxy)phenyl)pyridin-2-yl)ethane-1,2-diol (Compound Example No. 17, White Solid, 30%):): $^1$H NMR (400 MHz, CD$_3$OD): 8.4 (d, 1H, 2.6 Hz), 7.96-8.01 (m, 2H), 7.74 (dd, 1H, 7.6 and 7.8 Hz), 7.59-7.62 (m, 2H), 7.38-7.42 (m, 2H), 7.1-7.14 (m, 2H), 4.76-4.79 (m, 1H), 3.85-3.89 (m, 1H), 3.69-3.74 (m, 1H); LC/MS: m/z=377.1 [M+H]$^+$.

Example 4

Synthesis of (R)-1-(6-(4-((5-(trifluoromethyl)pyridin-2-yl)oxy)phenyl)pyridin-2-yl)ethane-1,2-diol (Compound Example No. 23) and Related Compounds (Compound Example Nos. 6, 11, 13, 14, 18, 22, and 24)

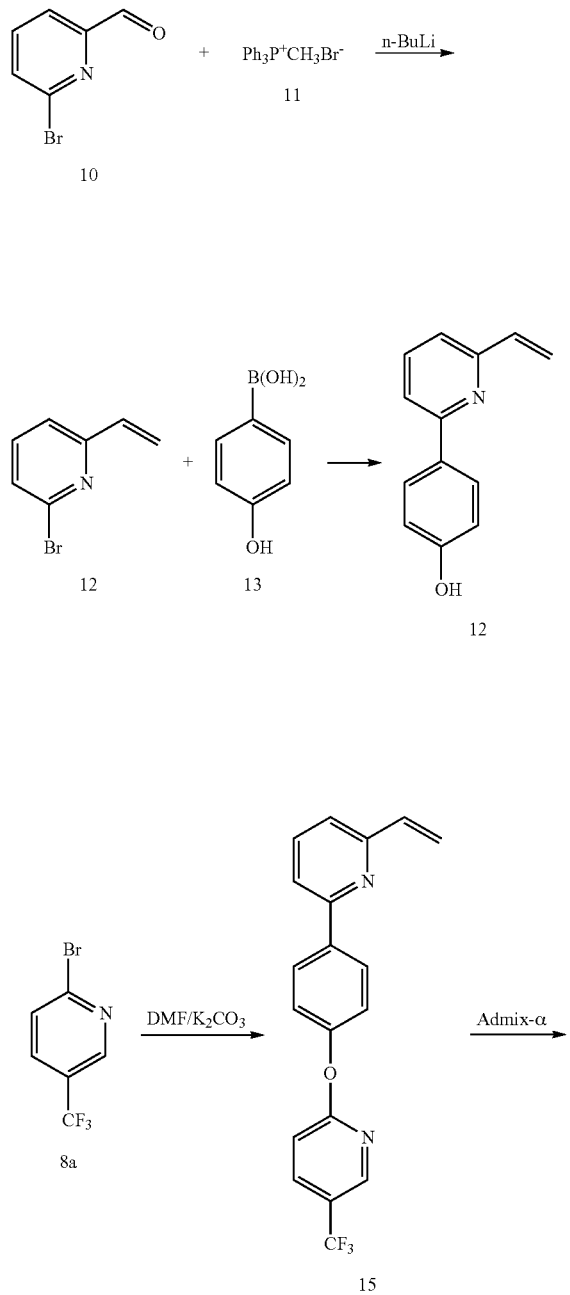

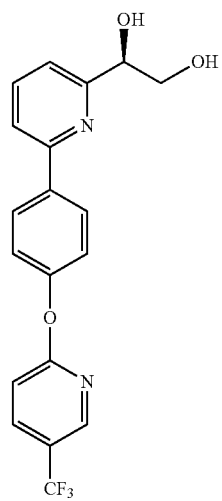

Compound Example No. 23

As described in Scheme 4, n-BuLi (22 mL, 2.5N in hexane) was added to a suspension of compound 11 (19 g, Aldrich) in 300 mL THF at −30° C. The mixture was stirred under argon at −20° C. for 1 h to give a yellow solution, and then it was added a solution of compound 10 (10 g, Accela Chembio) in 50 mL THF over 5 min. The reaction mixture was warmed to room temperature over 1 h and heated at 35° C. for 10 h. The reaction was quenched with water (150 mL) and extracted with $CHCl_3$ (3×150 mL). The combined organic layers were concentrated and purified by column chromatography ($CHCl_3$/hexanes 1/2) to give compound 12 as colorless oil (7 g): $^1$H NMR (400 MHz, $CDCl_3$): 7.42 (dd, 1H, 7.6 and 7.8 Hz), 7.27 (d, 1H, 7.6 Hz), 7.2 (dd, 1H, 0.7 and 7.6 Hz), 6.66 (dd, 1H, 10.2 and 17.5 Hz), 6.17 (dd, 1H, 1.0 and 17.3 Hz), 5.44 (dd, 1H, 0.8 and 17.3 Hz).

A mixture of compound 12 (4.5 g), $K_2CO_3$ (10 g), 13 (4 g) and Pd[(o-Tolyl)$_3$P]$_2$Cl$_2$ (400 mg) in 100 mL EtOH was heated under argon at 60° C. for 24 h. After cooling to room temperature, the reaction was quenched with water (100 mL) and extracted with $CHCl_3$ (2×200 mL). The combined organic layers were concentrated to give compound 14 as brown solid.

A mixture of compound 14 (0.3 g, 1.0 eq.), compound 8a (1.0 eq.), and $K_2CO_3$ (3 eq.) in 4 mL DMF was shaken at 95° C. for 24 h. The reaction mixture was diluted with water (20 mL) and extracted with $CHCl_3$ (2×40 mL). The combined organic layers were concentrated and purified by column chromatography (silica gel, $CHCl_3$/MeOH 10/0.5) to give compound 15 as white solid (200 mg, yield: 40%): $^1$H NMR (400 MHz, $CDCl_3$): 8.4 (m, 1H), 8.04-8.07 (m, 2H), 7.85 (dd, 1H, 2.6 and 8.5 Hz), 7.65 (dd, 1H, 7.6 and 7.8 Hz), 7.54 (dd, 1H, 0.8 and 7.7 Hz), 7.18-7.22 (m, 3H), 6.98 (d, 1H, 8.8 Hz), 6.83 (dd, 1H, 10.2 and 17.5 Hz), 6.17 (dd, 1H, 1.5 and 17.3 Hz), 5.44 (dd, 1H, 1.5 and 10.7 Hz).

Admix-α (0.43 g, Aldrich) was added to a solution of compound 15 (0.1 g) in 30 mL (t-BuOH/water 1/1) at 0° C. The reaction mixture was slowly warmed to room temperature for two days. The reaction mixture was diluted with water (40 mL) and extracted with $CHCl_3$. The organic layer was concentrated and purified by column chromatography (silica gel, EtOAc/hexanes 1/1) to get (R)-1-(6-(4-((5-(trifluoromethyl)pyridin-2-yl)oxy)phenyl)pyridin-2-yl)ethane-1,2-diol (Compound Example No. 23) as white solid (70 mg, yield 60%): ¹H NMR (400 MHz, CDCl₃): 8.35 (m, 1H), 7.96-8.01 (m, 2H), 7.92 (dd, 1H, 2.6 and 8.5 Hz), 7.62 (d, 1H, 7.7 Hz), 7.4 (d, 1H, 7.7 Hz), 7.18-7.22 (m, 2H), 7.03 (d, 1H, 8.7 Hz), 4.77-4.81 (m, 1H), 3.85-3.90 (m, 1H), 3.7-3.74 (m, 1H); LC/MS: m/z=377.4 [M+H]⁺.

Compound Example Nos. 11, 13, and 14 were prepared following the same procedure as Compound Example No. 23 using compounds 8c, 8g, and 8h instead of compound 8a:

(R)-4-(4-(6-(1,2-dihydroxyethyl)pyridin-2-yl)phenoxy)-3-(trifluoromethyl)benzonitrile (Compound Example No. 11, White Solid): ¹H NMR (400 MHz, CDCl₃): 7.92-8.01 (m, 3H), 7.77 (dd, 1H, 7.6 and 7.8 Hz), 7.66 (dd, 1H, 1.9 and 8.7 Hz), 7.62 (d, 1H, 7.6 Hz), 7.27 (d, 1H, 7.4 Hz), 7.12-7.15 (m, 2H), 6.94 (d, 1H, 8.8 Hz), 4.82-4.85 (m, 1H), 4.44 (br, 1H), 3.92-3.96 (m, 1H), 3.75-3.79 (m, 1H), 2.5 (br, 1H); LC/MS: m/z=401.0 [M+H]⁺.

(R)-4-(4-(6-(1,2-dihydroxyethyl)pyridin-2-yl)phenoxy)benzonitrile (Compound Example No. 13, White Solid): ¹H NMR (400 MHz, CDCl₃): 7.96-7.99 (m, 2H), 7.76 (dd, 1H, 7.6 and 7.8 Hz), 7.61 (d, 1H, 7.7 Hz), 7.55-7.58 (m, 2H), 7.24 (d, 1H, 7.4 Hz), 7.09-7.12 (m, 2H), 6.99-7.02 (m, 2H), 4.82-4.85 (m, 1H), 4.49 (br, 1H), 3.92-3.96 (m, 1H), 3.75-3.79 (m, 1H), 2.6 (br, 1H); LC/MS: m/z=333.1 [M+H]⁺.

(R)-5-(4-(6-(1,2-dihydroxyethyl)pyridin-2-yl)phenoxy)-2-(trifluoromethyl)benzonitrile (Compound Example No. 14, White Solid): ¹H NMR (400 MHz, CDCl₃): 7.92-8.03 (m, 2H), 7.77 (dd, 1H, 7.6 and 7.8 Hz), 7.66 (d, 1H, 8.7 Hz), 7.62 (d, 1H, 7.9 Hz), 7.24-7.35 (m, 3H), 7.11-7.14 (m, 2H), 4.82-4.85 (m, 1H), 4.44 (br, 1H), 3.92-3.96 (m, 1H), 3.75-3.79 (m, 1H), 2.55 (br, 1H); LC/MS: m/z=401.0 [M+H]⁺.

Compound Example Nos. 6, 18, 22, and 24 were prepared following the same procedure for Compound Example No. 23 using compounds 8a, 8c, 8g, and 8h and Admix-β (Aldrich) instead of Admix-α:

(S)-1-(6-(4-((5-(trifluoromethyl)pyridin-2-yl)oxy)phenyl)pyridin-2-yl)ethane-1,2-diol (Compound Example No. 24, White Solid): ¹H NMR (400 MHz, CDCl₃): 8.35 (m, 1H), 7.96-8.01 (m, 2H), 7.92 (dd, 1H, 2.6 and 8.5 Hz), 7.62 (d, 1H, 7.7 Hz), 7.4 (d, 1H, 7.7 Hz), 7.18-7.22 (m, 2H), 7.03 (d, 1H, 8.7 Hz), 4.77-4.81 (m, 1H), 3.85-3.90 (m, 1H), 3.7-3.74 (m, 1H); LC/MS: m/z=377.4 [M+H]⁺.

(S)-4-(4-(6-(1,2-dihydroxyethyl)pyridin-2-yl)phenoxy)-3-(trifluoromethyl)benzonitrile (Compound Example No. 22, White Solid): ¹H NMR (400 MHz, CDCl₃): 7.99-8.01 (m, 2H), 7.93 (d, 1H, 1.9 Hz), 7.77 (dd, 1H, 7.6 and 7.8 Hz), 7.66 (dd, 1H, 1.9 and 8.7 Hz), 7.62 (d, 1H, 7.6 Hz), 7.27 (d, 1H, 7.4 Hz), 7.12-7.15 (m, 2H), 6.94 (d, 1H, 8.8 Hz), 4.82-4.85 (m, 1H), 4.44 (br, 1H), 3.92-3.96 (m, 1H), 3.75-3.79 (m, 1H), 2.5 (br, 1H); LC/MS: m/z=401.0 [M+H]⁺.

(S)-4-(4-(6-(1,2-dihydroxyethyl)pyridin-2-yl)phenoxy)benzonitrile (Compound Example No. 6, White Solid): ¹H NMR (400 MHz, CDCl₃): 7.96-7.99 (m, 2H), 7.76 (dd, 1H, 7.6 and 7.8 Hz), 7.61 (d, 1H, 7.7 Hz), 7.55-7.58 (m, 2H), 7.24 (d, 1H, 7.4 Hz), 7.09-7.12 (m, 2H), 6.99-7.02 (m, 2H), 4.82-4.85 (m, 1H), 4.49 (br, 1H), 3.92-3.96 (m, 1H), 3.75-3.79 (m, 1H), 2.6 (br, 1H); LC/MS: m/z=333.1 [M+H]⁺.

(S)-5-(4-(6-(1,2-dihydroxyethyl)pyridin-2-yl)phenoxy)-2-(trifluoromethyl)benzonitrile (Compound Example No. 18, White Solid): ¹H NMR (400 MHz, CDCl₃): 7.92-8.03 (m, 2H), 7.77 (dd, 1H, 7.6 and 7.8 Hz), 7.66 (d, 1H, 8.7 Hz), 7.62 (d, 1H, 7.9 Hz), 7.24-7.35 (m, 3H), 7.11-7.14 (m, 2H), 4.82-4.85 (m, 1H), 3.92-3.96 (m, 1H), 3.75-3.79 (m, 1H), 2.55 (br, 1H); LC/MS: m/z=401.0 [M+H]⁺.

Example 5

General Procedure for the Synthesis of (R)-1-(6-(4-(4-(trifluoromethyl)phenoxy)phenyl)pyridin-2-yl)ethane-1,2-diol (Compound Example No. 5) and (S)-1-(6-(4-(4-(trifluoromethyl)phenoxy)phenyl)pyridin-2-yl)ethane-1,2-diol (Compound Example No. 4)

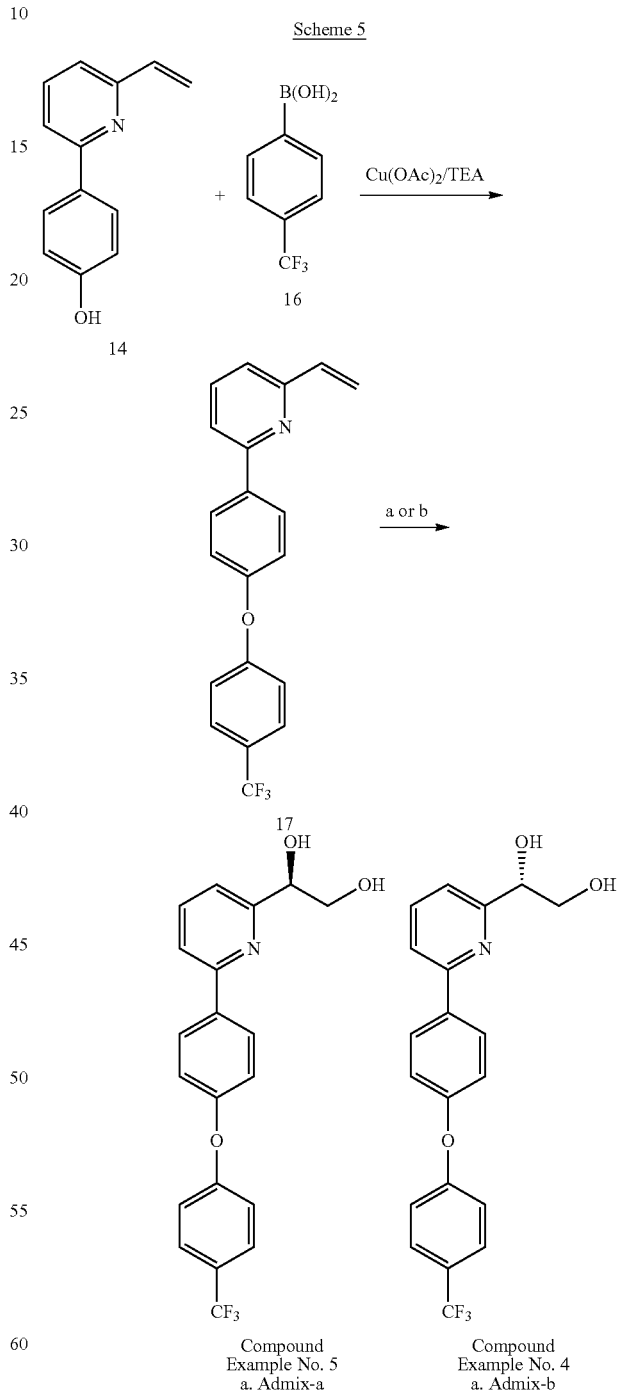

As described in Scheme 5, a mixture of compound 14 (200 mg, 1.0 eq.), compound 16 (1.1 eq., Combi-Blocks, LLC), triethylamine (4 eq.), Cu(OAc)₂ (0.3 eq., Aldrich), and 4 Å molecular sieve (0.4 g, Aldrich) in 15 mL of DCM was shaken at 40° C. for 96 h. After cooling to room temperature, the reaction mixture was filtered, diluted with water (20 mL), and extracted with CHCl₃ (3×20 mL). The combined organic layers were concentrated under vacuum. The residue was dissolved in t-BuOH/water (10 mL/10 mL), cooled in an ice-water bath, and Admix-α or Admix-β, 1.5 eq. (Aldrich) was added. The reaction mixture was warmed to room temperature over night and kept at room temperature for two days. The reaction mixture was diluted with water (30 mL), and extracted with CHCl₃ (3×30 mL). The combined organic layers were concentrated and purified by column chromatography (silica gel, CHCl₃/MeOH 10/0.5) to afford the products as white solids (~30% in two steps):

(R)-1-(6-(4-(4-(trifluoromethyl)phenoxy)phenyl)pyridin-2-yl)ethane-1,2-diol (Compound Example No. 5): ¹H NMR (400 MHz, CD₃OD): 8.01-8.03 (m, 2H), 7.85 (dd, 1H, 7.6 and 7.8 Hz), 7.68 (d, 1H, 7.6 Hz), 7.61-7.63 (m, 2H), 7.47 (d, 1H, 7.6 Hz), 7.13-7.17 (m, 4H), 4.84-4.87 (m, 1H), 3.93-3.97 (m, 1H), 3.77-3.82 (m, 1H); LC/MS: m/z=376.5 [M+H]⁺.

(S)-1-(6-(4-(4-(trifluoromethyl)phenoxy)phenyl)pyridin-2-yl)ethane-1,2-diol (Compound Example No. 4): ¹H NMR (400 MHz, CD₃OD/CD₃Cl 1/1): 7.93-7.96 (m, 2H), 7.76 (dd, 1H, 7.6 and 7.8 Hz), 7.61 (d, 1H, 7.6 Hz), 7.53-7.55 (m, 2H), 7.39 (d, 1H, 7.6 Hz), 7.04-7.09 (m, 4H), 4.76-4.79 (m, 1H), 3.85-3.89 (m, 1H), 3.69-3.74 (m, 1H); LC/MS: m/z=376.5 [M+H]⁺.

Example 6

Synthesis of (S)-2-({6-[4-(4-Fluoro-phenoxyl)-phenyl]-pyridin-2-ylmethyl}-amino)propionamide (Compound Example No. 88)

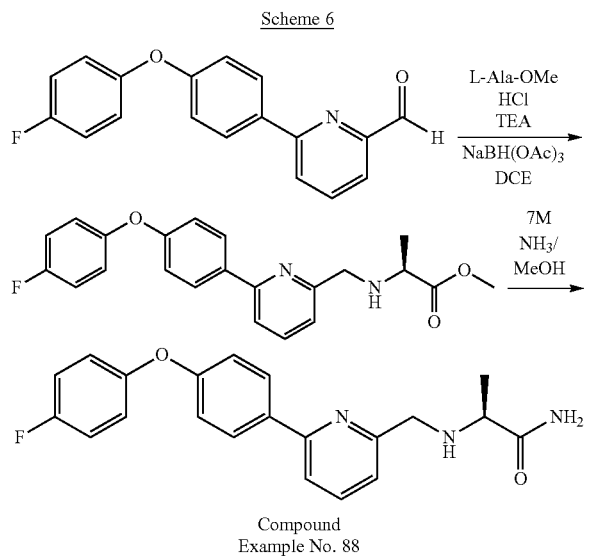

Compound Example No. 88

As described in Scheme 6, Na(OAc)₃BH (216 mg, 1.02 mmol) was added to a solution of aldehyde (200 mg, 0.68 mmol), triethylamine (0.94 mL, 0.68 mmol), L-alanine methyl ester (95 mg, 0.68 mmol) in dichloroethane (15 mL) under argon atmosphere. The reaction mixture was stirred for 15 h at room temperature. After the reaction was complete, ethyl acetate (8.0 mL) was added to reaction mixture which was then washed with sat. NaHCO₃. The organic phase was dried over anhydrous sodium sulfate and the solvent was removed in vacuo to give the oily residue. The crude product was chromatographed to give the ester (228 mg, 88% yield). Rf: 0.3 (EtOAc: Hexanes=1:1), LC/MS: m/z=381 [M+H]⁺.

The ester (60 mg, 0.16 mmol) was dissolved in 7N NH₃/MeOH (5 mL) and stirred for 2 h. After the reaction was complete, the solvent was removed. The residue was purified by preparative TLC to give (S)-2-({6-[4-(4-fluoro-phenoxyl)-phenyl]-pyridin-2-ylmethyl}-amino)propionamide (Compound Example No. 88) as white solid (43 mg, 74% yield). LC/MS: m/z=366 [M+H]⁺, ¹H NMR (400 MHz, CDCl₃): 8.06 (d, J=8.8 Hz, 2H), 7.82 (t, J=7.7 Hz, 1H), 7.71 (d, J=7.6 Hz, 1H), 7.32 (d, J=6.9 Hz, 1H), 7.03-7.18 (m, 6H), 3.91 (q, J=14 Hz, 2H), 3.3 (s, 1H), 1.35 (d, J=7.0 Hz, 3H).

Example 7

Synthesis of (S)-1-{4-((S)-1,2-Dihydroxy-ethyl)-6-[4-(4-fluoro-phenoxy)-phenyl]-pyridin-2-yl}-ethane-1,2-diol (Compound Example No. 26) and (R)-1-{4-((R)-1,2-Dihydroxy-ethyl)-6-[4-(4-fluoro-phenoxy)-phenyl]-pyridin-2-yl}-ethane-1,2-diol (Compound Example No. 19)

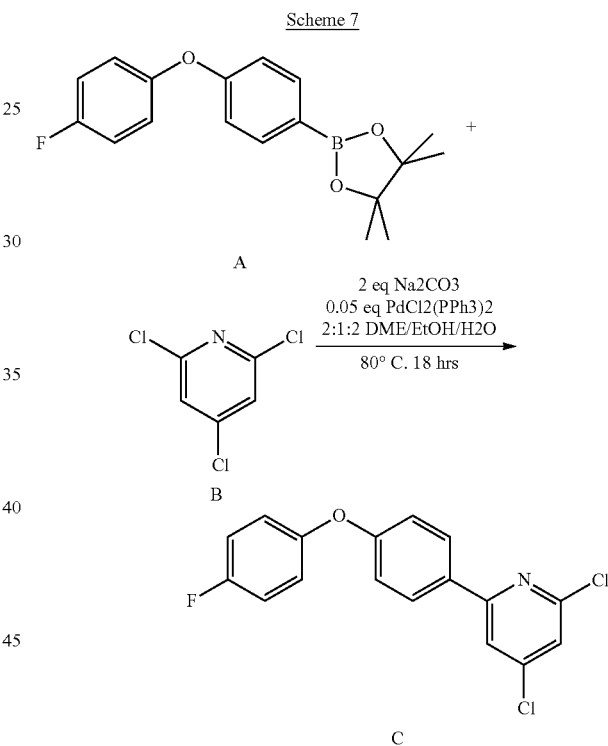

As described in Scheme 7, in a 50-mL vial with a screw-top septum, 4-(4'-fluorophenoxy)phenyl pinacol boronate (compound A) (3 g, 9.55 mmol) was reacted with 2,4,6-trichloropyridine (compound B) (1.73 grams, 9.55 mmol, Sigma Aldrich), sodium carbonate (2 g, 19.1 mmol), and PdCl₂(PPh₃)₂ (335 mg, 0.48 mmol, Sigma Aldrich), in a 20-mL solution of 2 parts dimethoxyethane, 1 part ethanol, and 2 parts water. The reaction mixture was heated to 80° C. overnight. When the reaction was complete as indicated by LC/MS, the mixture was diluted with water (100 mL) and extracted with ethyl acetate (2×100 mL). The organic layers were combined, dried over sodium sulfate, and concentrated. The residue was chromatographed by CombiFlash® (220-gram silica gel, 0-100% EtOAc/Hexane) to provide 2,4-dichloro-6-[4-(4-fluoro-phenoxy)-phenyl]-pyridine (compound C) as a waxy solid (1 g, 3 mmol). ¹H NMR (CHCl₃): 7.97-7.92 (m, 2H), 7.60-7.57 (m, 1H), 7.27-7.24 (m, 1H), 7.11-6.99 (m, 6H). LC/MS: m/z 333.

Scheme 8

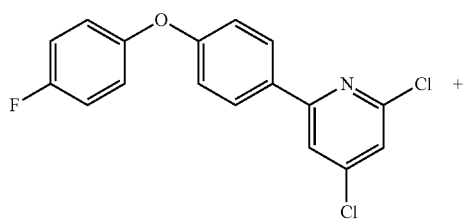

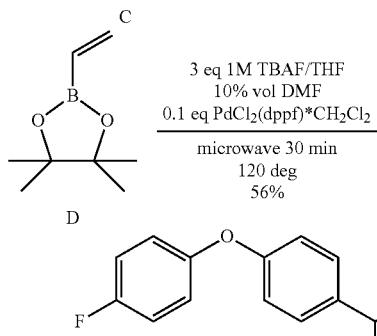

As described in Scheme 8, in a 20-mL microwaveable vial with a crimp-cap septum, compound C (824 mg, 2.47 mmol) was treated with vinyl boronic acid pinacol ester (compound D) (953 mg, 4.94 mmol, Sigma Aldrich), and PdCl$_2$(dppf)*CH$_2$Cl$_2$ (202 mg, 0.247 mmol, Sigma Aldrich), under nitrogen in a solution of tetra-n-butylammonium fluoride (2.5 mL, 1 M in THF, Sigma Aldrich) and dimethylformamide (0.3 mL). The mixture was heated to 120° C. for 30 min. When the reaction was complete, the mixture was adsorbed onto silica gel and chromatographed by CombiFlash® (40-gram silica gel, 0-40% EtOAc/Hexane) to provide 2-[4-(4-Ffluoro-phenoxy)-phenyl]-4,6-divinyl-pyridine (compound E) (435 mg, 1.37 mmol) as a clear oil.

Scheme 9

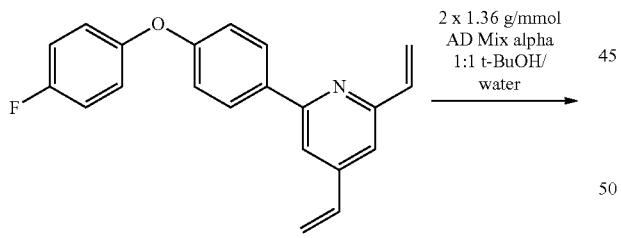

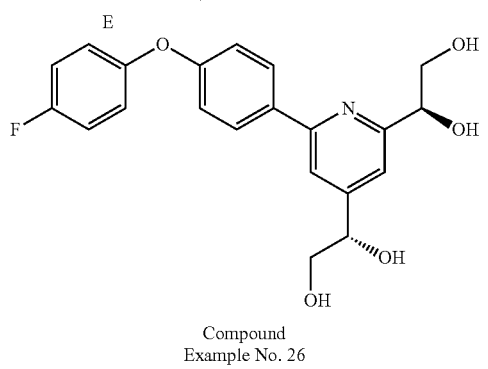

Compound Example No. 26

As described in Scheme 9, In a 50-mL vial with a screw-top septa, compound E (103 mg, 0.325 mmol) was suspended in a 1:1 solution of tert-butanol (3 mL) and water (3 mL) and cooled in an ice water bath for 10 min. AD Mix alpha (884 mg, Sigma Aldrich) was added to the suspension in one portion. The mixture was allowed to warm to room temperature and stir for 18 h. When the reaction was complete, the mixture was diluted with 20 mL water and extracted ethyl acetate (2×20 mL). The organic layer was dried over sodium sulfate, concentrated under vacuum, and chromatographed by CombiFlash® (40-gram silica gel, 0-30% EtOAc/Hexane) to provide (S)-1-{4-((S)-1,2-Dihydroxy-ethyl)-6-[4-(4-fluoro-phenoxy)-phenyl]-pyridin-2-yl}-ethane-1,2-diol (Compound Example No. 26, 29 mg, 0.075 mmol) as a white solid. $^1$H NMR (DMSO-d$_6$): 8.09-8.03 (m, 2H), 7.69 (s, 1H), 7.44 (s, 1H), 7.32-7.23 (m, 2H), 7.18-7.11 (m, 2H), 7.11-7.05 (m, 2H), 5.52-5.47 (m, 1H), 5.43-5.38 (m, 1H), 4.85-4.78 (m, 1H), 4.74-4.69 (m, 1H), 4.67-4.58 (m, 2H), 3.81-3.72 (m, 1H), 3.58-3.47 (m, 3H). LC/MS: m/z 385.

Scheme 10

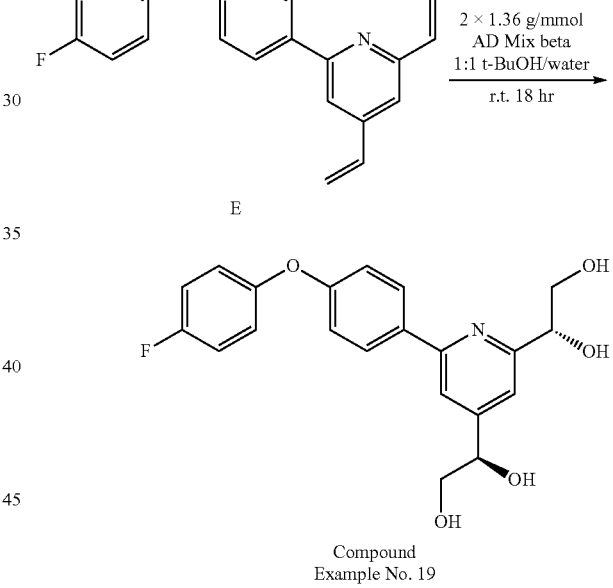

Compound Example No. 19

As described in Scheme 10, in a 50-mL vial with a screw-top septa, compound E (331 mg, 1.04 mmol) was suspended in a 1:1 solution of tert-butanol (3 mL) and water (3 mL) and cooled in an ice water bath for 10 min. AD Mix beta (2.84 g, Sigma Aldrich) was added to the suspension in one portion. The mixture was allowed to warm to room temperature and stir for 18 h. When the reaction was complete, the mixture was diluted with water (20 mL) and extracted ethyl acetate (2×20 mL). The organic layer was dried over sodium sulfate, concentrated under vacuum, and chromatographed by CombiFlash® (40-gram silica gel, 0-30% EtOAc/Hexane) to provide (R)-1-1-{4-((R)-1,2-dihydroxy-ethyl)-6-[4-(4-fluoro-phenoxy)-phenyl]pyridin-2-yl}-ethane-1,2-diol (Compound Example No. 19, 177 mg, 0.46 mmol) as a white solid. $^1$H NMR (DMSO-d$_6$): 8.09-8.03 (m, 2H), 7.69 (s, 1H), 7.44 (s, 1H), 7.32-7.23 (m, 2H), 7.18-7.11 (m, 2H), 7.11-7.05 (m, 2H), 5.52-5.47 (m, 1H), 5.43-5.38 (m, 1H), 4.85-4.78 (m, 1H), 4.74-4.69 (m, 1H), 4.67-4.58 (m, 2H), 3.81-3.72 (m, 1H), 3.58-3.47 (m, 3H). LC/MS: m/z 385.

Example 8

Synthesis of 2-(2,5,8,11-tetraoxadodecy)-6-(4-(4-trifluoromethyl)phenoxy)phenyl)pyridine (Compound Example No. 1) and 2-(2,5,8,11,14,17,20,23-octaoxatetracosyl)-6-(4-(4-trifluoromethyl)phenoxy)phenyl)pyridine (Compound Example No. 2)

mg, 0.72 mmol) in DMF (1 mL). After stirring for 15 min at room temperature, the reaction mixture was heated to 50° C. and stirred for 2 h. The solvent was removed, and the residue was purified by column chromatography (12 gram silica gel, 0-100% EtOAc/Hexane) to give the 2-(2,5,8,11-tetraoxadodecy)-6-(4-(4-trifluoromethyl)phenoxy)phenyl)pyridine (Compound Example No. 1) (39 mg, 0.079 mmol). $^1$H NMR (400 MHz, CDCl$_3$): 8.01 (d, J=8.8 Hz, 2H), 7.70 (t, J=7.7 Hz, 1H), 7.59 (d, J=8.3 Hz, 3H), 7.44 (d, J=7.7 Hz, 1H), 7.14 (d, J=8.8 Hz, 2H), 4.77 (s, 2H), 3.63-3.81 (m, 10H), 3.53-3.57 (m, 2H), 3.38 (s, 3H). LC/MS: m/z=492 [M+H]

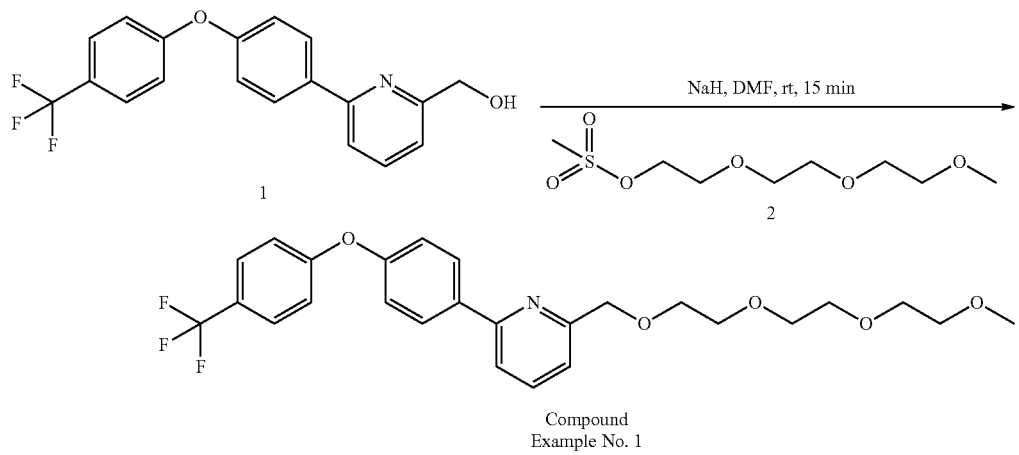

Scheme 11

Compound Example No. 1

As described in Scheme 11, to a solution of compound 1 (190 mg, 0.55 mmol) in DMF (20 mL) at room temperature was added NaH (40 mg, 1.6 mmol) and the resulting mixture was stirred at room temperature for 15 min under nitrogen. To this mixture was added a solution of compound 2 (170

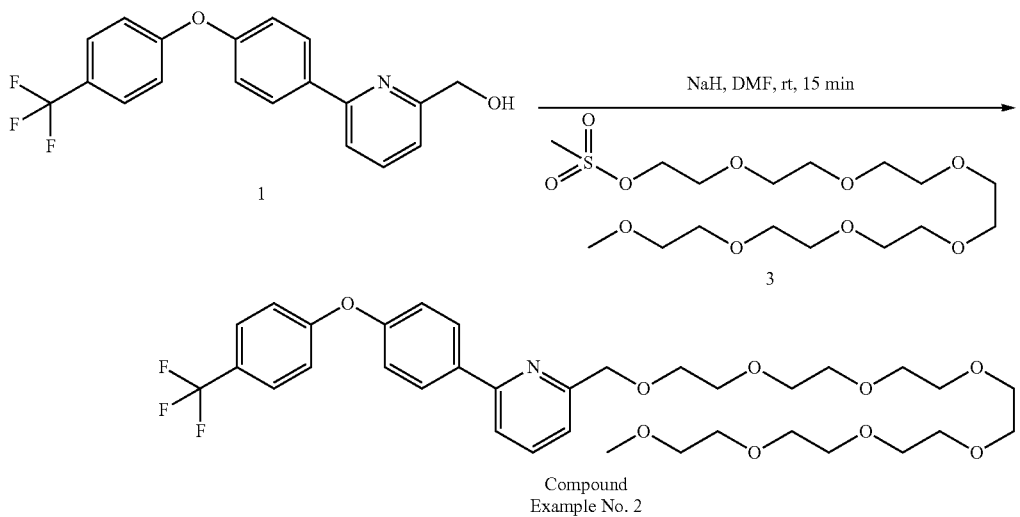

Scheme 12

Compound Example No. 2

As described in Scheme 12, 2-(2,5,8,11,14,17,20,23-octaoxatetracosyl)-6-(4-(4-trifluoromethyl)phenoxy)phenyl)pyridine (Compound Example No. 2) was synthesized similarly to Compound Example No. 1 by using compound 3 instead of compound 2. $^1$H NMR (400 MHz, CD$_3$OD): 8.07 (d, J=8.8 Hz, 2H), 7.87 (t, J=7.9 Hz, 1H), 7.74 (d, J=7.7 Hz, 1H), 7.67 (d, J=9.2 Hz, 2H), 7.48 (d, J=7.7 Hz, 1H), 7.17 (d, J=9.0 Hz, 4H), 4.73 (s, 2H), 3.56-3.79 (m, 28H), 3.33 (s, 3H). LC/MS: m/z=668 [M+H]

Example 9

Synthesis of 1-(2-(((6-(4-(4-fluorophenoxy)phenyl)pyridin-2-yl)methyl)amino)ethyl)imidazolidin-2-one (Compound Example No. 62)

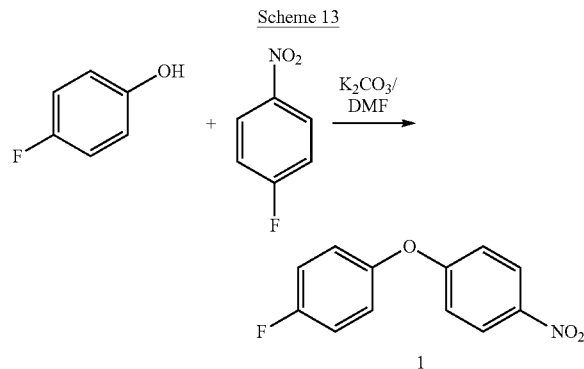

Step 1: Synthesis of 1-fluoro-4-(4-nitrophenoxy)benzene (Compound 1)

Method A:

As described in Scheme 13, a 500 mL round bottom flask was charged with 4-fluorophenol (11.2 g, 0.1 mmol), 4-fluoro-4-nitrobenzene (14.1 g, 0.1 mol), K$_2$CO$_3$ (27.6 g, 0.2 mol) and DMF (50 mL). The reaction mixture was stirred vigorously at 120° C. for 4 h, cooled to room temperature, and then poured into 300 mL water. The resulting mixture was extracted with ethyl acetate. The combined organic layers were dried over MgSO$_4$ and concentrated to give compound 1 as an off-white solid which was used in the next step without further purification (23.3 g, 100% yield). (m/z+H)=234).

Method B:

As described in Scheme 13, mixture of 4-fluorophenol (30 g, 0.27 mol), 1-fluoro-4-nitrobenzene (38 g, 0.27 mol) and K$_2$CO$_3$ (37.8 g, 0.27 mol) in DMF (300 mL) was heated at 95° C. overnight. The reaction mixture was cooled to room temperature and diluted with ethyl acetate (150 mL). The organic layer was washed with water. The organic layer was dried over anhydrous MgSO$_4$ and concentrated under reduced pressure to give an oily residue. The residue was purified by automated column chromatography on silica gel using a CombiFlash® system (5% EtOAc in Hexanes) to give compound 1 as brown crystals (44 g, 70% yield, R$_f$=0.7, eluent (30% diethyl ether in hexanes), $^1$H NMR (400 MHz, CD$_3$Cl): 8.2 (d, J=9.4 Hz, 2H), 7.04-7.17 (m, 4H), 6.99 (d, J=9.4, 2H)).

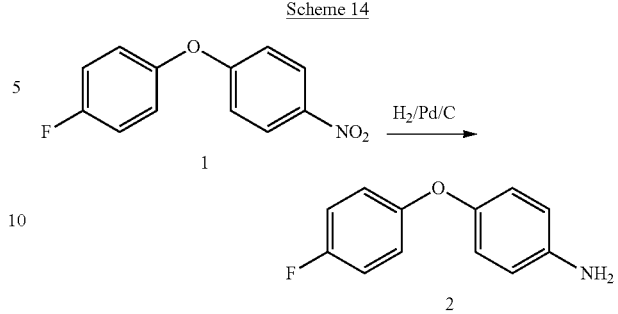

Step 2: Synthesis of 4-(4-fluorophenoxy)aniline (Compound 2)

Method A:

Compound 1 (23.3 g, 0.1 mol) was dissolved in ca. 50 mL MeOH and to this solution two spatulas of palladium on carbon (5%) (ca. 50 mg) were added. The reaction mixture was purged with nitrogen and hydrogen (three times) and stirred overnight at room temperature under a balloon of hydrogen. The palladium on carbon was removed by filtration and the filtrate was concentrated by rotary evaporation to give compound 2 as an off-white solid (20.4 g, 100% yield, (m/z+H)=204).

Method B:

Compound 1 (10 g, 42.9 mmol) was dissolved in 10% ethyl acetate in methanol (250 mL) and 10% palladium on carbon (2.0 g) was added. The reaction mixture was stirred for 5.0 h at room temperature. After the reaction was complete, the mixture was filtered through a pad of celite. The filtrate was concentrated to give compound 2 as a reddish brown solid which was used in the next step without purification (8.5 g, 97% yield, R$_f$=0.2, eluent (25% ethyl acetate in hexanes).

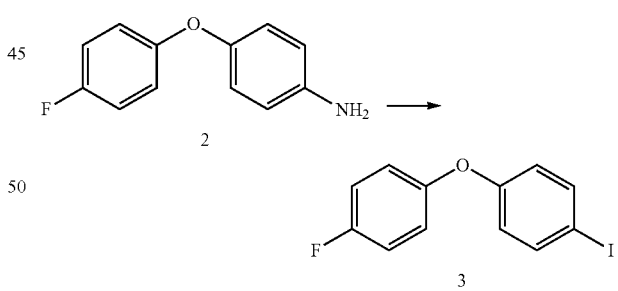

Step 3: Synthesis of 1-fluoro-4-(4-iodophenoxyl)benzene (Compound 3)

Method A:

To a DME (272 mL) solution of compound 2 (20.4 g, 0.1 mol) was added a solution of H$_2$SO$_4$ (41 mL concentrated H$_2$SO$_4$ in 204 mL of H$_2$O) dropwise. The resulting mixture was cooled to 0° C. and a solution of NaNO$_2$ (10.3 g, 0.15 mol) in H$_2$O (68 mL) was added over 20 min. After the addition was complete, the reaction mixture was stirred at 0° C.-5° C. for an additional 30 min and a solution of NaI (75 g, 0.5 mol) in H₂O (204 mL) was added dropwise at 0° C. After the addition was complete, the mixture was stirred for and additional 30 min and diluted with EtOAc. The organic layer was collected and washed with an aqueous solution of Na₂S₂O₃ and brine and dried over MgSO₄. The solvent was removed by evaporation and the residue solidified instantly. The pale solid product (compound 3) was used in the next step without further purification (96% yield, (m/z+H)=315).

Method B:

To a solution of p-TsOH.H₂O (56.0 g, 300 mmol) in acetonitrile (500 mL), was added compound 2. The suspension was cooled to 0-5° C. and stirred for 15 min. A solution of NaNO₂ (13.8 g, 200 mmol) and KI (41.5 g, 250 mmol) in H₂O (150 mL) was added slowly thereto. During the addition, N₂ evolved. The reaction mixture was stirred for 1 h at room temperature. After the reaction was complete, saturated NaHCO₃ was added to adjust the pH to 9~10 and 2M Na₂S₂O₃ (6.0 mL) was added. The aqueous layer was separated and extracted with ethyl acetate. The combined organic layers were dried with anhydrous MgSO₄ and concentrated under reduced pressure. The crude product was purified by automated column chromatography on silica gel using a CombiFlash® system (10% ethyl acetate in hexanes) to give compound 3 as a pale brown crystal (19.3 g, 67% yield, $R_f$=0.8, eluent (25% ethyl acetate in hexanes), LC/MS: m/z=315 [M+H]⁺).

Method B:

To a suspension of compound 3 (10 g, 31.8 mmol) in dioxane (320 mL) was added Pd(dppf)Cl₂.CH₂Cl₂ (0.82 g, 1.0 mmol) and reaction mixture was degassed by repeating argon/vacuum cycles. The suspension was stirred for 10 min at room temperature, bis(pinacolato)diboron (8.9 g, 35.0 mmol) and potassium acetate (0.97 g, 95.4 mmol) were added, and the reaction mixture was heated at 90° C. for 18 h under argon. Upon cooling to room temperature, the mixture was filtered through a pad of celite and concentrated under reduced pressure. The residue was purified by automated column chromatography on silica gel using a CombiFlash® system (5% ethyl acetate in hexanes) to give compound 4 as a pale brown solid (9.0 g, 90% yield, $R_f$=0.4, eluent (10% ethyl acetate in hexanes), LC/MS: m/z=315 [M+H]⁺, ¹H NMR (400 MHz, CD₃Cl): 7.67 (d, J=8.6 Hz, 2H), 7.06-6.96 (m, 4H), 6.93 (d, J=8.6 Hz, 2H), 1.33 (s, 12H)).

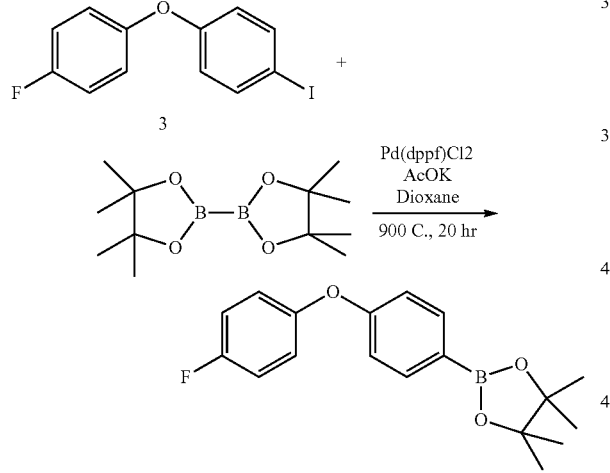

Scheme 16

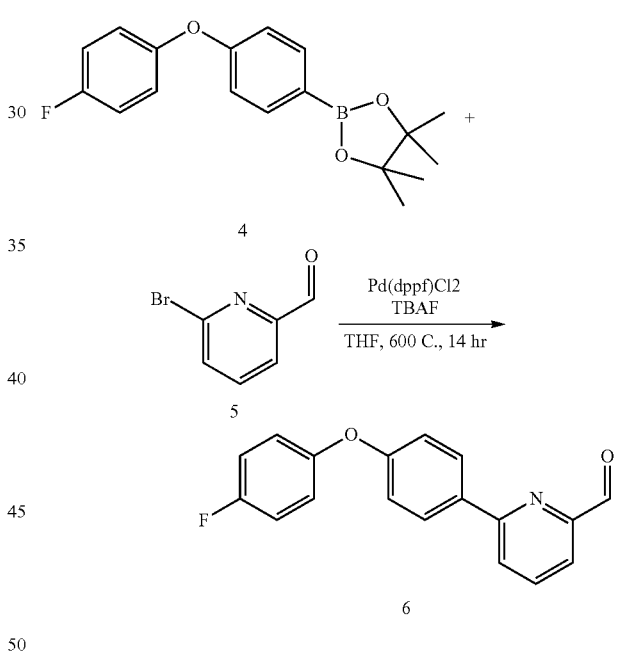

Scheme 17

Step 4: Synthesis of 2-(4-(4-fluorophenoxy)phenyl)-4,4,5,5-tetramethyl-1,3,2-dioxaborolane (Compound 4)

Method A:

A 100 mL round bottom flask was charged with compound 3 (Netchem, 5 g, 15.9 mmol), pinacol diborane (4.43 g, 17.4 mmol), KOAc (4.68 g, 47.7 mmol), Pd(dppf)Cl₂ (402 mg, 0.49 mmol) and dioxane (60 mL). The reaction mixture was purged with argon and then stirred at 90° C. under argon for 20 h. The reaction mixture was cooled to room temperature, diluted with EtOAc, and dried over MgSO₄. The EtOAc was evaporated and the residue was purified by column chromatography on silica gel (hexanes/EtOAc) to give compound 4 as a white solid (2.5 g, 50% yield, (m/z+H)=315).

Step 5: Synthesis of Compound 6

According to Scheme 17, a 100 mL round bottom flask was charged with compound 4 (3.14 g, 10 mmol), bromopyridine aldehyde 5 (Aldrich, 1.86 g, 10 mmol), Pd(dppf)Cl₂ (408 mg, 0.50 mmol) and a THF solution of TBAF (1N in THF). The mixture was purged with argon and then stirred at 60° C. under argon for 20 h. The reaction mixture was cooled to room temperature and diluted with EtOAc. The EtOAc was isolated and dried over MgSO₄. The EtOAc was evaporated and the residue was subjected to flash column chromatography (hexanes/EtOAc) to give compound 6 as white solid (yield 75%) (m/z+H) 294.

Scheme 18

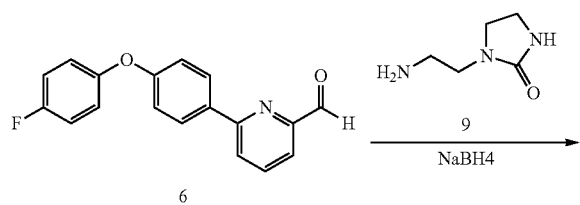

Step 6: Synthesis of 1-(2-(((6-(4-(4-fluorophenoxy)phenyl)pyridin-2-yl)methyl)amino)ethyl)imidazolidin-2-one According to Scheme 18, a mixture of the compound 6 (100 mg, 0.34 mmol) and amine 9 (44 mg, 0.34 mmol) in THF (5 mL) was stirred for 14 h at room temperature. NaBH$_4$ (13 mg, 0.34 mmol) was added thereto, and the mixture was stirred at room temperature for 20 min. The solvent was evaporated and the residue was subjected to flash column chromatography (silica gel, eluent: EtOAc/MeOH) to give 1-(2-(((6-(4-(4-fluorophenoxy)phenyl)pyridin-2-yl)methyl)amino)ethyl)imidazolidin-2-one (Compound Example No. 62) (100 mg, 72%). LC/MS: m/z=407 [M+H]$^+$, $^1$H NMR (400 MHz, CD$_3$OD): 7.95 (d, J=9.0 Hz, 2H), 7.70 (t, J=7.5 Hz, 1H), 7.6 (d, J=7.6 Hz, 1H), 7.19 (d, J=8.56, 1H), 6.9-7.06 (m, 6H), 3.83 (s, 2H), 3.17-3.19 (m, 6H), 2.70 (t, J=6.39 Hz, 2H).

Example 10

Synthesis of 2-(((6-(4-(4-fluorophenoxy)phenyl)pyridin-2-yl)methyl)(2-(2-oxoimidazolidin-1-yl)ethyl)amino)acetonitrile (Compound Example No. 69)

Scheme 19

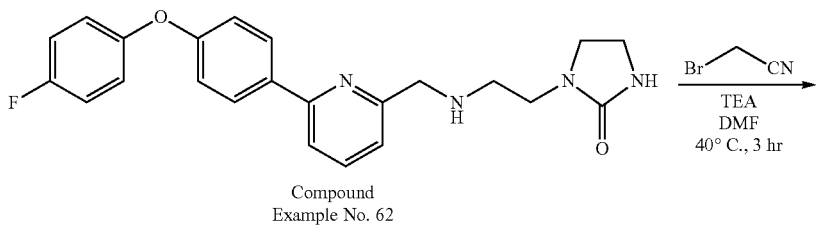

Compound Example No. 62

Compound Example No. 69

According to Scheme 19, a mixture of Compound Example No. 62 (300 mg, 0.73 mmol), 2-bromoacetonitrile (106 mg, 0.88 mmol) and TEA in DMF (5 mL) was stirred at 40° C. for 3 h. The mixture was diluted with EtOAc and water. The EtOAc was isolated, washed with brine, dried over MgSO$_4$, and concentrated. The residue was subjected to flash column chromatography (silica gel, eluent: EtOAc) to give 2-(((6-(4-(4-fluorophenoxy)phenyl)pyridin-2-yl)methyl)(2-(2-oxoimidazolidin-1-yl)ethyl)amino)acetonitrile (Compound Example No. 69) (300 mg, 92%). LC/MS: m/z=446 [M+H]$^+$, $^1$H NMR (400 MHz, CD$_3$OD): 8.02 (d, J=8.61 Hz, 2H), 7.83 (t, J=7.7 Hz, 1H), 7.72 (d, J=8.0 Hz, 1H), 7.40 (d, J=7.8, 1H), 6.9-7.01 (m, 6H), 3.91 (s, 2H), 3.84 (s, 1H), 3.23-3.4 (m, 6H), 2.81 (t, J=5.7 Hz, 2H)

Example 11

Synthesis of 2-(((6-(4-(4-fluorophenoxy)phenyl) pyridin-2-yl)methyl)(2-(2-oxoimidazolidin-1-yl) ethyl)amino)acetamide (Compound Example No. 72)

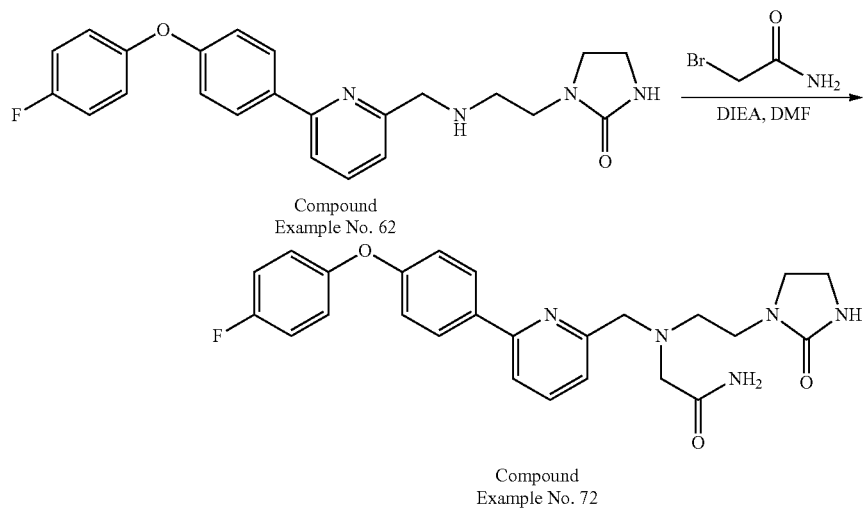

According to Scheme 20, Compound Example No. 62 (100 mg, 0.25 mmol), 2-bromoacetamide (34 mg, 0.25 mmol) and DIEA (0.1 mL) were dissolved in 1.5 mL of DMF. The mixture was heated at 140° C. for 20 min in a microwave oven, cooled to room temperature, and worked-up with EtOAc. The EtOAc was removed and the residue was recrystallized from EtOAc/MeOH to give 2-(((6-(4-(4-fluorophenoxy)phenyl)pyridin-2-yl)methyl)(2-(2-oxoimidazolidin-1-yl)ethyl)amino) acetamide (Compound Example No. 72) (100 mg, 87%) as white solid. LC/MS: m/z=464 [M+H]$^+$, $^1$H NMR (400 MHz, DMSO-d$_6$): 8.80 (d, J=8.9 Hz, 2H), 7.78-7.85 (m, 2H), 7.5 (s, 1H), 7.35 (d, J=7.1 Hz, 1H), 7.04-7.29 (m, 7H), 6.25 (s, 1H), 3.80 (s, 1H), 3.07-3.32 (m, 8H), 2.60 (t, J=5.9 Hz, 2H)

Example 12

Synthesis of 1-(2-(((6-(4-(4-(trifluoromethyl)phenoxy)phenyl)pyridin-2-yl)methyl)amino)ethyl)imidazolidin-2-one (Compound Example No. 61)

Scheme 21

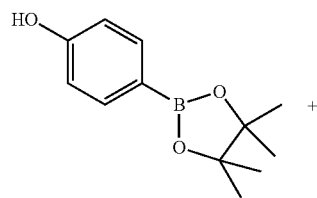 +

-continued

Step 1: Synthesis of Compound 7

According to Scheme 21, a 50 mL round bottom flask was charged with 4-hydroxyl phenyl borate (2.2 g, 10 mmol), 6-bromopyridine aldehyde (1.86 g, 10 mmol), Pd(PPh$_3$)$_2$Cl$_2$ (0.5 mmol), Na$_2$CO$_3$ (2.76 g, 20 mmol) and DME/EtOH/H$_2$O (5 mL/2.5 mL/5 mL). The mixture was purged with argon and stirred at 90° C. under argon for 14 h. The reaction mixture was cooled to room temperature, acidified to pH 1 with conc. HCl and extracted with EtOAc. The EtOAc was isolated and dried over MgSO$_4$. The EtOAc was evaporated and the residue was subjected to flash column chromatography (hexanes/EtOAc) to give compound 7 as yellow solid (yield 75%) (m/z+H) 200.

181

Scheme 22

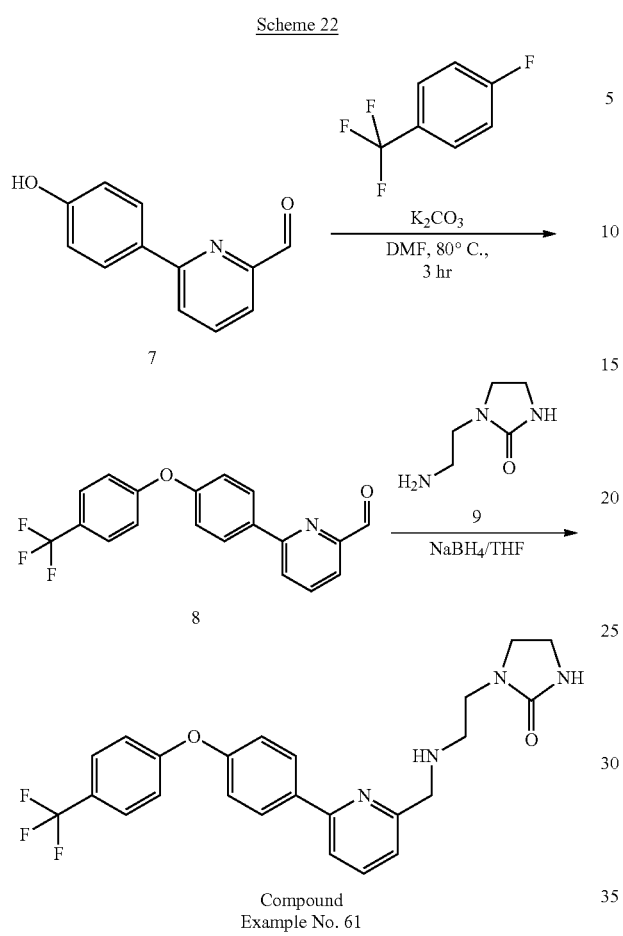

Step 2: Synthesis of 1-(2-(((6-(4-(4-(trifluoromethyl)phenoxy)phenyl)pyridin-2-yl)methyl)amino)ethyl)imidazolidin-2-one According to Scheme 22, a 20 mL round bottom flask was charged with compound 7 (150 mg, 0.75 mmol), 4-fluoro trifluorobenzene (123 mg, 0.75 mmol), and K$_2$CO$_3$ (138 mg g, 1 mmol) in 3 mL DMF. The mixture was stirred at 80° C. for 3 h. The reaction mixture was cooled to room temperature and worked up with EtOAc. The EtOAc layer was isolated, dried over MgSO$_4$, and evaporated to dryness. The crude product was used for next step without further purification (258 mg, yield 100%) (m/z+H)=344.

A mixture of compound 8 (117 mg, 0.34 mmol) and amine 9 (44 mg, 0.34 mmol) in THF (5 mL) was stirred for 14 h at room temperature. NaBH$_4$ (13 mg, 0.34 mmol) was added thereto, and the mixture was stirred at room temperature for 20 min. The solvent was evaporated and the residue was subjected to flash column chromatography (silica gel, eluent: EtOAc/MeOH) to give 1-(2-(((6-(4-(4-(trifluoromethyl)phenoxy)phenyl)pyridin-2-yl)methyl)amino)ethyl)imidazolidin-2-one (Compound Example No. 61) (108 mg, 70%). LC/MS: m/z=457 [M+H]$^+$; $^1$H NMR (400 MHz, CD$_3$OD): 8.18 (d, J=9.0 Hz, 2H), 7.79-7.80 (m, 2H), 7.70 (d, J=8.6 Hz, 2H), 7.36 (d, J=7.5 Hz, 2H), 7.15-7.23 (m. 3H), 4.11 (s, 2H), 3.34-3.51 (m, 6H), 2.80 (t, J=6.1 Hz, 2H)

182

Example 13

Synthesis of 4-(4-(6-(((2-(2-oxoimidazolidin-1-yl)ethyl)amino)methyl)pyridin-2-yl)phenoxy)benzonitrile (Compound Example No. 67)

Scheme 23

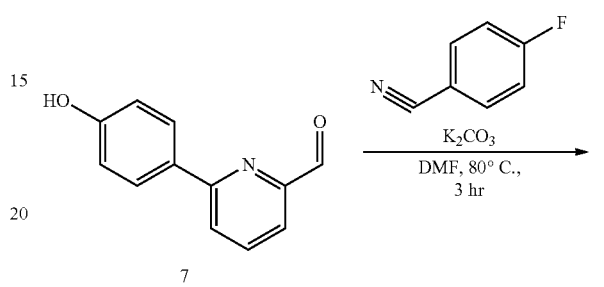

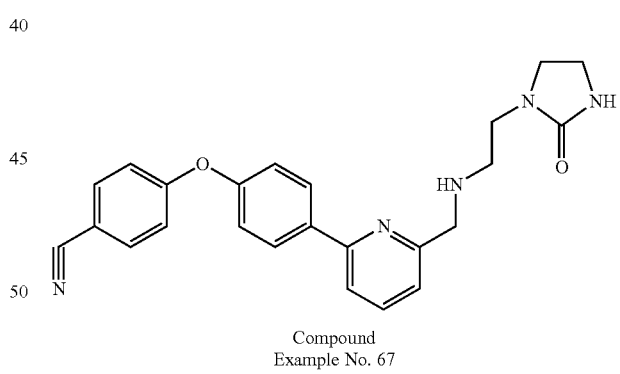

According to Scheme 23, 4-(4-(6-(((2-(2-oxoimidazolidin-1-yl)ethyl)amino)methyl)pyridin-2-yl)phenoxy)benzonitrile (Compound Example No. 67) was synthesized in 60% yield in a similar way as that of Compound Example No. 61 in Scheme 22. LC/MS: m/z=414 [M+H]$^+$, $^1$H NMR (400 MHz, CD$_3$OD): 8.17 (d, J=9.06 Hz, 2H), 7.85 (t, J=7.7 Hz, 1H), 7.7-7.8 (m, 3H), 7.3 (d, J=7.7 Hz, 1H), 7.2-7.13 (m, 4H), 4.0 (s, 2H), 3.28-3.50 (s, 6H), 2.84 (t, J=6.1 Hz, 2H).

Example 14

Synthesis of 1-(2-(((6-(4-((5-(trifluoromethyl)pyridin-2-yl)oxy)phenyl)pyridin-2-yl)methyl)amino)ethyl)imidazolidin-2-one (Compound Example No. 68)

Example 15

Synthesis of 4-(4-(6-(((2-(2-oxoimidazolidin-1-yl)ethyl)amino)methyl)pyridin-2-yl)phenoxy)-3-(trifluoromethyl)benzonitrile (Compound Example No. 65)

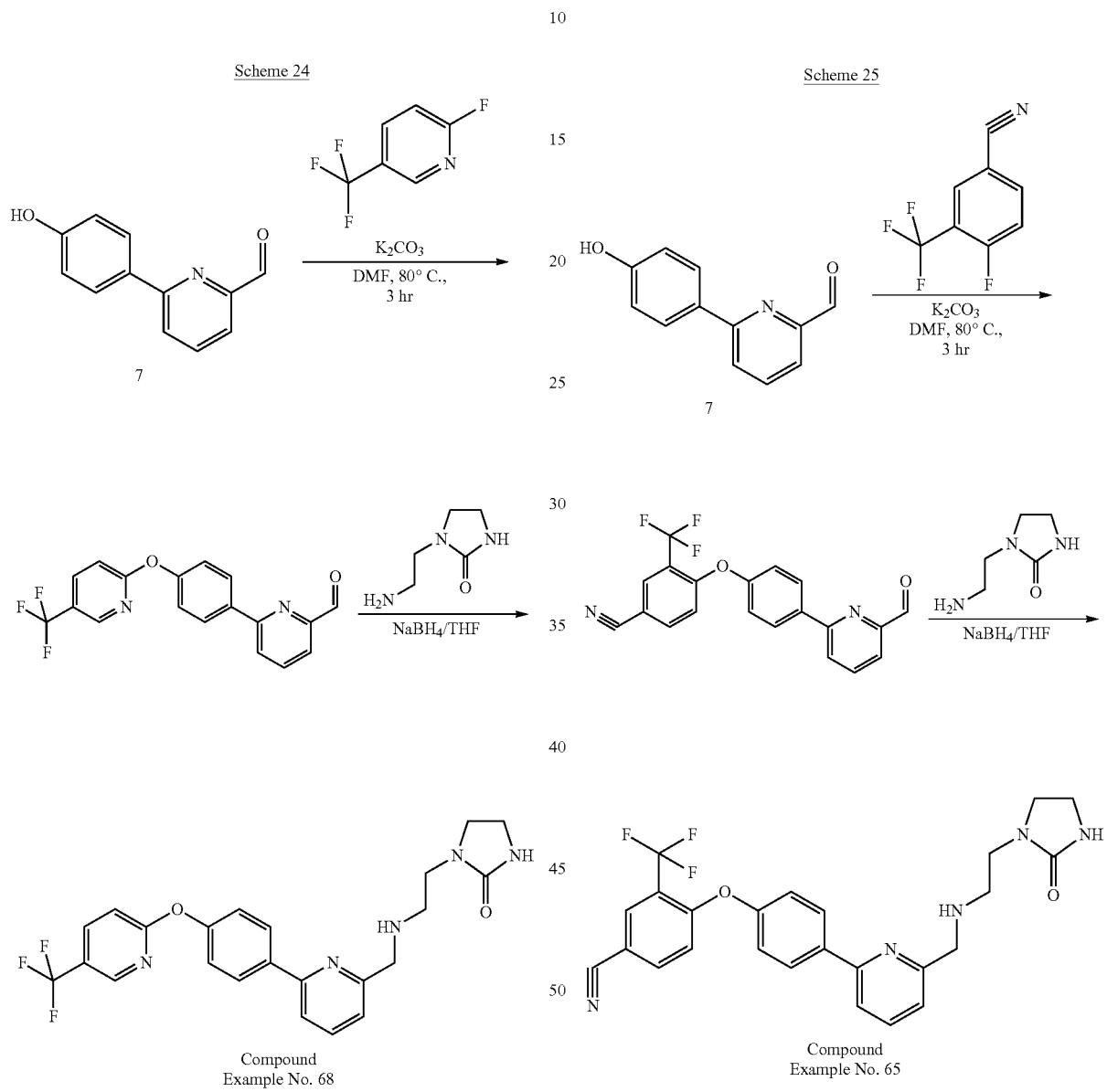

According to Scheme 24, 1-(2-(((6-(4-((5-(trifluoromethyl)pyridin-2-yl)oxy)phenyl)pyridin-2-yl)methyl)amino)ethyl)imidazolidin-2-one (Compound Example No. 68) was synthesized in 75% yield in a similar way as that of Compound Example No. 61 in Scheme 22. LC/MS: m/z=458 [M+H]+, 1H NMR (400 MHz, CD3OD): 8.35 (s, 1H), 7.07-8.13 (m, 3H), 7.62-7.80 (m, 2H), 7.13-7.28 (m, 3H), 7.09 (d, J=8.8 Hz, 1H), 3.87 (s, 2H), 3.13-3.39 (m, 6H), 2.65-2.76 (m, 2H).

According to Scheme 25, 4-(4-(6-(((2-(2-oxoimidazolidin-1-yl)ethyl)amino)methyl)pyridin-2-yl)phenoxy)-3-(trifluoromethyl)benzonitrile (Compound Example No. 65) was synthesized in 75% yield in a similar way as that of Compound Example No. 61 in Scheme 22. LC/MS: m/z=482 [M+H]+, 1H NMR (400 MHz, CD3OD): 8.23 (d, J=8.8 Hz, 2H), 8.2 (d, J=2.0 Hz, 1H), 7.78-7.97 (m, 3H), 7.4 (d, J=6.4 Hz, 2H), 7.3 (d, J=9.0 Hz, 2H), 7.1 (d, J=8.8 Hz, 1H), 3.3-3.5 (m, 6H), 2.85 (t, J=6.1 Hz, 2H).

Example 16

Synthesis of 2-(4-(6-(((2-(2-oxoimidazolidin-1-yl)ethyl)amino)methyl)pyridin-2-yl)phenoxy)-5-(trifluoromethyl)benzonitrile (Compound Example No. 63)

Example 17

Synthesis of 1-(2-(((6-(4-((3-chloro-5-(trifluoromethyl)pyridin-2-yl)oxy)phenyl)pyridin-2-yl)methyl)amino)ethyl)imidazolidin-2-one (Compound Example No. 66)

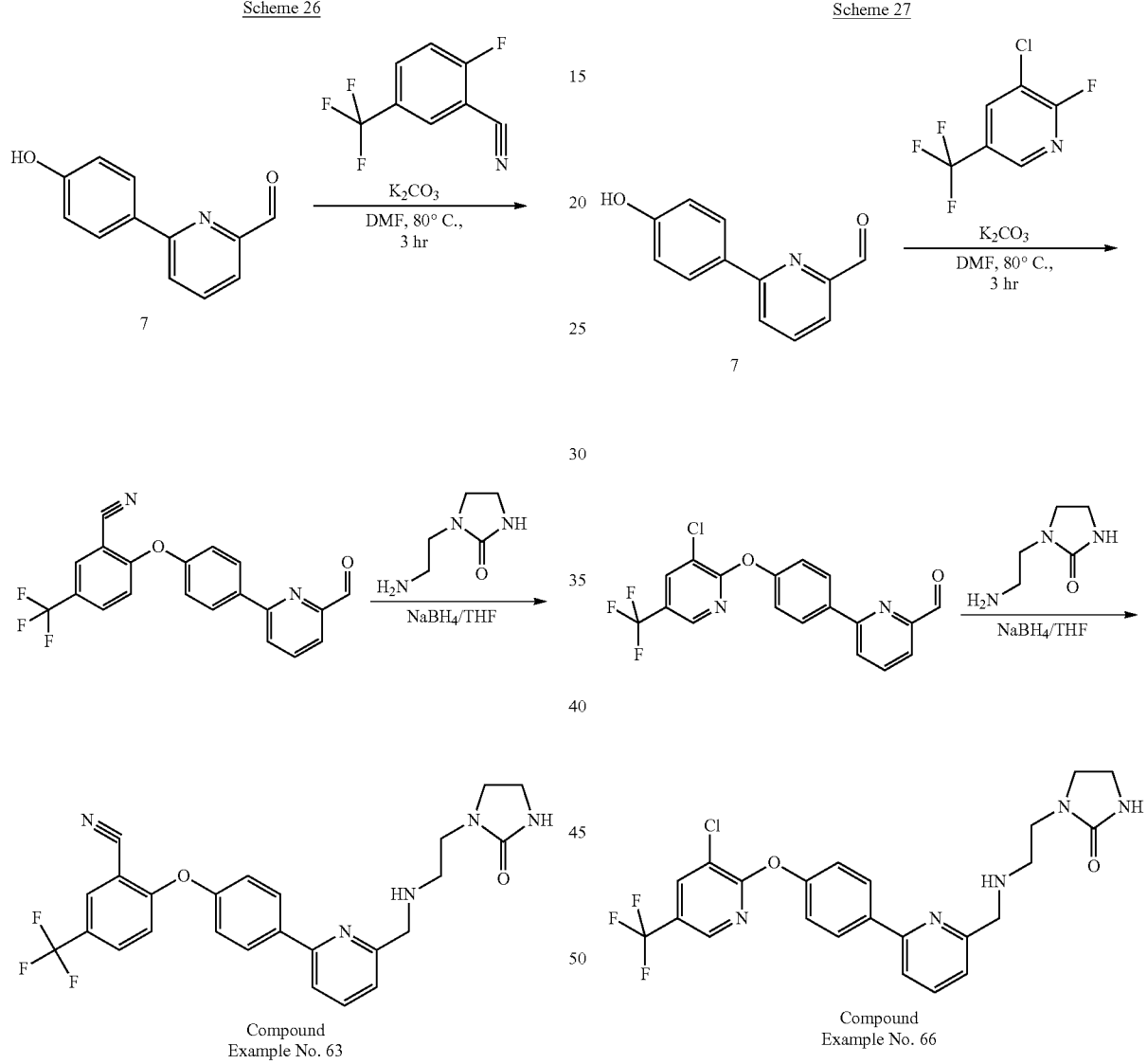

According to Scheme 26, 2-(4-(6-(((2-(2-oxoimidazolidin-1-yl)ethyl)amino)methyl)pyridin-2-yl)phenoxy)-5-(trifluoromethyl)benzonitrile (Compound Example No. 63) was synthesized in 75% yield in a similar way as that of Compound Example No. 61 in Scheme 22. LC/MS: m/z=482 [M+H]$^+$, $^1$H NMR (400 MHz, CD$_3$OD): 8.25 (d, J=8.5 Hz, 2H), 8.1 (s, 1H), 7.75-7.94 (m, 3H), 7.28-7.37 (m, 3H), 7.14 (d, J=8.8 Hz, 1H), 4.02 (s, 2H), 3.3-3.5 (m, 6H), 2.86 (t, J=6.1 Hz, 2H).

According to Scheme 27, 1-(2-(((6-(4-((3-chloro-5-(trifluoromethyl)pyridin-2-yl)oxy)phenyl)pyridin-2-yl)methyl)amino)ethyl)imidazolidin-2-one (Compound Example No. 66) was synthesized in 75% yield in a similar way as that of Compound Example No. 61 in Scheme 22. LC/MS: m/z=492 [M+H]$^+$, $^1$H NMR (400 MHz, CD$_3$OD): 8.36 (m, 1H), 8.32 (d, J=2.2 Hz, 1H), 8.18 (d, J=8.8 Hz, 2H), 7.78-7.88 (m, 2H), 7.30-7.36 (m, 3H), 3.99 (s, 2H), 3.33-3.47 (m, 6H), 2.84 (t, d=6.3 Hz, 2H).

Example 18

Synthesis of 1-(2-(((6-(4-(4-(methylsulfonyl)phenoxy)phenyl)pyridin-2-yl)methyl)amino)ethyl)imidazolidin-2-one (Compound Example No. 71)

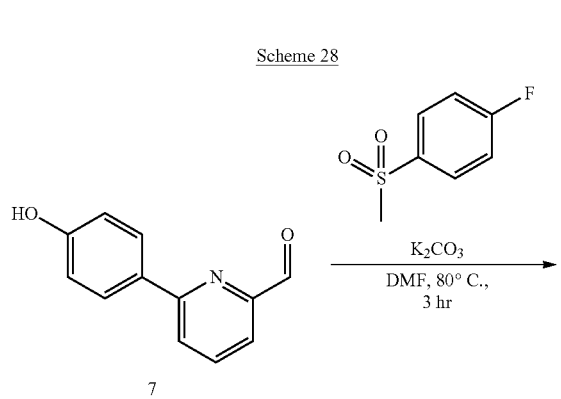

Example 19

Synthesis of 5-(4-(6-(((2-(2-oxoimidazolidin-1-yl)ethyl)amino)methyl)pyridin-2-yl)phenoxy)-2-(trifluoromethyl)benzonitrile (Compound Example No. 70)

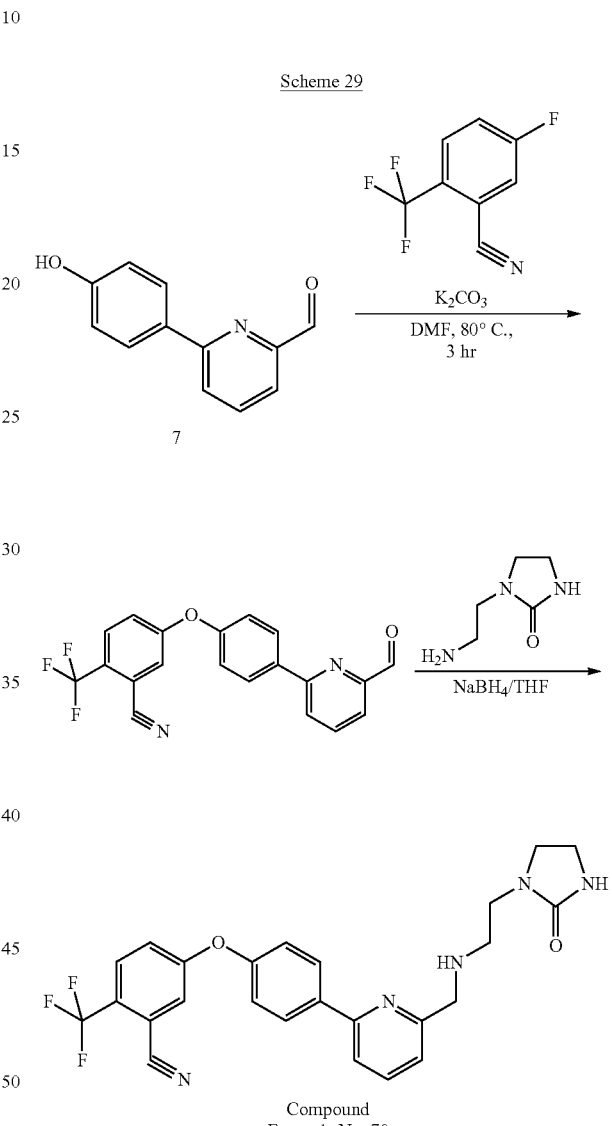

According to Scheme 28, 1-(2-(((6-(4-(4-(methylsulfonyl)phenoxy)phenyl)pyridin-2-yl)methyl)amino)ethyl)imidazolidin-2-one (Compound Example No. 71) was synthesized in 65% yield in a similar way as that of Compound Example No. 61 in Scheme 22. LC/MS: m/z=467 [M+H]$^+$, $^1$H NMR (400 MHz, CD$_3$OD): 8.13 (d, J=9.0 Hz, 2H), 7.95-8.0 (m, 4H), 7.38-7.4 (m, 1H), 7.21-7.29 (m, 4H), 4.52 (s, 2H), 3.5-3.60 (m, 4H), 3.35-3.47 (m, 4H), 3.15 (s, 3H).

According to Scheme 29, 5-(4-(6-(((2-(2-oxoimidazolidin-1-yl)ethyl)amino)methyl)pyridin-2-yl)phenoxy)-2-(trifluoromethyl)benzonitrile (Compound Example No. 70) was synthesized in 86% yield in a similar way as that of Compound Example No. 61 in Scheme 22. LC/MS: m/z=482 [M+H]$^+$, $^1$H NMR (400 MHz, CD$_3$OD): 8.03 (d, J=9.0 Hz, 2H), 7.63-7.70 (m, 2H), 7.54 (d, J=7.7 Hz, 1H), 7.32 (d, J=2.4 Hz, 1H), 7.20-7.25 (m, 2H), 7.08-7.15 (d, J=8.8 Hz, 2H), 4.48 (br, s, 1H), 3.40-3.46 (m, 2H), 3.41-3.46 (m, 2H), 3.30-3.37 (m, 4H), 2.87 (t, J=6.3 Hz, 2H).

Example 20

Synthesis of 1-(2-((2-(6-(4-(4-fluorophenoxy)phenyl)pyridin-2-yl)ethyl)amino)ethyl)imidazolidin-2-one (Compound Example No. 64)

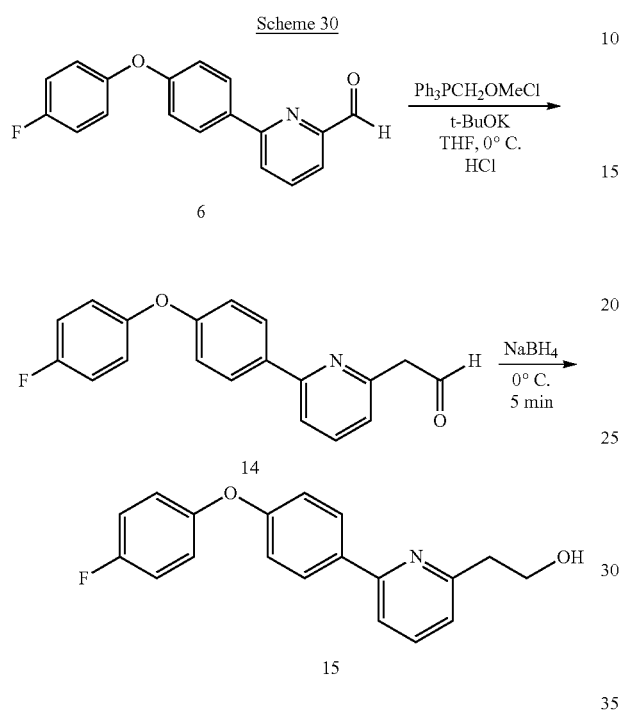

Scheme 30

Step 1: Synthesis of Compound 15

According to Scheme 30, at 0° C., a suspension of Ph₃PCH₂OMeCl (0.16 g, 0.46 mmol) in THF (10 mL) under argon was treated with t-BuOK (57.8 mg, 0.6 mmol) in one portion. The red orange suspension was stirred for additional 10 min, then compound 6 was added in 3 portions. The mixture was stirred at 0° C. for additional 15 min, quenched with H₂O/HCl (2 N), and worked up with ether. The ether was removed and compound 14 was used for next step without further purification.

Compound 14 was dissolved in methanol and cooled to 0° C. A NaBH₄ aqueous solution (2 N) was added to the above mixture dropwise. The reaction mixture was extracted with EtOAc, washed with brine, and dried over MgSO₄. Removal of EtOAc followed by flash column chromatography (Hexanes/EtOAc) gave compound 15 as a sticky oil (Yield 70% over 2 steps) (m/z+H) 310.

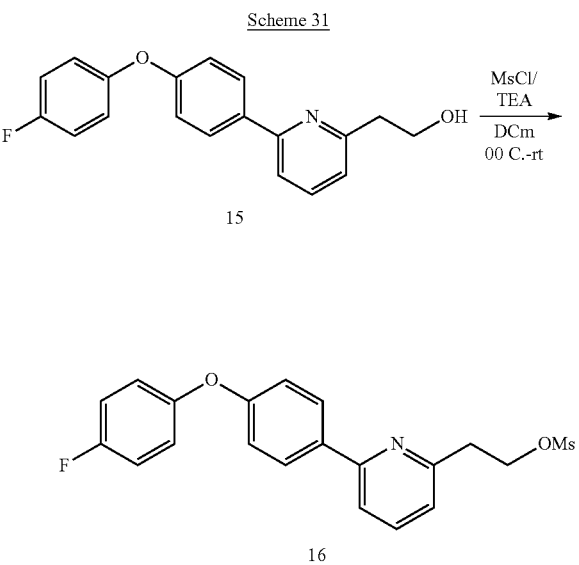

Scheme 31

Step 2: Synthesis of Compound 16

According to Scheme 31, compound 15 (100 mg, 0.32 mmol) and TEA (0.1 mL) were dissolved in DCM (3 mL) and cooled to 0° C. MsCl (37 mg, 0.34 mmol) was added to the mixture slowly and the resulting mixture was stirred at 0° C. for 30 min and then worked up with DCM. Removal of the DCM gave compound 16, which was used for next step without further purification (m/z+H) 388.

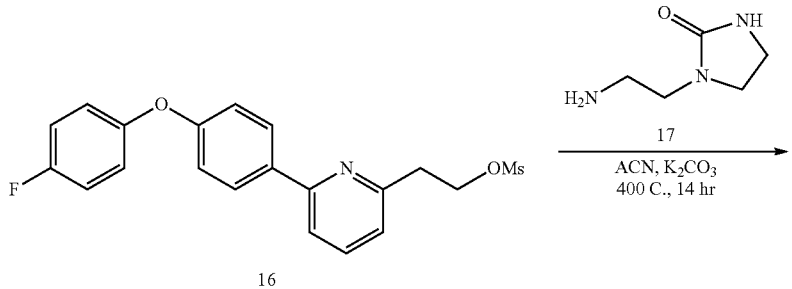

Scheme 32

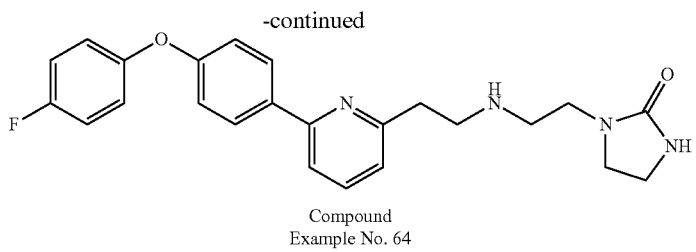

Compound Example No. 64

Step 3: Synthesis of 1-(2-(((2-(6-(4-(4-fluorophenoxy)phenyl)pyridin-2-yl)ethyl)amino)ethyl)imidazolidin-2-one According to Scheme 32, a mixture of compound 16 (50 mg, 0.13 mmol), 2-aminoethyl imidazolidone (compound 17) (30 mg, 0.13 mmol), and $K_2CO_3$ (50 mg, 0.36 mmol) in acetonitrile (3 mL) was stirred at 40° C. for 14 h, worked up with EtOAc, and purified by reverse phase (C18) column chromatography ($H_2O$/ACN with 0.1% TFA) to give 1-(2-((2-(6-(4-(4-fluorophenoxy)phenyl)pyridin-2-yl)ethyl) amino)ethyl)imidazolidin-2-one (Compound Example No. 64) as white solid (yield 70%). LC/MS: m/z=421 [M+H]$^+$, $^1$H NMR (400 MHz, MeOH-d$_4$): 7.5-7.9 (4H, m), 6.8-7.3 (7H, m), 2.9-3.6 (12H, m).

Example 21

Synthesis of 1-(2-(((2-(4-(4-fluorophenoxy)phenyl)pyridin-4-yl)methyl)amino)ethyl)imidazolidin-2-one (Compound Example No. 105)

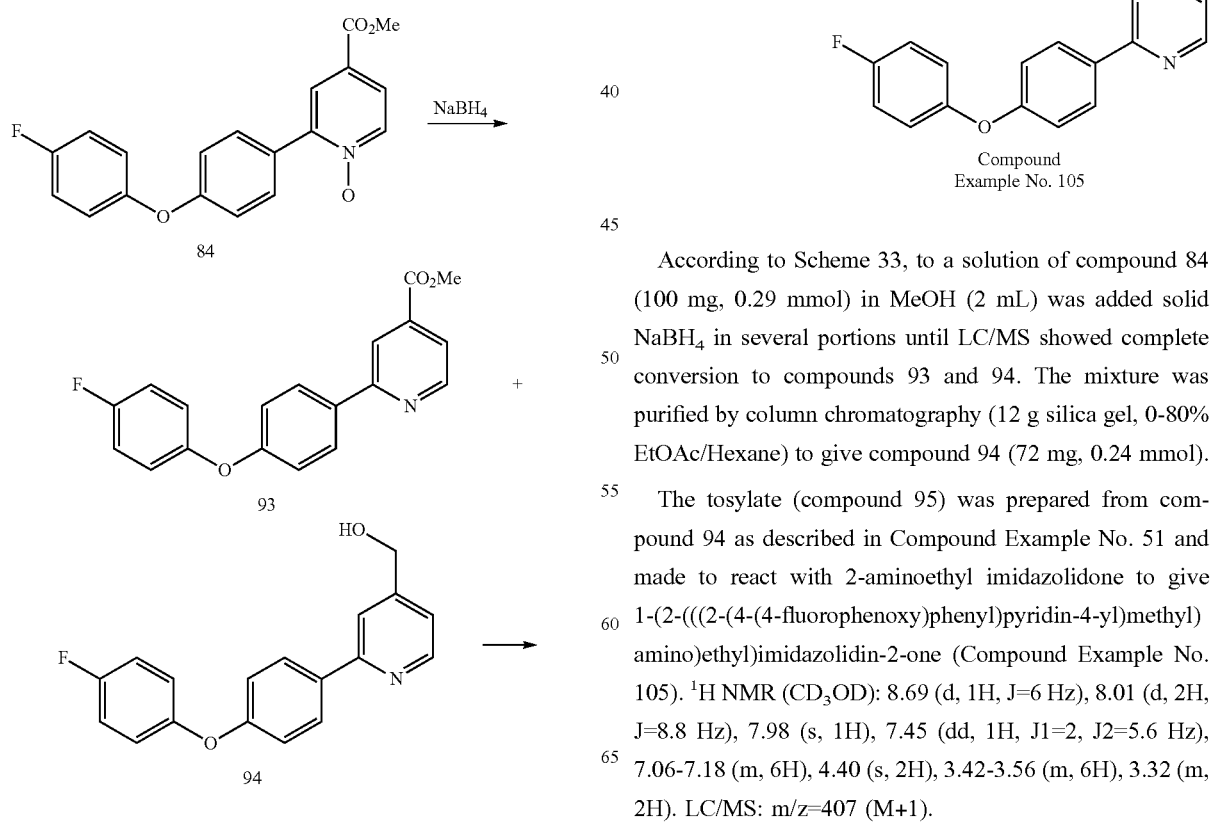

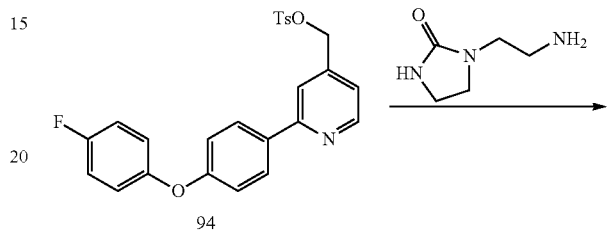

Compound Example No. 105

According to Scheme 33, to a solution of compound 84 (100 mg, 0.29 mmol) in MeOH (2 mL) was added solid NaBH$_4$ in several portions until LC/MS showed complete conversion to compounds 93 and 94. The mixture was purified by column chromatography (12 g silica gel, 0-80% EtOAc/Hexane) to give compound 94 (72 mg, 0.24 mmol).

The tosylate (compound 95) was prepared from compound 94 as described in Compound Example No. 51 and made to react with 2-aminoethyl imidazolidone to give 1-(2-(((2-(4-(4-fluorophenoxy)phenyl)pyridin-4-yl)methyl) amino)ethyl)imidazolidin-2-one (Compound Example No. 105). $^1$H NMR (CD$_3$OD): 8.69 (d, 1H, J=6 Hz), 8.01 (d, 2H, J=8.8 Hz), 7.98 (s, 1H), 7.45 (dd, 1H, J1=2, J2=5.6 Hz), 7.06-7.18 (m, 6H), 4.40 (s, 2H), 3.42-3.56 (m, 6H), 3.32 (m, 2H). LC/MS: m/z=407 (M+1).

Example 22

Synthesis of 6-(4-(4-fluorophenoxy)phenyl)-4-(3-phenylureido)picolinamide (Compound Example No. 84) and 2-(3-(2-carbamoyl-6-(4-(4-fluorophenoxy)phenyl)pyridin-4-yl)ureido)acetic acid (Compound Example No. 87)

Scheme 34

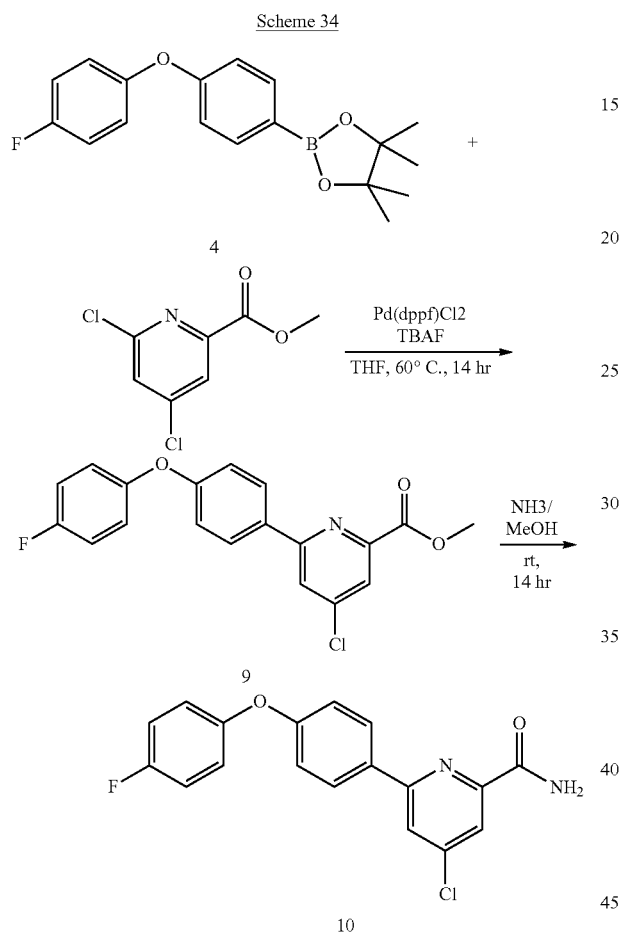

Scheme 35

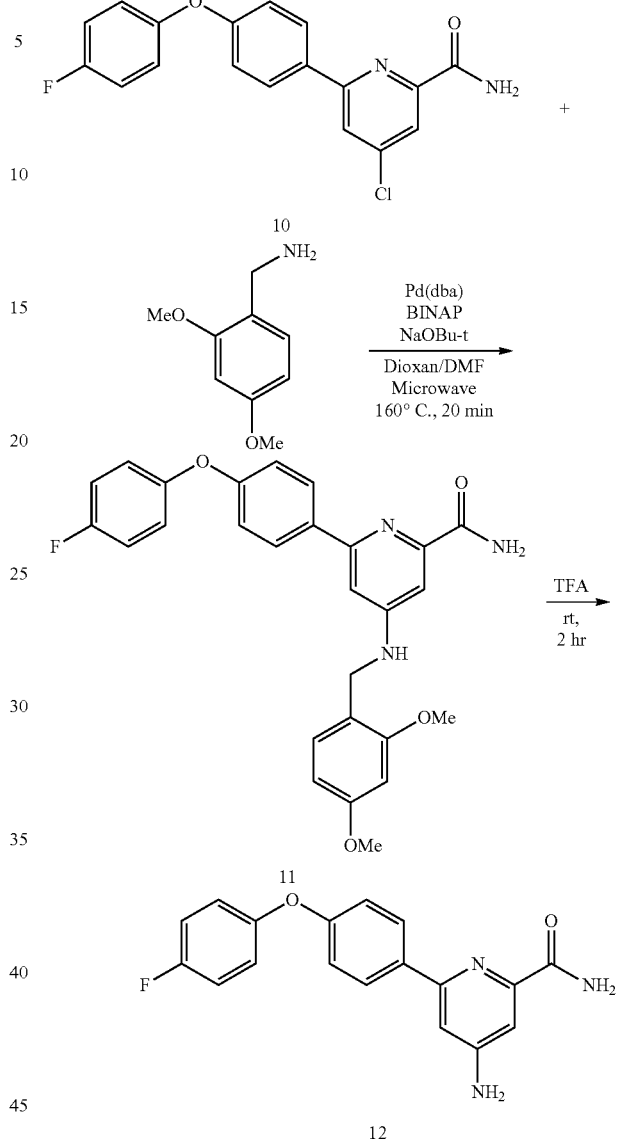

Step 1: Synthesis of Pyridine amide 10

According to Scheme 34, a 100 mL round bottom flask was charged with diphenyl ether borate 4 (3.14 g, 10 mmol), 2,4-dichloropyridine ester (Astatech, 2.05 g, 10 mmol), Pd(dppf)Cl$_2$ (408 mg, 0.50 mmol) and a THF solution of TBAF (1N in THF). The mixture was purged with argon and stirred at 60° C. under argon for 14 h. The reaction mixture was cooled to room temperature and diluted with EtOAc. The EtOAc was isolated and dried over MgSO$_4$. The EtOAc was evaporated and the residue was subjected to flash column chromatography (hexanes/EtOAc) to give compound 9 as white solid (yield 75%) (m/z+H) 358.

Compound 9 was dissolved in 7 N NH3 in MeOH and stirred at room temperature for 14 h. The solvent was removed to give compound 10, which was used for next step without further purification (m/z+H) 343.

Step 2: Synthesis of Compound 12

According to Scheme 35, a 10 mL microwavable vial was charged with compound 10 (250 mg, 0.73 mmol), 2,4-dimethoxybenzylamine (Aldrich, 0.54 mL, 3.63 mmol), Pd$_2$(dba)$_3$ (21 mg, 0.036 mmol), NaOBu-t (140 mg, 1.46 mmol), BINAP (45 mg, 0.07 mmol) and dioxane/DMF (3 mL/1 mL). The mixture was purge with argon and then stirred at 160° C. under microwave for 20 min. The reaction mixture was cooled to room temperature and diluted with EtOAc. The EtOAc was isolated and dried over MgSO$_4$. The EtOAc was evaporated and the residue was subjected to flash column chromatography (hexanes/EtOAc) to give compound 11 as white solid (yield 55%) (m/z+H) 474.

Compound 11 was dissolved in TFA and stirred at room temperature for 2 h. The TFA was removed and the residue was dissolved in EtOAc, which was washed with sat. NaHCO3 and brine. The EtOAc was isolated and concentrated to give crude 12, which was used for next step without further purification (m/z+H) 324.

Example 23

Synthesis of 2-(3-(2-carbamoyl-6-(4-(4-fluorophenoxy)phenyl)pyridin-4-yl)ureido)acetic acid (Compound Example No. 87)

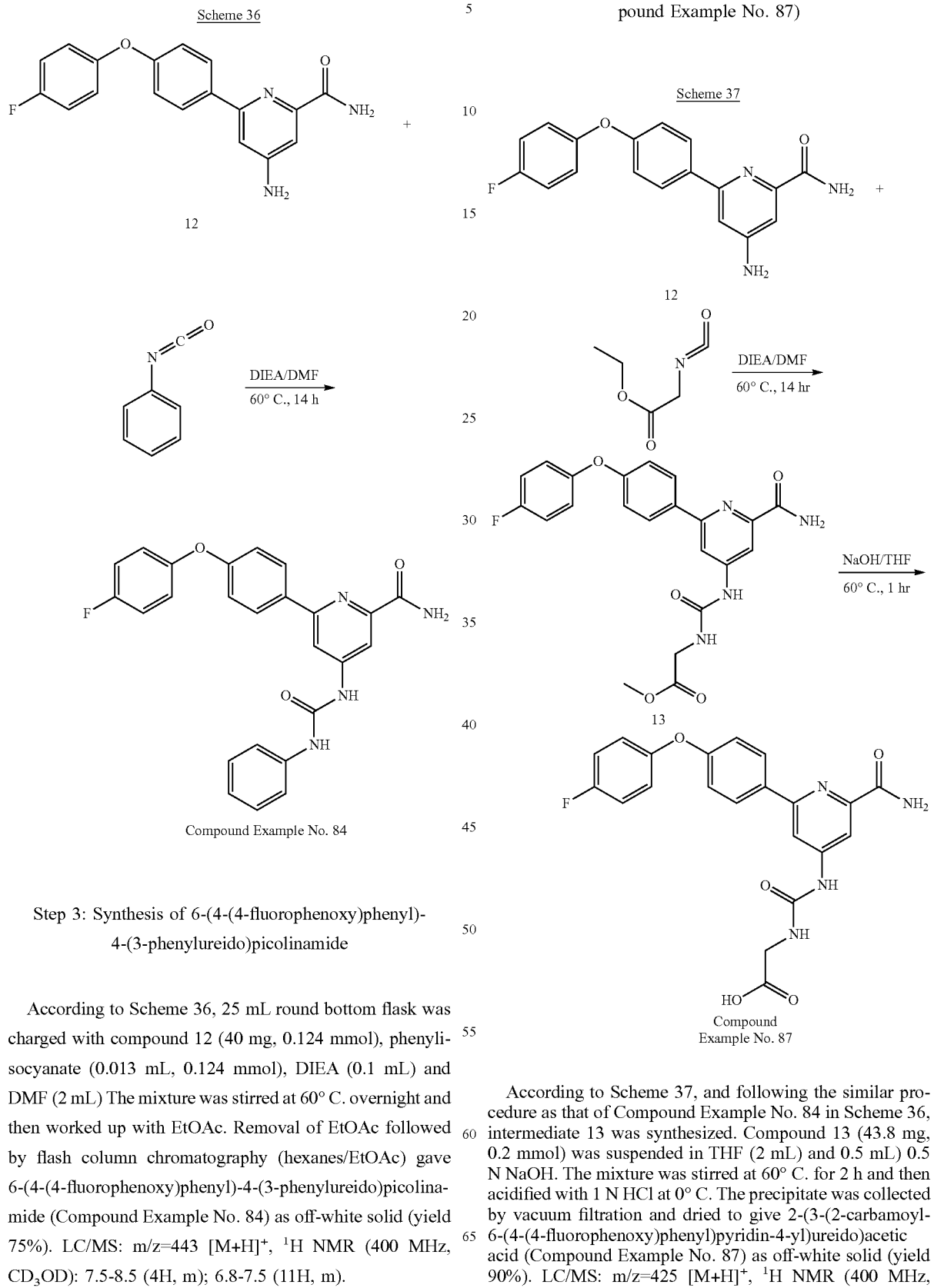

Compound Example No. 84

Step 3: Synthesis of 6-(4-(4-fluorophenoxy)phenyl)-4-(3-phenylureido)picolinamide According to Scheme 36, 25 mL round bottom flask was charged with compound 12 (40 mg, 0.124 mmol), phenylisocyanate (0.013 mL, 0.124 mmol), DIEA (0.1 mL) and DMF (2 mL) The mixture was stirred at 60° C. overnight and then worked up with EtOAc. Removal of EtOAc followed by flash column chromatography (hexanes/EtOAc) gave 6-(4-(4-fluorophenoxy)phenyl)-4-(3-phenylureido)picolinamide (Compound Example No. 84) as off-white solid (yield 75%). LC/MS: m/z=443 [M+H]$^+$, $^1$H NMR (400 MHz, CD$_3$OD): 7.5-8.5 (4H, m); 6.8-7.5 (11H, m).

Compound Example No. 87

According to Scheme 37, and following the similar procedure as that of Compound Example No. 84 in Scheme 36, intermediate 13 was synthesized. Compound 13 (43.8 mg, 0.2 mmol) was suspended in THF (2 mL) and 0.5 mL) 0.5 N NaOH. The mixture was stirred at 60° C. for 2 h and then acidified with 1 N HCl at 0° C. The precipitate was collected by vacuum filtration and dried to give 2-(3-(2-carbamoyl-6-(4-(4-fluorophenoxy)phenyl)pyridin-4-yl)ureido)acetic acid (Compound Example No. 87) as off-white solid (yield 90%). LC/MS: m/z=425 [M+H]$^+$, $^1$H NMR (400 MHz, DMSO-d$_6$): 9.5 (1H, s); 9.1 (1H, s), 8.8 (1H, s), 7.9 (1H, s), 6.3-8.8 (10H, m), 3.8 (2H, s).
Example 24
General Synthesis of 4-Amino Substituted Pyridines
Scheme 38
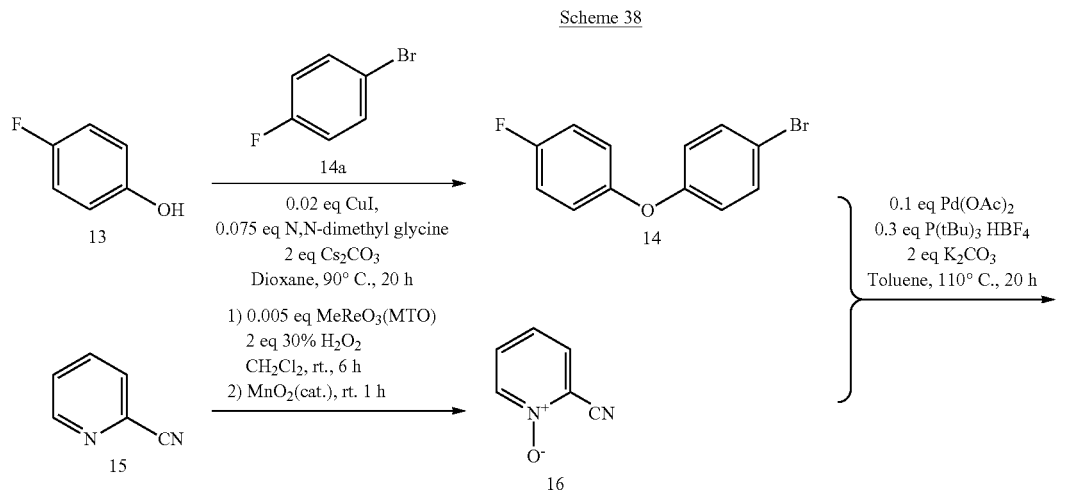
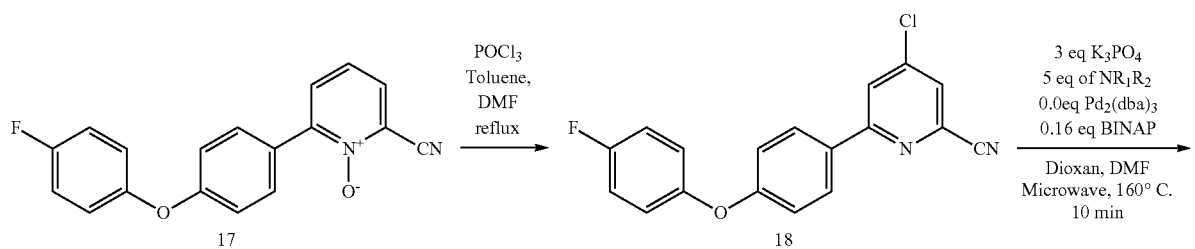
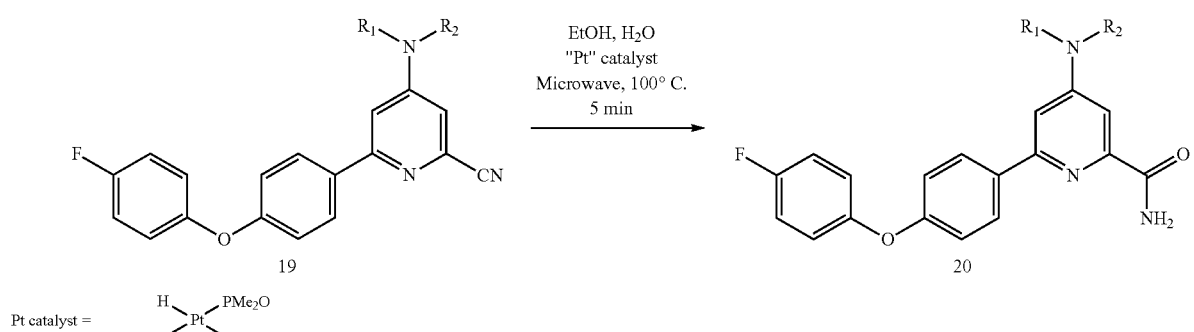

Compound 18 was synthesized according to the procedures reported in the literature (J. Org. Chem. 1998, 63, 1740-1741) as shown in Scheme 38.

A suspension of compound 18, amine NHR$_1$R$_2$ (5 eq.), K$_3$PO$_4$ (3 eq.), Pd$_2$(dba)$_3$ (0.08 eq.), BINAP (0.16 eq.) in dioxane (0.45 mL) and DMF (0.05 mL) was blanked with argon, then heated at 160° C. in a Microwave oven (Biotage, Initiator 2.5) for 10-30 min. After cooling to room temperature, the reaction mixture was purified by column chromatography (4 g silica gel, 20-60% EtOAc/Hexane) to give compound 19.

To a solution of compound 19 in EtOH (2 mL) and H$_2$O (2 mL) was added platinum catalyst (0.01 eq., Strem) and heated at 100° C. oil bath for 10 min. After cooling to room temperature, the reaction mixture was extracted with EtOAc (4×20 mL) and the combined organic layers were dried over Na$_2$SO$_4$, filtered and concentrated. The residue was purified either by silica gel column chromatography using MeOH/CH$_2$Cl$_2$ (containing 1% NH$_3$) as the eluent or by C18 column chromatography (reverse phase HPLC) to give compound 20.

Example 25

Synthesis of 6-(4-(4-fluorophenoxy)phenyl)-4-((2-morpholinoethyl)amino)picolinamide (Compound Example No. 53)

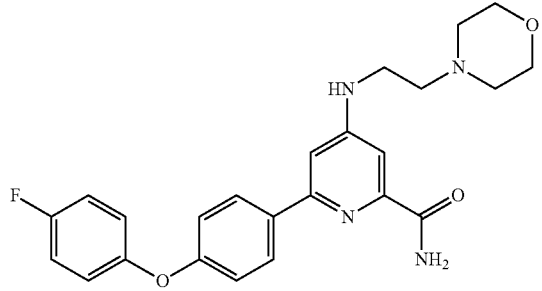 [SMILES: NC(=O)c1cc(NCCN2CCOCC2)cc(-c2ccc(Oc3ccc(F)cc3)cc2)n1]

6-(4-(4-fluorophenoxy)phenyl)-4-((2-morpholinoethyl) amino)picolinamide (Compound Example No. 53) was prepared according to general procedure of Scheme 38. $^1$H NMR (CD$_3$OD): 8.07 (m, 2H), 7.29 (m, 2H), 7.0-7.2 (m, 6H), 3.74 (t, 4H, J=4.8 Hz), 3.43 (t, 2H, J=6.4 Hz), 2.67 (t, 2H, J=6.4 Hz), 2.57 (m, 4H). LC/MS: m/z=437 (M+1)

Example 26

Synthesis of 4-((3-(1H-imidazol)-1-yl)propyl) amino)-6-(4-(4-fluorophenoxy)phenylpicolinonitrile (Compound Example No. 110)

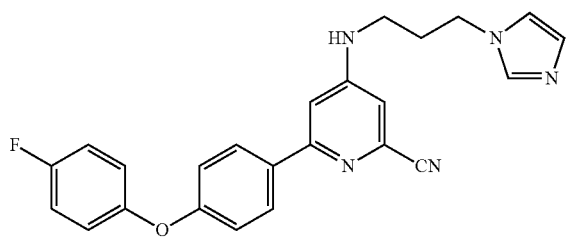 [SMILES: N#Cc1cc(NCCCn2ccnc2)cc(-c2ccc(Oc3ccc(F)cc3)cc2)n1]

4-((3-(1H-imidazol)-1-yl)propyl)amino)-6-(4-(4-fluorophenoxy)phenyl picolinonitrile (Compound Example No. 110) was prepared according to general procedure of Scheme 38. $^1$H NMR (CD$_3$OD): 8.97 (s, 1H), 7.88 (d, 2H, J=9.2 Hz), 7.70 (t, 1H, J=2 Hz), 7.60 (t, 1H, J=2 Hz), 7.0-7.18 (m, 6H), 4.40 (t, 2H, J=7.6 Hz), 3.36 (t, 2H, J=6.8 Hz), 2.25 (m, 2H). LC/MS: m/z=414 (M+1).

Example 27

Synthesis of 6-(4-(4-fluorophenoxy)phenyl)-4-(piperazin-1-yl)picolinamide (Compound Example No. 55)

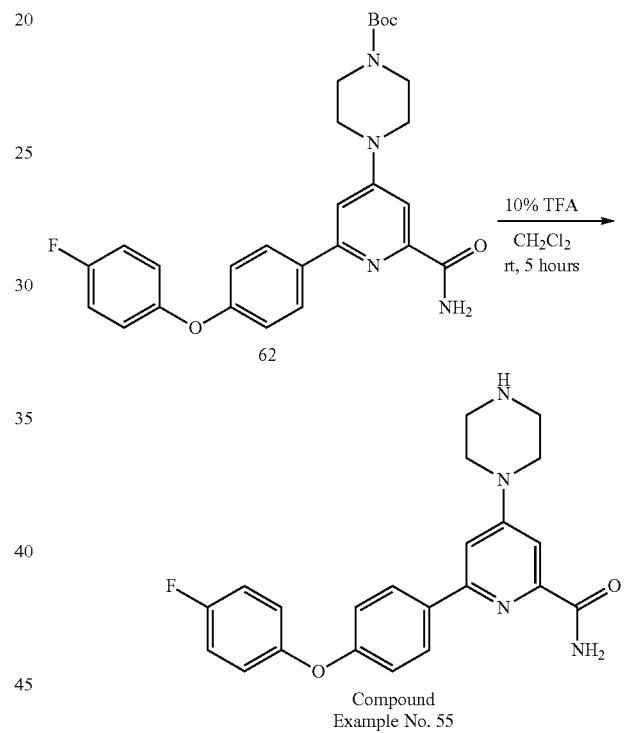

According to Scheme 39, compound 62, which was prepared according to the general procedure of Scheme 38, was treated with 10% TFA in CH$_2$Cl$_2$ at room temperature for 5 h, the reaction mixture was concentrated, and the residue was purified via C18 column reverse HPLC to obtain 6-(4-(4-fluorophenoxy)phenyl)-4-(piperazin-1-yl)picolinamide (Compound Example No. 55)$^1$H NMR (CD$_3$OD): 8.08 (m, 2H), 7.63 (d, 1H, J=2.4 Hz), 7.47 (d, 1H, J=2.4 Hz), 7.06-7.18 (m, 6H), 3.84 (t, 4H, J=4 Hz), 3.41 (t, 4H, J=5.2 Hz). LC/MS: m/z=393 (M+1).

6-(4-(4-fluorophenoxy)phenyl)-4-(piperazin-1-yl)pyridine-2-yl)(piperazin-1-yl)methanone (Compound Example No. 78) was isolated as a minor impurity in the synthesis of Compound Example No. 55. $^1$H NMR (CD$_3$OD): 7.85 (d, 2H, J=9.2 Hz), 7.31 (d, 1H, J=2.4 Hz), 7.12 (d, 1H, J=2.4 Hz), 6.93-7.09 (m, 6H), 3.93 (m, 2H), 3.82 (m, 2H), 3.75 (t, 4H, J=5.2 Hz), 3.306 (t, 4H, J=5.2 Hz), 3.27 (b, 4H). LC/MS: m/z=462 (M+1).

Example 28

Synthesis of 4-(4-carbamimidoylpiperazin-1-yl)-6-(4-(4-fluorophenoxy)phenyl)picolinamide (Compound Example No. 80)

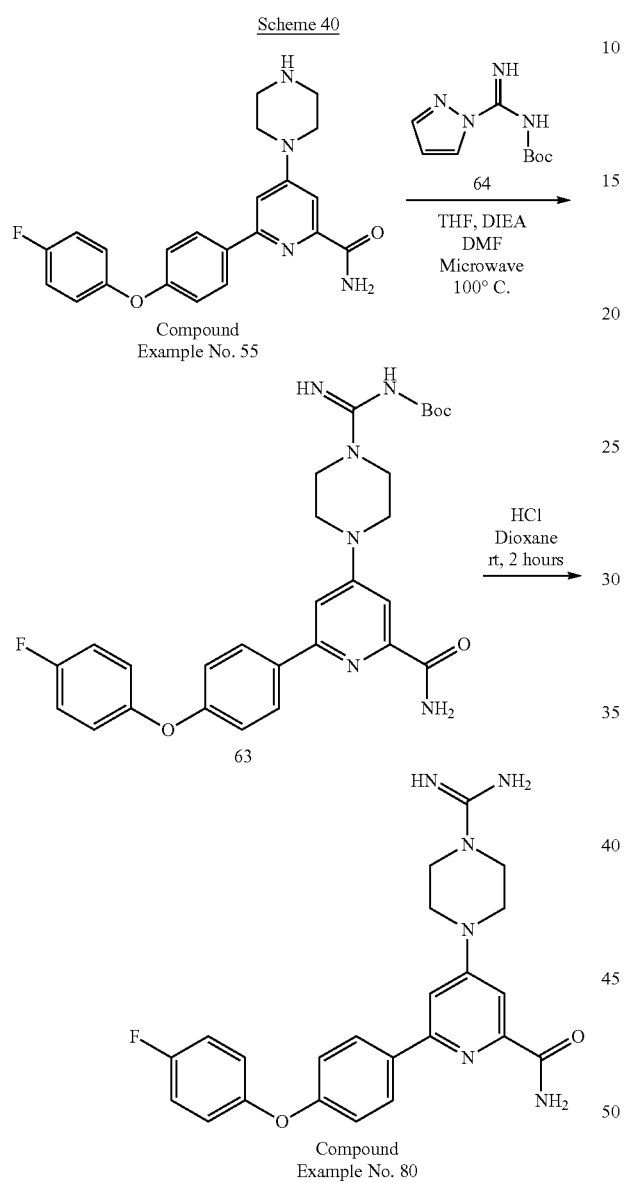

Example 29

Synthesis of 4-(2-cyano-6-(4-(4-fluorophenoxy)phenyl)pyridin-4-yl)piperazine-1-carboximidamide (Compound Example No. 83)

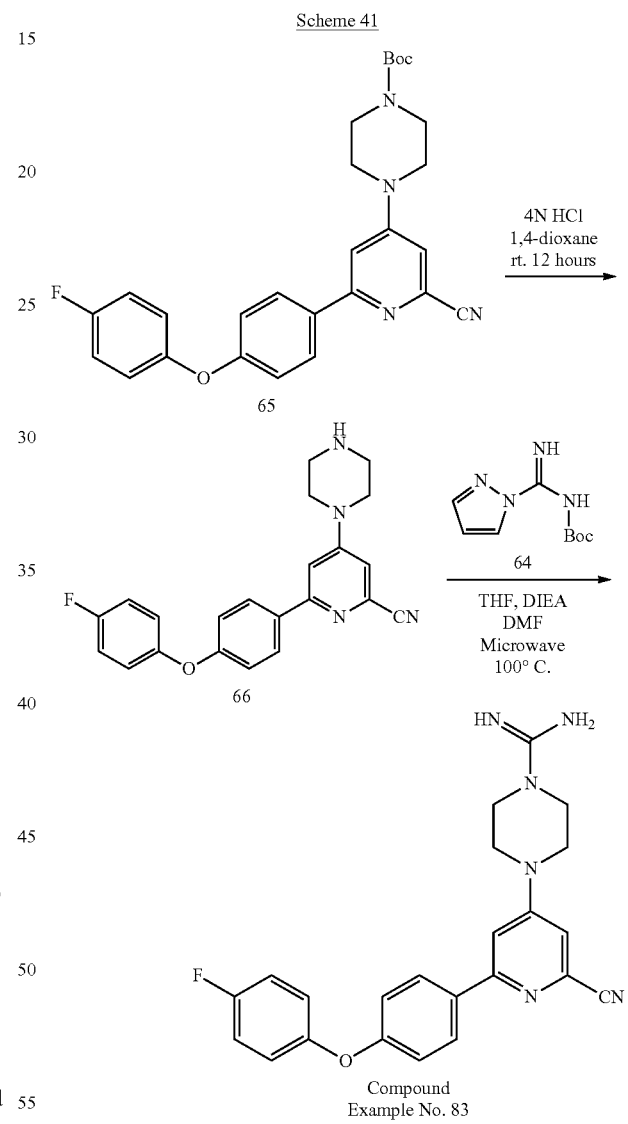

According to Scheme 40, a solution of Compound Example No. 55 (180 mg, 0.46 mmol), compound 64 (143 mg, 0.68 mmol, Aldrich), DIEA (254 µL, 1.38 mmol) in THF (4 mL) and DMF (0.04 mL) was heated at 100° C. (Biotage, Initiator 2.5 Microwave) for 10 min. After cooling to room temperature, the mixture was purified by column chromatography (12 g silica gel, 0-100% EtOAc/Hexane) to give compound 63.

Compound 63 was treated with 4 N HCl in 1,4-dioxane (Aldrich) at room temperature to remove the Boc protecting group. The resulting mixture was concentrated and purified by C18 reverse phase HPLC to give 4-(4-carbamimidoylpiperazin-1-yl)-6-(4-(4-fluorophenoxy)phenyl)picolinamide (Compound Example No. 80) (66 mg, 0.15 mmol). $^1$H NMR (CD$_3$OD): 7.80 (d, 2H, J=9.2 Hz), 7.56 (s, 1H), 7.34 (s, 2H, NH), 7.23 (d, 1H, J=2.4 Hz), 7.01-7.12 (m, 6H), 3.91 (bs, 4H), 3.71 (m, 4H). LC/MS: m/z=435 (M+1).

According to Scheme 41, to a solution of compound 65 (266 mg, 0.56 mmol), which was prepared according general procedure of Scheme 38, in EtOAc (6 mL) was added 4 N HCl in 1,4-dioxane (2 mL, 8 mol). The resulting solution was stirred at room temperature for 12 h. The solvent was removed and the precipitate was rinsed with EtOAc. Compound 66 was obtained as the HCl salt (246 mg, 0.55 mmol, 2HCl).

A solution of compound 66 (98 mg, 0.24 mmol), compound 64 (50 mg), and Et$_3$N (0.3 mL, 2 mmol) in DMF (3 mL) was heated at 90° C. in an oil bath for 12 h. After cooling to room temperature, the mixture was purified by C18 reverse phase HPLC to give 4-(2-cyano-6-(4-(4-fluorophenoxy)phenyl)pyridin-4-yl)piperazine-1-carboximidamide (Compound Example No. 83) as yellow solid (4.7 mg, 0.01 mmol). $^1$H NMR (CD$_3$OD): 7.98 (d, 2H, J=8.8 Hz), 7.38 (b, 1H, NH), 7.35 (d, 1H, J=2.4 Hz), 7.28 (d, 1H, J=2.4 Hz), 7.03-7.17 (m, 6H), 3.72 (m, 8H). LC/MS: m/z=417 (M+1).

Example 30

Synthesis of 6-(4-(4-fluorophenoxy)phenyl)-4-((piperidin-4-ylmethyl)amino)picolinamide (Compound Example No. 57)

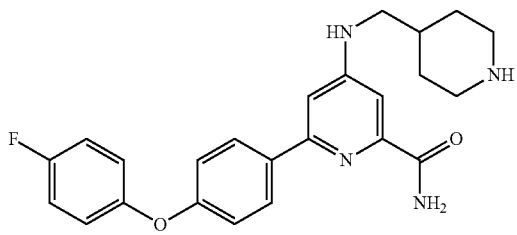 [SMILES: NC(=O)c1cc(NCC2CCNCC2)cc(-c2ccc(Oc3ccc(F)cc3)cc2)n1]

6-(4-(4-fluorophenoxy)phenyl)-4-((piperidin-4-ylmethyl)amino)picolinamide (Compound Example No. 57) was prepared according general procedure of Scheme 38. $^1$H NMR (CD$_3$OD): 7.84 (d, 2H, J=8.8 Hz), 7.43 (b, 1H), 7.12-7.23 (m, 7H), 3.45 (m, 4H), 3.04 (t, 2H, J=12 Hz), 2.11 (m, 3H), 1.56 (m, 2H). LC/MS: m/z=421 (M+1).

Example 31

Synthesis of 4-((2-(1,1-dioxidothiomorpholino)ethyl)amino)-6-(4-(4-fluorophenoxy phenyl)picolinamide (Compound Example No. 48)

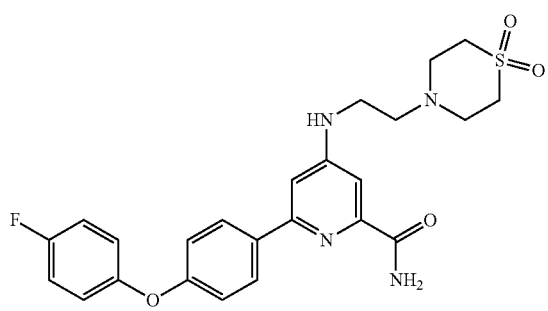 [SMILES: NC(=O)c1cc(NCCN2CCS(=O)(=O)CC2)cc(-c2ccc(Oc3ccc(F)cc3)cc2)n1]

4-((2-(1,1-dioxidothiomorpholino)ethyl)amino)-6-(4-(4-fluorophenoxy)phenyl)picolinamide (Compound Example No. 48) was prepared according general procedure of Scheme 38. $^1$H NMR (CD$_3$OD): 8.05 (m, 2H), 7.29 (m, 1H), 7.01-7.16 (m, 7H), 3.39 (t, 2H, J=6.4 Hz), 3.04-3.14 (m, 8H), 2.82 (m, 2H). LC/MS: m/z=485 (M+1).

Example 32

Synthesis of 4-((3-(1H-imidazol-1-yl)propyl)amino)-6-(4-(4-fluorophenoxy)phenyl)picolinamide (Compound Example No. 54)

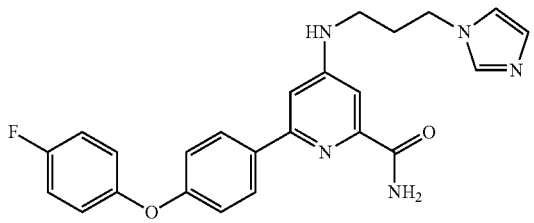 [SMILES: NC(=O)c1cc(NCCCn2ccnc2)cc(-c2ccc(Oc3ccc(F)cc3)cc2)n1]

4-((3-(1H-imidazol-1-yl)propyl)amino)-6-(4-(4-fluorophenoxy)phenyl)picolinamide (Compound Example No. 54) was prepared according general procedure of Scheme 38. $^1$H NMR (CD$_3$OD): 8.89 (s, 1H), 7.78 (d, 2H, J=8.4 Hz), 7.61 (t, 1H, J=2 Hz), 7.51 (t, 1H, J=2 Hz), 7.22 (d, 1H, J=2 Hz), 6.96-7.10 (m, 7H), 4.32 (t, 2H, J=7.6 Hz), 3.39 (t, 2H, J=7.2 Hz), 2.22 (m, 2H). LC/MS: m/z=432 (M+1).

Example 33

Synthesis of 6-(4-(4-fluorophenoxy)phenyl)-4-((2-(2-oxoimidazolidin-1-yl)ethyl)amino) picolinamide (Compound Example No. 58)

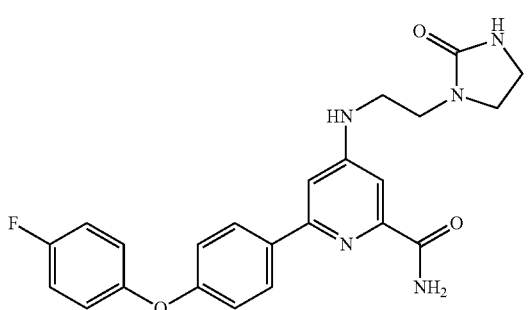

6-(4-(4-fluorophenoxy)phenyl)-4-((2-(2-oxoimidazolidin-1-yl)ethyl)amino) picolinamide (Compound Example No. 58) was prepared according general procedure of Scheme 38. $^1$H NMR (CD$_3$OD): 8.32 (d, 1H, J=2 Hz), 8.17 (d, 1H, J=2 Hz), 8.14 (d, 2H, J=8.8 Hz), 7.06-7.20 (m, 6H), 4.06 (m, 2H), 3.67 (m, 4H), 3.23 (t, 2H, J=6 Hz). LC/MS: m/z=436 (M+1).

Example 34

Synthesis of 4-(((1-2(2-amino-2-oxoethyl)piperidin-4-yl)methyl)amino)-6-(4-(4-fluorophenoxy)phenyl) picolinamide (Compound Example No. 52)

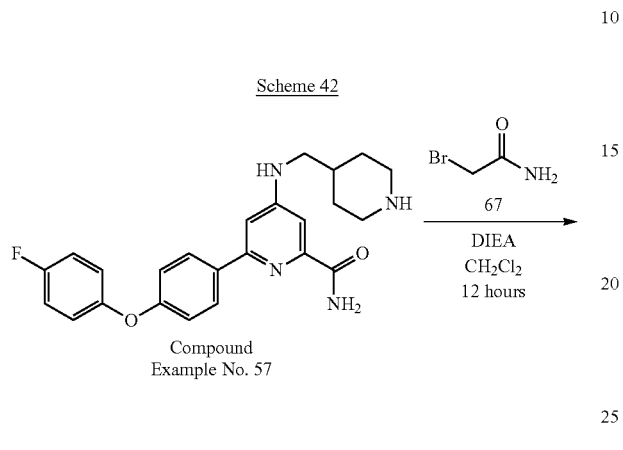

According to Scheme 42, to a solution of Compound Example No. 57 (174 mg HCl salt, 0.4 mmol) and DIEA (0.173 mL 1.2 mmol) in CH$_2$Cl$_2$ (5 mL) was added compound 67 (54 mg, 0.4 mmol). The resulting solution was stirred at room temperature for 12 h. After removal of the solvent, the residue was purified by column chromatography (40 g silica gel, 0-50% MeOH/CH$_2$Cl$_2$) and further purified by C18 reverse column chromatography to give 4-(((1-2(2-amino-2-oxoethyl)piperidin-4-yl)methyl)amino)-6-(4-(4-fluorophenoxy)phenyl)picolinamide (Compound Example No. 52) (40 mg, 0.08 mmol). $^1$H NMR (CD$_3$OD): 7.93 (d, 2H, J=9.2 Hz), 7.14 (d, 1H, J=2.4 Hz), 6.90-7.05 (m, 7H), 3.06 (d, 2H, J=6.8 Hz), 2.89 (s, 2H), 2.83 (d, 2H, J=11 Hz), 2.06 (t, 2H, J=11 Hz), 1.72 (d, 2H, J=12 Hz), 1.56 (m, 1H), 1.33 (m, 2H). LC/MS: m/z=478 (M+1).

Example 35

Synthesis of 6-(4-(4-fluorophenoxy)phenyl)-4-(4-(pyrimidin-2-yl)piperazin-1-yl)picolinamide (Compound Example No. 74)

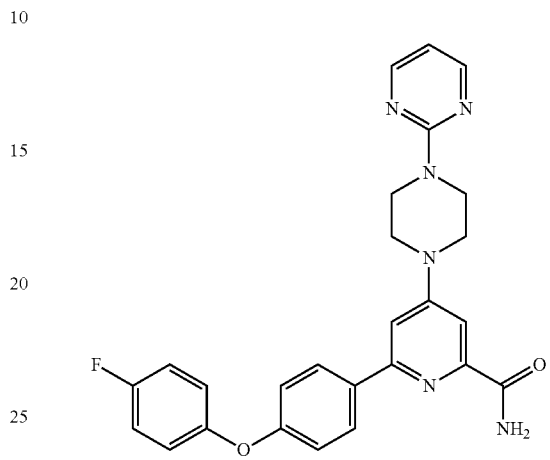

6-(4-(4-fluorophenoxy)phenyl)-4-(4-(pyrimidin-2-yl)piperazin-1-yl) picolinamide (Compound Example No. 74) was prepared according general procedure of Scheme 38. $^1$H NMR (CD$_3$OD): 8.38 (d, 2H, J=4.4 Hz), 8.07 (bd, 1H, NH), 7.96 (s, 1H), 7.94 (s, 1H), 7.67 (b, 1H), 7.16 (s, 1H), 7.04-7.11 (m, 6H), 6.59 (t, 1H, J=4.4 Hz), 5.57 (b, 1H, NH), 4.03 (m, 4H), 3.63 (m, 4H). LC/MS: m/z=471 (M+1).

Example 36

Synthesis of 6-(4-(4-fluorophenoxy)phenyl)-4-((pyrimidin-2-ylmethyl)amino)picolinamide (Compound Example No. 49)

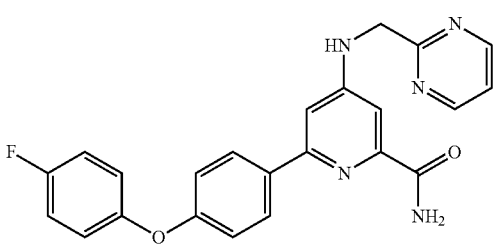 [SMILES: NC(=O)c1cc(NCc2ncccn2)cc(-c2ccc(Oc3ccc(F)cc3)cc2)n1]

6-(4-(4-fluorophenoxy)phenyl)-4-((pyrimidin-2-ylmethyl)amino)picolinamide (Compound Example No. 49) was prepared according general procedure of Scheme 38. $^1$H NMR (CD$_3$OD): 8.82 (m, 2H), 7.83 (m, 2H), 7.46 (m, 2H), 7.10-7.25 (m, 7H), 4.91 (s, 2H). LC/MS: m/z=416 (M+1).

Example 37

Synthesis of 4-(2-cyano-6-(4-(4-fluorophenoxy)phenyl)pyridine-4-yl)-N-isopropylpiperazine-1-carboxamide (Compound Example No. 82) and 4-(2-carbamoyl-6-(4-(4-fluorophenoxy)phenyl)pyridine-4-yl)-N-isopropylpiperazine-1-carboxamide (Compound Example No. 73)

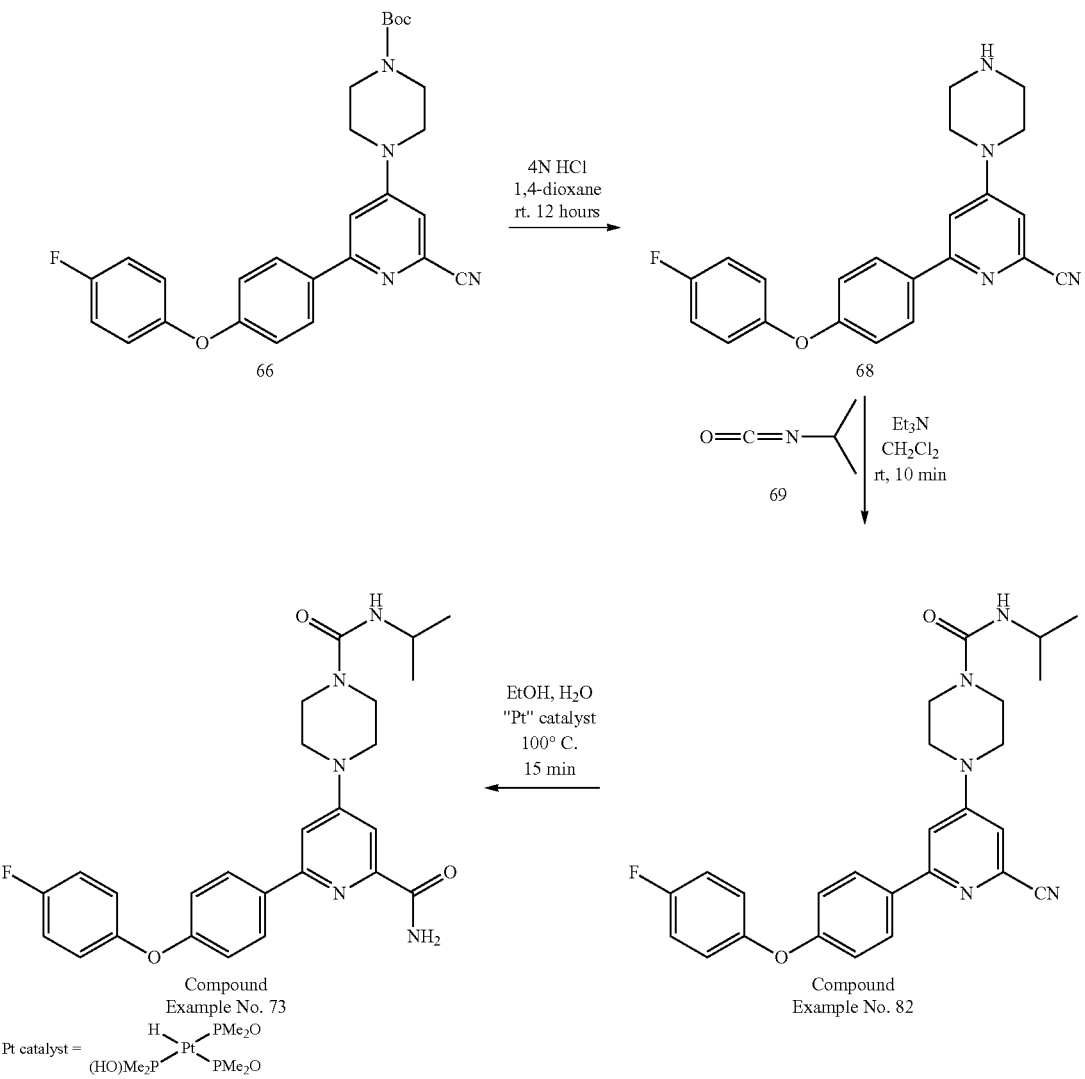

According to Scheme 43, a solution of compound 66 (266 mg, 0.56 mmol) in 4N HCl in 1,4-dioxane (5 mL) was stirred at room temperature for 12 h. The solvent was removed and the solid was washed with EtOAc/Hexane. Compound 68 was obtained (246 mg, 0.5 mmol) as white solid (HCl salt).

To a solution of compound 68 (95 mg, 0.21 mmol) and Et$_3$N (0.151 mL, 1.05 mmol) in CH$_2$Cl$_2$ was added compound 69 (18 mg, 0.21 mmol) and the resulting solution was stirred at room temperature for 10 min. The mixture was purified without aqueous workup by column chromatography (12 g silica gel, 0-100% EtOAc/Hexane) to give 4-(2-cyano-6-(4-(4-fluorophenoxy)phenyl)pyridine-4-yl)-N-isopropylpiperazine-1-carboxamide (Compound Example No. 82). $^1$H NMR (CDCl$_3$): 7.83 (d, 2H, J=9.2 Hz), 6.91-7.02 (m, 8H), 4.14 (b, 1H, NH), 3.94 (m, 1H), 3.54 (m, 4H), 3.48 (m, 4H), 1.12 (d, 6H, J=6.4 Hz). LC/MS: m/z=460 (M+1).

To a solution of Compound Example No. 82 in EtOH (2 mL) and H$_2$O (2 mL) was added the platinum catalyst and the reaction mixture was heated at 100° C. in an oil bath for 10 min. After cooling to room temperature, the mixture was extracted with EtOAc (4×20 mL) and the organic layer was dried over Na$_2$SO$_4$, filtered, and concentrated. The residue was purified by column chromatography (12 g silica gel, MeOH/CH$_2$Cl$_2$, 0-20% with 1% NH$_3$) to give 4-(2-carbamoyl-6-(4-(4-fluorophenoxy)phenyl)pyridine-4-yl)-N-isopropylpiperazine-1-carboxamide (Compound Example No. 73) (29 mg, 0.06 mmol). $^1$H NMR (CD$_3$OD): 8.01 (m, 2H), 7.45 (s, 1H), 7.28 (s, 1H), 6.94-7.07 (m, 6H), 6.14 (d, 0.66H, J=8 Hz, NH), 3.83 (m, 1H), 3.50 (m, 4H), 3.46 (m, 4H), 1.10 (d, 6H, J=7.6 Hz). LC/MS: m/z=478 (M+1).

Example 38

Synthesis of 4-(4-carbamoylpiperidin-1-yl)-6-(4-(4-fluorophenoxy)phenyl)picolinamide (Compound Example No. 56)

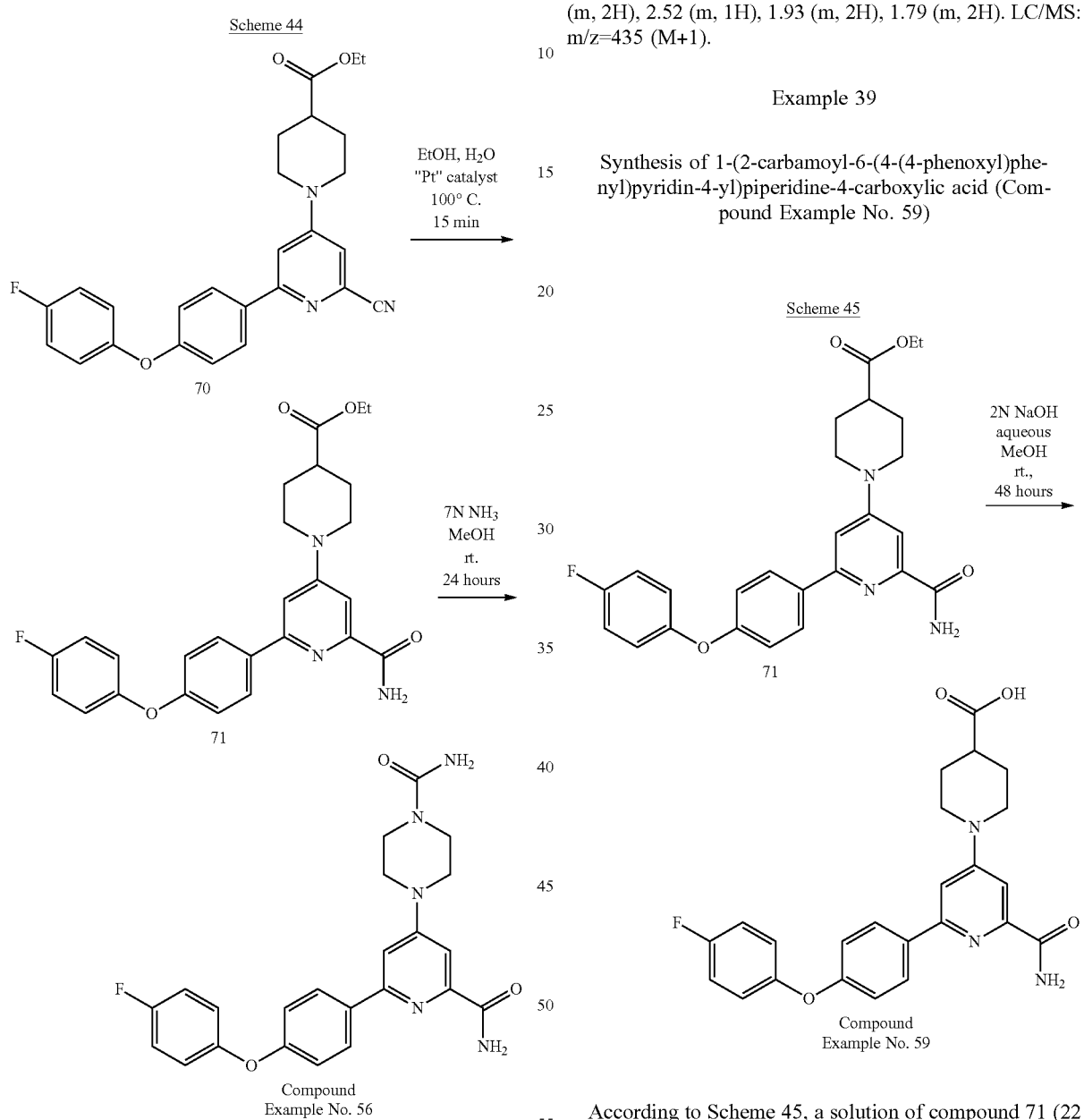

According to Scheme 44, a solution of compound 70 (89 mg, 0.2 mmol), which was prepared according general procedure of Scheme 38, and the platinum catalyst in EtOH (2.5 mL) and H₂O (1 mL) was heated at 100° C. (Biotage, Initiator 2.5 Microwave) for 15 min. After cooling to room temperature, the reaction mixture was extracted with EtOAc (4×20 mL) and the combined organic layers were dried over Na₂SO₄, filtered, and concentrated. The residue was purified by column chromatography (12 silica gel, 0-100% EtOAc/Hexane) to give compound 71 (69 mg, 0.14 mmol). Compound 71 (47 mg, 0.1 mmol) was treated with 7N NH₃ in methanol at room temperature for 24 h. After concentration, the resulting solid was recrystallized in methanol to give 4-(4-carbamoylpiperidin-1-yl)-6-(4-(4-fluorophenoxy)phenyl)picolinamide (Compound Example No. 56) (11 mg, 0.025 mmol). ¹H NMR (CD₃OD): 8.08 (d, 2H, J=9.2 Hz), 7.94 (s, 0.6H, NH), 7.53 (d, 1H, J=2.8 Hz), 7.35 (d, 1H, J=2.8 Hz), 7.02-7.15 (m, 6H), 4.17 (d, 2H, J=13 Hz), 3.04 (m, 2H), 2.52 (m, 1H), 1.93 (m, 2H), 1.79 (m, 2H). LC/MS: m/z=435 (M+1).

Example 39

Synthesis of 1-(2-carbamoyl-6-(4-(4-phenoxyl)phenyl)pyridin-4-yl)piperidine-4-carboxylic acid (Compound Example No. 59)

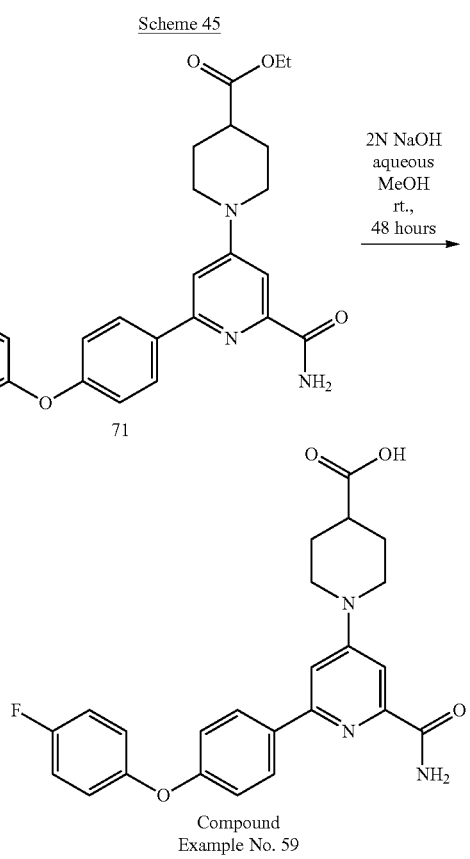

According to Scheme 45, a solution of compound 71 (22 mg, 0.047 mmol) in 2 N NaOH aqueous (2 mL, 4 mmol) and MeOH (1 mL) was stirred at room temperature for 48 h. The methanol was then removed under vacuum. The residue was adjusted to pH 3 with aqueous HCl and then extracted with EtOAc (2×5 mL). The organic layer was dried over Na₂SO₄, filtered, and concentrated to give 1-(2-carbamoyl-6-(4-(4-phenoxyl)phenyl)pyridin-4-yl)piperidine-4-carboxylic acid (Compound Example No. 59) (15 mg, 0.034 mmol). ¹H NMR (DMSO-d₆): 8.30 (m, 2H), 8.18 (m, 1H, NH), 7.67 (m, 1H, NH), 7.49 (m, 2H), 7.33 (m, 2H), 7.20 (m, 2H), 7.12 (m, 2H), 4.12 (m, 2H), 3.15 (m, 2H), 1.97 (m, 2H), 1.65 (m, 2H). LC/MS: m/z=436 (M+1).

Example 40

Synthesis of 4-(2-carbamoyl-6-(4-(4-fluorophenoxy)phenyl)pyridine-4-yl)piperazine-1-carboxamide (Compound Example No. 76)

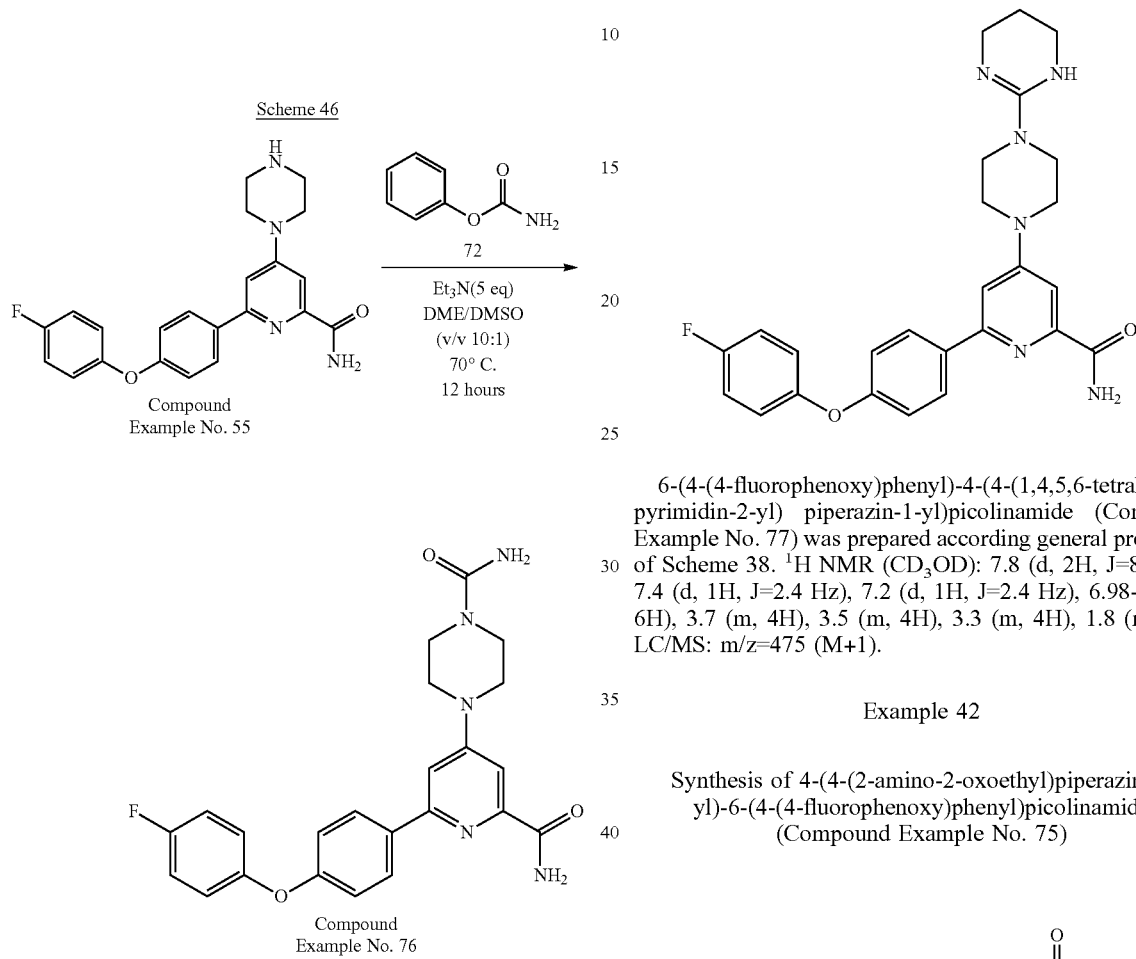

According to Scheme 46, a solution of Compound Example No. 55 (404 mg, 0.87 mmol, 2HCl salt), 72 (137 mg, 1 mmol), and Et$_3$N (0.63 mL, 4.3 mmol) in DME (10 mL) and DMSO (1 mL) was heated at 70° C. for 12 h. After cooling to room temperature, the mixture was purified by column chromatography without workup (40 g silica gel, 0-50% MeOH, CH$_2$Cl$_2$) to give 4-(2-carbamoyl-6-(4-(4-fluorophenoxy)phenyl)pyridine-4-yl)piperazine-1-carboxamide (Compound Example No. 76) as white solid (130 mg, 0.30 mmol). $^1$H NMR (CD$_3$OD): 8.56 (b, 1H, NH), 8.05 (b, 3H, contains NH), 7.61 (s, 1H), 7.43 (s, 1H), 7.31 (m, 2H), 7.11-7.18 (m, 4H), 3.70 (m, 4H), 3.49 (m, 4H). LC/MS: m/z=436 (M+1).

Example 41

Synthesis of 6-(4-(4-fluorophenoxy)phenyl)-4-(4-(1,4,5,6-tetrahydropyrimidin-2-yl)piperazin-1-yl) picolinamide (Compound Example No. 77)

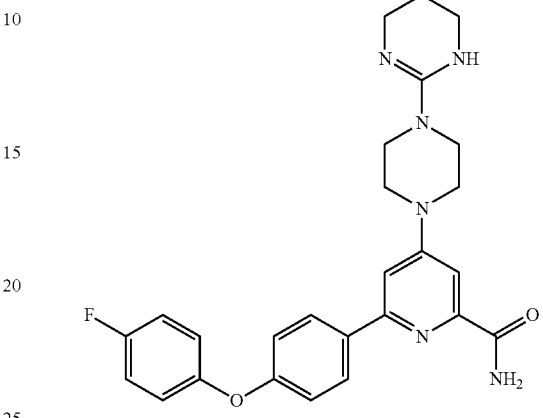

6-(4-(4-fluorophenoxy)phenyl)-4-(4-(1,4,5,6-tetrahydropyrimidin-2-yl) piperazin-1-yl)picolinamide (Compound Example No. 77) was prepared according general procedure of Scheme 38. $^1$H NMR (CD$_3$OD): 7.8 (d, 2H, J=8.8 Hz), 7.4 (d, 1H, J=2.4 Hz), 7.2 (d, 1H, J=2.4 Hz), 6.98-7.1 (m, 6H), 3.7 (m, 4H), 3.5 (m, 4H), 3.3 (m, 4H), 1.8 (m, 2H). LC/MS: m/z=475 (M+1).

Example 42

Synthesis of 4-(4-(2-amino-2-oxoethyl)piperazin-1-yl)-6-(4-(4-fluorophenoxy)phenyl)picolinamide (Compound Example No. 75)

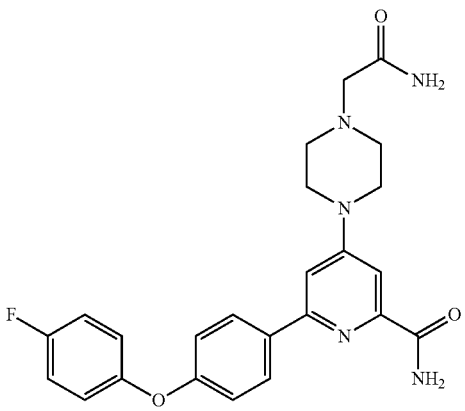 [SMILES: NC(=O)CN1CCN(c2cc(C(N)=O)nc(-c3ccc(Oc4ccc(F)cc4)cc3)c2)CC1]

4-(4-(2-amino-2-oxoethyl)piperazin-1-yl)-6-(4-(4-fluorophenoxy)phenyl)picolinamide (Compound Example No. 75) was synthesized similarly to Compound Example No. 52 in Scheme 42. $^1$H NMR (CD$_3$OD): 8.09 (d, 2H, J=9.2 Hz), 7.54 (d, 1H, J=2.4 Hz), 7.36 (d, 1H, J=2.4 Hz), 7.02-7.16 (m, 6H), 3.57 (m, 4H), 3.09 (s, 2H), 2.71 (m, 4H). LC/MS: m/z=450 (M+1).

Example 43

Synthesis of 2-(4-(2-chloro-6-(4-(4-fluorophenoxy)phenyl)pyridine-4-yl)piperazin-1-yl)acetamide (Compound Example No. 109)

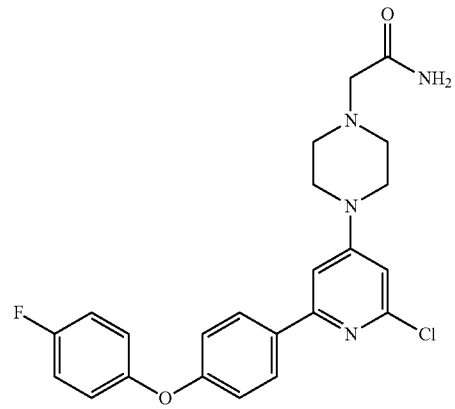 [SMILES: NC(=O)CN1CCN(c2cc(Cl)nc(-c3ccc(Oc4ccc(F)cc4)cc3)c2)CC1]

2-(4-(2-chloro-6-(4-(4-fluorophenoxy)phenyl)pyridine-4-yl)piperazin-1-yl) acetamide (Compound Example No. 109) was synthesized similarly to Compound Example No. 52 in Scheme 42. $^1$H NMR (CD$_3$OD): 7.79 (d, 2H, J=8.8 Hz), 6.90-7.06 (m, 7H), 6.69 (d, 1H, J=2 Hz), 3.43 (m, 4H), 2.98 (s, 2H), 2.58 (m, 4H). LC/MS: m/z=441 (M+1).

Example 44

Synthesis of (R)-1-6-(4-(4-fluorophenoxy)phenyl)-4-piperazin-1-yl)pyridin-2-yl)ethan-1,2-diol (Compound Example No. 21)

Scheme 47

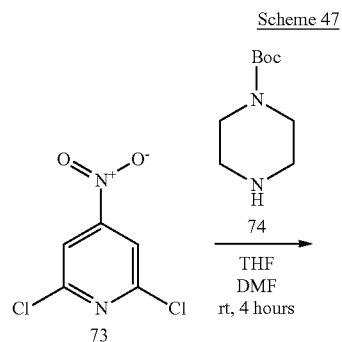

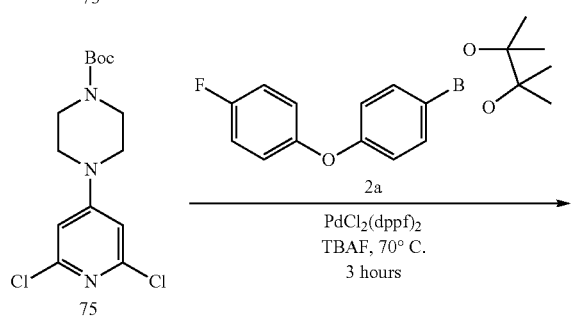

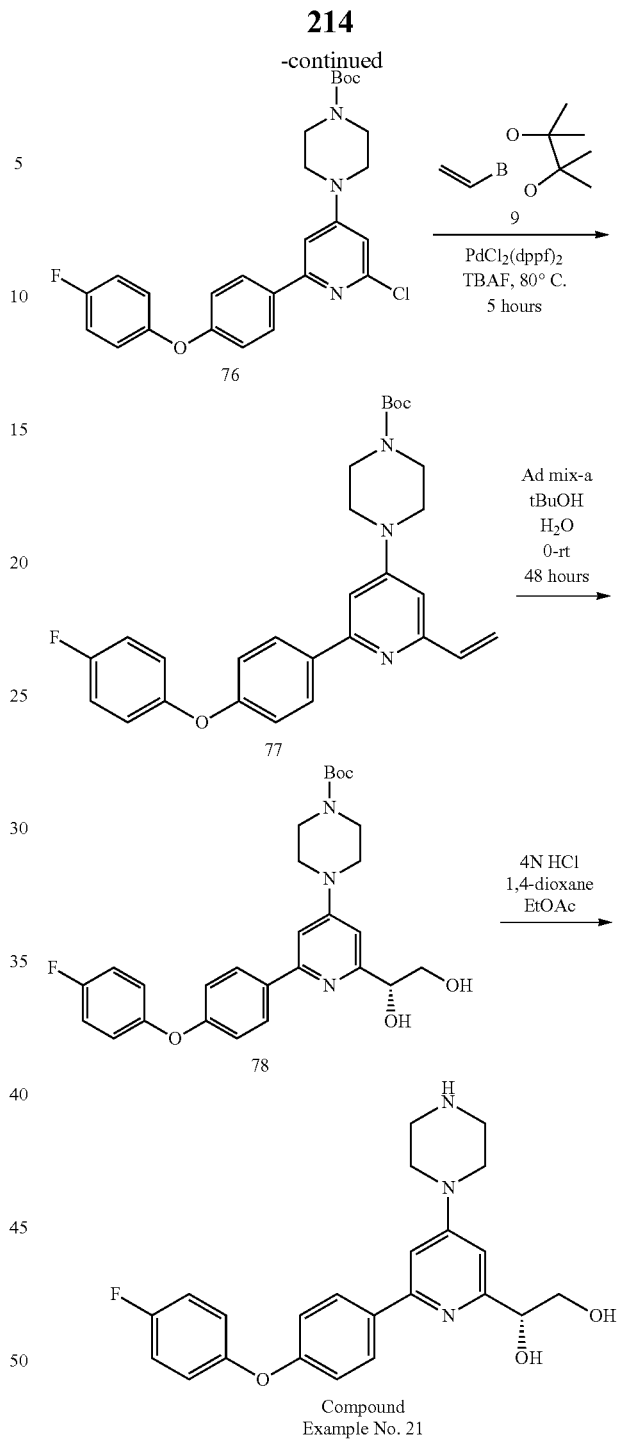

According to Scheme 47, a solution of compound 73 (1.2 g, 6.25 mmol, Aldrich), compound 74 (1.2 g, 6.25 mmol, Aldrich), Et$_3$N (0.9 mL, 6.25 mmol) in THF (10 mL) and DMF (3 mL) was stirred at room temperature for 4 h. After concentration, the residue was purified by column chromatography (40 g silica gel, 0-10% EtOAc/Hexane) to give compound 75 (615 mg, 1.8 mmol). A suspension of compound 75 (357 mg, 1.1 mmol), compound 2a (337 mg, 1.1 mmol), PdCl$_2$(dppf)$_2$ (70 mg, 0.08 mmol, Aldrich) in TBAF (5 mL, 5 mmol) was heated at 70° C. for 1 h. After cooling to room temperature, the mixture was purified without workup by column chromatography (40 g silica gel, 0-20% EtOAc/Hexane) give compound 76 (293 mg, 0.6 mmol).

A suspension of compound 76 (293 mg, 0.6 mmol), compound 9 (92 mg, 0.6 mmol), and PdCl$_2$(dppf)$_2$ (39 mg, 0.05 mmol) in TBAF (2 mL, 2 mmol) was heated at 80° C. for 5 h. After cooling to room temperature, the mixture was purified by column chromatography without workup to obtain a mixture of compounds 77 and 76. The mixture was used without further purification. To a milky suspension of compound 77 in t-Butanol (1 mL) and H$_2$O (1 mL) at 0° C. was added in one portion of ADMix-α (816 mg). The resulting mixture was stirred vigorously at room temperature for 48 h. The reaction mixture was extracted with EtOAc (2×5 mL) and the combined organic layers were dried over Na$_2$SO$_4$, filtered, and concentrated. The residue was purified by column chromatography (12 g silica gel, 20-100% EtOAc/Hexane) to give compound 78 (44 mg, 0.087 mmol).

Compound 78 was treated with 4 N HCl in 1,4-dioxane (0.5 mL) and EtOAc (1 mL) for 12 h. After concentration, the residue was purified via C18 reverse HPLC to give (R)-1-6-(4-(4-fluorophenoxy)phenyl)-4-piperazin-1-yl) pyridin-2-yl)ethan-1,2-diol (Compound Example No. 21) as the TFA salt (28 mg, 0.068 mmol). $^1$H NMR (CD$_3$OD): 7.76 (d, 2H, J=9.2 Hz), 7.27 (d, 1H, J=2.8 Hz), 7.22 (d, 1H, J=2.8 Hz), 7.05-7.18 (m, 6H), 4.88 (t, 1H, J=5.2 Hz), 4.00 (m, 4H), 3.81 (m, 2H), 3.39 (m, 414). LC/MS: m/z=410 (M+1).

Example 45

Synthesis of (R)-1-6-(4-(4-fluorophenoxy)phenyl)-4-((2-morpholinoethyl)amino)pyridine-2-yl) ethan-1,2-diol (Compound Example No. 1H)

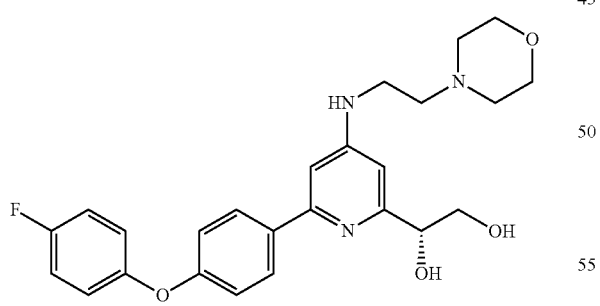

(R)-1-6-(4-(4-fluorophenoxy)phenyl)-4-((2-morpholino-ethyl)amino)pyridine-2-yl)ethan-1,2-diol (Compound Example No. 1H) was synthesized similarly to Compound Example No. 21 in Scheme 47. $^1$H NMR (CD$_3$OD): 8.39 (b, 1H, NH), 7.82 (m, 2H), 7.10-7.25 (m, 6H), 7.00 (s, 1H), 6.91 (s, 1H), 4.93 (m, 1H), 3.92 (m, 4H), 3.82 (m, 4H), 3.33 (m, 3H), 3.0-3.3 (b, 3H). LC/MS: m/z=454 (M+1).

Example 46

Synthesis of (R)-4-(2-(1,2-dihydroxyethyl)-6-(4-(4-fluorophenoxy)phenyl)pyridin-4-yl)-N-isopropylpiperazine-1-carboxamide (Compound Example No. 7)

Scheme 48

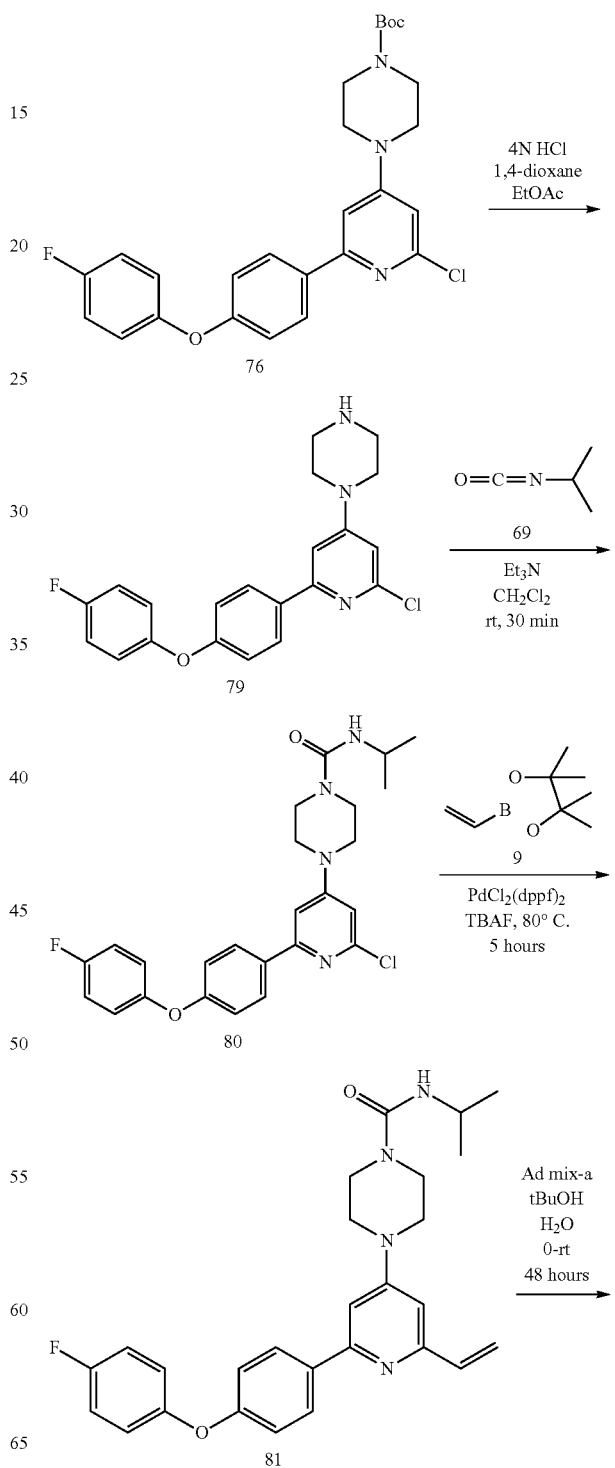

-continued

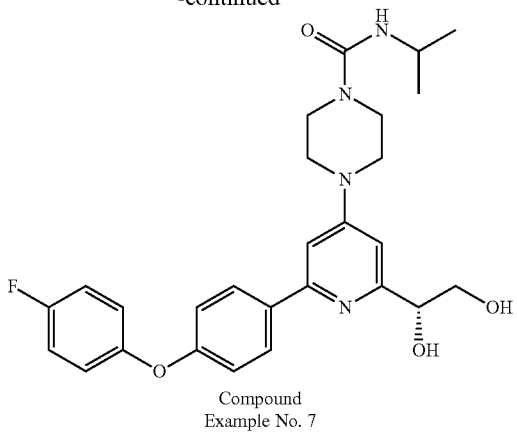

Compound Example No. 7

According to Scheme 48, a solution of compound 76 (220 mg, 0.46 mmol) in 4N HCl in 1,4-dioxane (2 mL, 8 mol) and EtOAc (5 mL) was stirred at room temperature for 12 h. The solvent was removed, the residue was rinsed with EtOAc, and the solvent was removed, to give compound 79 as HCl salt (217 mg, 0.46 mmol).

To a solution of compound 79 (150 mg, 0.33 mol) and Et$_3$N (0.142 mL, 0.99 mmol) in CH$_2$Cl$_2$ (5 mL) was added compound 69 (0.031 mL, 0.36 mmol). The resulting solution was stirred at room temperature for 30 min. The reaction mixture was purified by column chromatography without workup (12 g silica gel, 0-100% EtOAc/Hexane) to give compound 80.

Compound 80 was converted to (R)-4-(2-(1,2-dihydroxyethyl)-6-(4-(4-fluorophenoxy)phenyl)pyridin-4-yl)-N-isopropylpiperazine-1-carboxamide (Compound Example No. 7) similarly to the route used for Compound Example No. 21 in Scheme 47. $^1$H NMR (CD$_3$OD): 7.80 (d, 2H, J=8.8 Hz), 6.85-7.06 (m, 8H), 4.63 (dd, 1H, J1=4, J2=6.4 Hz), 3.79 (m, 2H), 3.61 (dd, 1H, J1=6.8, J2=11 Hz), 3.47 (m, 4H), 3.41 (m, 4H), 1.06 (d, 6H, J=6.4 Hz). LC/MS: m/z=495 (M+1).

Example 47

Synthesis of 2-(4-(4-fluorophenoxy)phenyl)-6-((2-(piperidin-1-yl)ethyl)carbamoyl)isonicotinic acid (Compound Example No. 85)

6-(4-(4-fluorophenoxy)phenyl)-N2-(2-(piperidin-1-yl)ethyl)pyridine-2,4-dicarboxamide (Compound Example No. 81); and 6-(4-(4-fluorophenoxy)phenyl)-N-(2-(piperidin-1-yl)ethyl)-4-(2H-tetrazol-5-yl) picolinamide (Compound Example No. 86)

Scheme 49

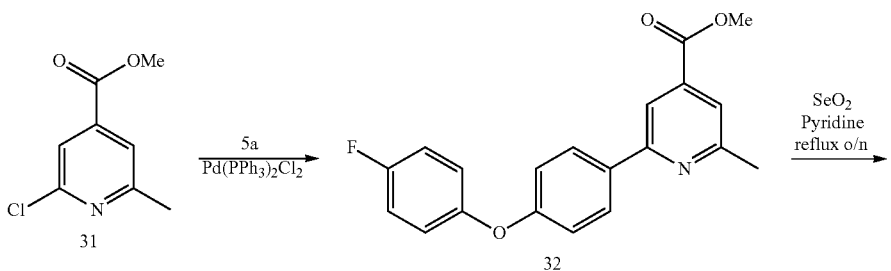

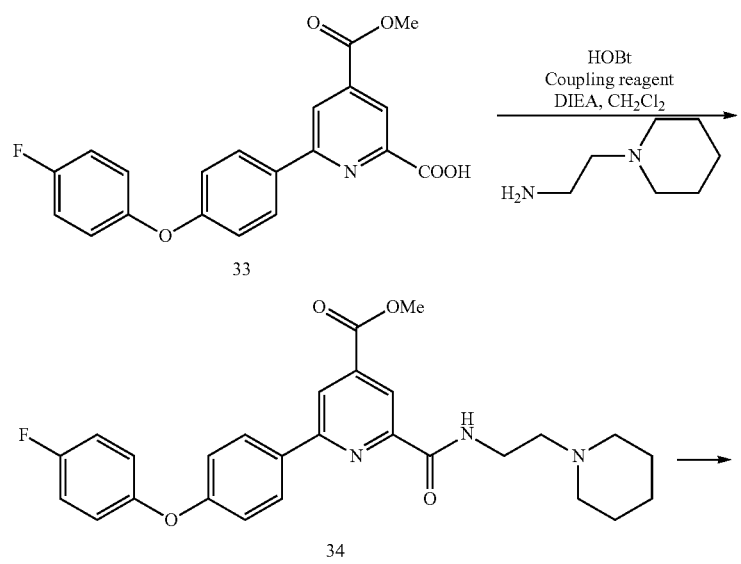

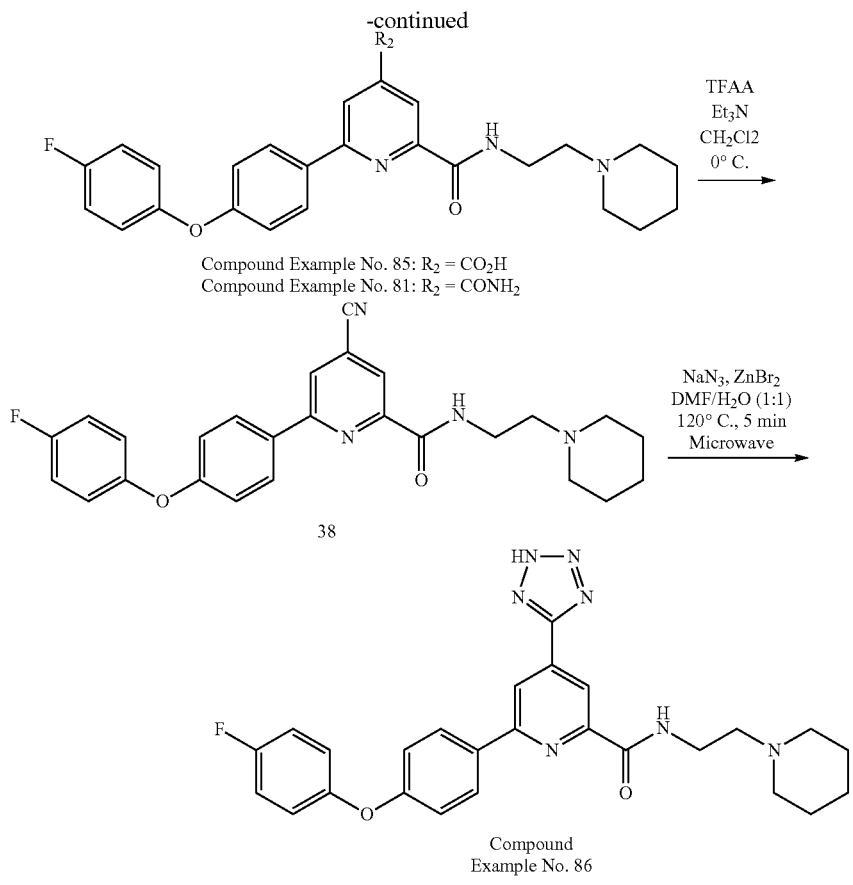

Coupling reagent: 1-[3-(dimethylaminopropyl]-3-ethylcarbodiimide HCl

According to Scheme 49, a solution of compound 31 (1.1 g, 5.9 mmol, Aldrich), 4-(4'-fluorophenoxy)phenyl pinacol boronate (1.85 g, 5.9 mmol), Pd(dppf)$_2$Cl$_2$ (385 mg, 0.47 mmol, Aldrich) in 1.0 M TBAF THF solution (10 mL) was heated at 75° C. for 3 h. After cooling to room temperature, the reaction mixture was purified by column chromatography (silica gel, 0-30% EtOAc/Hexane) to give compound 32 (1.0 g, 3.2 mmol).

A mixture of compound 32 (1 g, 3.2 mmol) and SeO$_2$ (32 mmol, Aldrich) in pyridine (100 mL) was heated at 100° C. for 48 h. The pyridine was removed under vacuum and the residue was purified by column chromatography (silica gel, 50% EtOAc/Hexane, then 30% MeOH/CH$_2$Cl$_2$) to give compound 33 (165 mg, 0.44 mmol) and recovered compound 32. A solution of compound 33 (165 mg, 0.45 mmol), 2-(piperidin-1-yl)-ethaneamine (73 μL, 0.5 mmol), HOBt (60 mg, 0.45 mmol, Aldrich), 1-[3-(dimethylamino) propyl]-3-ethylcarbodiimide hydrochloride (86 mg, 0.45 mmol, Aldrich), and DIEA (166 μL, 0.9 mmol) in CH$_2$Cl$_2$ (5 mL) was stirred at room temperature for 12 h. The reaction mixture was purified by column chromatography without work-up (12 g silica gel, 0-30% MeOH/CH$_2$Cl$_2$) to give compound 34 (100 mg, 0.21 mmol).

To a solution of compound 34 (60 mg, 0.125 mmol) in MeOH (2 mL) was added 2N NaOH aqueous solution (0.5 mL) and the resulting mixture was stirred for 24 h. After the solvent was removed under vacuum, H$_2$O (1 mL) was added, mixture was sonicated, and the aqueous solution was removed. The solid was washed with solvent (30% EtOAc/Hexane) and dried under vacuum to give 2-(4-(4-fluorophenoxy)phenyl)-6-((2-(piperidin-1-yl)ethyl)carbamoyl)isonicotinic acid (Compound Example No. 85) (34 mg, 0.07 mmol). $^1$H NMR (CD$_3$OD): 8.46 (d, 2H, J=15 Hz), 8.26 (d, 2H, J=9.2 Hz), 7.2-7.0 (m, 6H), 3.63 (t, 2H, J=6.8 Hz), 2.67 (t, 2H, J=6.8 Hz), 2.57 (m, 4H), 1.67 (m, 4H), 1.52 (m, 2H). LC/MS: m/z=464 (M+1).

A solution of compound 34 (40 mg, 0.084 mmol) in 7N NH$_3$ in methanol (2 mL) was stirred at room temperature for 12 h. After concentration to dryness, the residue was washed with solvent (30% EtOAc/Hexane) and then dried under vacuum to give 6-(4-(4-fluorophenoxy)phenyl)-N2-(2-(piperidin-1-yl)ethyl)pyridine-2,4-dicarboxamide (Compound Example No. 81) (16 mg, 0.035 mmol). $^1$H NMR (CD$_3$OD,): 8.46 (dd, 2H, J1=7.6, J2=1.6 Hz), 8.30 (d, 2H, J=8 Hz), 7.0-7.2 (m, 6H), 3.90 (t, 2H, J=6.4 Hz), 3.75 (bd, 2H, J=12 Hz), 3.41 (t, 2H, J=6 Hz), 3.02 (bt, 2H, J=13 Hz), 2.0 (bd, 2H, J=16 Hz), 1.82 (m, 3H), 1.57 (m, 1H). LC/MS: m/z=463 (M+1).

To a solution of compound 36 (39 mg, 0.084 mmol), Et$_3$N (36 μL, 0.24 mmol) in CH$_2$Cl$_2$ (2 mL) was added TFAA (0.16 mmol) at 0° C. After 5 min, the mixture was purified by column chromatography (12 g silica gel, 0-100% EtOAc/Hexane) to give compound 38 (27 mg, 0.061 mmol).

A suspension of compound 38 (64 mg, 0.14 mmol), NaN$_3$ (14 mg, 0.22 mmol), ZnBr$_2$ (50 mg, 0.22 mmol) in DMF (1.5 mL) and H$_2$O (1 mL) was heated at 120° C. for 10 min in a microwave (Biotage Initiator). The mixture was concentrated to dryness under vacuum and the residue was purified by column chromatography (12 g silica gel, 15-50% MeOH/CH$_2$Cl$_2$) to give 6-(4-(4-fluorophenoxy)phenyl)-N-(2-(piperidin-1-yl)ethyl)-4-(2H-tetrazol-5-yl)picolinamide (Compound Example No. 86) (40 mg, 0.082 mmol). $^1$H NMR (CD$_3$OD): 8.66 (dd, 2H, J1=14, J2=2 Hz), 8.56 (bs, 0.5H, interchangeable NH), 8.29 (d, 2H, J=8.8 Hz), 7.0-7.2 (m, 6H), 3.80 (t, 2H, J=6.4 Hz), 3.15 (b, 6H), 1.83 (m, 4H), 1.65 (b, 2H). LC/MS: m/z=488 (M+1).

Example 48

Synthesis of 6-(4-(4-fluorophenoxy)phenyl)-4-(hydroxymethyl)-N-(2-(piperidin-1-yl)ethyl) picolinamide (Compound Example No. 79)

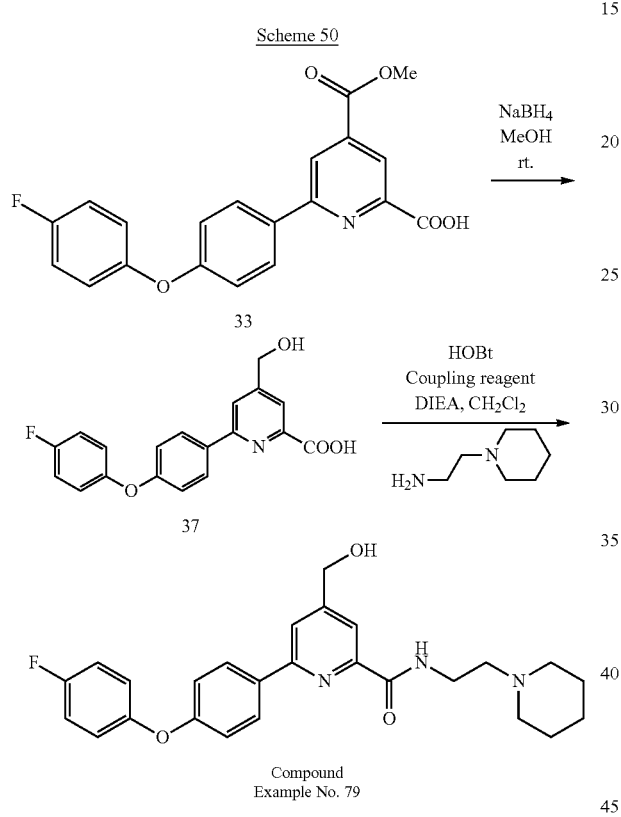

According to Scheme 50, to a solution of compound 33 (313 mg, 0.85 mmol) in MeOH (5 mL) was added NaBH$_4$ as a solid in several batches until LCMS indicated that no starting material remained. The reaction was then quenched at 0° C. with dilute HCl aqueous solution to pH 6. The methanol was removed under vacuum and the residue was diluted with H$_2$O (20 mL). The aqueous layer was extracted with EtOAc (3×50 mL), and the organic layer was dried over Na$_2$SO$_4$, filtered, and concentrated to dryness to give compound 37 (238 mg, 0.7 mmol).

A solution of compound 37 (77 mg, 0.23 mmol), 2-(piperidin-1-yl)-ethaneamine (37.4, 0.25 mmol), HOBt (30 mg, 0.23 mmol, Aldrich), 1-[3-(dimethylamino)propyl]-3-ethylcarbodiimide hydrochloride (43 mg, 0.23 mmol, Aldrich), and DIEA (166.4, 0.9 mmol) in CH$_2$Cl$_2$ (5 mL) was stirred at room temperature for 12 h. The mixture was purified by column chromatography without work-up (12 g silica gel, 0-15% MeOH/CH$_2$Cl$_2$), then C18 reverse column chromatography to give 6-(4-(4-fluorophenoxy)phenyl)-4-(hydroxymethyl)-N-(2-(piperidin-1-yl)ethyl)picolinamide (Compound Example No. 79) (30 mg, 0.067 mmol). $^1$H NMR (CD$_3$OD): 8.12 (d, 2H, J=8.8 Hz), 8.95 (d, 2H, J=6 Hz), 6.96-7.0 (m, 6H), 4.69 (s, 2H), 3.77 (t, 2H, J=6 Hz), 3.63 (bd, 2H, J=12 Hz), 3.29 (t, 2H, J=6 Hz), 2.91 (bt, 2H, J=12 Hz), 1.88 (bd, 2H, J=14 Hz), 1.71 (m, 1H). LC/MS: m/z=450 (M+1).

Example 49

Synthesis of 2-(4-(4-fluorophenoxy)phenyl)-6-methyl-N-(2-(piperidin-1-yl)ethyl)isonicotinamide (Compound Example No. 107)

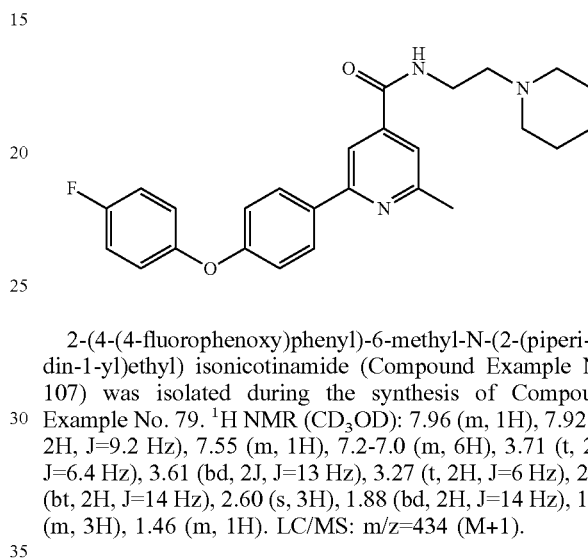

2-(4-(4-fluorophenoxy)phenyl)-6-methyl-N-(2-(piperidin-1-yl)ethyl) isonicotinamide (Compound Example No. 107) was isolated during the synthesis of Compound Example No. 79. $^1$H NMR (CD$_3$OD): 7.96 (m, 1H), 7.92 (d, 2H, J=9.2 Hz), 7.55 (m, 1H), 7.2-7.0 (m, 6H), 3.71 (t, 2H, J=6.4 Hz), 3.61 (bd, 2J, J=13 Hz), 3.27 (t, 2H, J=6 Hz), 2.90 (bt, 2H, J=14 Hz), 2.60 (s, 3H), 1.88 (bd, 2H, J=14 Hz), 1.71 (m, 3H), 1.46 (m, 1H). LC/MS: m/z=434 (M+1).

Example 50

Synthesis of 2-(5-(2-(4-(4-fluorophenoxy)phenyl)-6-methylpyridin-4-yl)-2H-tetrazol-2-yl)acetamide (Compound Example No. 108)

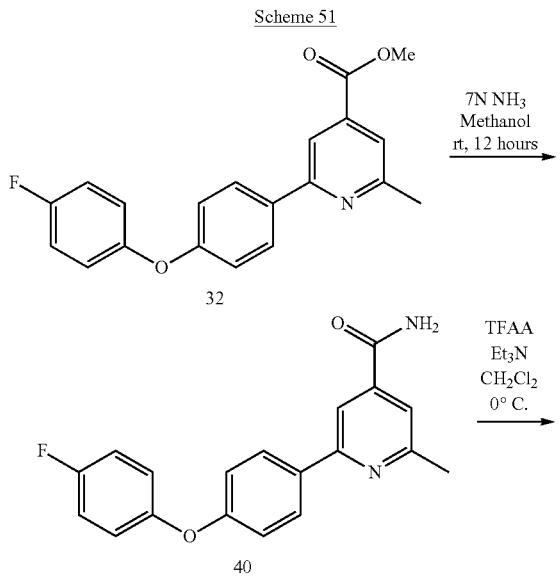

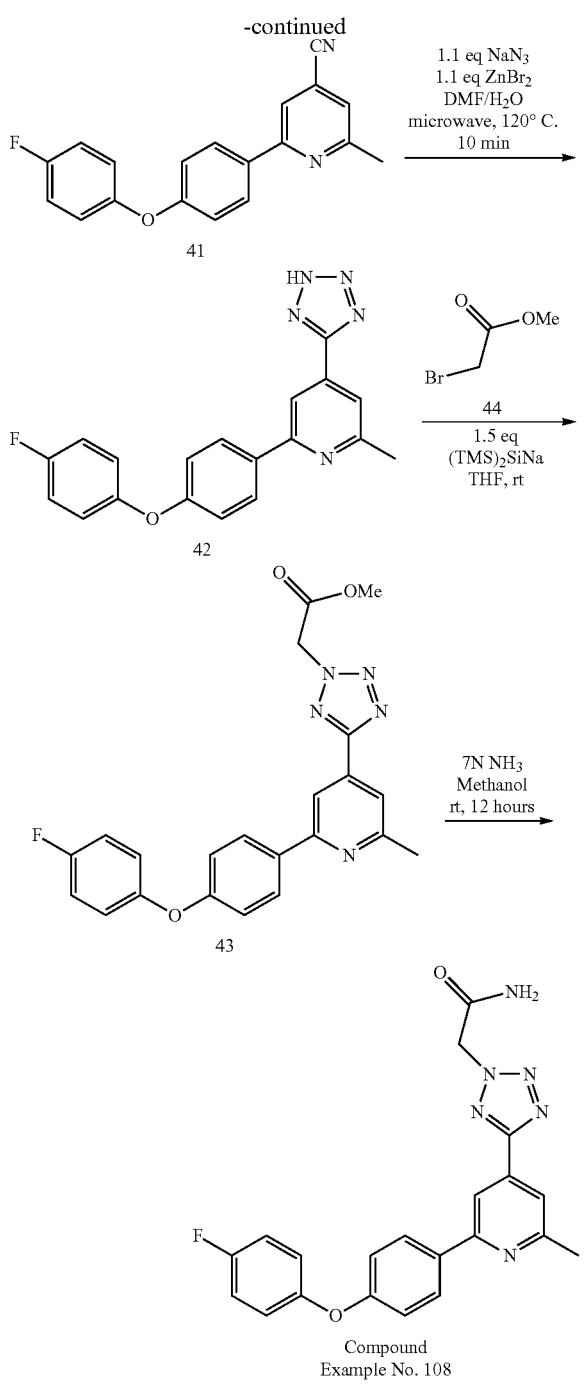

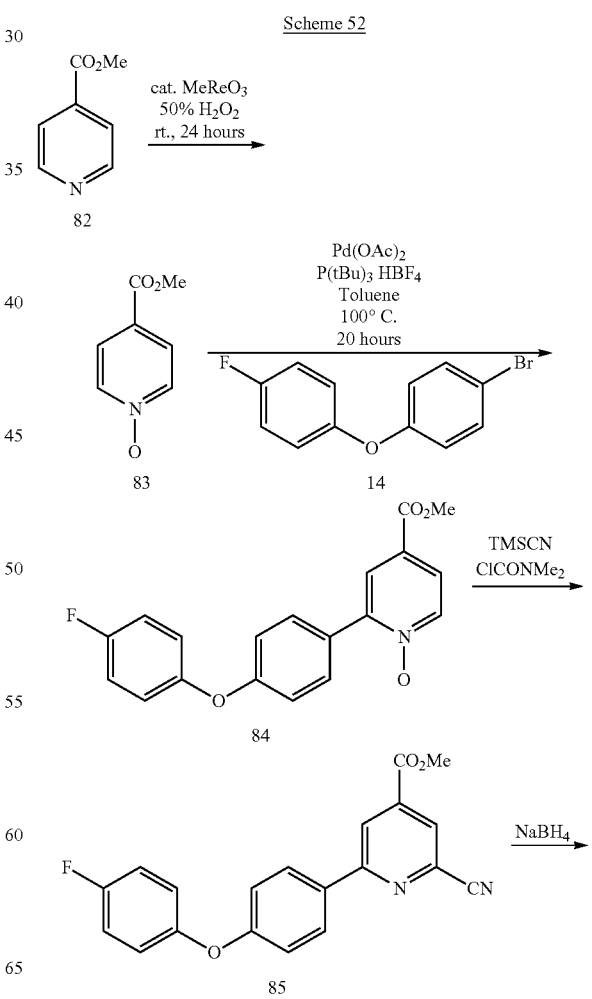

To a solution of compound 41 in DMF (2 mL) and H₂O (1 mL) was added NaN₃ (40 mg, 0.61 mmol) and ZnBr₂ (137 mg, 0.61 mmol). The resulting mixture was heated at 120° C. in a microwave oven (Biotage, Initiator) for 10 min. After removal of solvent under vacuum, the residue was purified by column chromatography (12 gram silica gel, 0-15% MeOH/CH₂Cl₂) to give compound 42 (110 mg, 0.34 mmol).

To a solution of compound 42 (110 mg, 0.34 mmol) in THF (0.5 mL) was added TMS₂NNa (0.51 mL, 0.51 mmol) at room temperature, followed by compound 44 (0.033 mL, 0.36 mmol). The resulting solution was stirred at room temperature for 4 h. After removal of solvent, the residue was dissolved in 7 N NH₃ in methanol (2 mL) at room temperature and stirred for 12 h. After removal of solvent the residue was purified by column chromatography (12 gram silica gel, 0-50% MeOH/CH₂Cl₂) to give 24542-(4-(4-fluorophenoxy)phenyl)-6-methylpyridin-4-yl)-2H-tetrazol-2-yl)acetamide (Compound Example No. 108) (9 mg, 0.022 mmol). ¹H NMR (CD₃OD): 8.18 (s, 1H), 7.94 (d, 2H, J=8.8 Hz), 7.79 (s, 1H), 6.96-7.0 (m, 6H), 5.47 (s, 2H), 2.59 (s, 3H). LC/MS: m/z=405 (M+1).

Example 51

Synthesis of 6-(4-(4-fluorophenoxy)phenyl)-4-(piperazin-1-ylmethyl)picolinamide (Compound Example No. 51)

According to Scheme 51, a solution of compound 32 (345 mg, 1 mmol) and 7N NH₃ in MeOH (2 mL) was stirred for 12 h. After removal of solvent under vacuum, the residue was purified by column chromatography (12 gram silica gel, 0-20% MeOH/CH₂Cl₂) to give compound 40 (330 mg, 1 mmol).

To a solution of compound 40 (330 mg, 1.0 mmol) in CH₂Cl₂ (2 mL) was added Et₃N (0.288 mL, 2 mmol) and TFAA (0.168 mL, 1.2 mmol) at 0° C. The resulting solution was stirred at 0° C. for 1 h. After removal of solvent under vacuum, the residue was purified by column chromatography (12 gram silica gel, 0-30% EtOAc/Hexane) to give compound 41 (168 mg, 0.55 mmol).

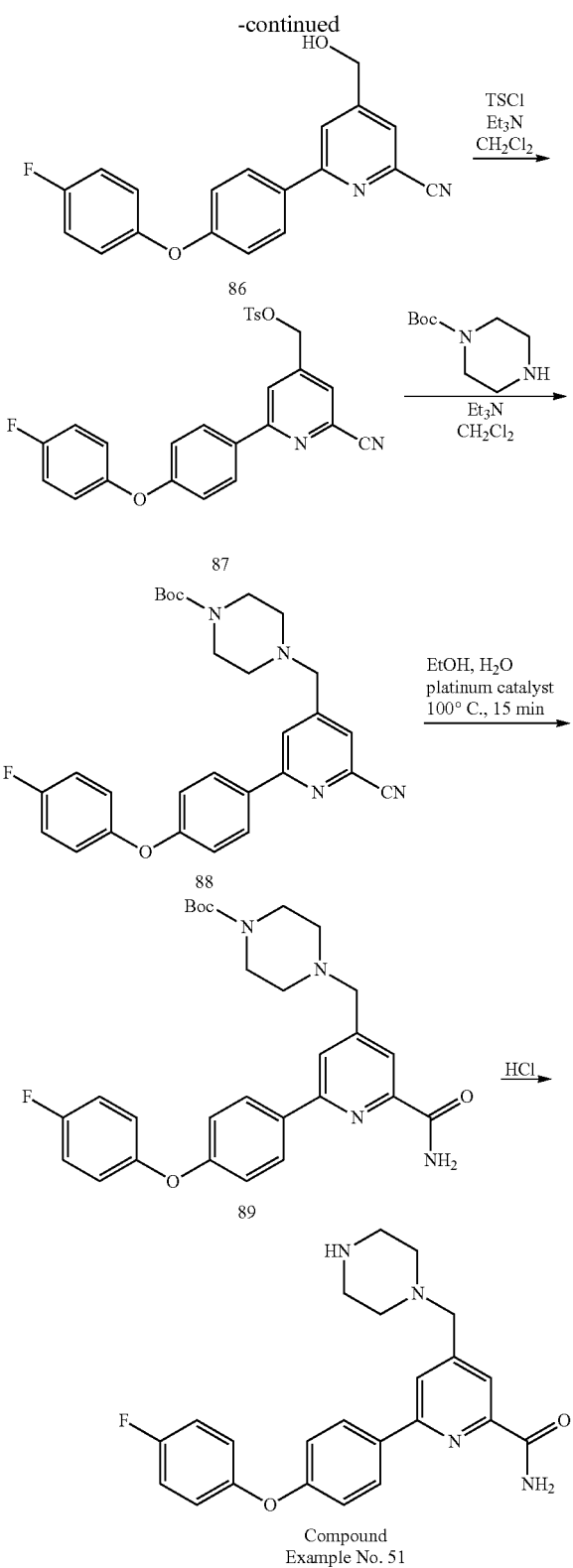

According to Scheme 52, to a solution of compound 82 (13.7 g, 0.1 mol) in CH₂Cl₂ at room temperature was added H₂O₂ (20 mL, 50% v/v, Aldrich), and methyltrioxorhennium (MTO, 250 mg, 1 mmol, Aldrich). The resulting mixture was stirred at room temperature for 12 h. MnO₂ (25 mg) was added and the mixture was left at room temperature for 1 h or until there is no more gas release (O₂) from the mixture. The organic layer of the mixture was separated, and the aqueous layer was extracted with CH₂Cl₂ (100 mL). The combined organic layers were dried over Na₂SO₄, filtered, and concentrated to dryness. The residue was washed with 30% EtOAc/Hexane and the solid was dried under vacuum to give compound 83 (12.7 g, 84 mmol).

A suspension of compound 83 (576 mg, 3.76 mmol), compound 14 (500 mg, 1.9 mmol), Pd(OAc)₂ (43 mg, 0.19 mmol, Aldrich), P(tBu)₃HBF₄ (165 mg, 0.57 mmol, Aldrich) and K₂CO₃ (524 mg, 3.8 mmol) in toluene (6 mL) was heated to reflux for 24 h. After cooling to room temperature, the reaction mixture was purified without work-up by column chromatography (40 g silica, EtOAc) to give compound 84 (265 mg, 0.78 mmol).

To a solution of compound 84 (265 mg, 0.78 mmol) in CH₂Cl₂ (2 mL) was added TMSCN (196 mg, 1.98 mmol, Aldrich) and ClCONMe₂ (181 μL, 1.98 mmol, Aldrich) at room temperature. The resulting mixture was stirred at room temperature for 12 h. Acetone (1 mL), followed by methanol (0.5 mL) were added sequentially. The mixture was concentrated to dryness and the residue was purified by column chromatography (40 g, 0-100% EtOAc/Hexane) to give compounds 85 (120 mg, 0.34 mmol) and 84 (100 mg, 0.29 mmol).

To a suspension of compound 85 (120 mg, 0.34 mmol) in methanol (5 mL) at 0° C., was added solid NaBH₄ in several batches, until LCMS indicated complete conversion to compound 86. The solvent was removed under vacuum and the residue was purified by column chromatography (12 g silica gel, 0-100% EtOAc/Hexane) to give compound 86 (114 mg, 0.34 mmol).

To a solution of compound 86 (114 mg, 0.34 mmol) in CH₂Cl₂ (2 mL) was added Et₃N (77 μL, 0.53 mmol) and p-toluenesulfonyl chloride (75 mg, 0.4 mmol, Aldrich). The resulting mixture was stirred at room temperature for 6 h. The mixture was purified by column chromatography (4 g silica gel, 10-40% EtOAc/Hexane) to give compound 87 (114 mg, 0.24 mmol).

To a solution of compound 87 (93 mg, 0.196 mmol) in CH₂Cl₂ (2 mL) was added Et₃N (69 μL, 0.48 mmol) and t-butyl piperazine-1-carboxylate. The resulting mixture was stirred at room temperature for 12 h. After removal of the solvent under vacuum, the residue was purified by column chromatography (4 g silica gel, 20-100% EtOAc/Hexane) to give compound 88 (90 mg, 0.18 mmol).

A suspension of compound 88 (90 mg, 0.18 mmol) and the platinum catalyst in EtOH (1.5 mL) and H₂O (1.5 mL) was heated at 100° C. in a microwave oven for 15 min. After cooling to room temperature, the mixture was extracted with EtOAc (4×10 mL) and the organic layer was dried over Na₂SO₄, filtered, and concentrated to dryness. The residue was purified by column chromatography (12 g silica gel, 0-60% EtOAc/Hexane) to give compound 89.

Compound 89 was treated with 4N HCl in 1,4-dioxane (1 mL) and EtOAc (2 mL) at room temperature for 12 h. After removal of the solvent, the residue was washed with Et₂O, washed with hexane, and dried under vacuum to give 6-(4-(4-fluorophenoxy)phenyl)-4-(piperazin-1-ylmethyl)picolinamide (Compound Example No. 51) (68 mg, 0.14 mmol, 2 HCl salt). ¹H NMR (CD₃OD): 8.26 (d, 2H, J=8.8 Hz), 8.25 (s, 1H), 8.13 (s, 1H), 7.09-7.20 (m, 6H), 4.24 (s, 2H), 3.48 (t, 4H, J=4.8 Hz), 3.22 (m, 4H).

LC/MS: m/z=407 (M+1).

Example 52

Synthesis of 2-(4-((2-carbamoyl-6-(4-(4-fluorophenoxy)phenyl)pyridine-4-yl)methyl)piperazin-1-yl) acetic acid (Compound Example 104)

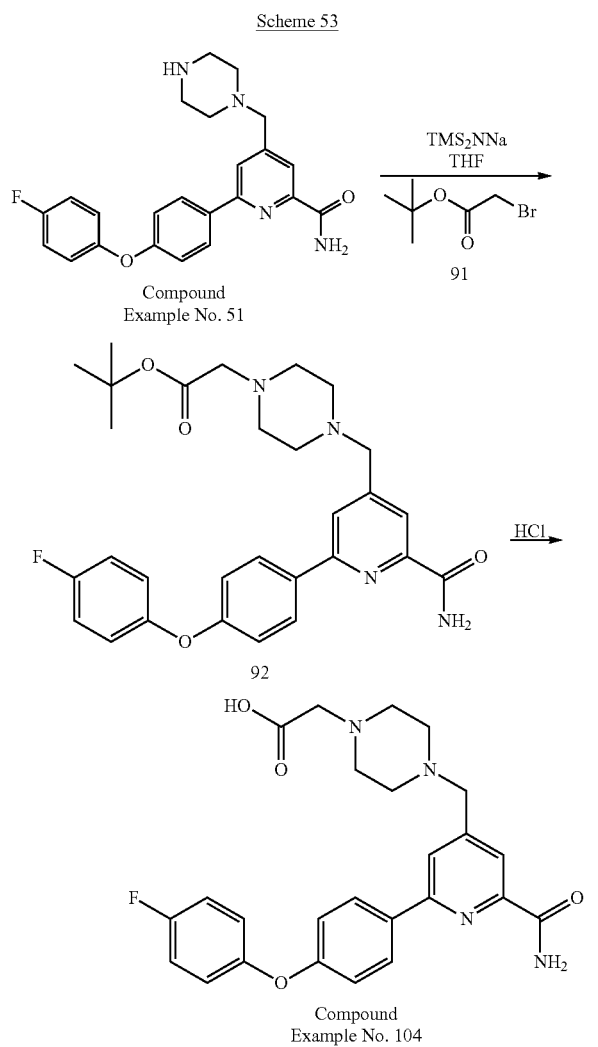

According to Scheme 53, to a solution of Compound Example No. 51 (68 mg, 0.14 mmol) in THF (2 mL) was added (TMS)$_2$NNa (1 mL, 1.0 M, 1 mmol, Aldrich) and compound 91 (54 mg, 0.28 mmol, Aldrich). The resulting mixture was heated at 50° C. for 2 h. The mixture was purified by column chromatography (12 g silica gel, 20-100% EtOAc/Hexane) to give compound 92.

Compound 92 was treated with 4N HCl in 1,4-dioxane (1 mL) and

EtOAc (2 mL) at room temperature for 2 h. After removal of the solvent under vacuum, the solid was washed with Et$_2$O and then dried under vacuum to give 2-(4-((2-carbamoyl-6-(4-(4-fluorophenoxy)phenyl)pyridine-4-yl)methyl)piperazin-1-yl) acetic acid (Compound Example 104) (7.4 mg, 0.014 mmol) as the HCl salt. $^1$H NMR (CD$_3$OD): 8.11 (d, 2H, J=8.9 Hz), 8.00 (s, 2H), 6.96-7.10 (m, 6H), 3.93 (m, 4H), 3.31 (m, 2H), 3.16 (s, 2H), 2.92 (m, 4H). LC/MS: m/z=465 (M+1).

Example 53

Synthesis of 6-(4-(4-fluorophenoxy)phenyl)-4-(((2-(2-oxoimidazolidin-1-yl)ethyl)amino)methyl)picolinonitrile (Compound Example No. 106)

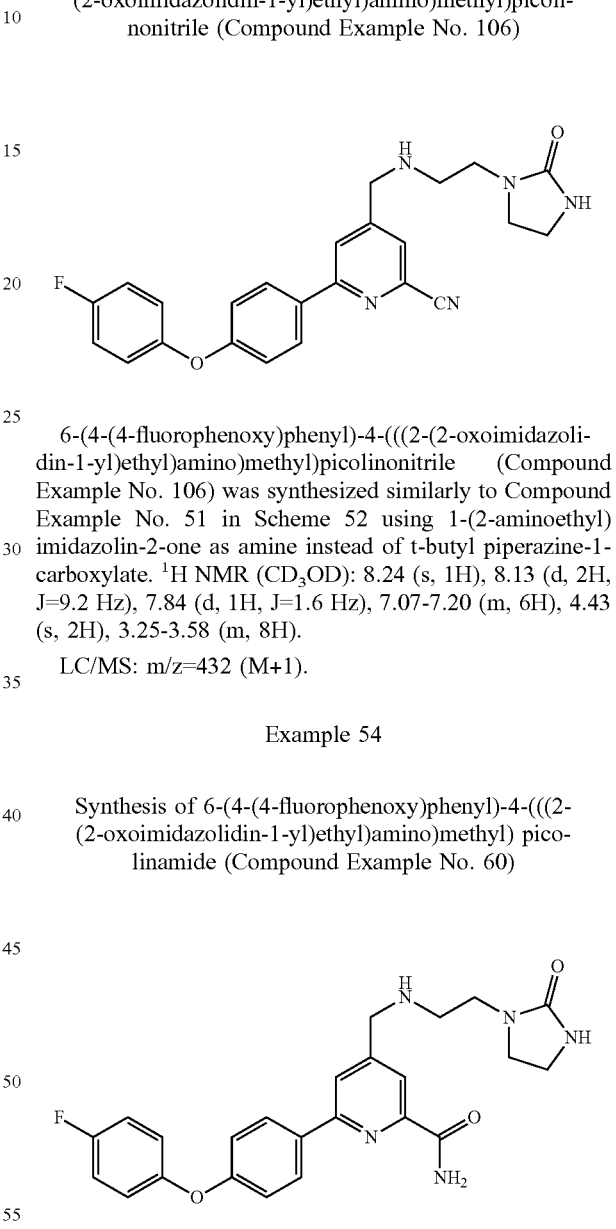

6-(4-(4-fluorophenoxy)phenyl)-4-(((2-(2-oxoimidazolidin-1-yl)ethyl)amino)methyl)picolinonitrile (Compound Example No. 106) was synthesized similarly to Compound Example No. 51 in Scheme 52 using 1-(2-aminoethyl) imidazolin-2-one as amine instead of t-butyl piperazine-1-carboxylate. $^1$H NMR (CD$_3$OD): 8.24 (s, 1H), 8.13 (d, 2H, J=9.2 Hz), 7.84 (d, 1H, J=1.6 Hz), 7.07-7.20 (m, 6H), 4.43 (s, 2H), 3.25-3.58 (m, 8H).

LC/MS: m/z=432 (M+1).

Example 54

Synthesis of 6-(4-(4-fluorophenoxy)phenyl)-4-(((2-(2-oxoimidazolidin-1-yl)ethyl)amino)methyl) picolinamide (Compound Example No. 60)

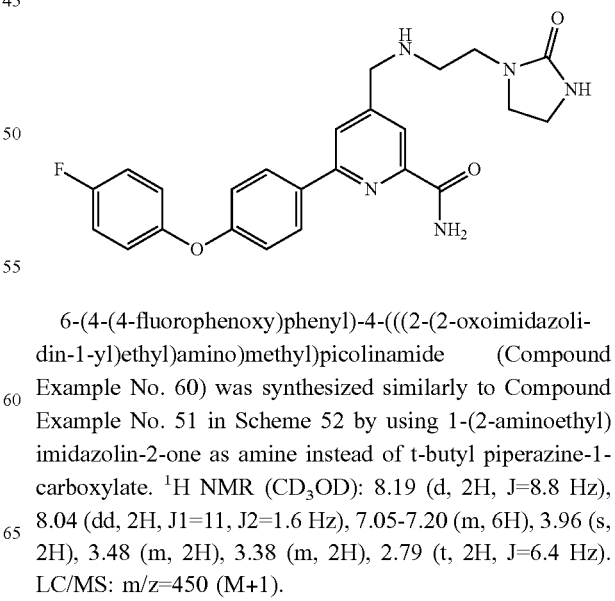

6-(4-(4-fluorophenoxy)phenyl)-4-(((2-(2-oxoimidazolidin-1-yl)ethyl)amino)methyl)picolinamide (Compound Example No. 60) was synthesized similarly to Compound Example No. 51 in Scheme 52 by using 1-(2-aminoethyl) imidazolin-2-one as amine instead of t-butyl piperazine-1-carboxylate. $^1$H NMR (CD$_3$OD): 8.19 (d, 2H, J=8.8 Hz), 8.04 (dd, 2H, J1=11, J2=1.6 Hz), 7.05-7.20 (m, 6H), 3.96 (s, 2H), 3.48 (m, 2H), 3.38 (m, 2H), 2.79 (t, 2H, J=6.4 Hz). LC/MS: m/z=450 (M+1).

Example 55

Synthesis of 6-(4-(4-fluorophenoxy)phenyl)-4-(methylsulfonamidomethyl)picolinamide (Compound Example No. 50)

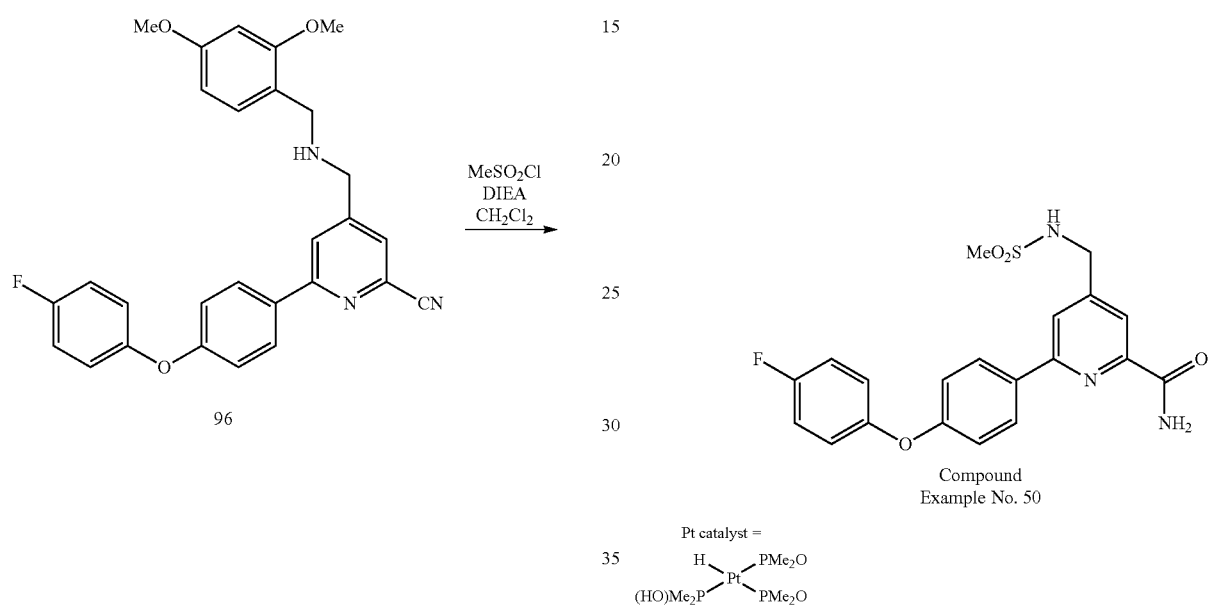

Scheme 54

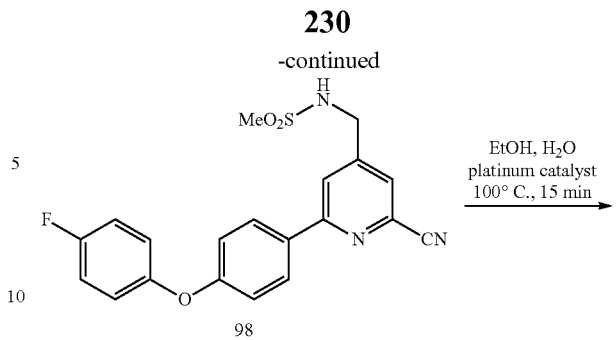

To a solution of compound 96 (43 mg, 0.092 mmol), which was synthesized similarly to compound 88 in Scheme 52, and DIEA (554, 0.3 mmol) in $CH_2Cl_2$ (2 mL) was added $MeSO_2Cl$ (11.50 μL, 0.15 mmol, Aldrich). The resulting mixture was stirred at room temperature for 2 h. The mixture was purified by column chromatography (12 g silica gel, 0-20% $MeOH/CH_2Cl_2$) to give compound 97.

Compound 97 was treated with trifluoroacetic acid (TFA, 2 mL, Aldrich) at room temperature for 12 h. After removal of solvent under vacuum, the residue was purified by column chromatography (12 g silica gel, 5-10% $MeOH/CH_2Cl_2$) to give compound 98.

Compound 98 was converted to 6-(4-(4-fluorophenoxy)phenyl)-4-(methylsulfonamidomethyl)picolinamide (Compound Example No. 50) using methodology as previously described. $^1$H NMR ($CD_3OD$): 8.20 (d, 2H, J=8.8 Hz), 8.07 (s, 2H), 7.06-7.19 (m, 6H), 4.45 (s, 2H), 3.01 (s, 3H). LC/MS: m/z=416 (M+1).

Example 56

Synthesis of Boronates: Compounds 5a-5f

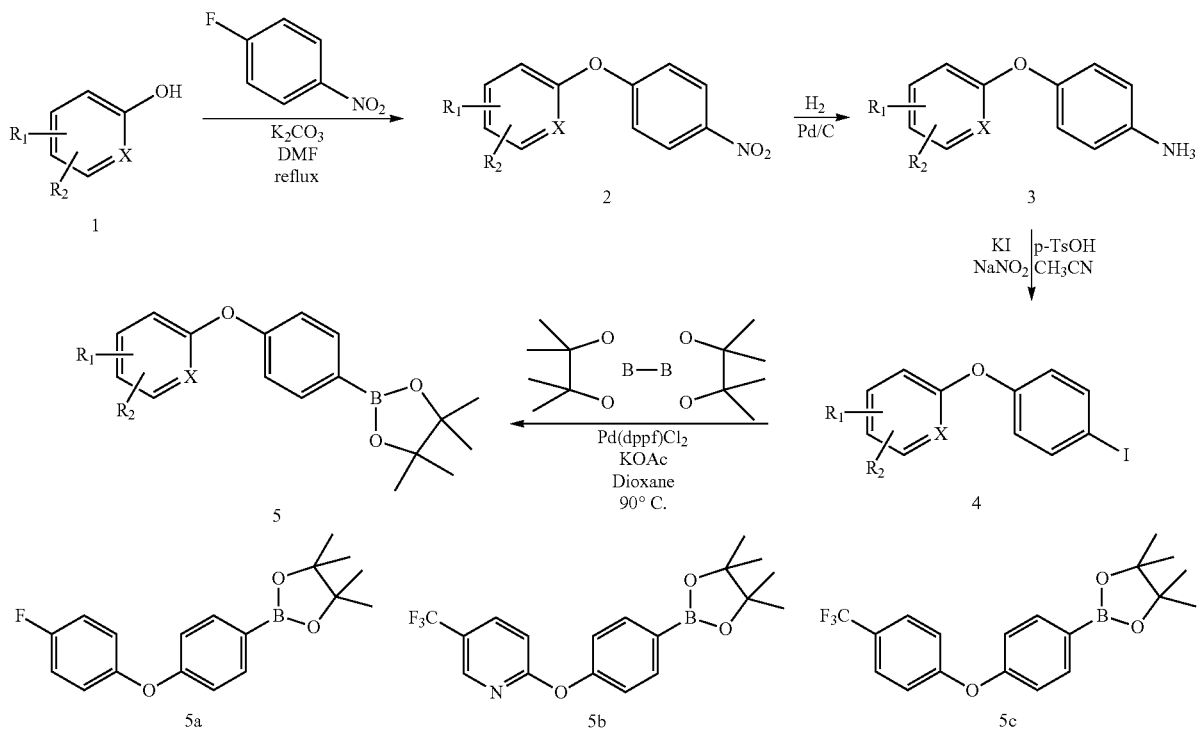

Scheme 55

Compound 2a: A mixture of 4-fluorophenol (30g, 0.27 mol, Aldrich), 1-fluoro-4-nitrobenzene (38g, 0.27 mol, Aldrich) and $K_2CO_3$ (37.8 g, 0.27 mol) in DMF (300 mL) was heated at 95° C. overnight. After the reaction mixture was cooled to room temperature, ethyl acetate (150 mL) was added. The organic layer was separated and washed with water. The organic layer was dried with anhydrous $MgSO_4$ and concentrated under the reduced pressure to give an oily residue. The residue was purified by column chromatography (5% EtOAc in Hexanes) to give compound 2a as brown crystals (44 g, 70%). $^1H$ NMR (400 MHz, $CDCl_3$): 8.2 (d, J=9.4 Hz, 2H), 7.04-7.17 (m, 4H), 6.99 (d, J=9.4, 2H).

Compound 3a: Compound 2a (10 g, 42.9 mmol) was dissolved in 10% ethyl acetate in methanol (250 mL) and 10% palladium on carbon (2.0g) was added. The mixture was degassed via vacuum and then filled with argon (Vacuum/argon). After degassing, the mixture was treated with a hydrogen balloon and stirred for 5.0 hr at room temperature, during the period the balloon was refilled with hydrogen so that a positive pressure of hydrogen was maintained throughout the reaction period. After the reaction was complete, the hydrogen balloon was removed. The mixture was degassed under vacuum and filled with argon. The mixture was then filtered through a pad of Celite. The filtrate was concentrated to give compound 3a as a reddish brown solid (8.5 g, 97%).

Compound 4a: To a solution of p-TsOH. $H_2O$ (56.0 g, 300 mmol) in acetonitrile (500 mL), compound 3a was added and cooled to 0-5° C. The suspension was stirred at 0° C. for 15 min and a solution of $NaNO_2$ (13.8g, 200 mmol), KI (41.5g, 250 mmol) in $H_2O$ (150 mL) was added slowly thereto. During the addition, $N_2$ was evolved. The reaction mixture was stirred for 1 h at room temperature. After the reaction was complete, saturated $NaHCO_3$ aqueous solution was added to adjust the pH to 9~10 and 2M $Na_2S_2O_3$ (6.0 mL) was added thereto. The aqueous layer was separated and extracted with ethyl acetate, the combined organic layer was dried with anhydrous $MgSO_4$ and then concentrated under the reduced pressure. The crude product was purified by column chromatography (silica gel, 10% ethyl acetate in hexanes) to give compound 4a as pale brown crystals (19.3 g, 67%). LC/MS: m/z=315 [M+H].

Compound 5a: To a suspension of compound 4a (10g, 31.8 mmol) in dioxane (320 mL), $Pd(dppf)_2Cl_2.CH_2Cl_2$ (0.82g, 1.0 mmol, Aldrich) was added and degassed by repeating with vac./argon. The suspension was stirred for 10 min at room temperature, bis(pinacolato)diboron (8.9 g, 35.0 mmol, NetChem, Inc.,) and potassium acetate (0.97 g, 95.4 mmol) were added thereto. The reaction mixture was heated at 90° C. for 18 h under the argon. Upon cooling to room temperature, the mixture was filtered through a pad of Celite and concentrated under the reduced pressure. The residue was purified by column chromatography (silica gel, 5% ethyl acetate in hexanes) to give compound 5a ad a pale brown solid (9.0 g, 90%). $^1H$ NMR (400 MHz, $CDCl_3$): 7.67 (d, J=8.6 Hz, 2H), 7.06-6.96 (m, 4H), 6.93 (d, J=8.6 Hz, 2H), 1.33 (s, 12H). LC/MS: m/z=315 [M+H].

Compound 5b: Compound 5b was synthesized the same way as described for 5a. $^1H$ NMR (400 MHz, $CDCl_3$): 8.47 (s, 1H), 8.13 (m, 1H), 7.83 (d, 2H, J=8.8 Hz), 7.21-7.15 (m, 3H), 1.38 (s, 12H).

Compound 5c: Compound 5c was synthesized the same way as described for 5a. $^1H$ NMR (400 MHz, $CD_3OD$): 7.69

(d, J=8.7 Hz, 2H), 7.57 (d, J=8.4 Hz, 2H), 7.03 (d, J=8.4 Hz, 2H), 1.25 (s, 12H). LC/MS: m/z=365 [M+H].

Scheme 56

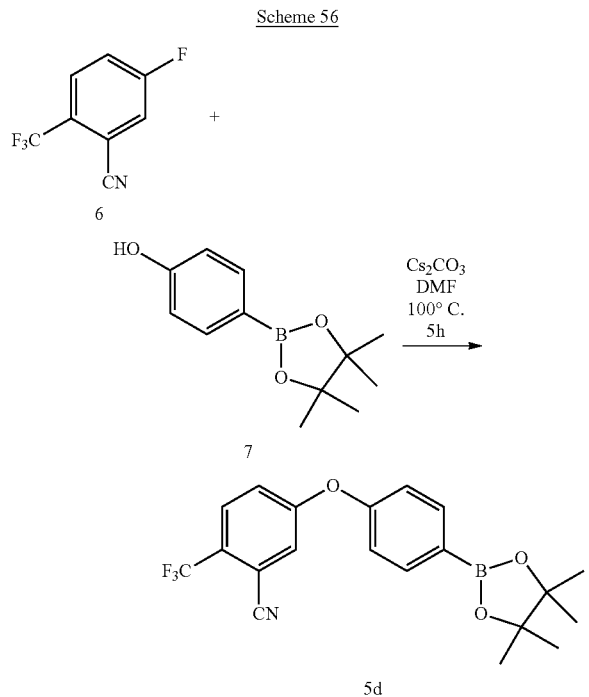

Compound 5d: A mixture of compound 6 (2.1 g, 10.9 mmol), compound 7 (2.4g, 10.9 mmol) and Cs$_2$CO$_3$ (3.5 g, 10.9 mmol) in DMF (14 mL) was heated at 100° C. for 4 hours. After cooling to room temperature, the mixture was filtered through a plug of silica gel and the plug was washed with EtOAc (50 mL). The filtrate was concentrated and the residue was to obtain compound 5d (2.3 g, 6.9 mmol). $^1$H NMR (400 MHz, CD$_3$OD): 7.81 (d, 2H, J=8.8 Hz), 7.63 (d, 1H, J=8.8 Hz), 7.26 (d, 1H, J=2.4 Hz), 7.17 (dd, 1H, J1=2.4, J2=8.8 Hz), 6.98 (d, 2H, J=8.8 Hz), 1.28 (s, 12H).

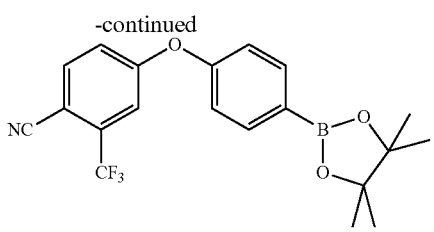

5e

Compound 5e: A suspension of compound 9 (53 g, 0.28 mol, Aldrich), compound 8 (64 g, 0.29 mol, Aldrich) and sodium carbonate (45 g, 0.42 mol) in DMF was heated at 100° C. for 12 hours. After cooling to room temperature the mixture was diluted with H$_2$O (600 mL) and extracted with EtOAc (2×300 mL). The organic layer was dried over sodium sulfate and concentrated to dryness. The product was collected by vacuum filtration and washed with DCM to give a first batch of crystalline compound 10a (~75 g). A suspension of compound 10a (20 g, 0.051 mol), bis pinacol boronate (13 g, 0.051 mol, NetChem), KOAc (10 g, 0.10 mol, Aldrich) and PdCl$_2$(dppf)$_2$CH$_2$Cl$_2$ (2.1 g, 2.57 mmol, Aldrich) in 1,4-dioxane (75 mL, Aldrich) was heated at 100° C. for 12 hours. After cooling to room temperature, the reaction mixture was diluted with water (500 mL) and extracted with EtOAc (2×300 m). The organic layer was washed with brine (250 mL), dried over sodium sulfate, and concentrated. The residue was purified via chromatograph (silica gel, 20% EtOAc/Hexane) to give compound 5e (11.45 g, 0.029 mol) as brown oil. $^1$H NMR (CDCl$_3$): 7.93-7.87 (m, 2H), 7.78-7.73 (m, 1H), 7.37-7.33 (m, 1H), 7.11-7.04 (m, 2H), 7.17-7.12 (m, 1H), 1.36 (s, 12H). LC/MS: m/z=389, [M+H].

Scheme 57

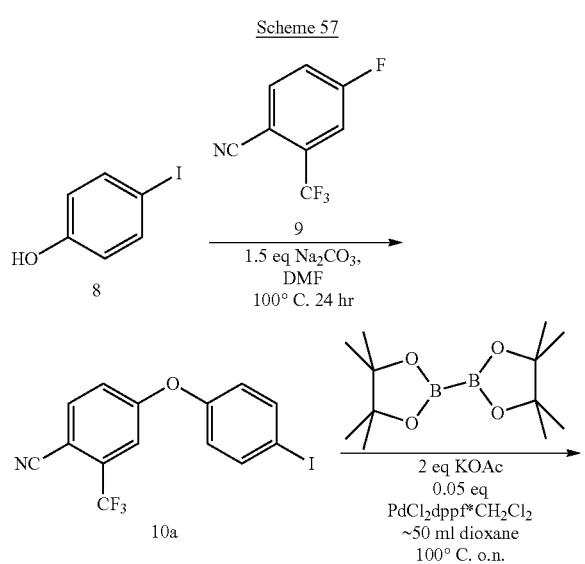

Scheme 58

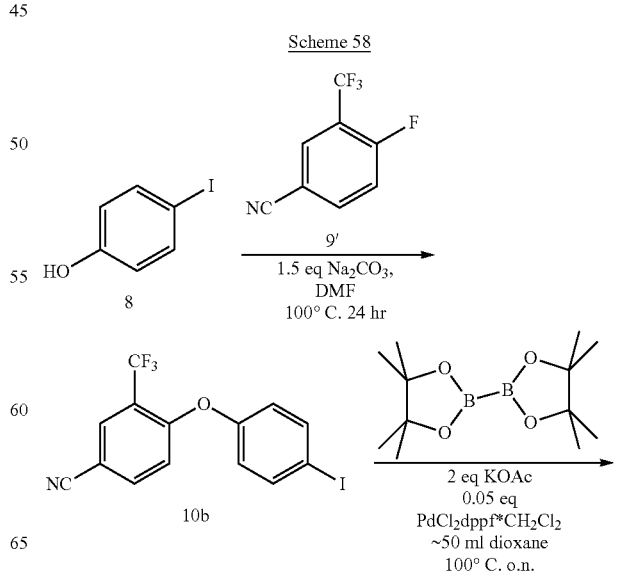

235

-continued

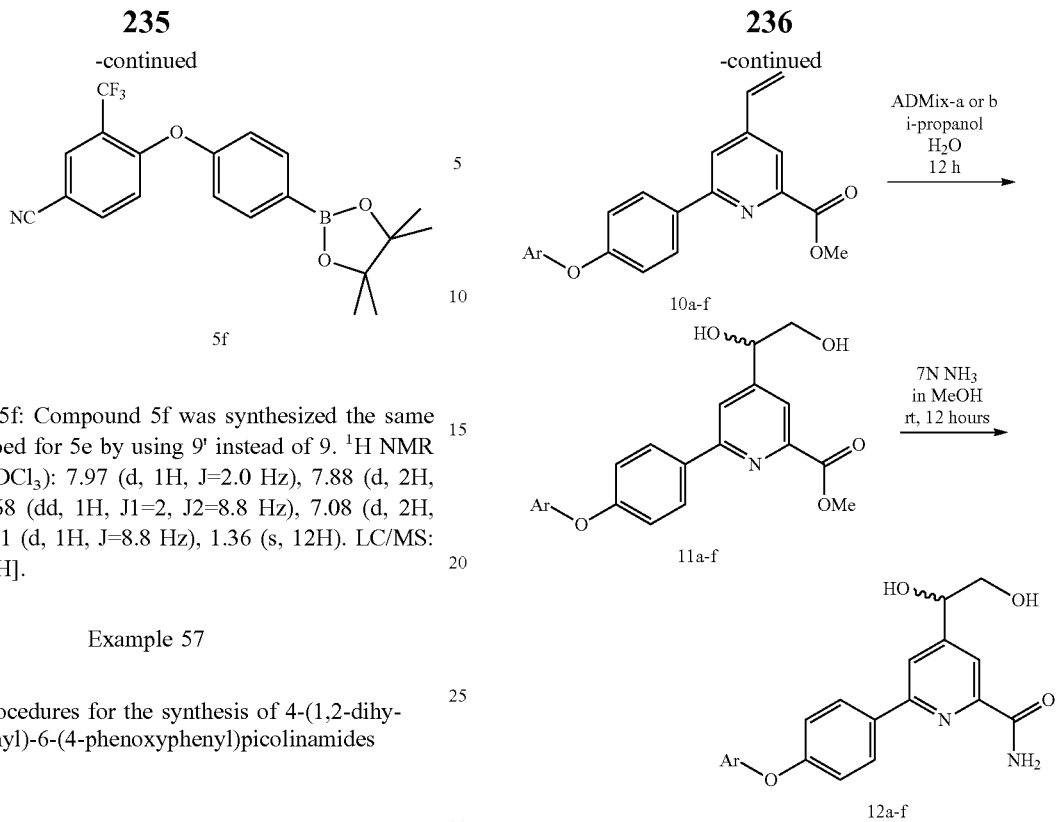

5f

Compound 5f: Compound 5f was synthesized the same way as described for 5e by using 9' instead of 9. ¹H NMR (400 MHz, CDCl₃): 7.97 (d, 1H, J=2.0 Hz), 7.88 (d, 2H, J=8.8 Hz), 7.68 (dd, 1H, J1=2, J2=8.8 Hz), 7.08 (d, 2H, J=8.8 Hz), 6.91 (d, 1H, J=8.8 Hz), 1.36 (s, 12H). LC/MS: m/z=390 [M+H].

Example 57

General procedures for the synthesis of 4-(1,2-dihydroxyethyl)-6-(4-phenoxyphenyl)picolinamides Scheme 59

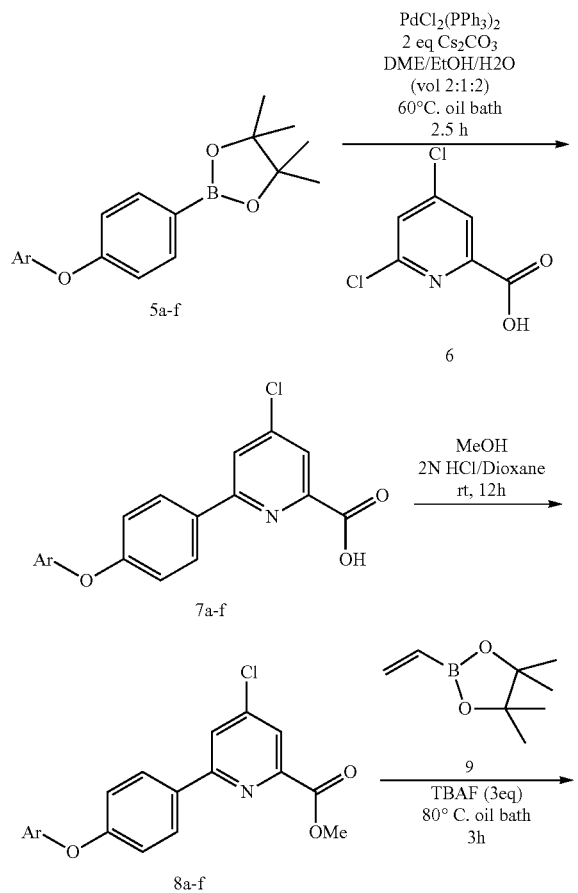

ADMix-a: (S)
ADMix-b: (R)

General Method 1

To a pressure bottle was added 4,7-dichloropiconilic acid 6 (1.3 g, 6.76 mmol, Astatech), compound 5c (2.46 g, 6.76 mmol), PdCl₂(PPh₃)₂ (379 mg, 0.5 mmol, Aldrich), Cs₂CO₃ (4.4 gram, 13.5 mmol, Aldrich), DME (16 mL), EtOH (8 mL), and H₂O (16 mL). The mixture was placed under argon and then heated at 60° C. in an oil bath for 3.5 h. After cooling to room temperature, brine (150 mL) was added and the pH of the mixture was adjusted to pH 1 with 4 N HCl aqueous solution. The mixture was then extracted with EtOAc (250 mL). The separated organic layer was dried with Na₂SO₄, filtered and concentrated to dryness. The residue was dissolved in MeOH, 4 N HCl in 1,4-dioxane (1 mL) was added, and the mixture was stirred at room temperature for 12 h. After concentration, the residue was purified via column chromatography (40 g silica gel, 0-50% EtOAc/Hexane) to give compound 8c (1.8 g, 4.4 mmol) as yellow liquid.

To a pressure bottle was added compound 8c (1.8g, 4.6 mmol), compound 9 (1.4 mL, 8.36 mmol, Aldrich), PdCl₂(dppf)₂ (300 mg, 0.37 mmol, Aldrich) and TBAF (14 mL, 14 mmol, Aldrich). The mixture was placed under Argon and heated at 80° C. oil bath for 3 hours. After cooling to room temperature, the mixture was purified via column chromatography (40 g silica gel, 0-30% EtOAc/Hexane, Combiflash®) to give compound 10c (680 mg) as yellow liquid.

To a milky suspension of compound 10c (680 mg, 1.7 mmol) in i-PrOH (5 mL) and H₂O (5 mL) at room temperature was added in one portion AD Mix-α (2.09 g, Aldrich). The resulting mixture was vigorously stirred at room temperature for 12 h. The reaction mixture was extracted with EtOAc (5×20 mL) and the organic was dried over Na₂SO₄, filtered and concentrated. The residue was purified via column chromatography (40 g silica gel, 0-100% EtOAc/Hexan) to give compound 11c (526 mg, 1.2 mmol).

Compound 11c (526 mg, 1.2 mmol) was dissolved in 7 N NH₃ in methanol (5 mL, 35 mmol, Aldrich) and stirred for 12 h at room temperature. The mixture was concentrated to dryness and the residue was triturated with a mixture of EtOAc in hexane and sonicated to induce precipitation. After removal of the clear solution, compound 12c was obtained as solid (300 mg, 0.7 mmol).

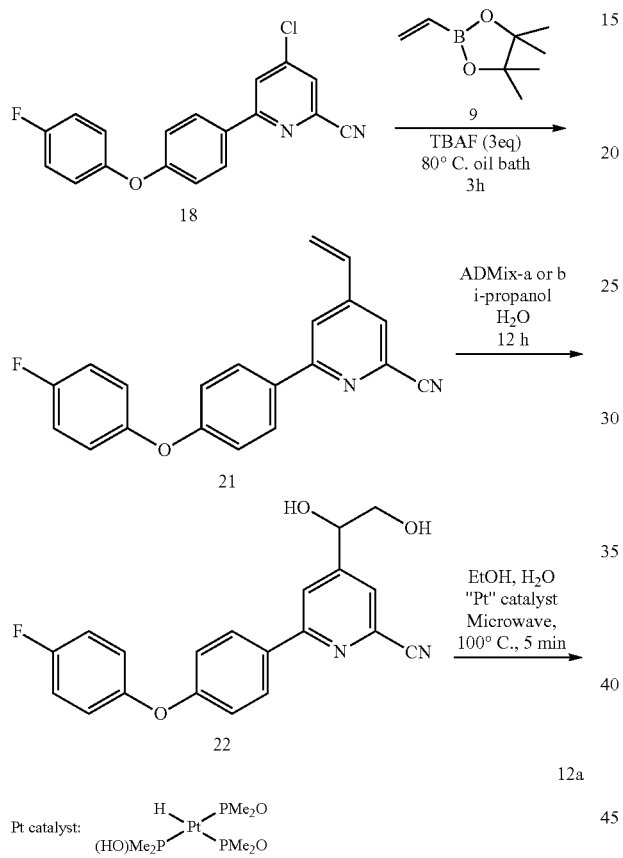

General Method 2

To a pressure bottle was added compound 18 (420 mg, 1.29 mmol), compound 9 (299 mg, 1.94 mmol), PdCl₂(dppf)₂ (85 mg, 0.1 mmol) and TBAF (3.89 mL, 3.89 mmol). The mixture was placed under argon and heated at 80° C. oil bath for 3 h. After cooling to room temperature, the mixture was poured on to the silica gel column and purified via chromatograph (40 g silica gel, 10-20% EtOAc/Hexane). The desired product 21 was obtained as solid. To a milky suspension of compound 21 in t-BuOH (5 mL) and H₂O (5 mL) at 0° C. was added in one portion of AD Mix-α (1.69 g, Aldrich). After addition, the ice bath was removed and the resulting mixture was vigorously stirred at room temperature for 12 hours. The mixture was extracted with EtOAc (5×20 mL) and the organic was dried with Na₂SO₄, filtered and concentrated to dryness. The residue was purified via column chromatography (40 g silica gel, 0-100% EtOAc/Hexane) to give compound 22 (350 mg, 1 mmol). To a milky suspension of compound 22 (350 mg, 1 mmol) in EtOH (2 mL) and H₂O (2 mL) was added Pt catalyst (Strem) and the mixture was then heated at 100° C. oil bath for 10 min. After cooling to room temperature, the resulting mixture was extracted with EtOAc (3×20 mL) and the combined organic layers were dried over Na₂SO₄, filtered and concentrated. The residue was purified via column chromatography (40 g silica gel, 50-100% EtOAc/Hexane) to give compound 12a.

Example 58

Synthesis of (S)-4-(1,2-dihydroxyethyl)-6-(4-(4-fluorophenoxy)phenyl)picolinonitrile (Compound Example No. 112)

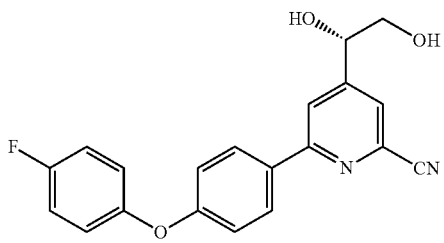 [SMILES: N#Cc1cc([C@H](O)CO)cc(-c2ccc(Oc3ccc(F)cc3)cc2)n1]

(S)-4-(1,2-dihydroxyethyl)-6-(4-(4-fluorophenoxy)phenyl)picolinonitrile was synthesized according to General Method 2 of Example 57. ¹H NMR (CD₃OD): 8.02 (s, 1H), 7.98 (d, 2H, J=9.2 Hz), 7.68 (s, 1H), 6.96-7.0 (m, 6H), 4.71 (t, 1H, J=5.2 Hz), 3.62 (m, 2H); LC/MS: m/z=351 (M+1).

Example 59

Synthesis of (S)-4-(1,2-dihydroxyethyl)-6-(4-(4-fluorophenoxy)phenyl)picolinamide (Compound Example No. 41)

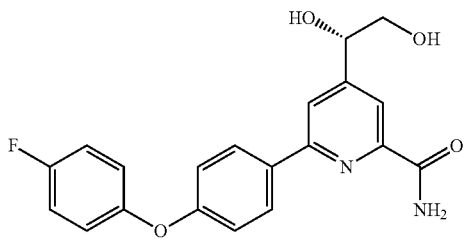 [SMILES: NC(=O)c1cc([C@H](O)CO)cc(-c2ccc(Oc3ccc(F)cc3)cc2)n1]

(S)-4-(1,2-dihydroxyethyl)-6-(4-(4-fluorophenoxy)phenyl)picolinamide was synthesized according to General Method 1 of Example 57. ¹H NMR (CD₃OD): 8.20 (d, 2H, J=8.8 Hz), 8.09 (s, 1H), 8.08 (s, 1H), 7.07-7.19 (m, 6H), 5.51 (0.6H, OH, partially exchanged hydrogen bond), 4.86 (t, 1H, J=6 Hz), 3.73 (m, 2H); LC/MS: m/z=369 (M+1).

Example 60

Synthesis of (R)-4-(1,2-dihydroxyethyl)-6-(4-(4-fluorophenoxy)phenyl)picolinonitrile (Compound Example No. 138)

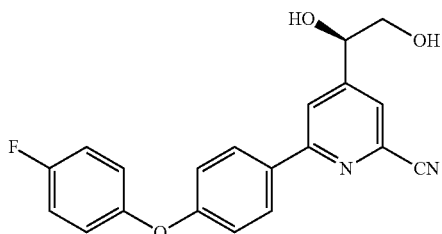

(R)-4-(1,2-dihydroxyethyl)-6-(4-(4-fluorophenoxy)phenyl)picolinonitrile was synthesized according to General Method 2 of Example 57. ¹H NMR (CDCl₃): 8.09 (d, 2H, J=9.2 Hz), 7.93 (s, 1H), 7.64 (s, 1H), 4.95 (dd, 1H, J1=3.2, J2=7.2 Hz), 3.94 (dd, 1H, J1=4, J2=11 Hz), 3.71 (dd, 1H, J1=7.6, J2=11 Hz); LC/MS: m/z=351 (M+1).

Example 61

Synthesis of (R)-4-(1,2-dihydroxyethyl)-6-(4-(4-fluorophenoxy)phenyl)picolinamide (Compound Example No. 40)

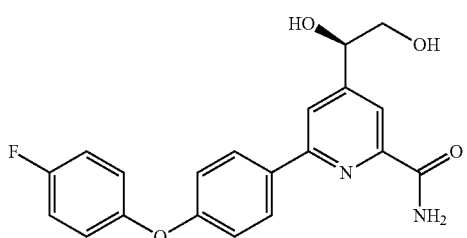

(R)-4-(1,2-dihydroxyethyl)-6-(4-(4-fluorophenoxy)phenyl)picolinamide was synthesized according to the General Method 2 of Example 57. ¹H NMR (DMS-d₆): 8.29 (d, 2H, J=8.8 Hz), 8.28 (bs, 1H, NH), 8.03 (s, 1H), 7.98 (s, 1H), 7.67 (bs, 1H, NH), 7.28 (m, 2H), 7.16 (m, 2H), 7.08 (d, 2H, J=8.8 Hz), 5.61 (d, 1H, OH, J=4.8 Hz), 4.85 (t, 1H, OH, J=5.6 Hz), 4.70 (m, 1H), 3.56 (m, 2H); LC/MS: m/z=369 (M+1).

Example 62

Synthesis of (S)-4-(1,2-dihydroxyethyl)-6-(4-((5-(trifluoromethyl)pyridin-2-yl)oxy)phenyl)picolinamide (Compound Example No. 139)

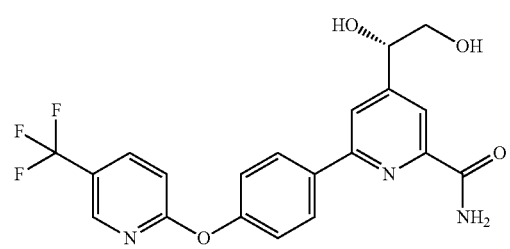 [SMILES: NC(=O)c1cc([C@H](O)CO)cc(-c2ccc(Oc3ccc(C(F)(F)F)cn3)cc2)n1]

(S)-4-(1,2-dihydroxyethyl)-6-(4-((5-(trifluoromethyl)pyridin-2-yl)oxy)phenyl)picolinamide was synthesized according to General Method 1 of Example 57. ¹H NMR (CD₃OD): 8.37 (s, 1H), 8.18 (d, 2H, J=9.2 Hz), 8.03 (m, 3H), 7.21 (d, 2H, J=9.2 Hz), 7.12 (s, 1H), 7.09 (s, 1H), 4.76 (m, 1H), 3.65 (m, 2H); LC/MS: m/z=420 (M+1).

Example 63

Synthesis of (R)-4-(1,2-dihydroxyethyl)-6-(4-((5-(trifluoromethyl)pyridin-2-yl)oxy)phenyl)picolinamide (Compound Example No. 132)

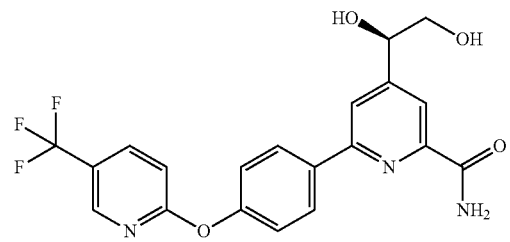 [SMILES: NC(=O)c1cc([C@@H](O)CO)cc(-c2ccc(Oc3ccc(C(F)(F)F)cn3)cc2)n1]

(R)-4-(1,2-dihydroxyethyl)-6-(4-((5-(trifluoromethyl)pyridin-2-yl)oxy)phenyl)picolinamide was synthesized according to General Method 1 of Example 57. ¹H NMR (CD₃OD): 8.48 (bs, 1H), 8.28 (d, 2H, J=8.8 Hz), 8.17 (m, 3H), 7.34 (d, 2H, J=8.8 Hz), 7.23 (d, 1H), 4.92 (m, 1H), 3.77 (m, 2H); LC/MS: m/z=420 (M+1).

Example 64

Synthesis of (S)-4-(1,2-dihydroxyethyl)-6-(4-(4-trifluorometyl)phenoxy)phenyl)picolinamide (Compound Example No. 30)

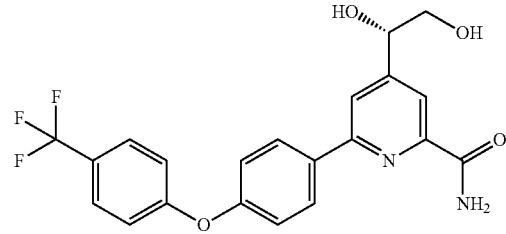 [SMILES: NC(=O)c1cc([C@H](O)CO)cc(-c2ccc(Oc3ccc(C(F)(F)F)cc3)cc2)n1]

(S)-4-(1,2-dihydroxyethyl)-6-(4-(4-trifluorometyl)phenoxy)phenyl) picolinamide was synthesized according to General Method 1 of Example 57. ¹H NMR (CD₃OD): 8.16 (d, 2H, J=9.2 Hz), 8.00 (s, 2H), 7.58 (d, 2H, J=8.4 Hz), 7.10 (m, 4H), 4.76 (m, 1H), 3.64 (m, 2H); LC/MS: m/z=419 (M+1).

Example 65

Synthesis (R)-4-(1,2-dihydroxyethyl)-6-(4-(4-trifluoromethyl)phenoxy)phenyl)picolinamide (Compound Example No. 103)

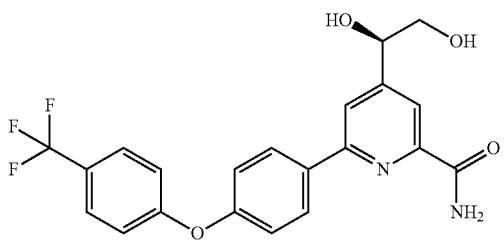 [SMILES: NC(=O)c1cc([C@@H](O)CO)cc(-c2ccc(Oc3ccc(C(F)(F)F)cc3)cc2)n1]

(R)-4-(1,2-dihydroxyethyl)-6-(4-(4-trifluoromethyl)phenoxy)phenyl) picolinamide was synthesized according to General Method 1 of Example 57. ¹H NMR (CD₃OD): 8.16 (d, 2H, J=9.2 Hz), 8.00 (s, 2H), 7.58 (d, 2H, J=8.4 Hz), 7.10 (m, 4H), 4.76 (m, 1H), 3.64 (m, 2H); LC/MS: m/z=419 (M+1).

Example 66

Synthesis of (S)-6-(4-(4-cyano-3-(trifluoromethyl)phenoxy)phenyl)-4-(1,2-dihydroxyethyl)picolinamide (Compound Example No. 31)

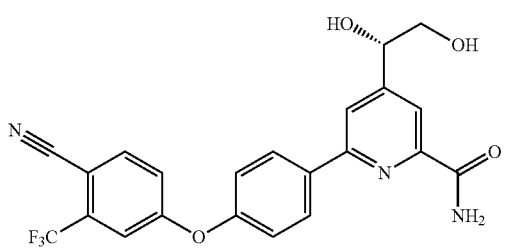

(S)-6-(4-(4-cyano-3-(trifluoromethyl)phenoxy)phenyl)-4-(1,2-dihydroxyethyl) picolinamide was synthesized according to General Method 1 of Example 57. ¹H NMR (CD₃OD): 8.23 (d, 2H, J=8.8 Hz), 8.03 (s, 2H), 7.88 (d, 1H, J=8.8 Hz), 7.41 (d, 1H, J=2.4 Hz), 7.26 (dd, 1H, J1=2.4, J2=8.4 Hz), 7.20 (d, 2H, J=8.8 Hz), 4.76 (m, 1H), 3.64 (m, 2H); LC/MS: m/z=444 (M+1).

Example 67

Synthesis (R)-6-(4-(4-cyano-3-(trifluoromethyl)phenoxy)phenyl)-4-(1,2-dihydroxyethyl)picolinamide (Compound Example No. 127)

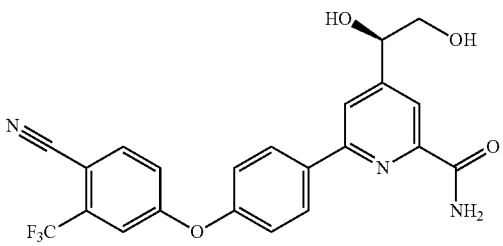 [SMILES: N#Cc1ccc(Oc2ccc(-c3cc([C@@H](O)CO)cc(C(N)=O)n3)cc2)cc1C(F)(F)F]

(R)-6-(4-(4-cyano-3-(trifluoromethyl)phenoxy)phenyl)-4-(1,2-dihydroxyethyl) picolinamide was synthesized according to General Method 1 of Example 57. ¹H NMR (CD₃OD): 8.34 (d, 2H, J=9.2 Hz), 8.14 (s, 2H), 8.03 (d, 1H, J=8.4 Hz), 7.53 (d, 1H, J=2.0 Hz), 7.37 (dd, 1H, J1=1.2, J2=8.0 Hz), 7.31 (m, 2H), 4.84 (m, 1H), 3.68 (m, 2H); LC/MS: m/z=444 (M+1).

Example 68

Synthesis of (S)-6-(4-(3-cyano-4-(trifluoromethyl)phenoxy)phenyl)-4-(1,2-dihydroxyethyl)picolinamide (Compound Example No. 33)

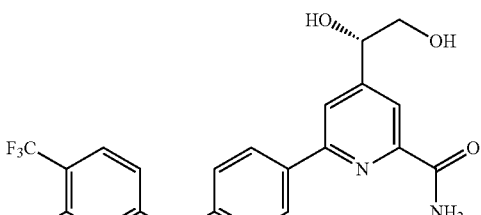

(S)-6-(4-(3-cyano-4-(trifluoromethyl)phenoxy)phenyl)-4-(1,2-dihydroxyethyl) picolinamide was synthesized according to General Method 1 of Example 57. ¹H NMR (CD₃OD): 8.21 (d, 2H, J=8.8 Hz), 8.02 (s, 2H), 7.80 (d, 1H, J=8.8 Hz), 7.53 (d, 1H, J=2.8 Hz), 7.33 (dd, 1H, J1=8.8, J2=2.8 Hz), 7.18 (d, 2H, J=9.2 Hz), 4.75 (m, 1H), 3.65 (m, 2H); LC/MS: m/z=444 (M+1).

Example 69

Synthesis of (R)-6-(4-(3-cyano-4-(trifluoromethyl) phenoxy)phenyl)-4-(1,2-dihydroxyethyl)picolinamide (Compound Example No. 34)

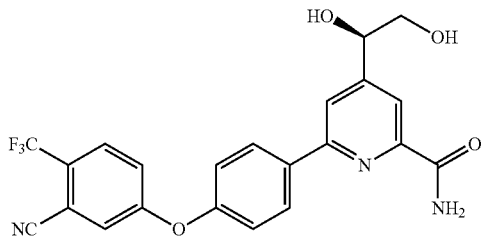 [SMILES: N#Cc1cc(Oc2ccc(-c3cc([C@@H](O)CO)cc(C(N)=O)n3)cc2)ccc1C(F)(F)F]

(R)-6-(4-(3-cyano-4-(trifluoromethyl)phenoxy)phenyl)-4-(1,2-dihydroxyethyl) picolinamide was synthesized according to General Method 1 of Example 57. $^1$H NMR (CD$_3$OD): 8.21 (d, 2H, J=8.8 Hz), 8.02 (s, 2H), 7.80 (d, 1H, J=8.8 Hz), 7.53 (d, 1H, J=2.8 Hz), 7.33 (dd, 1H, J1=8.8, J2=2.8 Hz), 7.18 (d, 2H, J=8.8 Hz), 4.75 (m, 1H), 3.65 (m, 2H); LC/MS: m/z=444 (M+1).

Example 70

Synthesis of (S)-6-(4-(4-cyano-2-(trifluoromethyl) phenoxy)phenyl)-4-(1,2-dihydroxyethyl)picolinamide (Compound Example No. 35)

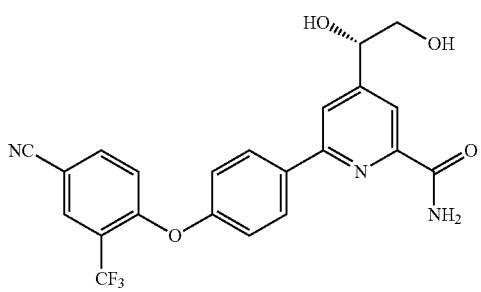 [SMILES: N#Cc1ccc(Oc2ccc(-c3cc([C@H](O)CO)cc(C(N)=O)n3)cc2)c(C(F)(F)F)c1]

(S)-6-(4-(4-cyano-2-(trifluoromethyl)phenoxy)phenyl)-4-(1,2-dihydroxyethyl) picolinamide was synthesized according to General Method 1 of Example 57. $^1$H NMR (600 MHz, CD$_3$OD): 8.30 (d, 2H, J=9 Hz), 8.17 (m, 1H), 8.12 (m, 1H), 7.93 (dd, 1H, J1=1.8, J2=8.4 Hz), 7.26 (d, 2H, J=7.8 Hz), 7.14 (d, 1H, J=9 Hz), 4.85 (m, 1H), 3.74 (m, 2H); LC/MS: m/z=444 (M+1).

Example 71

Synthesis of (R)-6-(4-(4-cyano-2-(trifluoromethyl) phenoxy)phenyl)-4-(1,2-dihydroxyethyl)picolinamide (Compound Example No. 36)

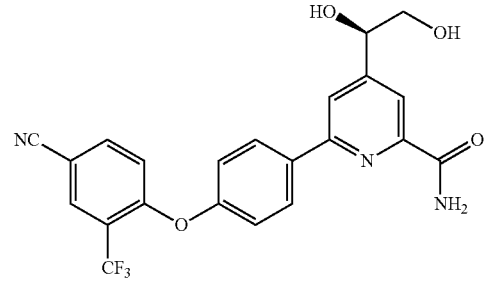 [SMILES: N#Cc1ccc(Oc2ccc(-c3cc([C@@H](O)CO)cc(C(N)=O)n3)cc2)c(C(F)(F)F)c1]

(R)-6-(4-(4-cyano-2-(trifluoromethyl)phenoxy)phenyl)-4-(1,2-dihydroxyethyl) picolinamide was synthesized according to General Method 1 of Example 57. $^1$H NMR (600 MHz, CD$_3$OD): 8.32 (d, 2H, J=9 Hz), 8.17 (m, 1H), 8.12 (m, 1H), 7.93 (m, 1H), 7.26 (d, 2H, J=9 Hz), 7.14 (d, 1H, J=9 Hz), 4.85 (m, 1H), 3.74 (m, 2H); LC/MS: m/z=444 (M+1).

Example 72

Synthesis of (S)-6-(4-(4-carbamoyl-2-(trifluoromethyl)phenoxy)phenyl)-4-(1,2-dihydroxyethyl)picolinamide (Compound Example No. 32)

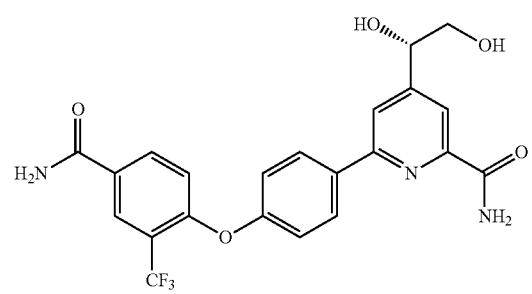 [SMILES: NC(=O)c1ccc(Oc2ccc(-c3cc([C@H](O)CO)cc(C(N)=O)n3)cc2)c(C(F)(F)F)c1]

(S)-6-(4-(4-carbamoyl-2-(trifluoromethyl)phenoxy)phenyl)-4-(1,2-dihydroxyethyl)picolinamide was synthesized according to General Method 2 of Example 57 using compound 5f. $^1$H NMR (600 MHz, CD$_3$OD): 8.32 (m, 3H), 8.12 (m, 3H), 7.23 (d, 2H, J=8.8 Hz), 7.11 (d, 1H, J=8.8 Hz), 3.78 (m, 2H); LC/MS: m/z=462 (M+1).

Example 73

Synthesis (S)-6-(4-(4-cyanophenoxyl)phenyl)-4-(1,2-dihydroxyethyl)picolinamide (Compound Example No. 37)

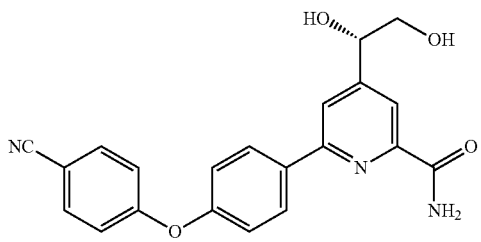 [SMILES: N#Cc1ccc(Oc2ccc(-c3cc([C@H](O)CO)cc(C(N)=O)n3)cc2)cc1]

(S)-6-(4-(4-cyanophenoxyl)phenyl)-4-(1,2-dihydroxyethyl)picolinamide was synthesized according to General Method 1 of Example 57. ¹H NMR (CD₃OD): 8.18 (d, 2H, J=8.8 Hz), 8.00 (s, 2H), 7.64 (d, 2H, J=8.4 Hz), 7.13 (d, 2H, J=8.4 Hz), 7.04 (d, 2H, J=8.8 Hz), 4.74 (m, 1H), 3.64 (m, 2H); LC/MS; m/z=376 (M+1).

Example 74

Synthesis of (R)-6-(4-(4-cyanophenoxyl)phenyl)-4-(1,2-dihydroxyethyl) picolinamide (Compound Example No. 38)

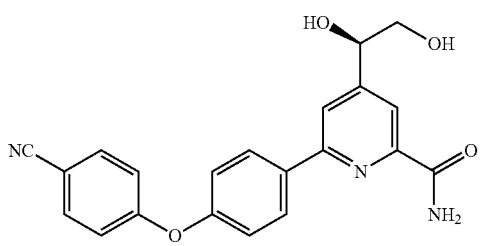 [SMILES: N#Cc1ccc(Oc2ccc(-c3cc([C@@H](O)CO)cc(C(N)=O)n3)cc2)cc1]

(R)-6-(4-(4-cyanophenoxyl)phenyl)-4-(1,2-dihydroxyethyl) picolinamide was synthesized according to General Method 1 of Example 57. ¹H NMR (CD₃OD): 8.18 (d, 2H, J=8.8 Hz), 8.00 (s, 2H), 7.64 (d, 2H, J=8.4 Hz), 7.13 (d, 2H, J=8.4 Hz), 7.04 (d, 2H, J=8.8 Hz), 4.74 (m, 1H), 3.64 (m, 2H); LC/MS: m/z=376 (M+1).

Example 75

Synthesis of (S)-6-(5-chloro-2-fluorophenoxy)phenyl)-4-(1,2-dihydroxyethyl) picolinamide (Compound Example No. 39)

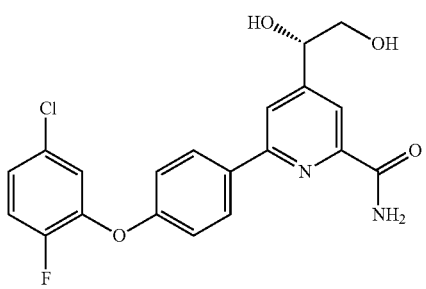 [SMILES: NC(=O)c1cc([C@H](O)CO)cc(-c2ccc(Oc3cc(Cl)ccc3F)cc2)n1]

(S)-6-(5-chloro-2-fluorophenoxy)phenyl)-4-(1,2-dihydroxyethyl)picolinamide was synthesized according to General Method 1 of Example 57. ¹H NMR (CD₃OD): 8.11 (d, 2H, J=8.8 Hz), 7.97 (m, 2H), 7.21-7.08 (m, 3H), 7.01 (d, 2H, J=8.8 Hz), 4.75 (m, 1H), 3.63 (m, 2H); LC/MS: m/z=403 (M+1).

Example 76

Synthesis of (R)-6-(5-chloro-2-fluorophenoxy)phenyl)-4-(1,2-dihydroxyethyl) picolinamide (Compound Example No. 123)

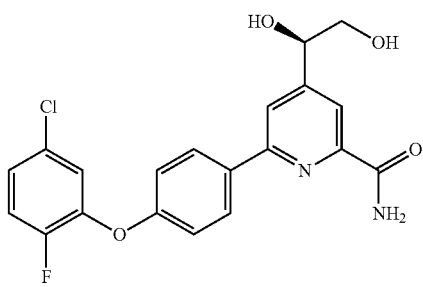 [SMILES: NC(=O)c1cc([C@@H](O)CO)cc(-c2ccc(Oc3cc(Cl)ccc3F)cc2)n1]

(R)-6-(5-chloro-2-fluorophenoxy)phenyl)-4-(1,2-dihydroxyethyl)picolinamide was synthesized according to General Method 1 of Example 57. ¹H NMR (CD₃OD): 8.11 (d, 2H, J=8.8 Hz), 7.97 (m, 2H), 7.21-7.08 (m, 3H), 7.01 (d, 2H, J=8.8 Hz), 4.75 (m, 1H), 3.63 (m, 2H); LC/MS: m/z=403 (M+1).

Example 77

Synthesis of (S)-4-(1,2-dihydroxyethyl)-6-(4-(4-fluorophenoxy)phenyl)-N-(2-(piperidin-1-yl)ethyl) picolinamide (Compound Example No. 42)

Scheme 61

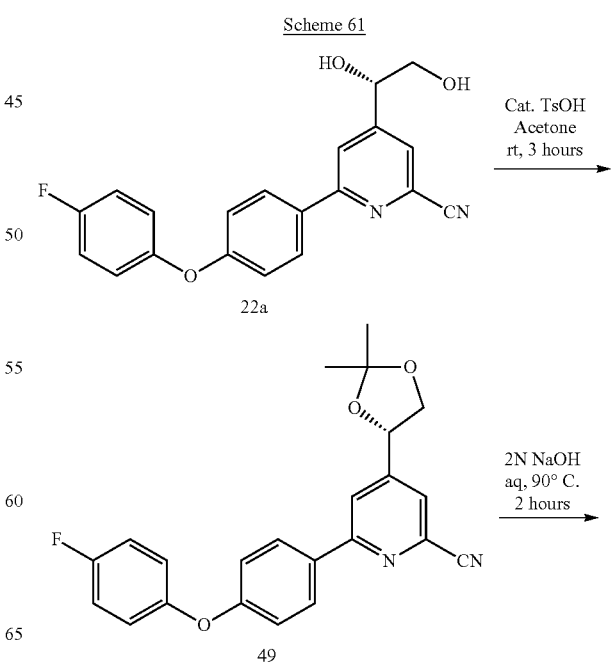

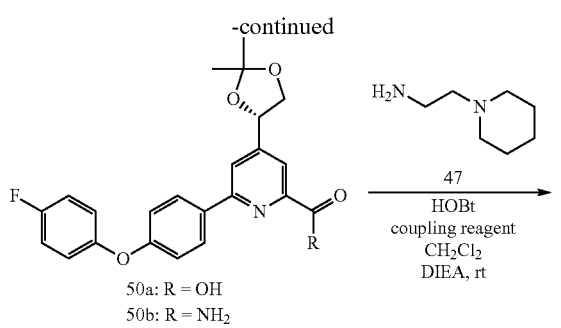

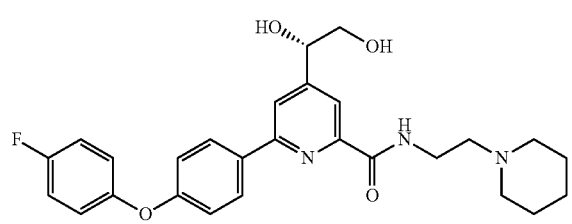

Compound Example No. 42

Coupling reagent: N-(3-dimethylaminopropyl)-N'-ethylcarbodiimide hydrogen chloride (Aldrich)

A solution of compound 22a (65 mg, 0.18 mmol) and a catalytic amount of TsOH in acetone was stirred at room temperature for 3 h. After removal of solvent under vacuum, the residue was treated with 2N NaOH aqueous at 90° C. for 2 h. After cooling to room temperature, the solvent was removed to give a mixture of compounds 50a and 50b. The mixture of compounds 50a and 50b was treated with HOBT (24.3 mg, 0.18 mmol), coupling agent, DIEA (99 µL, 0.54 mmol) and compound 47 (23 mg, 0.18 mmol) in $CH_2Cl_2$ for 12 h. The reaction mixture was purified via column chromatography (12 silica, 0-30% MeOH in $CH_2Cl_2$ containing 1% $NH_3$ aqueous solution) to give (S)-4-(1,2-dihydroxyethyl)-6-(4-(4-fluorophenoxy)phenyl)-N-(2-(piperidin-1-yl)ethyl)picolinamide (Compound Example No. 42 (12 mg, 0.025 mmol). $^1$H NMR ($CD_3OD$): 8.12 (d, 2H, J=9.2 Hz), 7.97 (s, 1H), 7.96 (s, 1H), 6.96-7.0 (m, 6H), 4.74 (t, 1H, J=5.2 Hz), 3.63 (m, 2H), 3.56 (m, 2H), 2.52-2.73 (b, 6H), 1.61 (m, 4H), 1.45 (m, 2H); LC/MS: m/z=480 (M+1).

Example 78

Synthesis of (R)-4-(1,2-dihydroxyethyl)-6-(4-(4-fluorophenoxy)phenyl) isonicotinamide (Compound Example No. 89)

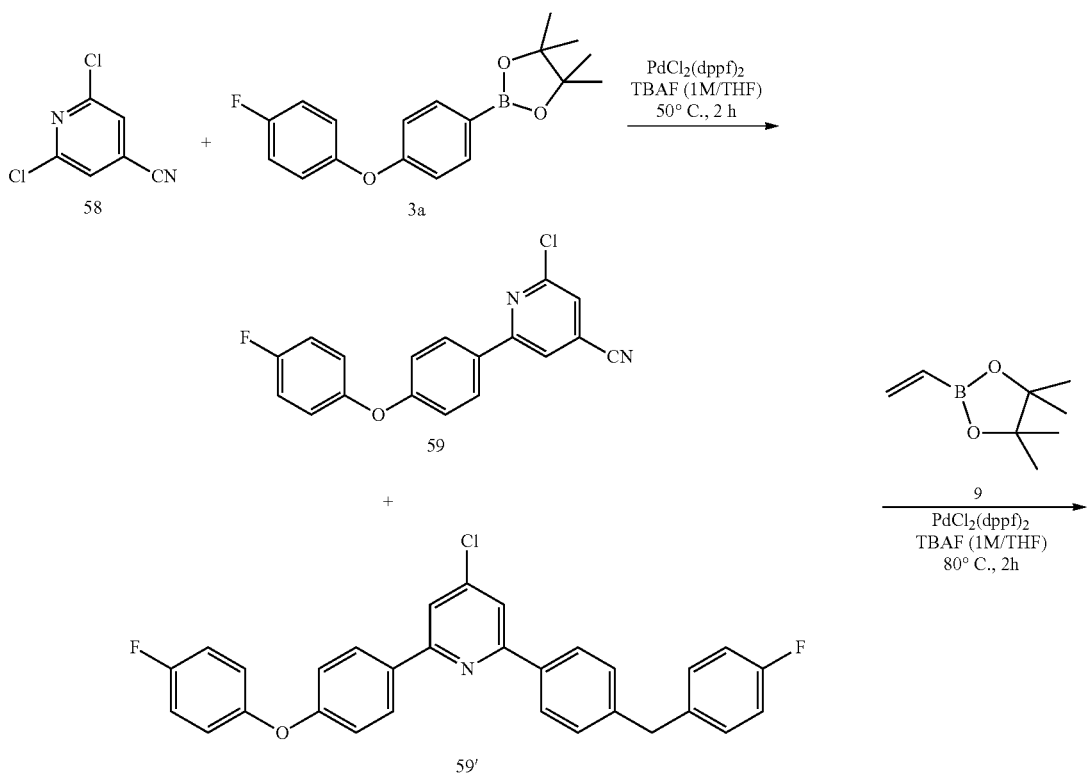

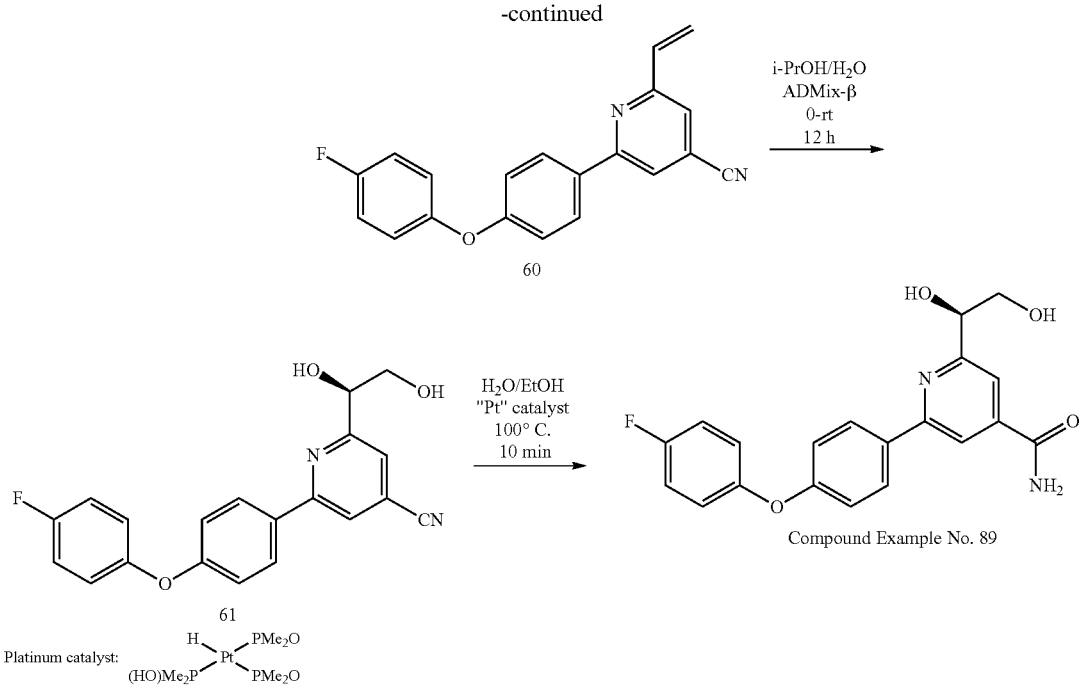

A solution of compound 58 (500 mg, 2.89 mmol, Aldrich), compound 3a (908 mg, 2.89 mmol), PdCl$_2$(dppf)$_2$ (169 mg, 0.23 mmol, Aldrich) in TBAF (9 mL, 9 mmol, Aldrich) under pressure was placed under argon and then heated at 60° C. in an oil bath for 2 h. After cooling to room temperature, the reaction mixture was purified via column chromatography without aqueous workup (40 g silica gel, 0-30% EtOAc/Hexane) to obtain a mixture (0.7 g) of compounds 59 and 59' as a liquid.

A solution of the mixture of compounds 59 and 59', PdCl$_2$(dppf)$_2$ (141 mg, 0.17 mmol, Aldrich) in TBAF (6 mL, 6 mmol, Aldrich) placed under argon and heated at 80° C. in an oil bath for 0.5 h. After cooling to room temperature, the mixture was purified without aqueous workup via column chromatography (40 g silica gel, 0-20% EtOAc/Hexane) to obtain a mixture (540 mg) of compounds 60 and 59'.

To a milky suspension of the mixture of compounds 60 and 59' (540 mg, 1.7 mmol) in 2-PrOH (5 mL) and H$_2$O (5 mL) was added in one portion of ADMix-β ((2.21 g, Aldrich) and the resulting mixture was stirred at room temperature for 12 h. The mixture was extracted with EtOAc (4×20 mL) and the combined organic layers were dried over Na$_2$SO$_4$, filtered and concentrated. The residue was purified via column chromatography (40 g silica gel, 0-80% EtOAc/Hexane) to give compound 61.

To a solution of compound 61 in EtOH (2 mL) and H$_2$O (2 mL) was added platinum catalyst and the reaction mixture heated at 100° C. in an oil bath for 10 min. After cooling to room temperature, the mixture was extracted with EtOAc (4×20 mL) and the combined organic layers were dried over Na$_2$SO$_4$, filtered and concentrated. The residue was recrystallized from methanol to give (R)-4-(1,2-dihydroxyethyl)-6-(4-(4-fluorophenoxy)phenyl) isonicotinamide (Compound Example No. 89) (86 mg, 0.23 mmol) as white solid. $^1$H NMR (CD$_3$OD): 8.01 (m, 3H), 7.77 (m, 1H), 7.07-7.94 (m, 6H), 4.79 (m, 1H), 3.87 (dd, 1H, J1=4, J2=11 Hz), 3.71 (dd, 1H, J1=4, J2=11 Hz); LC/MS: m/z=369.

Example 79

Synthesis of (S)-2-(1,2-dihydroxyethyl)-6-(4-(4-fluorophenoxy)phenyl) isonicotinamide (Compound Example No. 97)

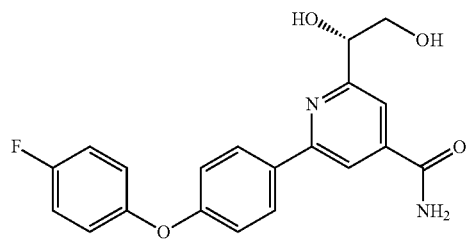 [SMILES: NC(=O)c1cc(-c2ccc(Oc3ccc(F)cc3)cc2)nc([C@H](O)CO)c1]

(S)-2-(1,2-dihydroxyethyl)-6-(4-(4-fluorophenoxy)phenyl)isonicotinamide was synthesized similarly to (R)-4-(1,2-dihydroxyethyl)-6-(4-(4-fluorophenoxy)phenyl) isonicotinamide as described in Example 78. $^1$H NMR (DMSO-d$_6$): 8.35 (bs, 1H, NH), 8.17 (m, 3H), 7.83 (s, 1H), 7.72 (bs, 1H, NH), 7.27 (t, 2H), 7.15 (m, 4H), 5.6 (s, 1H, OH), 4.8 (d, 1H, OH), 4.7 (m, 1H), 3.8 (m, 1H), 3.57 (m, 1H); LC/MS: m/z=369.

Example 80

Synthesis of (S)-6-(1,2-dihydroxyethyl)-4-(4-(4-fluorophenoxy)phenyl)picolinamide (Compound Example No. 95)

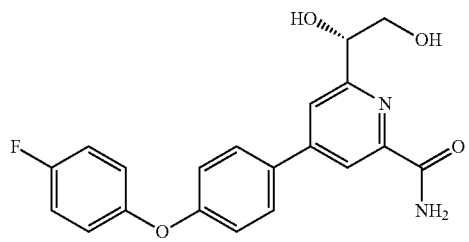 [SMILES: NC(=O)c1cc(-c2ccc(Oc3ccc(F)cc3)cc2)cc([C@H](O)CO)n1]

(S)-6-(1,2-dihydroxyethyl)-4-(4-(4-fluorophenoxy)phenyl)picolinamide was synthesized using methodology described in General Method 1 of Example 57. $^1$H NMR (DMSO-$d_6$): 8.3 (m, 3H), 8.0 (d, 2H), 7.7 (s, 1H), 7.3 (m, 2H), 7.18 (m, 2H), 7.1 (d, 2H), 5.65 (d, 1H, OH), 4.9 (d, 1H, OH), 4.7 (m, 1H), 3.5 (m, 2H); LC/MS: m/z=369.

Example 81

Synthesis of (R)-6-(1,2-dihydroxyethyl)-4-(4-(4-fluorophenoxy)phenyl)picolinamide (Compound Example No. 96)

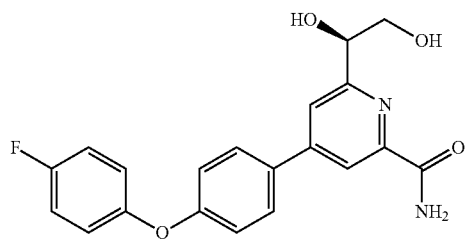 [SMILES: NC(=O)c1cc(-c2ccc(Oc3ccc(F)cc3)cc2)cc([C@@H](O)CO)n1]

(R)-6-(1,2-dihydroxyethyl)-4-(4-(4-fluorophenoxy)phenyl)picolinamide was synthesized using methodology described in General Method 1 of Example 57. $^1$H NMR (DMSO-$d_6$): 8.3 (m, 3H), 8.0 (d, 2H), 7.7 (s, 1H), 7.3 (m, 2H), 7.18 (m, 2H), 7.1 (d, 2H), 5.65 (d, 1H, OH), 4.9 (d, 1H, OH), 4.7 (m, 1H), 3.5 (m, 2H); LC/MS: m/z=369.

Example 82

Synthesis of (R)-4-(2,3-dihydroxypropyl)-6-(4-(4-fluorophenoxy)phenyl)picolinamide (Compound Example No. 134)

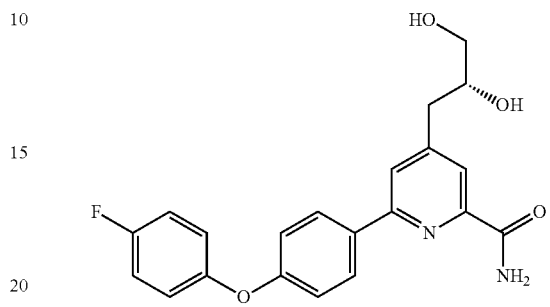

(R)-4-(2,3-dihydroxypropyl)-6-(4-(4-fluorophenoxy)phenyl)picolinamide was synthesized using methodology described in General Method 1 of Example 57. $^1$H NMR (DMSO-$d_6$): 8.09 (m, 2H), 7.85 (d, 2H), 7.70 (m, 2H), 7.30 (t, 2H), 7.18 (m, 2H), 7.10 (d, 2H), 4.70 (m, 2H), 4.00 (m, 1H), 3.40 (m, 2H), 3.04 (m, 1H), 2.80 (m, 1H); LC/MS: m/z=383.

Example 83

Synthesis of (S)-4-(2,3-dihydroxypropyl)-6-(4-(4-fluorophenoxy)phenyl)picolinamide (Compound Example No. 135)

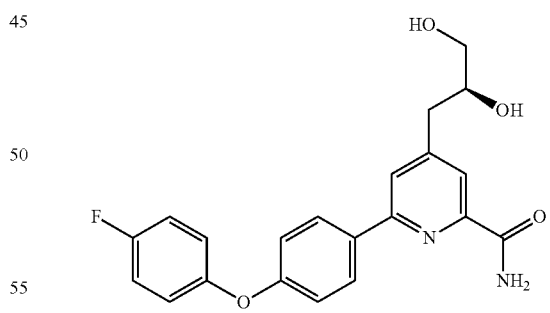

(S)-4-(2,3-dihydroxypropyl)-6-(4-(4-fluorophenoxy)phenyl)picolinamide was synthesized using methodology described in General Method 1 of Example 57. $^1$H NMR (DMSO-$d_6$): 8.09 (m, 2H), 7.87 (d, 2H), 7.70 (m, 2H), 7.30 (t, 2H), 7.18 (m, 2H), 7.10 (d, 2H), 4.70 (m, 2H), 4.00 (m, 1H), 3.40 (m, 2H), 3.04 (m, 1H), 2.80 (m, 1H); LC/MS: m/z=383.

Example 84

Synthesis 4-((1S,2S)-1,2-dihydroxypropyl)-6-(4-(4-fluorophenoxy)phenyl) picolinamide (Compound Example No. 129)

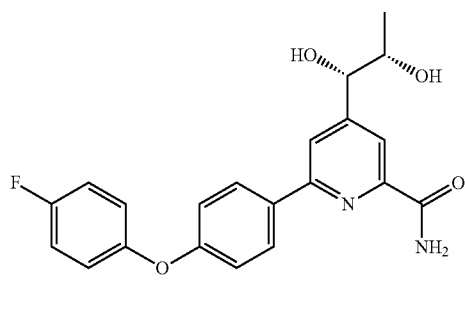 [SMILES: C[C@H](O)[C@@H](O)c1cc(C(N)=O)nc(-c2ccc(Oc3ccc(F)cc3)cc2)c1]

4-((1S,2S)-1,2-dihydroxypropyl)-6-(4-(4-fluorophenoxy)phenyl)picolinamide was isolated as by-product during the synthesis of (S)-4-(2,3-dihydroxypropyl)-6-(4-(4-fluorophenoxy)phenyl) picolinamide. $^1$H NMR (DMSO-d$_6$): 8.39 (s, 1H), 8.12 (s, 1H), 7.84 (m, 3H), 7.67 (s, 1H), 7.27 (m, 2H), 7.16 (m, 2H), 7.11 (d, 2H), 5.40 (bs, 1H), 4.50 (m, 2H), 4.0 (m, 1H), 1.0 (m, 3H); LC/MS: m/z=383.

Example 85

Synthesis of 4-((1R,2R)-1,2-dihydroxypropyl)-6-(4-(4-fluorophenoxy)phenyl)picolinamide (Compound Example No. 131)

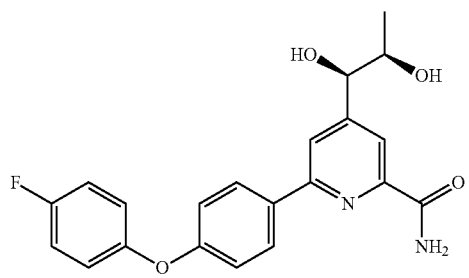 [SMILES: C[C@@H](O)[C@H](O)c1cc(C(N)=O)nc(-c2ccc(Oc3ccc(F)cc3)cc2)c1]

4-((1R,2R)-1,2-dihydroxypropyl)-6-(4-(4-fluorophenoxy)phenyl)picolinamide was isolated as a by product during the synthesis of Compound Example No. 133. $^1$H NMR (DMSO-d$_6$): 8.39 (s, 1H), 8.17 (s, 1H), 7.84 (m, 3H), 7.70 (s, 1H), 7.32 (m, 2H), 7.20 (m, 2H), 7.16 (d, 2H), 5.40 (m, 1H), 4.50 (m, 2H), 4.0 (m, 1H), 1.0 (m, 3H); LC/MS: m/z=383.

Example 86

Synthesis of 6-(4-(4-fluorophenoxy)phenyl)-4-((pyridine-3-ylmethyl)amino) picolinamide, 6-(4-(4-fluorophenoxy)phenyl)-4-((pyridine-4-ylmethyl)amino) picolinamide, and 6-(4-(4-fluorophenoxy)phenyl)-4-((pyridine-2-ylmethyl)amino) picolinamide Compound Example Nos. 45-47

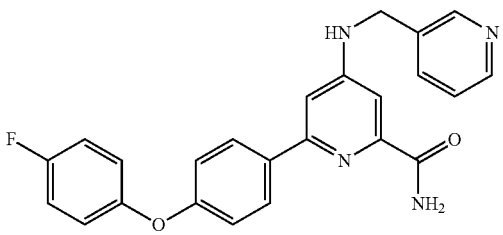 [SMILES: NC(=O)c1cc(NCc2cccnc2)cc(-c2ccc(Oc3ccc(F)cc3)cc2)n1]

6-(4-(4-fluorophenoxy)phenyl)-4-((pyridine-3-ylmethyl)amino)picolinamide (Compound Example No. 45) was synthesized according to general procedure of Example 24 in 80% yield as a white solid. $^1$H NMR (CD$_3$CN): 8.2-8.9 (m, 3H), 7.6-7.9 (m, 3H), 6.8-7.5 (m, 8H), 4.8 (s, 2H); (m/z+H)=415.

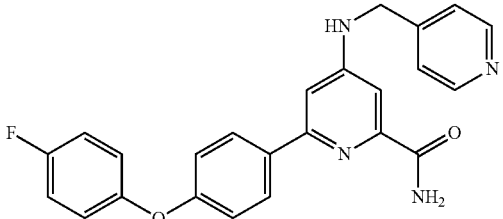

6-(4-(4-fluorophenoxy)phenyl)-4-((pyridine-4-ylmethyl)amino)picolinamide (Compound Example No. 46) was synthesized according to general procedure of Example 24 in 80% yield as a white solid. $^1$HNMR (CD$_3$CN): 8.9 (s, br, 2H), 7.6-7.9 (m, 4H), 6.8-7.5 (m, 9H), 4.8 (s, 2H).

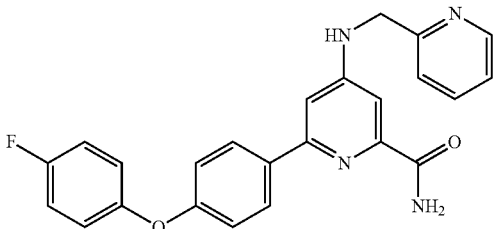

6-(4-(4-fluorophenoxy)phenyl)-4-((pyridine-2-ylmethyl)amino)picolinamide (Compound Example No. 47) was synthesized according to general procedure of Example 24. $^1$H NMR (CD$_3$OD): 8.44 (m, 1H), 7.89 (d, 2H, J=8.8 Hz), 7.71 (dt, 1H, J1=1.6, J2=7.6 Hz), 7.38 (d, 1H, J=7.6 Hz), 7.23 (dd, 1H, J1=6, J2=7.6 Hz), 7.19 (d, 1H, J=2.4 Hz), 7.06-6.90 (m, 6H), 4.51 (s, 2H); LC/MS: m/z=415 (M+1).

Example 87

Synthesis of 6-(4-(4-fluorophenoxy)phenyl)-1',2',3',6'-tetrahydro-[4,4'-bipyridine]-2-carboxamide (Compound Example No. 122)

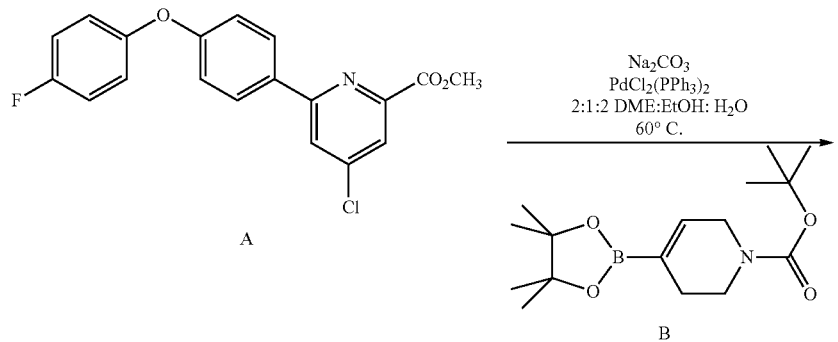

Scheme 63

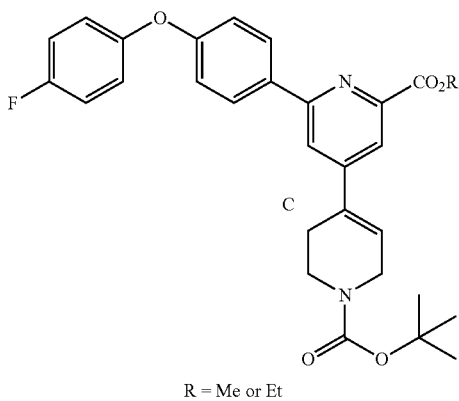

R = Me or Et

To a flask containing methyl 4-chloro-6-(4-(4-fluorophenoxy)phenyl)picolinate (compound A) (0.5g, 1.4 mmol) was added tert-butyl 4-(4,4,5,5-tetramethyl-1,3,2-dioxaborolan-2-yl)-5,6-dihydropyridine-1(2H)-carboxylate (compound B) (0.45 g, 1.47 mmol), dimethoxyethane (1.4 mL), and ethanol (0.7 mL). Sodium carbonate (0.296 g, 2.8 mmol) was dissolved in water (1.4 mL) and this solution was added to the reaction mixture. The reaction mixture was then evacuated and flushed with argon 3 times. Bis(triphenylphine) dichloropalladium was added and the reaction mixture was heated at 60° C. for 1.5 h at which time analysis of an aliquot of the reaction mixture indicated the reaction was complete. The ethanol was removed under reduced pressure and the residue was partitioned between ethyl acetate (50 mL) and water (50 mL). The layers were separated, the aqueous layer was washed with ethyl acetate (20 mL) and the combined organic layers were dried (magnesium sulfate) and concentrated under reduced pressure to yield the crude product. Purification by column chromatography (silica gel, hexane/ethyl acetate gradient) yielded an approximately one to one mixture of the methyl and ethyl esters of compound C. This material was used as is for the next step.

Scheme 64

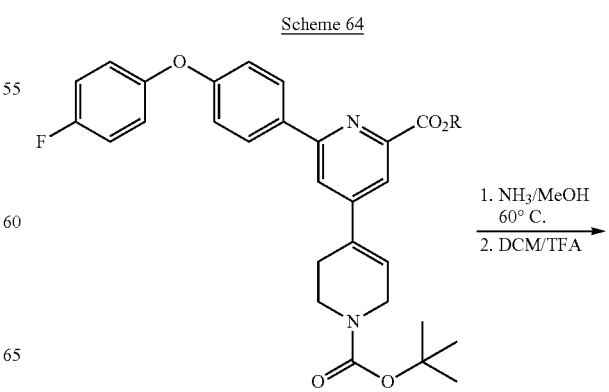

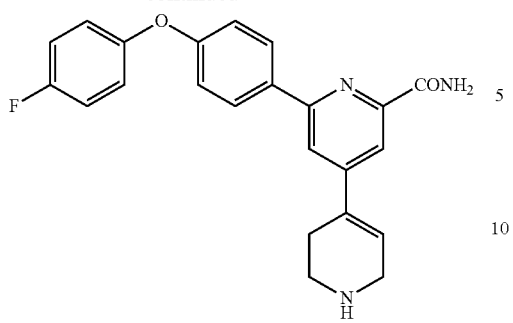

Compound C as a mixture of esters from Scheme 63 was dissolved in 5 mL of 7N ammonia in methanol and heated at 60° C. for 18 h. The reaction mixture was concentrated under reduced pressure to yield a pale yellow solid which was taken up in dichloromethane (10 mL) and trifluoroacetic acid (2 mL). The reaction mixture was stirred for 16 h at ambient temperature. The solvent was removed under reduced pressure and the residue was purified by column chromatography (silica gel; methanol/ethyl acetate gradient) to give 6-(4-(4-fluorophenoxy)phenyl)-1',2',3',6'-tetrahydro-[4,4'-bipyridine]-2-carboxamide (Compound Example No. 122).

Example 88

6-(4-(4-fluorophenoxy)phenyl)-4-methyl(phenyl)amino)picolinamide (Compound Example No. 43)

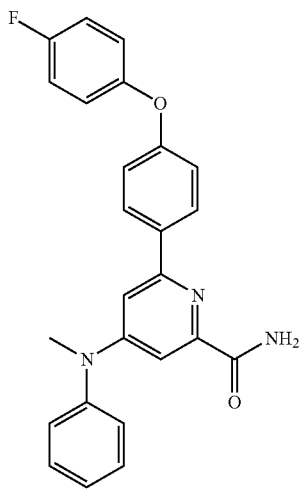 [SMILES: CN(c1ccccc1)c1cc(C(N)=O)nc(-c2ccc(Oc3ccc(F)cc3)cc2)c1]

$^1$H NMR (DMSO-d$_6$): 7.93 (bd, 1H, NH), 7.63 (bd, 1H, NH), 7.56 (m, 3H), 7.47 (m, 2H), 7.39 (d, 2H), 7.25 (m, 3H), 7.12 (m, 2H), 7.02 (d, 2H), 6.79 (s, 1H), 3.5 (s, 3H); LC/MS: m/z=414 (M+1).

Example 89

4-((2-cyanoethyl)(phenyl)amino)-6-(4-(4-fluorophenoxy)phenylpicolinamide (Compound Example No. 44)

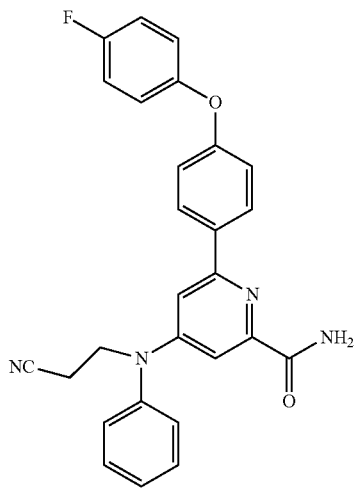 [SMILES: N#CCCN(c1ccccc1)c1cc(C(N)=O)nc(-c2ccc(Oc3ccc(F)cc3)cc2)c1]

$^1$H NMR (DMSO-d$_6$): 8.12 (bs, 1H, NH), 7.69 (bs, 1H, NH), 7.61 (s, 1H), 7.51 (m, 4H), 7.43 (d, 2H), 7.38 (d, 1H), 7.24 (t, 2H), 7.12 (m, 2H), 7.01 (d, 2H), 6.59 (s, 1H), 4.31 (t, 2H), 2.85 (t, 2H); LC/MS: m/z=453 (M+1).

Example 90

4-(4-(4-fluorophenoxy)phenyl)-6-methyl(phenyl)amino)picolinamide (Compound Example No. 113)

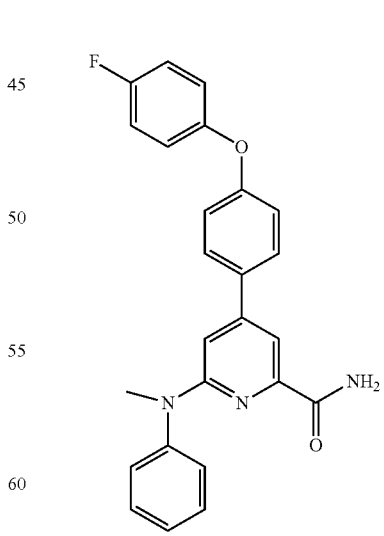

$^1$H NMR (DMSO-d$_6$): 8.19 (m, 3H), 7.58 (bs, 1H, NH), 7.51 (t, 2H), 7.34 (m, 3H), 7.25 (m, 3H), 7.15 (m, 3H), 7.04 (d, 2H), 3.40 (s, 3H); LC/MS: m/z=414 (M+1).

Example 91

6-(4-(4-fluorophenoxy)phenyl)-4-methyl(phenyl)amino)picolinic acid (Compound Example No. 114)

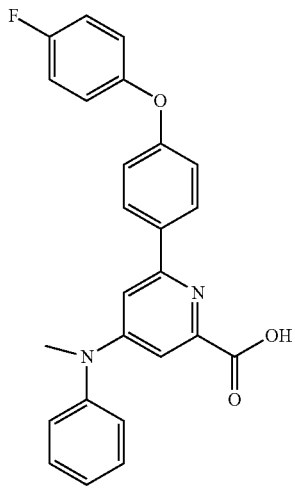 [SMILES: CN(c1ccccc1)c1cc(C(=O)O)nc(-c2ccc(Oc3ccc(F)cc3)cc2)c1]

$^1$H NMR (DMSO-d$_6$): 12.80 (bs, 1H, CO$_2$H), 7.50 (m, 3H), 7.40 (t, 2H), 7.32 (m, 2H), 7.19 (m, 3H), 7.05 (m, 2H), 6.96 (d, 2H), 6.74 (s, 1H), 3.40 (s, 3H); LC/MS: m/z=415 (M+1).

Example 92

6-((2-cyanoethyl)(phenyl)amino)-4-(4-(4-fluorophenoxy)phenyl)picolinamide (Compound Example No. 115)

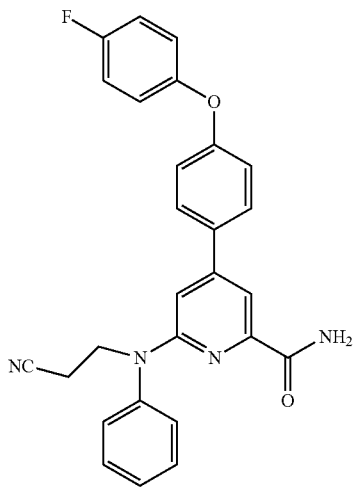 [SMILES: N#CCCN(c1ccccc1)c1cc(-c2ccc(Oc3ccc(F)cc3)cc2)cc(C(N)=O)n1]

$^1$H NMR (DMSO-d$_6$): 8.24 (d, 2H), 8.17 (s, 1H), 7.56 (m, 3H), 7.40 (m, 4H), 7.27 (m, 2H), 7.14 (m, 2H), 7.06 (d, 2H), 7.02 (s, 1H), 4.20 (t, 2H), 2.80 (t, 2H); LC/MS: m/z=453 (M+1).

Example 93

4-((6-carbamoyl-4-(4-(4-fluorophenoxy)phenyl)pyridine-2-yl)(methyl)amino)benzoic acid (Compound Example No. 116)

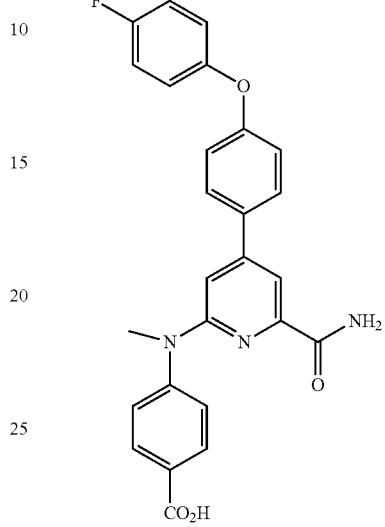

$^1$H NMR (DMSO-d$_6$): 8.28 (m, 3H), 8.08 (d, 2H), 7.70 (s, 1H, NH), 7.50 (m, 3H), 7.40 (s, 1H), 7.32 (t, 2H), 7.20 (m, 2H), 7.10 (d, 2H), 3.50 (s, 3H); LC/MS: m/z=458 (M+1).

Example 94

6-((4-carboxyphenyl)(methyl)amino)-4-(4-(4-fluorophenoxy)phenyl)picolinic acid (Compound Example No. 117)

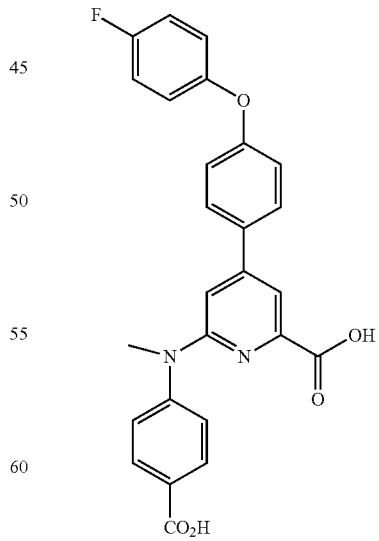

$^1$H NMR (DMSO-d$_6$): 8.01 (d, 2H), 7.78 (m, 3H), 7.51 (d, 2H), 7.32 (m, 3H), 7.20 (m, 2H), 7.11 (d, 2H), 3.60 (s, 3H); LC/MS: m/z=459 (M+1).

Example 95

4-((2-cyanoethyl)phenyl)amino)-6-(4-(4-fluorophenoxy)phenyl)picolinic acid (Compound Example No. 118)

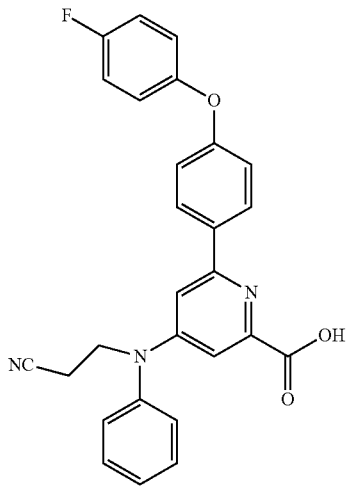 [SMILES: N#CCCN(c1ccccc1)c1cc(C(=O)O)nc(-c2ccc(Oc3ccc(F)cc3)cc2)c1]

¹H NMR (DMSO-d₆): 7.62 (s, 1H), 7.52 (m, 4H), 7.44 (d, 2H), 7.38 (t, 1H), 7.24 (t, 2H), 7.12 (m, 2H), 7.01 (d, 2H), 6.62 (s, 1H), 4.25 (t, 2H), 2.92 (t, 2H); LC/MS: m/z=454 (M+1).

Example 96

4-(4-(4-fluorophenoxy)phenyl)-6-(methyl(phenyl)amino)picolinic acid (Compound Example No. 119)

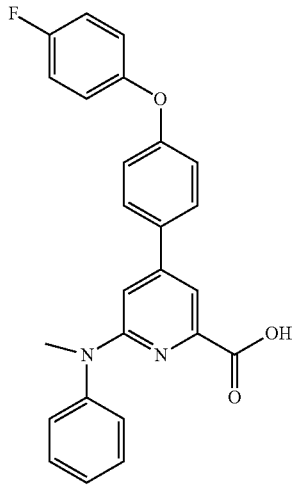 [SMILES: CN(c1ccccc1)c1cc(-c2ccc(Oc3ccc(F)cc3)cc2)cc(C(=O)O)n1]

¹H NMR (DMSO-d₆): 8.18 (d, 2H), 7.60 (m, 2H), 7.42 (m, 3H), 7.34 (m, 3H), 7.21 (m, 3H), 7.15 (d, 2H), 3.50 (s, 3H); LC/MS: m/z=415 (M+1).

Example 97

6-((4-carboxyphenyl)(methyl)amino)-4-(4-(4-fluorophenoxy)phenyl)picolinic acid (Compound Example No. 120)

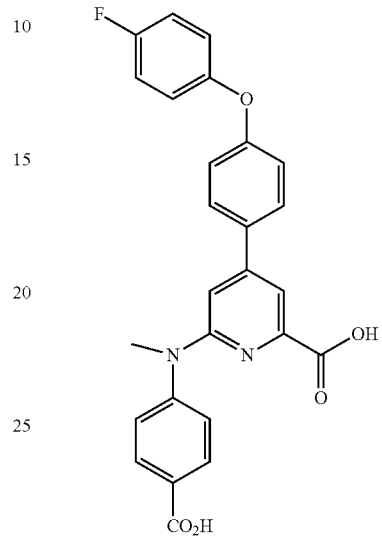

¹H NMR (DMSO-d₆): 8.12 (d, 2H), 8.01 (d, 2H), 7.44 (m, 3H), 7.32 (s, 1H), 7.27 (t, 2H), 7.13 (m, 2H), 7.08 (d, 2H), 3.50 (s, 3H); LC/MS: m/z=459 (M+1).

Example 98

6-((carboxymethyl)(phenyl)amino)-4-(4-(4-fluoeophenoxy)phenyl)picolinic acid (Compound Example No. 121)

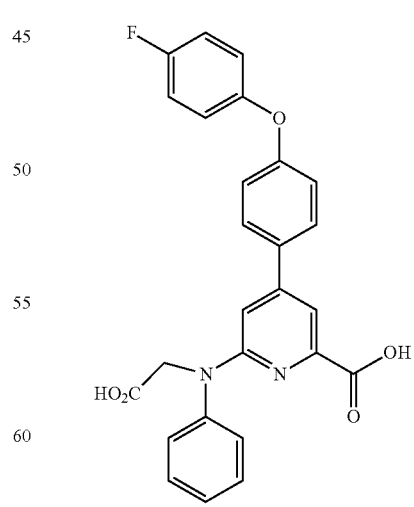

¹H NMR (DMSO-d₆): 8.12 (d, 2H), 7.60 (m, 2H), 7.44 (m, 3H), 7.30 (m, 3H), 7.20 (m, 2H), 7.12 (m, 3H), 4.70 (s, 2H); LC/MS: m/z=459 (M+1).

Example 99

4-((2-carbamoyl-6-(4-(4-fluorophenoxy)phenyl)pyridine-4-yl)(methyl)amino)benzoic acid (Compound Example No. 91)

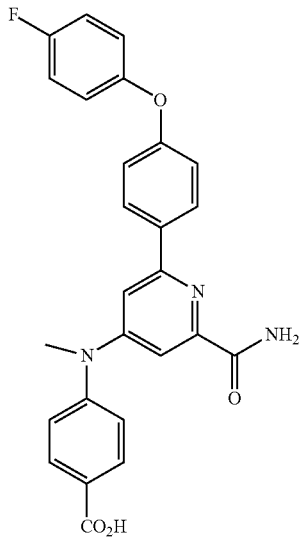 [SMILES: CN(c1ccc(C(=O)O)cc1)c1cc(C(N)=O)nc(-c2ccc(Oc3ccc(F)cc3)cc2)c1]

$^1$H NMR (DMSO-do): 7.95 (s, 1H, NH), 7.90 (d, 2H), 7.61 (s, 1H, NH), 7.55 (m, 3H), 7.23 (m, 4H), 7.12 (m, 2H), 7.04 (d, 2H), 6.81 (s, 1H), 3.50 (s, 3H); LC/MS: m/z=458 (M+1).

Example 100

4-((carboxymethyl)(phenyl)amino)-6-(4-(4-fluoeophenoxy)phenyl)picolinic acid (Compound Example No. 92)

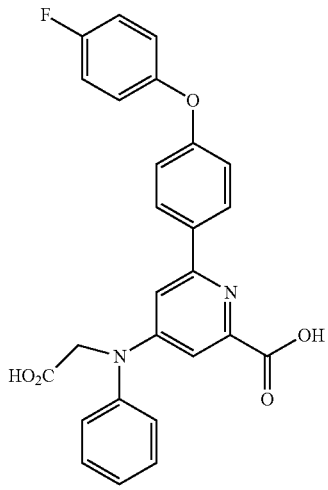 [SMILES: O=C(O)CN(c1ccccc1)c1cc(C(=O)O)nc(-c2ccc(Oc3ccc(F)cc3)cc2)c1]

$^1$H NMR (DMSO-d$_6$): 7.59 (s, 1H), 7.55 (d, 2H), 7.46 (m, 4H), 7.34-7.21 (m, 3H), 7.12 (m, 2H), 7.03 (d, 2H), 6.78 (s, 1H), 4.70 (s, 2H); LC/MS: m/z=459 (M+1).

Example 101

1-(2-carboxy-6-(4-(4-fluorophenoxy)phenyl)pyridine-4-yl)-1H-indole-3-carboxylic acid (Compound Example No. 93)

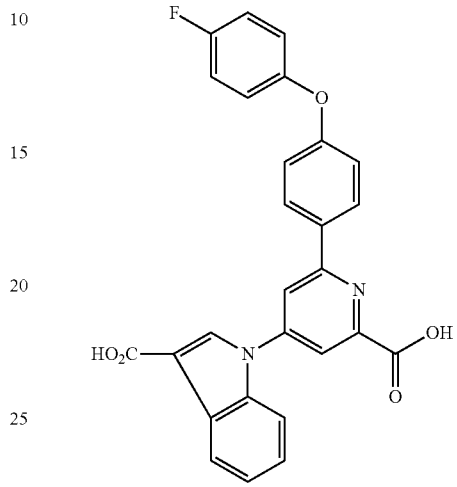

$^1$H NMR (DMSO-d$_6$): 8.61 (bs, 1H), 8.31 (s, 1H), 8.11 (bs, 1H), 8.05 (s, 1H), 7.9-7.8 (m, 3H), 7.2 (m, 2H), 7.12-7.0 (m, 6H); LC/MS: m/z=469 (M+1).

Example 102a 6-((2-cyanoethyl)phenyl)amino)-4-(4-(4-fluorophenoxy)phenyl)picolinic acid (Compound Example No. 94)

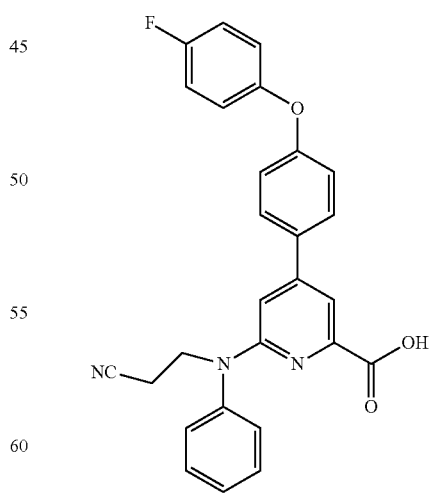

$^1$H NMR (DMSO-d$_6$): 8.19 (d, 2H), 7.60 (t, 2H), 7.46 (m, 4H), 7.30 (t, 2H), 7.19 (m, 2H), 7.11 (d, 2H), 7.06 (s, 1H), 4.30 (t, 2H), 2.85 (t, 2H); LC/MS: m/z=454 (M+1).

Example 102b 6-((2-amino-2-oxoethyl)(phenyl)amino)-4-(4-(4-fluorophenoxy)phenyl)picolinamide (Compound Example No. 98)

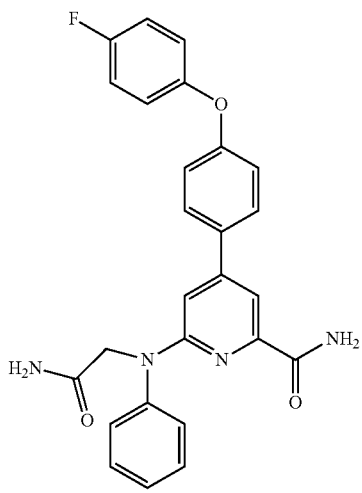 [SMILES: NC(=O)CN(c1ccccc1)c1cc(-c2ccc(Oc3ccc(F)cc3)cc2)cc(C(N)=O)n1]

$^1$H NMR (DMSO-d$_6$): 8.15 (bs, 1H, NH), 8.10 (m, 2H), 7.66-7.30 (m, 7H), 7.25 (m, 3H0, 7.17-7.0 (m, 6H), 4.4 (m, 2H); LC/MS: m/z=457 (M+1).

Example 103

4-(4-cyano-1H-indol-1-yl)-6-(4-(4-fluorophenoxy)phenyl)picolinamide (Compound Example No. 99)

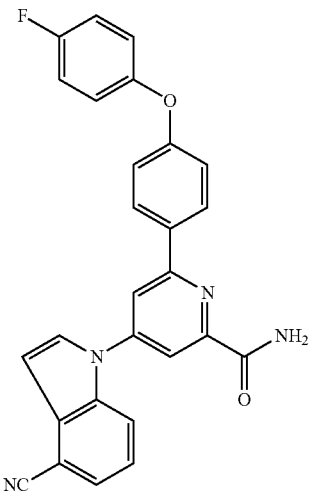 [SMILES: N#Cc1cccc2c1ccn2-c1cc(C(N)=O)nc(-c2ccc(Oc3ccc(F)cc3)cc2)c1]

$^1$H NMR (DMSO-d$_6$): 8.68 (d, 1H), 8.65 (s, 1H), 8.21 (s, 2H), 8.12 (bs, 1H, NH), 8.07 (d, 2H), 7.90 (bs, 1H, NH), 7.75 (d, 1H), 7.48 (t, 1H), 7.30 (t, 2H), 7.20 (m, 2H), 7.15 (d, 2H), 6.98 (s, 1H); LC/MS: m/z=449 (M+1).

Example 104

6-(4-cyano-1H-indol-1-yl)-4-(4-(4-fluorophenoxy)phenyl)picolinamide (Compound Example No. 100)

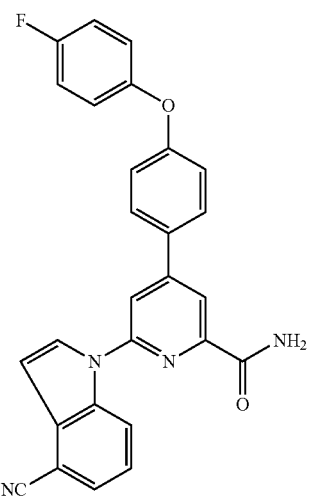 [SMILES: N#Cc1cccc2c1ccn2-c1cc(-c2ccc(Oc3ccc(F)cc3)cc2)cc(C(N)=O)n1]

$^1$H NMR (DMSO-d$_6$): 8.50 (m, 3H), 8.47 (d, 2H), 8.12 (m, 2H), 7.90 (bs, 1H, NH), 7.78 (m, 1H), 7.49 (m, 1H), 7.29 (m, 2H), 7.2-7.1 (m, 4H), 7.0 (s, 1H); LC/MS: m/z=449 (M+1).

Example 105

4-(4-cyano-1H-indol-1-yl)-6-(4-(4-fluorophenoxy)phenyl)picolinic acid (Compound Example No. 101)

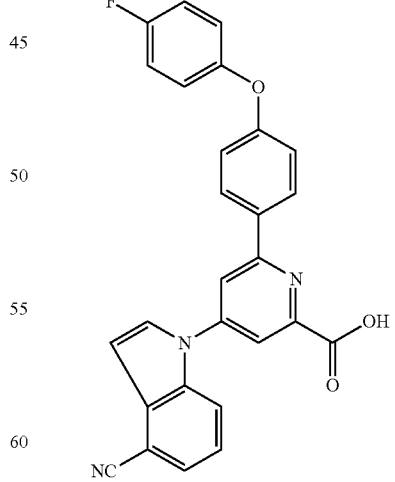

$^1$H NMR (DMSO-d$_6$): 9.01 (d, 1H), 8.55 (s, 1H), 8.10 (s, 1H), 7.97 (m, 3H), 7.70 (d, 1H), 7.40 (t, 1H), 7.29 (t, 2H), 7.19 (m, 2H), 7.12 (d, 2H), 6.90 (s, 1H); LC/MS: m/z=450 (M+1).

Example 106

4-((2-amino-2-oxoethyl)(phenyl)amino)-6-(4-(4-fluorophenoxy)phenyl)picolinamide (Compound Example No. 102)

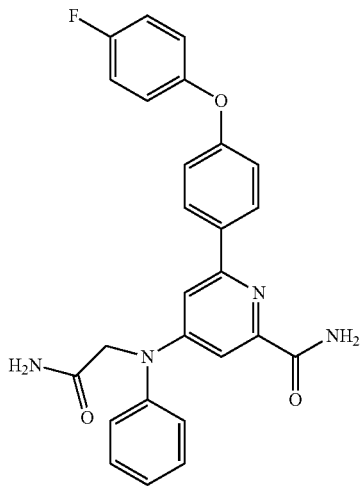 [SMILES: NC(=O)CN(c1ccccc1)c1cc(C(N)=O)nc(-c2ccc(Oc3ccc(F)cc3)cc2)c1]

$^1$H NMR (DMSO-$d_6$): 7.83 (bs, 1H), 7.73 (bs, 1H), 7.58 (m, 2H), 7.58-7.45 (m, 6H), 7.34-7.21 (m, 3H), 7.13 (m, 3H), 7.02 (d, 2H), 6.75 (s, 1H), 4.42 (s, 2H); LC/MS: m/z=457 (M+1).

Example 107

6-(4-cyano-1H-indol-1-yl)-4-(4-(4-fluorophenoxy)phenyl)picolinic acid (Compound Example No. 126)

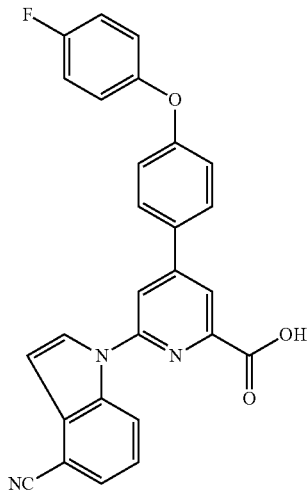

$^1$H NMR (DMSO-$d_6$): 8.26 (m, 3H), 8.10 (d, 1H), 8.0 (d, 2H), 7.75 (d, 1H), 7.46 (t, 1H), 7.30 (t, 2H), 7.17 (m, 2H), 7.09 (d, 2H), 6.95 (s, 1H); LC/MS: m/z=449 (M).

Example 108

1-(2-carboxy-6-(4-(4-fluorophenoxy)phenyl)pyridine-4-yl)-1H-indole-6-carboxylic acid (Compound Example No. 130)

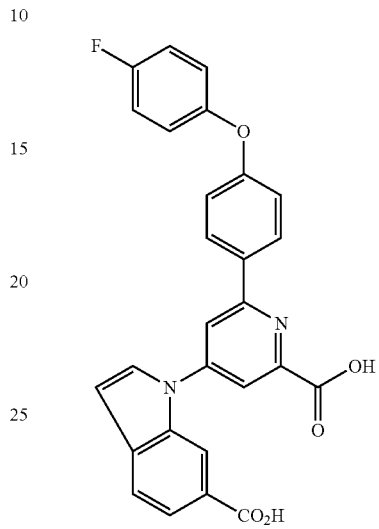

$^1$H NMR (DMSO-$d_6$): 9.25 (bs, 0.7H, CO$_2$H), 8.24 (d, 1H), 8.11 (s, 1H), 7.96 (m, 3H), 7.79 (d, 1H), 7.50 (d, 1H), 7.29 (t, 2H), 7.20 (m, 2H), 7.13 (d, 2H), 6.7 (d, 1H); LC/MS: m/z=468 (M).

Example 109

(S)-6-(4-(3-cyano-4-(trifluoromethyl)phenoxy)phenyl)-N-(2,3-dihydroxypropyl) picolinamide (Compound Example No. 90)

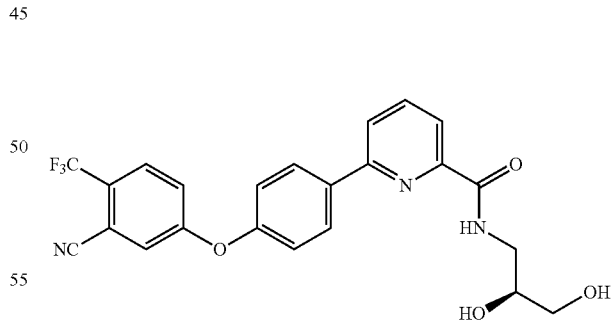

$^1$H NMR (CD$_3$OD): 8.22 (d, 2H, J=8.8 Hz), 8.02-7.93 (m, 3H), 7.80 (d, 1H, J=8.8 Hz), 7.53 (d, 1H, J=2.4 Hz), 7.33 (dd, 1H, J1=2.8, J2=9.2 Hz), 7.18 (d, 2H, J=8 Hz), 3.77 (m, 1H), 3.59 (dd, 1H, J1=4.8, J2=14 Hz), 3.50 (d, 2H, J=5.6 Hz), 3.40 (dd, 1H, J1=6.8, J2=14 Hz); LC/MS: m/z=458 (M+H).

Example 110

(S)-4-(6-(1,2-dihydroxyethyl)pyridin-2-yl)-N-(4-fluorophenyl)benzenesulfonamide (Compound Example No. 104)

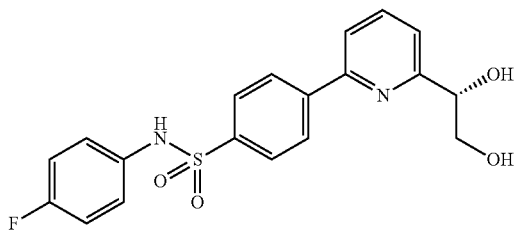 [SMILES: O=S(=O)(Nc1ccc(F)cc1)c1ccc(-c2cccc([C@H](O)CO)n2)cc1]

$^1$H NMR (CD$_3$OD): 8.17 (d, 2H, J=8.8 Hz), 7.91 (t, 1H, J=8 Hz), 7.82 (d, 2H, J=8.4 Hz), 7.57 (d, 1H, J=7.6 Hz), 7.12 (m, 2H), 6.98 (m, 2H), 4.84 (m, 1H), 3.94 (dd, 1H, J1=4.4, J2=12 Hz), 3.78 (dd, 1H, J1=6.4, J2=12 Hz); LC/MS: m/z=389 (M+H).

Example 111

(S)-6-(4-(4-chloro-2-fluorophenoxy)phenyl)-4-(1,2-dihydroxyethyl)picolinamide (Compound Example No. 140)

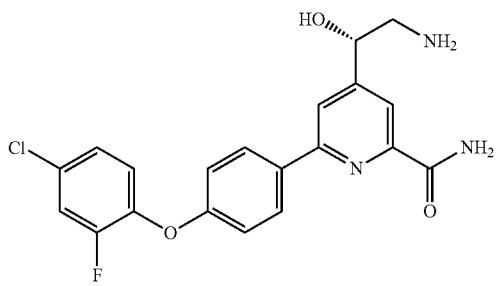 [SMILES: NC[C@@H](O)c1cc(C(N)=O)nc(-c2ccc(Oc3ccc(Cl)cc3F)cc2)c1]

$^1$H NMR (CD$_3$OD): 8.21 (d, 2H, J=8.8 Hz), 8.09 (m, 2H), 7.42 (dd, 1H, J1=2.4, J2=10 Hz), 7.27 (m, 1H), 7.22 (t, 1H, J=8.8 Hz), 7.10 (d, 2H, J=8.8 Hz), 4.86 (m, 1H), 3.74 (m, 2H); LC/MS: m/z=403 [M+H].

Example 112

(R)-6-(4-(4-chloro-2-fluorophenoxy)phenyl)-4-(1,2-dihydroxyethyl)picolinamide (Compound Example No. 141)

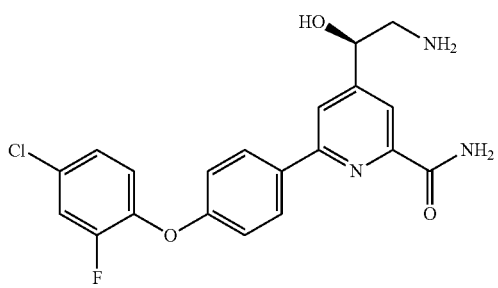 [SMILES: NC[C@H](O)c1cc(C(N)=O)nc(-c2ccc(Oc3ccc(Cl)cc3F)cc2)c1]

$^1$H NMR (CD$_3$OD): 8.11 (d, 2H, J=8.8 Hz), 7.98 (m, 2H), 7.31 (dd, 1H, J1=2.4, J2=10 Hz), 7.17 (m, 1H), 7.11 (t, 1H, J=8.8 Hz), 6.99 (d, 2H, J=8.8 Hz), 4.755 (m, 1H), 3.64 (m, 2H); LC/MS: m/z=403 [M+H].

Example 113

Synthesis of 4-((R)-1,2-dihydroxy-ethyl)-6-[3-(4-fluoro-phenoxy)-phenyl]-pyridine-2-carboxylic acid amide (Compound Example No. 142)

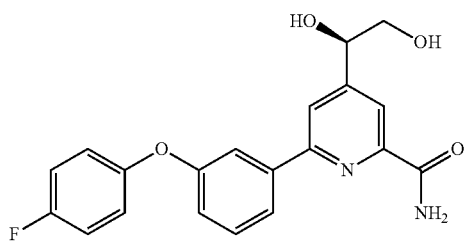 [SMILES: NC(=O)c1cc([C@@H](O)CO)cc(-c2cccc(Oc3ccc(F)cc3)c2)n1]

2-[3-(4-fluoro-phenoxy)-phenyl]-4,4,5,5-tetramethyl-[1,3,2]dioxaborolane

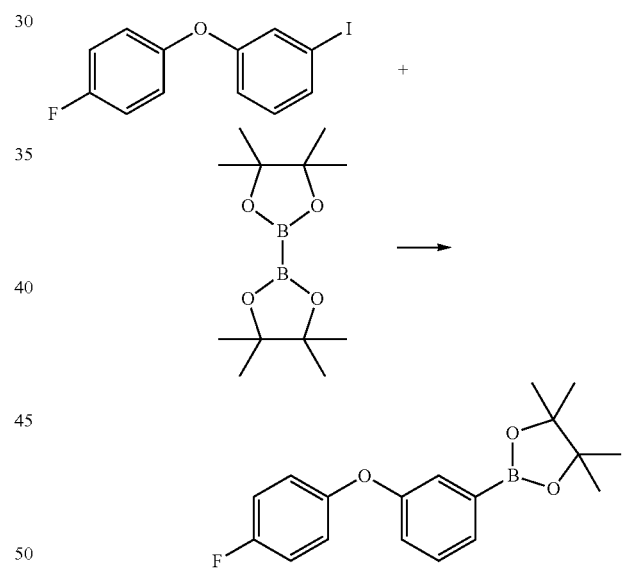

A 250 ml round bottom flask was charged with 4-fluoro-3'-iodophenyl ether (5 g, Synquest), 4,4,5,5,4',4',5',5'-octamethyl-[2,2']bi[[1,3,2]dioxaborolanyl] (4 g, 15.9 mmol), potassium acetate (4.68 g, 47.7 mmol), and 0 PdCl$_2$dppf*CH$_2$Cl$_2$ (0.649 g, 0.8 mmol) in 15 ml dioxane. The flask was purged with nitrogen and heated to 100° C. for 20 h. When the reaction was complete, the mixture was diluted with 500 ml brine and extracted with diethyl ether (2×250 ml). The combined organic layers were dried over sodium sulfate and concentrated under reduced pressure. The boronate was chromatographed by combiflash using a 120 gram silica column and a gradient of EtOAc (40% max) in hexane. The concentrated residue was taken up in a minimum of IPA and heated in a water bath until the suspension dissolved and was then allowed to cool to room temperature. The cooled solution was sonicated to give a precipitate. The solid was collected by vacuum filtration to provide 1.9 g of 2-[3-(4-fluoro-phenoxy)-phenyl]-4,4,5,5-tetramethyl-[1,3,2]dioxaborolane as an off-white solid (30% yield) in very high purity. $^1$H NMR (CHCl$_3$): 7.57-7.51 (m, 1H), 7.44-7.39 (m, 1H), 7.37-7.31 (m, 1H), 7.09-6.92 (m, 5H), 1.35-1.31 (s, 12H). LC/MS: m/z=314 [M]$^+$.

4-Chloro-6-[3-(4-fluoro-phenoxy)-phenyl]-pyridine-2-carboxylic acid ethyl ester

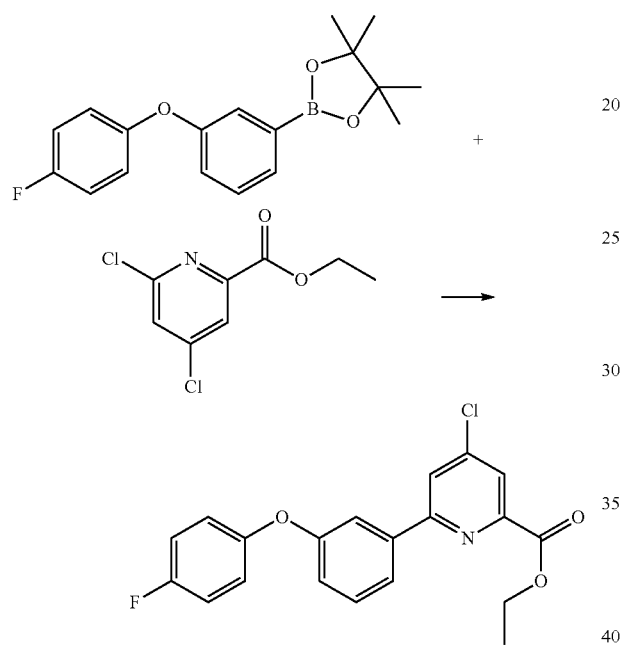

In a 50-ml vial with a screw-top septum, 2-[3-(4-fluoro-phenoxy)-phenyl]-4,4,5,5-tetramethyl-[1,3,2]dioxaborolane (0.500 g, 1.59 mmol) was dissolved in 6 ml DME, 3 ml EtOH, and 6 ml water. The boronate was then treated with one equivalent of 4,6-dichloro-pyridine-2-carboxylic acid ethyl ester (Anichem), PdCl$_2$(PPh$_3$)$_2$ (0.078 g, 0.11 mmol), and cesium carbonate (1.04 g, 3.18 mmol). The vial was purged with argon and heated to 90° C. for 10 hours, at which time the reaction was complete. The reaction mixture was diluted with 50 ml water and the aqueous layer acidified with about 10 ml 4N aq. HCl. The desired material was extracted with EtOAc (2×50 ml). The combined organic layers were dried over sodium sulfate and concentrated under reduced pressure. The residue was purified by combiflash using a 40-gram silica column and a gradient of EtOAc (100% max) in hexane to provide 0.445 g of 4-chloro-6-[3-(4-fluoro-phenoxy)-phenyl]-pyridine-2-carboxylic acid ethyl ester.

4-chloro-6-[3-(4-fluoro-phenoxy)-phenyl]-pyridine-2-carboxylic acid amide

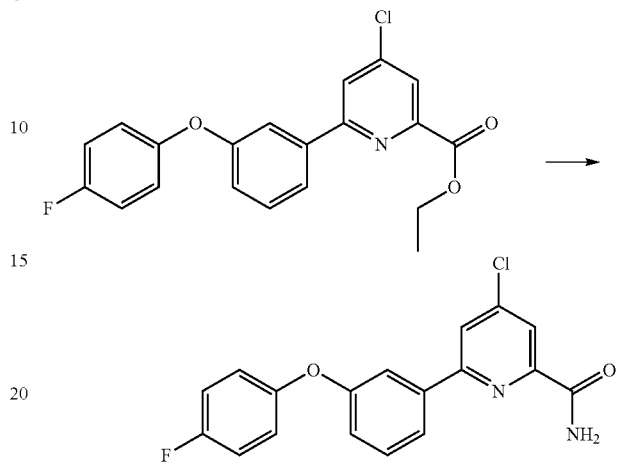

In a 50-ml vial with a screw-top septum, 4-chloro-6-[3-(4-fluoro-phenoxy)-phenyl]-pyridine-2-carboxylic acid ethyl ester (0.445 g) was dissolved in 3 ml methanol. 7N NH$_3$/MeOH (6 ml) was added to the solution and stirred for 3 hours, at which time the reaction was complete. The reaction mixture was concentrated under reduced pressure and the residue was suspended in about 3 ml methanol. The suspension was collected by vacuum filtration and washed with cold methanol to provide 0.267 g of 4-chloro-6-[3-(4-fluoro-phenoxy)-phenyl]-pyridine-2-carboxylic acid amide as a very pure yellow solid (65% yield).

6-[3-(4-Fluoro-phenoxy)-phenyl]-4-vinyl-pyridine-2-carboxylic acid amide

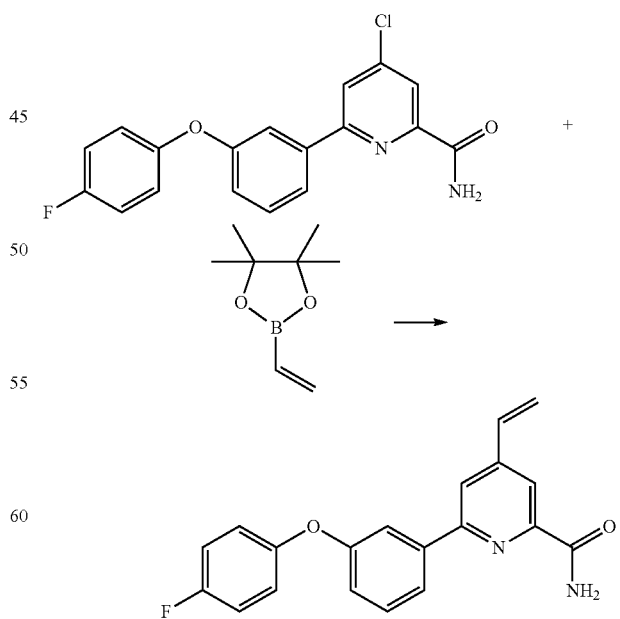

A 5 ml sealed microwave tube was charged with 4-chloro-6-[3-(4-fluoro-phenoxy)-phenyl]-pyridine-2-carboxylic acid amide (0.267 g, 0.78 mmol), vinyl boronic acid pinacol ester (0.180 g, 1.17 mmol, Aldrich) in three equivalents of TBAF/THF. The mixture was heated to 120° C. by microwave for 45 minutes. The mixture was chromatographed without workup by combiflash using a 40-gram silica column with a gradient of methanol (30% max) in chloroform to provide 0.130 g of 6-[3-(4-fluoro-phenoxy)-phenyl]-4-vinyl-pyridine-2-carboxylic acid amide as a clear oil in good purity (50% yield).

4-((R)-1,2-Dihydroxy-ethyl)-6-[3-(4-fluoro-phenoxy)-phenyl]-pyridine-2-carboxylic acid amide

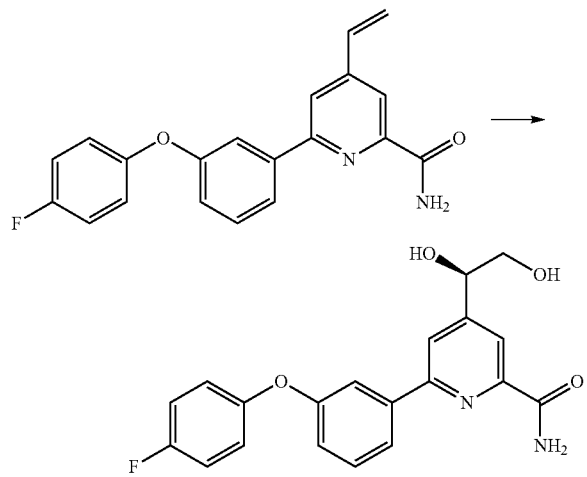

To a scintillation vial was added 6-[3-(4-fluoro-phenoxy)-phenyl]-4-vinyl-pyridine-2-carboxylic acid amide (0.066 g), 5 ml IPA, 5 ml water, and 0.270 g AD Mix beta. After the oxidation reaction was complete, the mixture was partitioned between 50 ml water and 50 ml EtOAc. The organic layer was separated, concentrated under reduced vacuum, and chromatographed by combiflash using a 12-gram silica column using a gradient of MeOH (0-40%) in chloroform as the eluent. The compound was purified further by prep TLC (100% EtOAc) followed by crystallization from chloroform and hexane to provide 0.019 g of 4-((R)-1,2-dihydroxy-ethyl)-6-[3-(4-fluoro-phenoxy)-phenyl]-pyridine-2-carboxylic acid amide as a white solid (26% yield) in very high purity. ¹H NMR (CHCl₃) 8.80-8.73 (m, 1H), 8.22-8.14 (m, 1H), 7.79-7.74 (m, 1H), 7.71-7.64 (m, 1H), 7.56-7.47 (s, 1H), 7.31-7.03 (m, 7H), 5.55-5.47 (m, 1H), 4.86-4.80 (m, 1H), 4.77-4.69 (m, 1H), 3.55-3.44 (m, 1H). LC/MS: m/z=368[M]⁺.

Example 114

Synthesis of 4-((S)-1,2-Dihydroxy-ethyl)-6-(4'-fluoro-biphenyl-4-yl)pyridine-2-carboxylic acid (Compound Example No. 154)

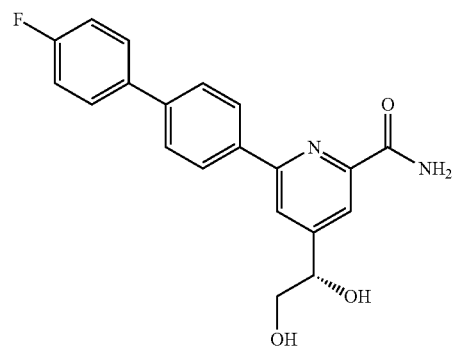 [SMILES: NC(=O)c1cc([C@H](O)CO)cc(-c2ccc(-c3ccc(F)cc3)cc2)n1]

Step 1: Synthesis of 4-bromo-4'-fluoro-1,1'-biphenyl

To THF (90 mL) degassed by purging argon was added 4-flouroiodobenzene (4.5g, 20.2 mmol), 4-bromophenylboronic acid (4g, 20.2 mmol), and tetrabutylammonium fluoride (1M in THF, 40.5 mL, 40.5 mmol), and the mixture was degassed again. Pd(dppf)Cl₂ (732 mg, 1 mmol) was added and the mixture was degassed again for 15 minutes. The reaction mixture was heated at 65° C. in an oil bath overnight. TLC (heptane eluent) showed the reaction was complete. The reaction mixture was diluted with ethyl acetate and extracted with brine. The organic layer was dried (sodium sulfate) and concentrated to yield the crude product. Purification by column chromatography (60-120 mesh silica, heptane eluent) yielded 3.2 g of 4-bromo-4'-fluoro-1,1'-biphenyl.

Step 2: Synthesis of 2-(4'-fluoro-[1,1'-biphenyl]-4-yl)-4,4,5,5-tetramethyl-1,3,2-dioxaborolane To DMF (32 mL) degassed by purging with argon was added 4-bromo-4'-fluoro-1,1'-biphenyl (3.2 g, 12.7 mmol), bis(pinacolato)diboron (3.56 g, 14.0 mmol) and potassium acetate (3.76 g, 30.0 mmol), and the mixture was degassed again. Pd(dppf)Cl₂ (276 mg, 0.38 mmol) was added and the mixture was degassed again for 15 minutes. The reaction mixture was heated at 53° C. in an oil bath overnight. The reaction was checked by TLC (heptane eluent), shown to be incomplete, and heated to 65° C. for an additional 4 h.

TLC showed some starting material remaining. The reaction mixture was diluted with ethyl acetate and extracted with brine. The organic layer was dried (sodium sulfate) and concentrated under reduced pressure to obtain the crude product. Purification by column chromatography (60-120 mesh silica gel, 0 to 5% ethyl acetate/heptane eluent) yielded 3.1 g of 2-(4'-fluoro-[1,1'-biphenyl]-4-yl)-4,4,5,5-tetramethyl-1,3,2-dioxaborolane.

Step 3: Synthesis of methyl 6-chloro-4-(4'-fluoro-[1,1'-biphenyl]-4-yl)picolinate (compound I) and methyl 4-chloro-6-(4'-fluoro-[1,1'-biphenyl]-4-yl) picolinate (compound II)

To THF (62 mL) degassed by purging argon was added 2-(4'-fluoro-[1,1'-biphenyl]-4-yl)-4,4,5,5-tetramethyl-1,3,2- dioxaborolane (3.1 g, 10.3 mmol), methyl 4,6-dichloropicolinate (2.132 g, 10.3 mmol) and tetrabutylammonium fluoride (1M in THF, 20.7 mL, 20.7 mmol), and the mixture was degassed again. Pd(dppf)Cl$_2$ (372 mg, 0.51 mmol) was added and the reaction mixture was degassed again for 15 minutes. The reaction mixture was heated at 50° C. in an oil bath overnight. TLC (silica gel, 4/1 heptane/ethyl acetate) showed the reaction had not gone to completion. After heating at 55° C. for an additional four hours, TLC showed almost complete reaction. The reaction was diluted with ethyl acetate and extracted with brine. The organic layer was dried (sodium sulfate) and concentrated under reduced pressure to obtain the crude product which was purified by column chromatography (230-400 mesh silica gel) to give compound I (1.0 g) which eluted with 0-6% ethyl acetate in heptane and compound II (0.80 g) which eleuted with 8-12% ethyl acetate in heptane.

Step 4: Synthesis of methyl 6-(4'-fluoro-[1,1'-biphenyl]-4-yl)-4-vinylpicolinate To THF (16 mL) degassed by purging argon was added methyl 4-chloro-6-(4'-fluoro-[1,1'-biphenyl]-4-yl)picolinate (compound II, 800 mg, 0.83 mmol), vinyl boronic acid pinacol ester (360 mg, 2.9 mmol), and tetrabutylammonium fluoride (1M in THF, 4.68 mL), and the reaction mixture was degassed. Pd(dppf)Cl$_2$ (85.6 mg, 0.04 mmol) was added and the reaction was degassed for an additional 15 minutes. The reaction mixture was heated at 60° C. in an oil bath for overnight. TLC (silica gel, 4/1 heptane/ethyl acetate) showed the reaction had not gone to completion. Additional reaction time had no effect, so the reaction was cooled, diluted with ethyl acetate, and extracted with brine. The organic layer was dried (sodium sulfate) and concentrated under vacuum to obtain the crude product which was purified by column chromatography (230-400 mesh silica gel, 0-8% ethyl acetate in heptane as eluent) to yield 600 mg of methyl 6-(4'-fluoro-[1,1'-biphenyl]-4-yl)-4-vinylpicolinate.

Step 5: Synthesis of 6-(4'-fluoro-[1,1'-biphenyl]-4-yl)-4-vinylpicolinamide

Methyl 6-(4'-fluoro-[1,1'-biphenyl]-4-yl)-4-vinylpicolinate (600 mg, 1.8 mmol) was dissolved in 10 mL of methanol in a pressure tube. Into the tube was condensed about 10 mL ammonia at −20° C. to −30° C. The pressure tube was tightly closed and the resulting solution was stirred at room temperature for overnight. TLC (silica gel, 10% methanol in chloroform) showed the reaction had gone to completion. The ammonia was removed by nitrogen purge and the methanol was removed under reduced pressure to obtain 300 mg of 6-(4'-fluoro-[1,1'-biphenyl]-4-yl)-4-vinylpicolinamide which was pure enough to take to next step without purification.

Step 6: Synthesis of (S)-4-(1,2-dihydroxyethyl)-6-(4'-fluoro-[1,1'-biphenyl]-4-yl)picolinamide 6-(4'-fluoro-[1,1'-biphenyl]-3-yl)-4-vinylpicolinamide (0.2 g, 0.78 mmol) was added to the clear solution of AD-mix alpha (0.8 g) in 1:1 mixture of IPA (10 mL) and water (10 mL). The resulting slurry was stirred at room temperature overnight. TLC (20% methanol in chloroform) showed the reaction had not gone to completion. The reaction mixture was quenched by adding 10 mL of 10% aqueous NaHSO$_3$ solution and extracted with ethyl acetate. The organic layers were washed with brine, dried over sodium sulfate, and concentrated under reduced pressure to obtain the crude compound. Purification by column chromatography (230-400 mesh silica gel, 0-5% methanol in CHCl$_3$ yielded 130 mg of (S)-4-(1,2-dihydroxyethyl)-6-(4'-fluoro-[1,1'-biphenyl]-4-yl)picolinamide $^1$H NMR (DMSO-d$_6$): 8.35 (bs, 1H), 8.22 (bs, 1H), 7.98-7.89 (bm 3H), 7.89-7.78 (m, 4H), 7.70 (bs, 1H), 7.25 (bm, 2H), 5.62 (m, 1H), 4.72 (m 2H), 3.75 (m, 2H). LC/MS: m/z=453[M+1]$^+$.

Example 115

The following compounds were prepared using the synthetic methodology described above:

({6-Carbamoyl-4-[4-(4-fluoro-phenoxy)-phenyl]-pyridin-2-yl}phenyl-amino)-acetic acid (Compound Example No. 143)

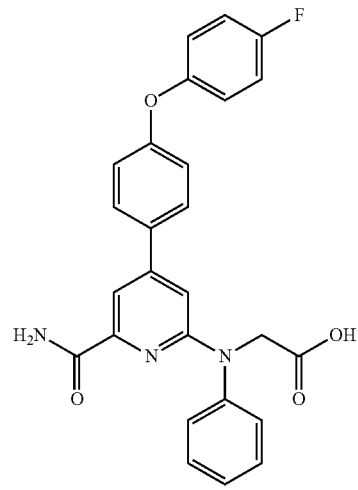 [SMILES: NC(=O)c1cc(-c2ccc(Oc3ccc(F)cc3)cc2)cc(N(CC(=O)O)c2ccccc2)n1]

$^1$H NMR (DMSO-d$_6$): 8.05 (bs, 1H), 7.95 (m, 2H), 7.45 (m, 1H), 7.27-7.12 (bm, 3H), 7.08-6.92 (bm, 6H), 4.0 (s, 2H). LC/MS: m/z=458 [M+1]$^+$.

277

3-({6-Carbamoyl-4-[4-(4-fluoro-phenoxy)-phenyl]-pyridin-2-yl}phenyl-amino)-propionic acid (Compound Example No. 144)

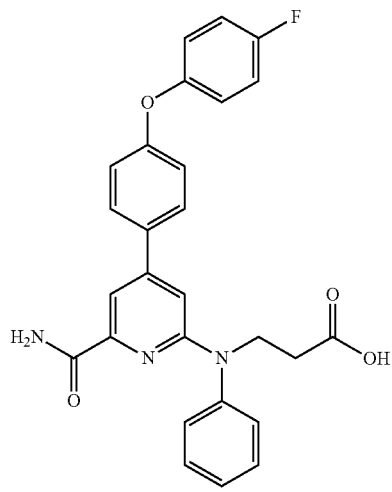 [SMILES: NC(=O)c1cc(-c2ccc(Oc3ccc(F)cc3)cc2)cc(N(CCC(=O)O)c2ccccc2)n1]

$^1$H NMR (DMSO-d$_6$): 12.4 (bs, 1H), 9.36 (bs, 1H), 8.42 (m, 2H), 7.80- (m, 2H), 7.68- (m, 2H), 7.40-7.05 (bm, 9H), 7.36-7.20 (bm, 4H), 6.95 (bm, 1H), 3.45 (s, 2H), 2.55 (s, 2H). LC/MS: m/z=472[M+1]$^+$.

3-({2-Carbamoyl-6-[4-(4-fluoro-phenoxy)-phenyl]-pyridin-4-yl}phenyl-amino)-propionic acid (Compound Example No. 145)

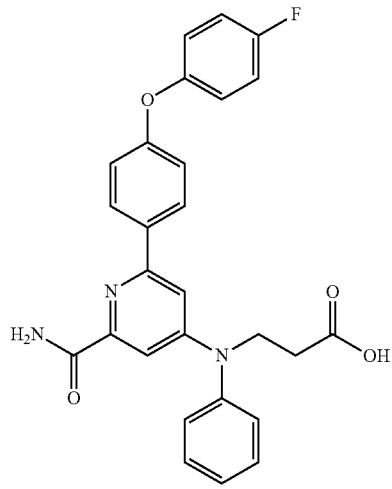 [SMILES: NC(=O)c1cc(N(CCC(=O)O)c2ccccc2)cc(-c2ccc(Oc3ccc(F)cc3)cc2)n1]

$^1$H NMR (DMSO-d$_6$): 12.4 (bs, 1H), 9.16 (bs, 1H), 8.12 (m, 2H), 7.55 (m, 1H), 7.50-7.38 (bm, 3H), 7.36-7.20 (bm, 4H), 7.20-7.02 (bm, 5H), 3.45 (s, 2H), 2.55 (s, 2H). LC/MS: m/z=472[M+1]$^+$.

278

4-[4-(4-Cyano-phenoxy)-phenyl]-6-(methyl-phenyl-amino)-pyridine2-carboxylic acid amide (Compound Example No. 146)

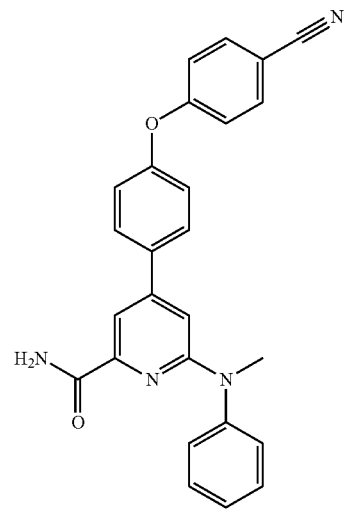 [SMILES: CN(c1ccccc1)c1cc(-c2ccc(Oc3ccc(C#N)cc3)cc2)cc(C(N)=O)n1]

$^1$H NMR (DMSO-d$_6$): 8.38-8.22 (bm, 3H), 7.70 (m, 2H), 7.65-7.52 (bm, 3H), 7.45-7.30 (bm, 4H), 7.30-7.18 (bm, 5H), 3.60 (s, 3H). LC/MS: m/z=421[M+1]$^+$.

6-[4-(4-Cyano-phenoxy)-phenyl]-4-(methyl-phenyl-amino)-pyridine-2-carboxylic acid amide (Compound Example No. 147)

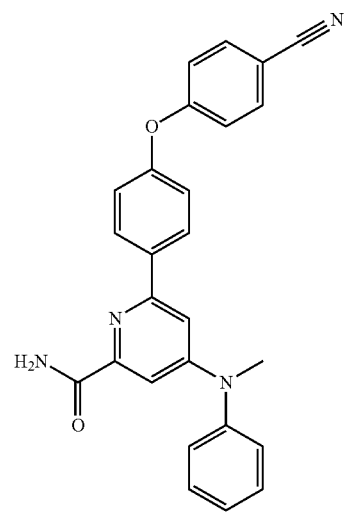 [SMILES: CN(c1ccccc1)c1cc(C(N)=O)nc(-c2ccc(Oc3ccc(C#N)cc3)cc2)c1]

$^1$H NMR (DMSO-d$_6$): 7.95 (bs 1H), 7.84 (bm 2H), 7.70-7.58 (bm, 4H), 7.48 (m, 2H), −7.40 (m, 2H), 7.30 (bm, 1H), 7.23 (m, 2H), 7.19 (m, 2H), 6.82 (s, 1H). LC/MS: m/z=421[M+1]$^+$.

6-(Methyl-phenyl-amino)-4-[4-(4-trifluoromethyl-phenoxy)phenyl]-pyridine-2-carboxylic acid amide (Compound Example No. 148)

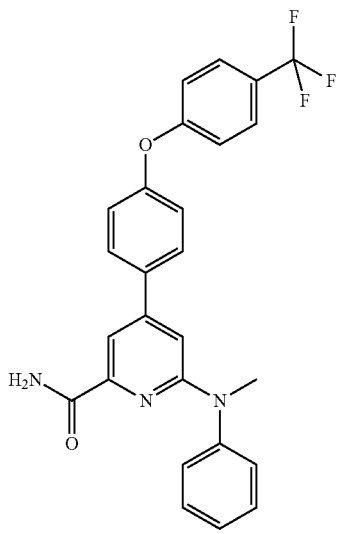

¹H NMR (DMSO-d₆): 8.38-8.18 (bm, 3H), 7.78 (bm, 2H), 7.63-7.48 (bm, 3H), 7.42-7.27 (bm, 4H), 7.27-7.12 (bm, 5H), 3.60 (s, 3H). LC/MS: m/z=464[M+1]⁺.

4-(Methyl-phenyl-amino)-6-[4-(4-trifluoromethyl-phenoxy)phenyl]-pyridine-2-carboxylic acid amide (Compound Example No. 149)

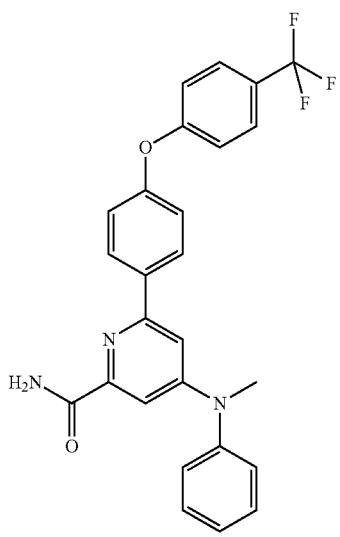 [SMILES: CN(c1ccccc1)c1cc(C(N)=O)nc(-c2ccc(Oc3ccc(C(F)(F)F)cc3)cc2)c1]

¹H NMR (DMSO-d₆): 7.97 (bs, 1H), 7.75 (bm, 2H), 7.50-7.45 (bm, 2H), 7.30 (bm 1H), 7.23-7.18 (bm, 4H), 6.82 (s, 1H), 3.60 (s, 3H). LC/MS: m/z=464[M+1]⁺.

6-[4-(4-Fluoro-phenoxy)-phenyl]-4-{phenyl-[2-(2H-tetrazol-5-yl)-ethyl]-amino}-pyridine-2-carboxylic acid amide (Compound Example No. 150)

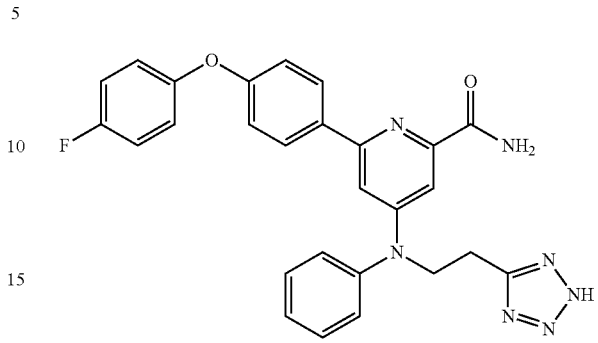

¹H NMR (DMSO-d6): 8.15 (bs, 1H), 7.72 (bs, 1H), 7.58-7.45 (bm, 5H), 7.30-7.20 (bm 3H), 7.25 (bm, 2H), 7.12 (bm, 2H), 7.03 (bm, 2H), 6.62 (s, 1H), 4.32 (m, 2H), 3.15 (m, 2H). LC/MS: m/z=496[M+1]⁺.

4-[4-(4-Fluoro-phenoxy)-phenyl]-6-{phenyl-[2-(2H-tetrazol-5-yl)-ethyl]-amino}-pyridine-2-carboxylic acid amide (Compound Example No. 151)

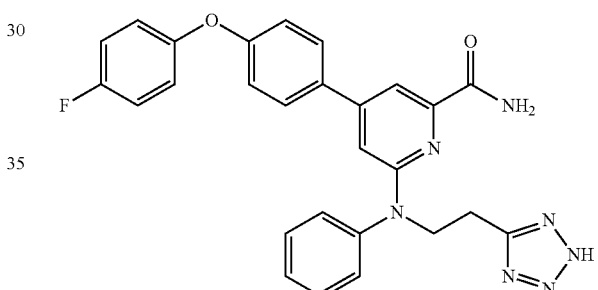

¹H NMR (DMSO-d₆): 8.15 (m, 3H), 7.58-7.50 (bm, 3H), 7.42-7.38 (bm 1H), 7.35-7.20 (bm, 5H), 7.15 (bm, 2H), 7.05 (bm, 3H), 4.23 (m, 2H), 3.15 (m, 2H). LC/MS: m/z=496 [M+1]⁺.

6-[4-(4-Fluoro-phenoxy)-phenyl]-4-{phenyl-[2-(2H-tetrazol-5-yl)ethyl]-amino}-pyridine-2-carboxylic acid (Compound Example No. 152)

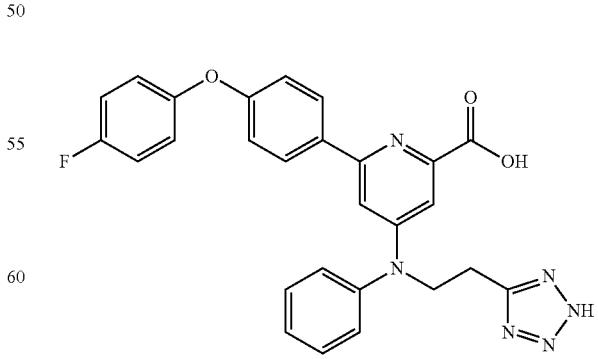

¹H NMR (DMSO-d₆): 7.60 (s, 1H), 7.58-7.48 (bm, 4H), 7.38-7.20 (bm 5H), 7.15 (bm, 2H), 7.02 (bm, 2H), 4.23 (m, 2H), 3.15 (m, 2H). LC/MS: m/z=497[M+1]⁺.

4-[4-(4-Fluoro-phenoxy)-phenyl]-6-{phenyl-[2-(2H-tetrazol-5-yl)ethyl]-amino}-pyridine-2-carboxylic acid (Compound Example No. 153)

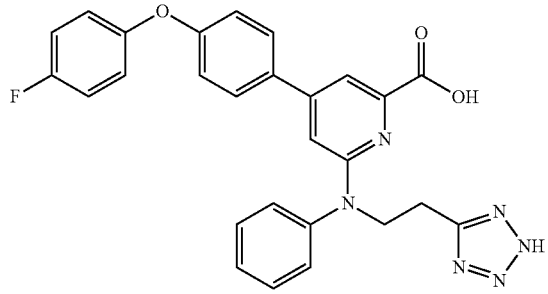

$^1$H NMR (DMSO-d$_6$): 8.08 (m, 2H), 7.55 (m, 2H), 7.41 (bm 1H), 7.32-7.22 (bm, 5H), 7.14 (bm, 2H), 7.18 (bm, 2H), 7.0 (bs 1H), 4.33 (m, 2H), 3.35 (m, 2H). LC/MS: m/z=497 [M+1]$^+$.

4-((R)-1,2-Dihydroxy-ethyl)-6-(4'-fluoro-biphenyl-4-yl)pyridine-2-carboxylic acid amide (Compound Example No. 155)

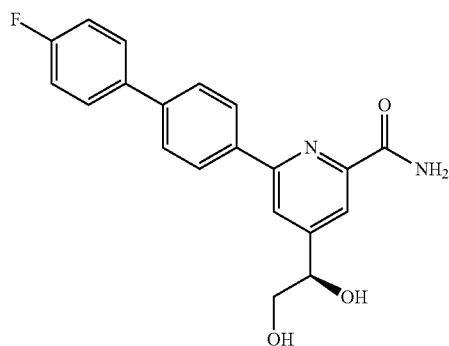 [SMILES: NC(=O)c1cc([C@@H](O)CO)cc(-c2ccc(-c3ccc(F)cc3)cc2)n1]

$^1$H NMR (DMSO-d$_6$): 8.35 (bs, 1H), 8.22 (bs, 1H), 7.98-7.89 (bm 3H), 7.89-7.78 (m, 4H), 7.35 (bm, 2H), 5.62 (m, 1H), 4.72 (m 2H), 3.75 (m, 2H). LC/MS: m/z=353 [M+1]$^+$.

6-((S)-1,2-Dihydroxy-ethyl)-4-[4-(4-trifluoromethoxy-phenoxy)phenyl]-pyridine-2-carboxylic acid amide (Compound Example No. 156)

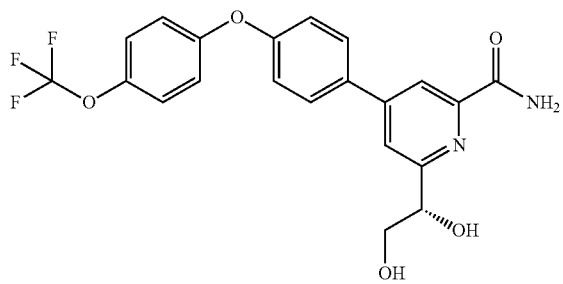 [SMILES: NC(=O)c1cc(-c2ccc(Oc3ccc(OC(F)(F)F)cc3)cc2)cc([C@H](O)CO)n1]

$^1$H NMR (DMSO-d$_6$): 8.38-8.28 (bm, 3H), 8.05 (bs, 1H), 8.00 (bs, 1H), 7.42 (bs, 2H), 7.18 (m, 4H), 5.62 (m, 1H), 4.87 (m 1H), 4.72 (m 1H), 3.75 (m, 2H). LC/MS: m/z=435 [M+1]$^+$.

6-((R)-1,2-Dihydroxy-ethyl)-4-[4-(4-trifluoromethoxy-phenoxy)phenyl]-pyridine-2-carboxylic acid amide (Compound Example No. 157)

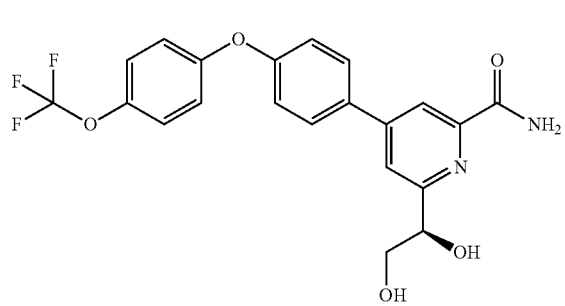 [SMILES: NC(=O)c1cc(-c2ccc(Oc3ccc(OC(F)(F)F)cc3)cc2)cc([C@@H](O)CO)n1]

$^1$H NMR (DMSO-d$_6$): 8.38-8.28 (bm, 3H), 8.05 (bs, 1H), 8.00 (bs, 1H), 7.42 (bs, 2H), 7.18 (m, 4H), 5.62 (m, 1H), 4.87 (m 1H), 4.72 (m 1H), 3.75 (m, 2H). LC/MS: m/z=435 [M+1]$^+$.

6-((S)-1,2-Dihydroxy-ethyl)-4-[4-(3-trifluoromethoxy-phenoxy)phenyl]-pyridine-2-carboxylic acid amide (Compound Example No. 158)

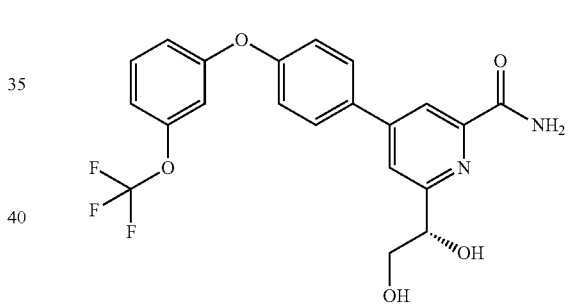

$^1$H NMR (DMSO-d$_6$): 8.38-8.28 (bm, 3H), 8.05 (bs, 1H), 8.00 (bs, 1H), 7.68 (bs, 1H), 7.55 (bm, 1H), 7.23-7.16 (bm 3H), 7.15-7.08 (m, 2H), 5.62 (m, 1H), 4.87 (m 1H), 4.72 (m 1H), 3.75 (m, 2H). LC/MS: m/z=435[M+1]$^+$.

4-((S)-1,2-Dihydroxy-ethyl)-6-[4-(4-trifluoromethoxy-phenoxy)phenyl]-pyridine-2-carboxylic acid amide (Compound Example No. 159)

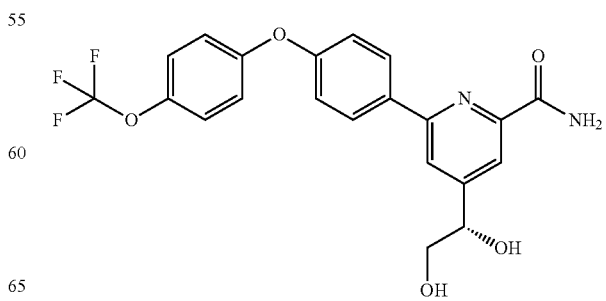

¹H NMR (DMSO-d₆): 8.35 (bs, 1H), 8.16 (bs, 1H), 7.95-7.85 (bm, 3H), 7.68 (bm, 1H), 7.48-7.42 (bm 2H), 7.27-7.18 (m, 4H), 5.62 (m, 1H), 4.87 (m 2H), 3.75 (m, 2H). LC/MS: m/z=435[M+1]⁺.

6-((S)-1,2-Dihydroxy-ethyl)-4-(4'-fluoro-biphenyl-4-yl)pyridine-2-carboxylic acid amide (Compound Example No. 160)

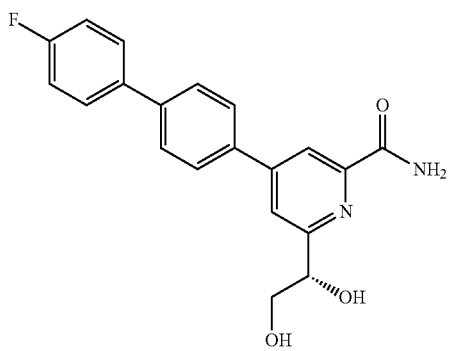 [SMILES: NC(=O)c1cc(-c2ccc(-c3ccc(F)cc3)cc2)cc([C@H](O)CO)n1]

¹H NMR (DMSO-d₆): 8.42-8.38 (bm, 3H), 8.14 (bs, 1H), 8.03 (bs, 1H), 7.87-7.78 (bm, 4H), 7.72 (bs, 1H), 7.38-7.30 (bm 2H), 5.62 (m, 1H), 4.87 (m 1H), 4.72 (m 1H), 3.75 (m, 2H). LC/MS: m/z=453[M+1]⁺.

4-((R)-1,2-Dihydroxy-ethyl)-6-[4-(4-trifluoromethoxy-phenoxy)phenyl]-pyridine-2-carboxylic acid amide (Compound Example No. 161)

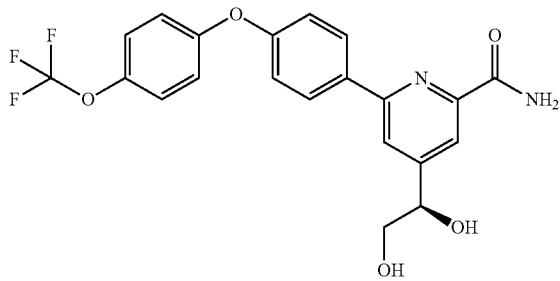 [SMILES: NC(=O)c1cc([C@@H](O)CO)cc(-c2ccc(Oc3ccc(OC(F)(F)F)cc3)cc2)n1]

¹H NMR (DMSO-d₆): 8.35 (bs, 1H), 8.16 (bs, 1H), 7.95-7.85 (bm, 3H), 7.68 (bm, 1H), 7.48-7.42 (bm 2H), 7.27-7.18 (m, 4H), 5.62 (m, 1H), 4.87 (m 2H), 3.75 (m, 2H). LC/MS: m/z=435[M+1]⁺.

6-((R)-1,2-Dihydroxy-ethyl)-4-(4'-fluoro-biphenyl-4-yl)pyridine-2-carboxylic acid amide (Compound Example No. 162)

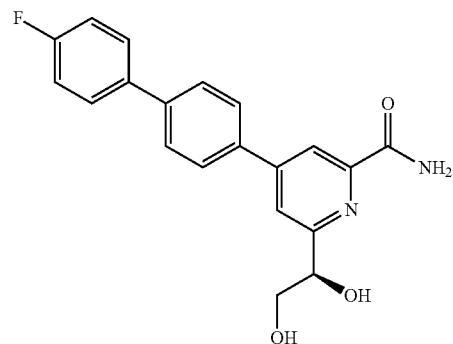 [SMILES: NC(=O)c1cc(-c2ccc(-c3ccc(F)cc3)cc2)cc([C@@H](O)CO)n1]

¹H NMR (DMSO-d₆): 8.42-8.38 (bm, 3H), 8.14 (bs, 1H), 8.03 (bs, 1H), 7.87-7.78 (bm, 4H), 7.72 (bs, 1H), 7.38-7.30 (bm 2H), 5.62 (m, 1H), 4.87 (m 1H), 4.72 (m 1H), 3.75 (m, 2H). LC/MS: m/z=453[M+1]⁺.

4-((S)-1,2-Dihydroxy-ethyl)-6-[4-(3-trifluoromethoxy-phenoxy)phenyl]-pyridine-2-carboxylic acid amide (Compound Example No. 163)

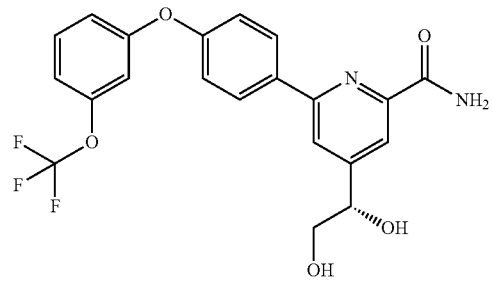

¹H NMR (DMSO-d₆): 8.40 (bs, 1H), 8.22 (bs, 1H), 7.98-7.92 (bm, 3H), 7.75 (bs, 1H), 7.62 (bm, 1H), 7.32-7.22 (bm 3H), 7.22-7.18 (m, 2H), 5.62 (m, 1H), 4.87 (m 2H), 3.75 (m, 2H). LC/MS: m/z=435[M+1]⁺.

4-((R)-1,2-Dihydroxy-ethyl)-6-[4-(3-trifluoromethoxy-phenoxy)phenyl]-pyridine-2-carboxylic acid amide (Compound Example No. 164)

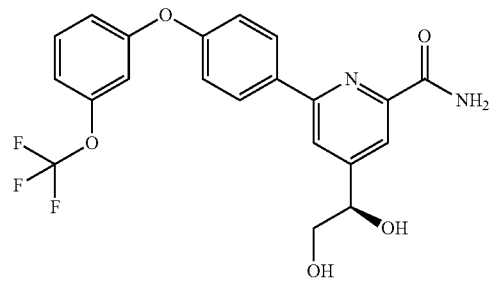 [SMILES: NC(=O)c1cc([C@@H](O)CO)cc(-c2ccc(Oc3cccc(OC(F)(F)F)c3)cc2)n1]

¹H NMR (DMSO-d₆): 8.35 (bs, 1H), 8.17 (bs, 1H), 7.92-7.88 (bm, 3H), 7.68 (bs, 1H), 7.55 (bm, 1H), 7.26-7.18

(bm 3H), 7.18-7.10 (m, 2H), 5.62 (m, 1H), 4.87 (m 2H), 3.75 (m, 2H). LC/MS: m/z=435[M+1]⁺.

(S)-2-((2-cyano-6-(4-(4-fluorophenoxy)phenyl)pyridin-4-yl)amino)propanamide (Compound Example No. 165)

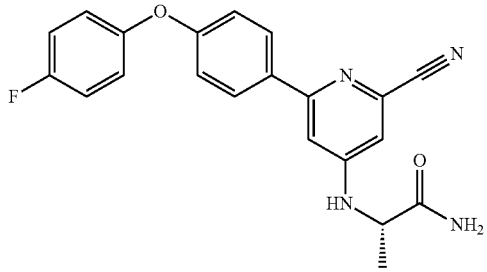 [SMILES: C[C@H](Nc1cc(C#N)nc(-c2ccc(Oc3ccc(F)cc3)cc2)c1)C(N)=O]

LC/MS: m/z=377.2 [M+H]⁺, ¹H NMR (400 MHz, DMSO-d₆): 7.94 (2H, d, J=8.8 Hz), 7.60 (1H, s), 7.36 (1H, d, J=7.5 Hz), 7.31-7.24 (2H, m), 7.22-7.12 (4H, m), 7.07 (2H, d, J=9.0 Hz), 6.99 (1H, br s), 4.16-4.06 (1H, m), 1.35 (3H, d, J=7.0 Hz).

(S)-2-((4-cyano-6-(4-(4-fluorophenoxy)phenyl)pyridin-2-yl)amino)propanamide (Compound Example No. 166)

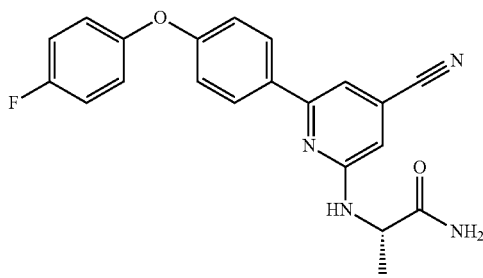 [SMILES: C[C@H](Nc1cc(C#N)cc(-c2ccc(Oc3ccc(F)cc3)cc2)n1)C(N)=O]

LC/MS: m/z=377.1 [M+H]⁺, ¹H NMR (400 MHz, DMSO-d₆): 8.12 (2H, d, J=9.0 Hz), 7.47 (1H, s), 7.42 (1H, s), 7.34 (1H, d, J=6.6 Hz), 7.31-7.24 (2H, m), 7.18-7.12 (2H, m), 7.01 (2H, d, J=8.8 Hz), 6.97 (1H, s), 6.84 (1H, s), 4.46-4.36 (1H, m), 1.34 (3H, d, J=7.0 Hz).

(S)-4-((1-amino-1-oxopropan-2-yl)amino)-6-(4-(4-fluorophenoxy)phenyl)picolinamide (Compound Example No. 167)

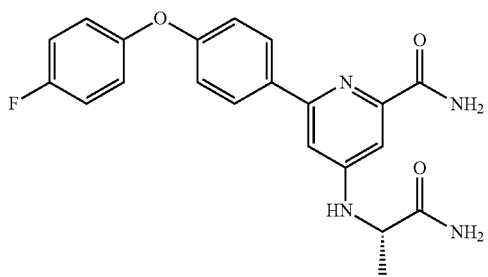 [SMILES: C[C@H](Nc1cc(C(N)=O)nc(-c2ccc(Oc3ccc(F)cc3)cc2)c1)C(N)=O]

LC/MS: m/z=395.1 [M+H]⁺, ¹H NMR (400 MHz, DMSO-d₆): 8.16-8.09 (3H, m), 7.57 (1H, s), 7.52 (1H, d, J=2.6 Hz), 7.31-7.22 (2H, m), 7.21-7.08 (5H, m), 7.05 (2H, d, J=9.0 Hz), 7.01 (1H, d, J=7.0 Hz), 4.10-4.01 (1H, m), 1.35 (3H, d, J=7.0 Hz).

(S)-2-((2-((S)-1,2-dihydroxyethyl)-6-(4-(4-fluorophenoxy)phenyl)pyridin-4-yl)amino)propanamide (Compound Example No. 168)

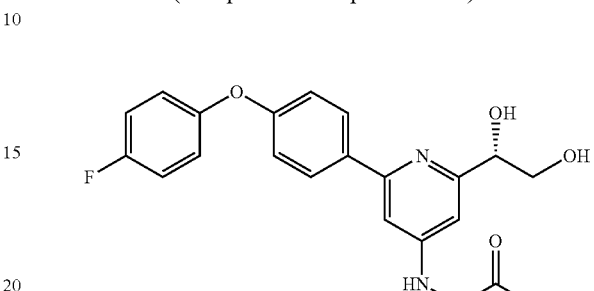

LC/MS: m/z=412.2 [M+H]⁺, ¹H NMR (400 MHz, DMSO-d₆): δ 7.92 (2H, d, J=8.8 Hz), 7.51 (1H, s), 7.29-7.22 (2H, m), 7.15-7.10 (2H, m), 7.09 (1H, s), 7.05 (2H, d, J=8.8 Hz), 6.83 (1H, s), 6.71 (1H, d, J=7.0 Hz), 6.64 (1H, s), 5.29-5.25 (1H, m), 4.81-4.73 (1H, m), 4.49-4.44 (1H, m), 3.99 (1H, p, J=7.0 Hz), 3.74-3.64 (1H, m), 3.48-3.39 (1H, m), 1.33 (3H, d, J=7.0 Hz).

Example 116

Representative compounds of the invention have been tested in the FLIPR® or FLIPR^TETRA® sodium dye assay with KCl assay for sodium channel blocking activity, which is described in detail above. Representative values are presented in TABLE 3.

TABLE 3

| Evaluation of compounds as sodium channel (Na_v) blockers | |
|---|---|
| Compound Ex. No. | Na_v1.7 IC50 (μM) ± SEM |
| 3 | 0.07 ± 0.01 |
| 4 | 0.12 ± 0.02 |
| 5 | 0.16 ± 0.07 |
| 6 | 0.27 ± 0.05 |
| 7 | 0.32 ± 0.02 |
| 8 | 0.47 ± 0.09 |
| 9 | 0.50 ± 0.18 |
| 10 | 0.52 ± 0.11 |
| 11 | 0.82 ± 0.09 |
| 12 | 0.89 ± 0.02 |
| 13 | 0.89 ± 0.08 |
| 14 | 1.30 ± 0.30 |
| 15 | 1.42 ± 0.24 |
| 16 | 1.71 ± 0.24 |
| 17 | 2.77 ± 0.41 |
| 18 | 2.80 ± 0.12 |
| 20 | 2.95 ± 0.76 |
| 21 | 2.97 ± 0.91 |
| 22 | 3.33 ± 0.2 |
| 23 | 4.89 ± 2.48 |
| 24 | 6.49 ± 2.94 |
| 27 | >20 |
| 29 | 2.65 ± 0.37 |
| 30 | 0.24 ± 0.07 |
| 31 | 0.61 ± 0.10 |

TABLE 3-continued

Evaluation of compounds as sodium channel (Na$_v$) blockers

| Compound Ex. No. | Na$_v$1.7 IC50 (μM) ± SEM |
|---|---|
| 32 | >20 |
| 33 | 0.50 ± 0.07 |
| 34 | 0.38 ± 0.08 |
| 35 | 0.40 ± 0.07 |
| 36 | 0.22 ± 0.04 |
| 37 | 0.44 ± 0.10 |
| 38 | 0.35 ± 0.07 |
| 39 | 0.13 ± 0.03 |
| 41 | 0.24 ± 0.04 |
| 42 | 1.25 ± 0.15 |
| 43 | 0.93 ± 0.17 |
| 44 | 3.29 ± 1.17 |
| 45 | 0.15 ± 0.01 |
| 46 | 0.48 ± 0.07 |
| 47 | 0.22 ± 0.06 |
| 48 | 0.09 ± 0.06 |
| 49 | 0.10 ± 0.03 |
| 50 | 0.14 ± 0.03 |
| 51 | 0.18 ± 0.3 |
| 52 | 0.20 ± 0.08 |
| 53 | 0.22 ± 0.06 |
| 54 | 0.22 ± 0.06 |
| 55 | 0.23 ± 0.06 |
| 56 | 0.31 ± 0.05 |
| 57 | 0.83 ± 0.02 |
| 58 | 1.57 ± 0.33 |
| 59 | 2.28 ± 0.20 |
| 60 | 0.16 ± 0.03 |
| 61 | 0.03 ± 0.01 |
| 62 | 0.07 ± 0.02 |
| 63 | 0.09 ± 0.03 |
| 64 | 0.10 ± 0.3 |
| 65 | 0.12 ± 0.02 |
| 66 | 0.13 ± 0.03 |
| 67 | 0.17 ± 0.01 |
| 68 | 0.18 ± 0.09 |
| 69 | 0.19 ± 0.05 |
| 70 | 0.23 ± 0.08 |
| 71 | 0.35 ± 0.05 |
| 72 | 0.76 ± 0.03 |
| 73 | 0.09 ± 0.03 |
| 74 | 0.09 ± 0.01 |
| 76 | 0.53 ± 0.07 |
| 77 | 4.27 ± 0.69 |
| 78 | 10-20 |
| 79 | 0.41 ± 0.03 |
| 80 | 1.30 ± 0.17 |
| 81 | 1.46 ± 0.43 |
| 82 | 1.94 ± 0.21 |
| 83 | 1.95 ± 0.52 |
| 84 | 4.11 ± 0.93 |
| 85 | 6.59 ± 2.17 |
| 86 | 9.21 ± 1.15 |
| 87 | >20 |
| 88 | 0.23 ± 0.09 |
| 89 | 7.13 ± 0.50 |
| 91 | >20 |
| 92 | 3.83 ± 0.64 |
| 93 | >20 μM |
| 94 | 2.17 ± 0.66 |
| 95 | 0.17 ± 0.08 |
| 96 | 0.12 ± 0.03 |
| 98 | 0.22 ± 0.07 |
| 99 | 0.10 ± 0.03 |
| 100 | 0.27 ± 0.03 |
| 101 | 0.27 ± 0.08 |
| 104 | 2.70 ± 0.26 |
| 105 | 0.53 ± 0.08 |
| 106 | 2.01 ± 0.44 |
| 107 | 0.40 ± 0.12 |
| 108 | 0.13 ± 0.01 |
| 109 | 3.77 ± 0.56 |
| 110 | 0.62 ± 0.08 |
| 111 | 0.71 ± 0.13 |
| 112 | 2.12 ± 0.54 |
| 113 | 0.36 ± 0.8 |
| 114 | 0.68 ± 0.6 |
| 115 | 0.08 ± 0.03 |
| 116 | 2.71 ± 0.73 |
| 117 | >20 |
| 118 | 2.5 ± 0.30 |
| 119 | 2.46 ± 0.80 |
| 120 | 9.3 ± 0.54 |
| 121 | 6.24 ± 0.81 |
| 122 | 0.14 ± 0.03 |
| 123 | 0.17 ± 0.03 |
| 124 | 2.50 ± 0.34 |
| 125 | 0.77 ± 0.13 |
| 126 | 1.05 ± 0.13 |
| 127 | 1.13 ± 0.11 |
| 128 | 1.29 ± 0.17 |
| 129 | 1.74 ± 0.35 |
| 130 | 2.47 ± 0.73 |
| 131 | 2.78 ± 0.46 |
| 132 | 2.78 ± 0.75 |
| 133 | 3.08 ± 0.59 |
| 134 | 3.90 ± 0.34 |
| 135 | 7.26 ± 0.34 |
| 136 | >20 |
| 137 | >20 |
| 140 | 0.07 ± 0.01 |
| 141 | 0.07 ± 0.01 |
| 142 | 5.30 ± 1.6 |
| 143 | >20 |
| 144 | >20 |
| 145 | 1.25 ± 0.03 |
| 146 | 0.09 ± 0.004 |
| 147 | 1.60 ± 0.26 |
| 148 | 0.25 ± 0.08 |
| 149 | 10-20 |
| 150 | 0.46 ± 0.04 |
| 151 | 0.16 ± 0.03 |
| 152 | 1.87 ± 0.68 |
| 153 | 2.13 ± 0.55 |
| 154 | 1.12 ± 0.07 |
| 155 | 2.78 ± 0.61 |
| 156 | 0.13 ± 0.02 |
| 157 | 0.12 ± 0.008 |
| 158 | 0.16 ± 0.01 |
| 159 | 0.30 ± 0.02 |
| 160 | 0.49 ± 0.12 |
| 161 | 1.38 ± 0.20 |
| 163 | 0.63 ± 0.07 |
| 164 | 0.49 ± 0.10 |
| 165 | 1.97 ± 0.49 |
| 166 | 4.32 ± 1.0 |
| 167 | 0.73 ± 0.10 |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:
1. A compound having Formula I:

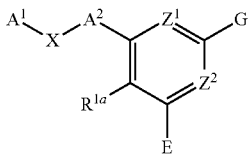

or a pharmaceutically acceptable salt, or solvate thereof, wherein:
$Z^1$ is $CR^{1b}$ and $Z^2$ is selected from the group consisting of N and N-oxide;
$R^{1a}$ and $R^{1b}$, which are identical or different, are selected from the group consisting of:
a) hydrogen;
b) halogen;
c) hydroxy;
d) cyano;
e) optionally substituted alkyl;
f) alkoxy;
g) haloalkoxy; and
h) haloalkyl;
$A^1$ is optionally-substituted phenyl;
X is —O—;
$A^2$ is optionally substituted phenyl;
G is selected from the group consisting of:
a) cyano;

b)

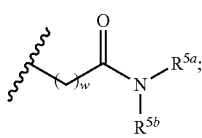

c)

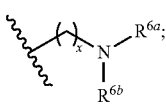

d)

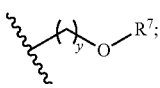

e)

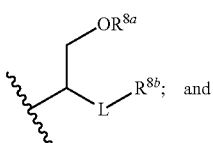

f)

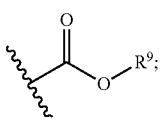

wherein:
$R^{5a}$ and $R^{5b}$, which are identical or different, are selected from the group consisting of:
a) hydrogen;
b) optionally substituted alkyl;
c) optionally substituted cycloalkyl;
d) optionally substituted heterocyclo;
e) optionally substituted aryl;
f) optionally substituted heteroaryl;
g) aralkyl;
h) hydroxyalkyl;
i) (cyano)alkyl;
j) (heterocyclo)alkyl;
k) (heteroaryl)alkyl;
l) (amino)alkyl;
m) (alkylamino)alkyl;
n) (dialkylamino)alkyl, and
o) —$(CH_2CH_2O)_m$—$R^{15a}$, or
$R^{5a}$ and $R^{5b}$ taken together with the nitrogen atom to which they are attached form an optionally substituted 3- to 8-membered heterocyclo;
$R^{6a}$ and $R^{6b}$, which are identical or different, are selected from the group consisting of:
a) hydrogen;
b) optionally substituted alkyl;
c) optionally substituted cycloalkyl;
d) optionally substituted heterocyclo;
e) optionally substituted aryl;
f) optionally substituted heteroaryl;
g) hydroxyalkyl
h) (heterocyclo)alkyl;
i) (heteroaryl)alkyl;
j) (amino)alkyl;
k) (alkylamino)alkyl;
l) (dialkylamino)alkyl;
m) (carboxamido)alkyl;
n) (cyano)alkyl, and
o) —$(CH_2CH_2O)_n$—$R^{15b}$; or
$R^{6a}$ and $R^{6b}$ taken together with the nitrogen atom to which they are attached form an optionally substituted 3- to 8-membered heterocyclo;
$R^7$ is selected from the group consisting of:
a) hydrogen;
b) optionally substituted alkyl;
c) optionally substituted cycloalkyl;
d) optionally substituted heterocyclo;
e) optionally substituted aryl;
f) optionally substituted heteroaryl;
g) (heterocyclo)alkyl;
h) (heteroaryl)alkyl;
i) (amino)alkyl;
j) (alkylamino)alkyl;
k) (dialkylamino)alkyl; and
l) —$(CH_2CH_2O)_o$—$R^{15c}$,
$R^{8a}$ and $R^{8b}$, which are identical or different, are selected from the group consisting of:
a) hydrogen;
b) optionally substituted alkyl; and
c) —$(CH_2CH_2O)_p$—$R^{15d}$,
L is selected from the group consisting of —O— and —$NR^{16}$—;
$R^9$ is selected from the group consisting of hydrogen, alkyl and —$(CH_2CH_2O)_q$—$R^{15e}$;
$R^{15a}$, $R^{15b}$, $R^{15c}$, $R^{15d}$, and $R^{15e}$, which are identical or different, are selected from the group consisting of hydrogen and optionally substituted alkyl;

$R^{16}$ is selected from the group consisting of hydrogen and optionally substituted alkyl;

m, n, o, p, and q are each independently 1, 2, 3, 4, 5, 6, 7, 8, 9, 10, or 11;

w is 0, 1, 2, 3, 4 or 5;

x and y are each independently 1, 2, 3, or 4;

E is selected from the group consisting of:
a) halogen;
b) optionally substituted heteroaryl;
c) optionally substituted heterocyclo;
d) hydroxyalkyl;

e)
E-1 f)
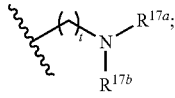
E-2 g)
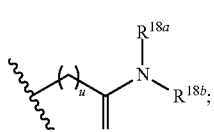
E-3 h)
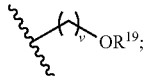
E-4 i)
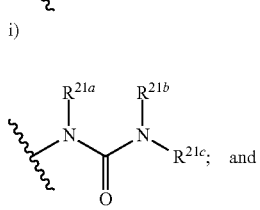
E-5 j)
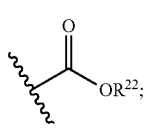
E-6 wherein:

$R^{17a}$ and $R^{17b}$, which are identical or different, are selected from the group consisting of:
a) hydrogen;
b) optionally substituted alkyl;
c) —SO$_2$R$^{24a}$;
d) —COR$^{24b}$;
e) optionally substituted aryl;
f) optionally substituted heteroaryl;
g) (heterocyclo)alkyl;
h) (heteroaryl)alkyl;
i) (amino)alkyl;
j) (alkylamino)alkyl;
k) (dialkylamino)alkyl;
l) (carboxamido)alkyl;
m) (cyano)alkyl; and
n) hydroxyalkyl; or $R^{17a}$ and $R^{1m}$ taken together with the nitrogen atom to which they are attached form an optionally substituted 3- to 8-membered heterocyclo;

$R^{18a}$ and $R^{18b}$, which are identical or different, are selected from the group consisting of:
a) hydrogen;
b) optionally substituted alkyl;
c) optionally substituted cycloalkyl;
d) optionally substituted aryl;
e) optionally substituted heteroaryl;
f) (heterocyclo)alkyl;
g) (heteroaryl)alkyl; and
h) (dialkylamino)alkyl; or $R^{18a}$ and $R^{18b}$ taken together with the nitrogen atom to which they are attached form an optionally substituted 3- to 8-membered heterocyclo;

$R^{19}$ is selected from the group consisting of hydrogen and optionally substituted alkyl;

$R^{20a}$ and $R^{20b}$, which are identical or different, are selected from the group consisting of hydrogen and optionally substituted alkyl, wherein at least one of $R^{20a}$ and $R^{20b}$ is optionally substituted alkyl;

$R^{21a}$ is selected from the group consisting of hydrogen and alkyl;

$R^{21b}$ and $R^{21b}$, which are identical or different, are selected from the group consisting of:
a) hydrogen;
b) optionally substituted alkyl;
c) optionally substituted cycloalkyl;
d) optionally substituted aryl;
e) optionally substituted heteroaryl;
f) (heterocyclo)alkyl;
g) (heteroaryl)alkyl; and
h) (dialkylamino)alkyl; or $R^{21b}$ and $R^{21c}$ taken together with the nitrogen atom to which they are attached form an optionally substituted 3- to 8-membered heterocyclo;

$R^{22}$ is selected from the group consisting of hydrogen and alkyl;

$R^{24a}$ is selected from the group consisting of optionally substituted alkyl, optionally substituted cycloalkyl, optionally substituted aryl, and optionally substituted heteroaryl;

$R^{24b}$ is selected from the group consisting of optionally substituted alkyl, optionally substituted cycloalkyl, optionally substituted aryl, and optionally substituted heteroaryl;

t and u are each independently 0, 1, 2, or 3; and v is 1, 2, or 3;

wherein:

1) when G is:

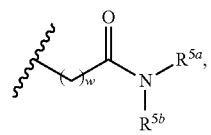
G-1 w is 0, and E is:

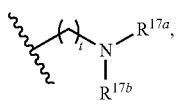
E-1 then R$^{17a}$ is not hydrogen or alkyl when R$^{17b}$ is hydrogen or alkyl;

2) when G is:

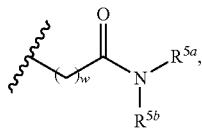
G-1 w is 0, and E is:

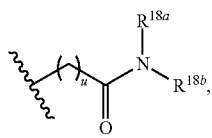
E-2 then u is 1, 2, or 3;

3) when G is:

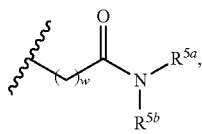
G-1 and R$^{5a}$ and R$^{5b}$ taken together with the nitrogen atom to which they are attached form an optionally substituted 3- to 8-membered heterocyclo, then said optional substituents are selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, alkylcarbonyl, arylcarbonyl, ureido, guanidino, optionally substituted alkyl, optionally substituted cycloalkyl, optionally substituted alkenyl, optionally substituted alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl;

4) when G is:

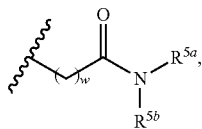
G-1 and w is 0, then E is not a morpholinyl group.

2. A compound having Formula I:

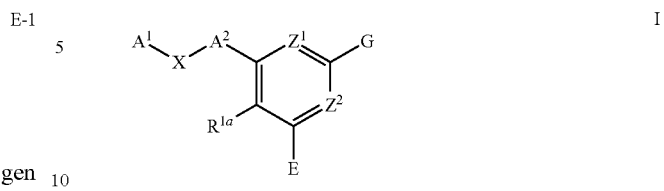
I or a pharmaceutically acceptable salt, or solvate thereof, wherein:

Z$^1$ is CH and Z$^2$ is selected from the group consisting of N and N-oxide;

R$^{1a}$ is hydrogen;

A$^1$ is optionally substituted phenyl;

X is selected from the group consisting of:
a) —O—; and
b) —(CR$^2$R$^3$)$_j$—, wherein:
at each occurrence R$^2$ and R$^3$, which are identical or different, are selected from the group consisting of hydrogen, fluoro, and optionally substituted alkyl; or each R$^2$ and R$^3$ are taken together to form an oxo group; or each R$^2$ and R$^3$ taken together with the carbon atom to which they are attached form a 3- to 8-membered optionally substituted cycloalkyl or optionally substituted heterocyclo;

j is 0 or 1,

A$^2$ is unsubstituted phenyl;

G is selected from the group consisting of:
a) cyano;

b)
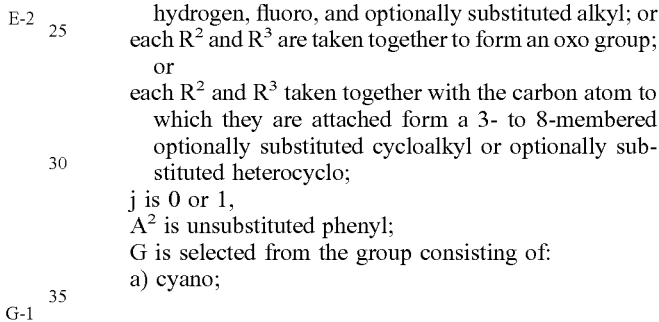
G-1 c)
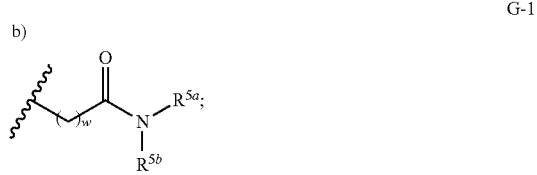
G-2 d)
G-3 e)
G-4

wherein:
R$^{5a}$ and R$^{5b}$ are hydrogen;
R$^{6a}$ is selected from the group consisting of:
a) hydroxyalkyl;
b) (heterocyclo)alkyl;

c) (heteroaryl)alkyl;
d) (amino)alkyl;
e) (alkylamino)alkyl;
f) (dialkylamino)alkyl;
g) (carboxamido)alkyl; and
h) (cyano)alkyl;

$R^{6b}$ is selected from the group consisting of hydrogen and (cyano)alkyl;

$R^7$ is —(CH$_2$CH$_2$O)$_o$—R$^{15c}$, $R^{8a}$ and $R^{8b}$ are hydrogen;

L is —O—;

$R^{15c}$ is selected from the group consisting of hydrogen and optionally substituted alkyl;

o is 1, 2, 3, 4, 5, 6, 7, 8, 9, 10, or 11;

w is 0;

x is 1 or 2, y is 1;

E is selected from the group consisting of:
a) halogen;
b) optionally substituted piperazine;
c) hydroxyalkyl;

d)

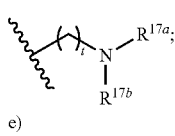

E-1 e)

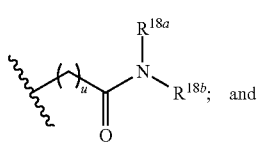

E-2; and f)

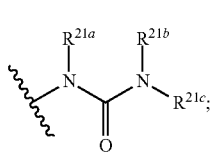

E-5 wherein:
$R^{17a}$ is selected from the group consisting of hydrogen and alkyl;
$R^{17b}$ is selected from the group consisting of:
a) optionally substituted aryl;
b) optionally substituted heteroaryl;
c) (heterocyclo)alkyl;
d) (heteroaryl)alkyl;
e) (amino)alkyl;
f) (alkylamino)alkyl;
g) (dialkylamino)alkyl;
h) (carboxamido)alkyl;
i) (cyano)alkyl;
j) hydroxyalkyl; and
k) —SO$_2$R$^{24a}$ $R^{18a}$ and $R^{18b}$ are hydrogen or optionally substituted alkyl;

$R^{21a}$ is selected from the group consisting of hydrogen and alkyl;

$R^{21b}$ and $R^{21c}$, which are identical or different, are selected from the group consisting of:

a) hydrogen;
b) optionally substituted alkyl;
c) optionally substituted cycloalkyl;
d) optionally substituted aryl;
e) optionally substituted heteroaryl;
f) (heterocyclo)alkyl;
g) (heteroaryl)alkyl; and
h) (dialkylamino)alkyl; or $R^{21b}$ and $R^{21c}$ taken together with the nitrogen atom to which they are attached form an optionally substituted 3- to 8-membered heterocyclo;

$R^{24a}$ is selected from the group consisting of optionally substituted alkyl, optionally substituted cycloalkyl, optionally substituted aryl, and optionally substituted heteroaryl;

t is 0 or 1; and u is 0;

with the provisos:
a) when G is cyano, or G-1, then E is optionally substituted piperazine, hydroxyalkyl, E-1, or E-5, or
b) when E is halogen, then G is G-2, G-3, or G-4.

3. The compound of claim 1 having Formula VI:

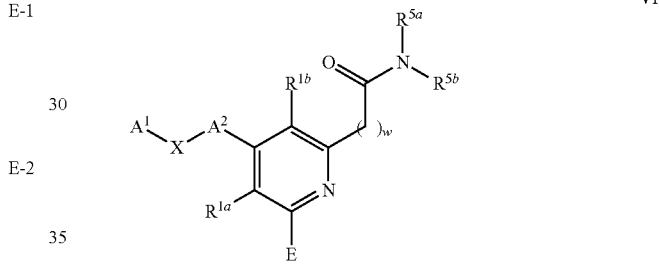

VI or a pharmaceutically acceptable salt, or solvate thereof.

4. The compound of claim 1 having Formula IX:

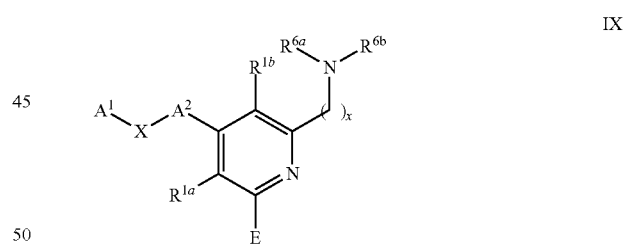

IX or a pharmaceutically acceptable salt, or solvate thereof.

5. The compound of claim 1 having Formula XV:

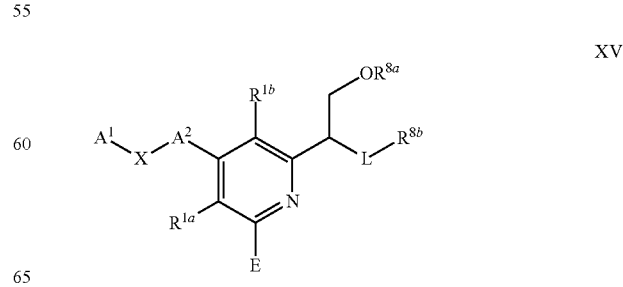

XV or a pharmaceutically acceptable salt, or solvate thereof.

6. The compound of claim 1 having Formula XVIII:

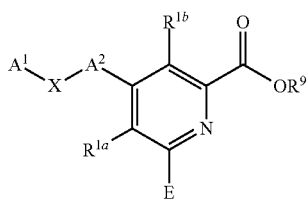

XVIII or a pharmaceutically acceptable salt, or solvate thereof.

7. The compound of claim 1, or a pharmaceutically acceptable salt, or solvate thereof, wherein $A^1$-X-$A^2$- is:

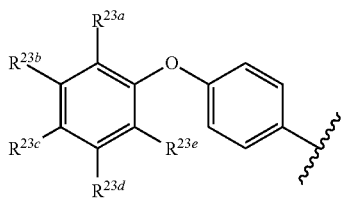

wherein:
$R^{23a}$, $R^{23b}$, $R^{23c}$, $R^{23d}$, $R^{23e}$, which are identical or different, are selected from the group consisting of:
a) hydrogen;
b) halo;
c) nitro;
d) cyano;
e) hydroxy;
f) amino;
g) alkylamino;
h) dialkylamino;
i) haloalkyl;
j) hydroxyalkyl;
k) alkoxy;
l) haloalkoxy;
m) aryloxy;
n) aralkyloxy;
o) alkylthio;
p) carboxamido;
q) sulfonamido;
r) alkylcarbonyl;
s) arylcarbonyl;
t) alkylsulfonyl;
u) arylsulfonyl;
v) ureido;
w) guanidino;
x) carboxy;
y) carboxyalkyl;
z) alkyl;
aa) optionally substituted cycloalkyl;
bb) optionally substituted alkenyl;
cc) optionally substituted alkynyl;
dd) optionally substituted aryl;
ee) optionally substituted heteroaryl; and
ff) optionally substituted heterocyclo; or
$R^{23a}$ and $R^{23b}$, or $R^{23b}$ and $R^{23c}$, or $R^{23c}$ and $R^{23d}$, or $R^{23d}$ and $R^{23e}$, taken together with the carbon atoms to which they are attached form a 5- or 6-membered optionally substituted cycloalkyl or heterocyclo group.

8. The compound of claim 1, or a pharmaceutically acceptable salt, or solvate thereof, wherein $R^{1a}$ and $R^{1b}$ are each hydrogen.

9. The compound of claim 8, or a pharmaceutically acceptable salt, or solvate thereof, wherein E is:

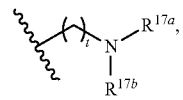

E-1 wherein t is 0 or 1; and
$R^{17a}$ and $R^{17b}$, which are identical or different, are selected from the group consisting of
a) hydrogen;
b) optionally substituted alkyl;
c) —$SO_2R^{24a}$;
d) optionally substituted aryl;
e) optionally substituted heteroaryl;
f) (heterocyclo)alkyl;
g) (heteroaryl)alkyl;
h) (carboxamido)alkyl;
i) (cyano)alkyl; and
j) hydroxyalkyl.

10. The compound of claim 8, or a pharmaceutically acceptable salt, or solvate thereof, wherein E is:

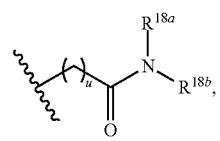

E-2 wherein
u is 0; and
$R^{18a}$ and $R^{18b}$, which are identical or different, are selected from the group consisting of:
a) hydrogen; and
b) optionally substituted alkyl.

11. The compound of claim 8, or a pharmaceutically acceptable salt, or solvate thereof, wherein E is:

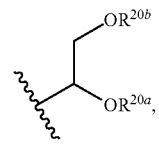

E-4 wherein
$R^{20a}$ and $R^{20b}$, which are identical or different, are selected from the group consisting of hydrogen and alkyl; wherein at least one of $R^{20a}$ and $R^{20b}$ is alkyl.

12. The compound of claim 1, or a pharmaceutically acceptable salt, solvate, or prodrug thereof, wherein E is:

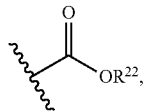

E-6 wherein $R^{22}$ is hydrogen.

13. The compound of claim 8, wherein E is optionally substituted heteroaryl or halogen.

14. A pharmaceutical composition, comprising the compound of claim 1, or a pharmaceutically acceptable salt, or solvate thereof, and a pharmaceutically acceptable carrier.

15. A method for treating pain in a mammal, comprising administering an effective amount of a compound as claimed in claim 1, or a pharmaceutically acceptable salt, or solvate thereof, to a mammal in need of such treatment.

16. The method of claim 15, wherein said pain is selected from the group consisting of chronic pain, inflammatory pain, neuropathic pain, acute pain, and surgical pain.

17. A method of modulating sodium channels in a mammal, comprising administering to the mammal at least one compound as claimed in claim 1.

18. The method of claim 17, wherein $Na_v1.7$ sodium channel is modulated.

19. The compound of claim 8, wherein E is hydroxyalkyl.

* * * * *